US006689581B1

(12) United States Patent
Rhodes et al.

(10) Patent No.: US 6,689,581 B1

(45) Date of Patent: Feb. 10, 2004

(54) POTASSIUM CHANNEL INTERACTORS AND USES THEREFOR

(75) Inventors: Kenneth Rhodes, Neshanic Station, NJ (US); Maria Betty, Mt. Laurel, NJ (US); Huai-Ping Ling, Princeton Junction, NJ (US); Wenqian An, Framingham, MA (US)

(73) Assignees: Wyeth, Madison, NJ (US); Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/350,614

(22) Filed: Jul. 9, 1999

Related U.S. Application Data

(63) Continuation-in-part of application No. 09/298,731, filed on Apr. 23, 1999, now Pat. No. 6,369,197.

(60) Provisional application No. 60/110,033, filed on Nov. 25, 1998, provisional application No. 60/109,333, filed on Nov. 20, 1998, and provisional application No. 60/110,277, filed on Nov. 30, 1998.

(51) Int. Cl.$^7$ ........................ C12N 15/12; C12N 15/63; C12N 15/00; C07H 21/04

(52) U.S. Cl. .................. 435/69.1; 435/320.1; 435/325; 536/23.5

(58) Field of Search ........................ 536/23.5; 435/69.1, 435/320.1, 325

(56) References Cited

FOREIGN PATENT DOCUMENTS

| | | |
|---|---|---|
| WO | WO 97/31112 | 8/1997 |
| WO | WO 98/16185 | 4/1998 |
| WO | WO 99/49038 | 9/1999 |

OTHER PUBLICATIONS

Bygrave FL, Roberts HR. Regulation of cellular calcium through signaling cross–talk involves an intricate interplay between the actions of receptors, G–proteins, and second messengers. FASEB J. 1995 Oct;9(13):1297–303.*

Christine MJ. Molecular and functional diversity of K+ channels. Clin Exp Pharmacol Physiol. 1995 Dec;22(12):944–51.*

Mikayama T. Molecular cloning and functional expression of a cDNA encoding glycosylation–inhibiting factor. Proc. Natl. Acad. Sci. USA vol. 90, pp. 10056–10060, 1993.*

Voet et al. Biochemistry. 1990. John Wiley & Sons, Inc.. pp. 126–128 and 228–234.*

Hiilier et al. "yo76e10.r1 Soares adult brain N2b4HB55y Homo sapiens clone IMAGE:183882 5', mRNA." EST. Accession H30608. Aug. 16, 1995.*

Bonaldo et al., GenBank Accession No. AA859724 [online], "Calcium–binding protein NCS–1" (Mar. 14, 1998).

Castagna, Michela et al. "Molecular Characteristics of Mammalian and Insect Amino Acid Transporters: Implications for Amino Acid Homeostatis" *The Journal of Experimental Biology* 200:269–286 (1997).

Lombardi, Stephen J. et al. "Structure–Activity Relationships of the $K_v\beta1$ Inactivation Domain and Its Putative Receptor Probed Using Peptide Analogs of Voltage–gated Potassium Channel α– and β–Supunits" *The Journal of Biogical Chemistry* 273(46):30092–30096 (Nov. 13, 1998).

National Cancer Intsitute–Cancer Genome Aanatomy Project, GenBank Accession No. AI038858 [online] , ". . . Homo sapiens cDNA clone IMAGE:1659605 3' similar to SW:VIS3_Rat P35333 Visinin–like Protein" (Jul. 01, 1998).

Kim, E. et al. "Clustering of Shaker–type $K^+$ channels by interaction with a family of membrane–associated guanylate kinases" *Nature* 378:85–88 (Nov. 2, 1995).

Scannevin, R.H. and Trimmer, J.S. "Cytoplasmic Domains of Voltage–Sensitive $K^+$Channels Involved in Mediating Protein–Protein Interactions" *Biochemical and Biophysical Research Communications* 232:585–589 (1997).

Sheng, M. and Kim, E. "Ion channel associated proteins" *Current Opinion in Neurobiology* 6:602–608 (1996).

Adachi, Y. et al., "Identification and Characterization of SET, a nuclear phosphoprotein encoded by the translocation break point in acute undifferentiated leukemia," *J. Biol. Chem.*, 269:2258–2262 (1994).

Bilbe,G., et al., "Restin: a novel intermediate filament–associated protein highly expressed in the Reed–Sternberg cells of Hodgkin's disease," *EMBO J.* 11 (6):2103–2113 (1992).

Buxbaum, Joseph D. , et al., "Calsenilin: A Calcium–binding protein that interacts with the presenilins and regulates the levels of a presenilin fragments", *Nature Medicine*, Vol, 4, No. 10, pp. 1177–1181 (1998).

Carrion, Angel M., et al., "DREAM is a $CA^{2+}$–regulated transcriptional repressor", *Nature*, vol. 398, pp 80–84 (1999).

(List continued on next page.)

*Primary Examiner*—Yvonne Eyler
*Assistant Examiner*—Joseph F. Murphy
(74) *Attorney, Agent, or Firm*—Lahive & Cockfield, LLP; Amy E. Mandragouras; Maria Laccotripe Zacharakis

(57) ABSTRACT

The invention provides isolated nucleic acids molecules, designated PCIP nucleic acid molecules, which encode proteins that bind potassium channels and modulate potassium channel mediated activities. The invention also provides antisense nucleic acid molecules, recombinant expression vectors containing PCIP nucleic acid molecules, host cells into which the expression vectors have been introduced, and nonhuman transgenic animals in which a PCIP gene has been introduced or disrupted. The invention still further provides isolated PCIP proteins, fusion proteins, antigenic peptides and anti-PCIP antibodies. Diagnostic methods utilizing compositions of the invention are also provided.

53 Claims, 42 Drawing Sheets

OTHER PUBLICATIONS

Cunningham, E. et al., "Phosphatidylinositol transfer protein dictates the rate of inositol trishosphate production by promoting the synthesis of PIP2," *Curr Biol.* 5(7):775–83 (1995).

DeCastro, E. et al., "Regulation of rhodopsin phosphorylation by a family of neuronal calcium sensors" *Biochem Biophys Res Commun.*;216(1):133–40 1995).

Dickerson,S.K., et al., "Isolation and sequence of cDNA clones encoding rat phosphatidylinositol transfer protein," *J. Biol. Chem.* 264 (28):16557–16564 (1989).

Dixon, J., "Role of the Kv4.3 K+ channel in ventricular muscle. A molecular correlate for the transient outward current" *Circ Res.*;79(4):659–68. (1996).

Endo, T.A. et al., "A new protein containing an SH2 domain that inhibits JAK kinase," *Nature.* 387(6636):921–4 (1997).

Fukuda, J. et al., "Breakdown of cytoskeletal filaments selectively reduces Na and Ca spikes in cultured mammal neurones," *Nature.* 294(5836):82–5 (1981).

Funkhouser, J.D.; 'Amino–terminal sequence of a phosholipid transfer protein from rat,lung, Biochem. Biophys. Res. Commun. 145:1310–1314 (1987).

Hoffman, D.A. et al., "K+ channel regulation of signal propagation in dendrites of hippocampal pyramidal neurons," *Nature.* 387(6636):869–75 (1997).

Hoffman, D.A. et al., "Downregulation of transient k+ channels in dendrites of hippocampal CA1 pyramidal neurons by activation of PKA and PKC," *J Neurosci.* 18(10):3521–8 (1998).

Honore, E. et al., "Different types of K+ channel current are generated by different levels of a single mRNA," *EMBO J.* 11(7):2465–71 (1992).

Hoppe–Seyler, "Purification and Characterization of two putative HLA class II associated proteins:PHAPI and PHAPII," *Biol. Chem.*, 375:113–126 (1994).

Jan, L.Y. et al., "How might the diversity of potassium channels be generated?" *Trends Neurosci.* 13(10);415–9 (1990).

Johnson, B.D. et al., "A cytoskeletal mechanism for Ca2+ channel metabolic dependence and inactivation by intracellular ca2+, " *Neuron.* 10(5):797–804 (1993).

Kaab, S. et al., "Molecular basis of transient outward potassium current downregulation in human heart failure: a decrease in Kv4.3 mRNA correlates with a reduction in current density" *Circulation.* 98(14):1383–93 (1998).

Levin, G. et al., "Phosphorylation of a K+ channel alpha subunit modulates the inactivation conferred by a beta subunit. Involvement of cytoskeleton," *J Biol Chem.* 271(46):29321–8 (1996).

Li, M., et al., "The myeloid leukemia–associated protein SET is a potent inhibitor of protein phosphatase 2A," *J. Biol. Chem.* 271 (19):11059–11062 (1996).

Masiakowski, P. et al., "Nerve growth factor induces the genes for two proteins related to a family of calcium–binding proteins in PC12 cells," *Proc Natl Acad Sci U S A.* 85(4);1277–81 (1988).

Nagase, T. et al., "Prediction of the coding sequence of unidentified human genes.XI. The complete sequences of 100 new cDNA clones from brain which code for large proteins in vitro," *DNA Res.* 5 (5):277–286 (1998).

Nagata, K. et al., "Replication factor encoded by a putative oncogene, set, associated with myeloid leukemogenesis," *Proc. Natl. Acad. Sci. U.S.A.*, 92:4279–4283 (1995).

Naka, T. et al., "Structure and function of a new STAT–induced STAT inhibitor," *Nature.* 387(6636):924–9 (1997).

Nakamura, T.Y. et al., "Modulation of Kv4 channels, key components of rat ventricular transient outward K+ current, by PKC," *Am J Physiol.* 273(4 Pt 2):H1775–86 (1997).

Nerbonne, J., "Regulation of voltage–gated K+ channel expression in the developing mammalian myocardium", *J. Neurobiol.*;37(1):37–59. (1998)Review.

Panaretou, C. et al., "Characterization of p150, an adaptor protein for the human phosphatidylinositol (Ptdlns) 3–kinase. Substrate presentation by phosphatidylinositol transfer protein to the p150.Ptdins 3–kinase complex," *J Biol Chem.* 272(4):2477–85 (1997).

Pierre,P., et al., "CLIP–170 links endocytic vesicles to microtubules," *Cell* 70 (6):887–900 (1992).

Pongs, O. et al., "Regulation of the activity of voltage–gated potassium channels by beta subunits" *Sem. Neurosci.* 7:137–146 (1995).

Prevarskaya, N.B. et al., "Role of tyrosine phosphorylation in potassium channel activation. Functional association with prolactin receptor and JAK2 tyrosine kinase," *J Biol Chem.* 270(41):24292–9 (1995).

Serodio, P. et al., "Cloning of a Novel Component of A–Type $K^+$ Channels Operating at Subthreshold Potential with Unique Expression in Heart and Brian" *Journal of Neurophysiology*, vol. 75, No. 5, pp. 2174–2179 (1996).

Sheng, M. et al., "Subcellular segregation of two A–type K+ channel proteins in rat central neurons," *Neuron.* 9(2):271–84 (1992).

Simon, H.U. et al., "Molecular characterization of hNRP, a cDNA encoding a human nucleosome–assembly–protein–I–related gene product invloved in the induction of cell proliferation," *Biochem. J.*, 297:389–397 (1994).

Starr, R. et al., "A family of cytokine–inducible inhibitors of signalling," *Nature.* 387(6636):917–21 (1997).

Touchot, N. et al., "Four additional members of the ras gene duperfamily isolated by an oligonucleotide strategy: Molecular cloning of YPT–related cDNAs from a rat brain library," *Proc natl Acad Sci U S A.* 84(23):8210–4 (1987).

Van Hille, B. et al., "Identification of two subunit A isoforms of the vacuolar H(+)–ATPase in human osteoclastoma," *J Biol Chem.* 268(10):7075–80 (1993).

Von Lindern, M. et al., "Can, a putative oncogene associated with myeloid leukemogenesis, may be activated by fusion of its 3' half to different genes: characterization of the set gene," *Mol. Cell Biol.*, 12:3346–3355 (1992).

* cited by examiner

HUMAN 1V DNA (CD:225-875)

GAATAGCCCCCTTTCACTTCTGAGTCCCTGCATGTGCGGGGCTGAAGAAGGAAGCCAGAAGCCTCCTAGCCTCGCCTCCA
CGTTTGCTGAATACCAAGCTGCAGGCGAGCTGCCGGGCGCTTTTCTCTCCTCCAATTCAGAGTAGACAAACCACGGGGAT
TTCTTTCCAGGGTAGGGGAGGGGCCGGGCCCGGGGTCCCAACTCGCACTCAAGTCTTCGCTGCCATGGGGGCCGTCATGG
GCACCTTCTCATCTCTGCAAACCAAACAAAGGCGACCCTCGAAAGATAAGATTGAAGATGAGCTGGAGATGACCATGGTT
TGCCATCGGCCCGAGGGACTGGAGCAGCTCGAGGCCCAGACCAACTTCACCAAGAGGGAGCTGCAGGTCCTTTATCGAGG
CTTCAAAAATGAGTGCCCCAGTGGTGTGGTCAACGAAGACACATTCAAGCAGATCTATGCTCAGTTTTTCCCTCATGGAG
ATGCCAGCACGTATGCCCATTACCTCTTCAATGCCTTCGACACCACTCAGACAGGCTCCGTGAAGTTCGAGGACTTTGTA
ACCGCTCTGTCGATTTTATTGAGAGGAACTGTCCACGAGAAACTAAGGTGGACATTTAATTTGTATGACATCAACAAGGA
CGGATACATAAACAAAGAGGAGATGATGGACATTGTCAAAGCCATCTATGACATGATGGGAAATACACATATCCTGTGC
TCAAAGAGGACACTCCAAGGCAGCATGTGGACGTCTTCTTCCAGAAAATGGACAAAAATAAAGATGGCATCGTAACTTTA
GATGAATTTCTTGAATCATGTCAGGAGGACGACAACATCATGAGGTCTCTCCAGCTGTTTCAAAATGTCATGTAACTGGT
GACACTCAGCCATTCAGCTCTCAGAGACATTGTACTAAACAACCACCTTAACACCCTGATCTGCCCTTGTTCTGATTTTA
CACACCAACTCTTGGGACAGAAACACCTTTTACACTTTGGAAGAATTCTCTGCTGAAGACTTTCTTATGGAACCCAGCAT
CATGTGGCTCAGTCTCTGATTGCCAACTCTTCCTCTTTCTTCTTCTTGAGAGAGACAAGATGAAATTTGAGTTTGTTTTG
GAAGCATGCTCATCTCCTCACACTGCTGCCCTATGGAAGGTCCCTCTGCTTAAGCTTAAACAGTAGTGCACAAAATATGC
TGCTTACGTGCCCCCAGCCCACTGCCTCCAAGTCAGGCAGACCTTGGTGAATCTGGAAGCAAGAGGACCTGAGCCAGATG
CACACCATCTCTGATGGCCTCCCAAACCAATGTGCCTGTTTCTCTTCCTTTGGTGGGAAGAATGAGAGTTATCCAGAACA
ATTAGGATCTGTCATGACCAGATTGGGAGAGCCAGCACCTAACATATGTGGGATAGGACTGAATTATTAAGCATGACATT
GTCTGATGACCCAAACTGCCCCG

HUMAN 1V PROTEIN

MGAVMGTFSSLQTKQRRPSKDKIEDELEMTMVCHRPEGLEQLEAQTNFTKRELQVLYRGFKNECPSGVVNEDTFKQIYAQ

FFPHGDASTYAHYLFNAFDTTQTGSVKFEDFVTALSILLRGTVHEKLRWTFNLYDINKDGYINKEEMMDIVKAIYDMMGK

YTYPVLKEDTPRQHVDVFFQKMDKNKDGIVTLDEFLESCQEDDNIMRSLQLFQNVM

Fig. 1

RAT 1vN (r1vN) DNA (CD: 339-1037)

GGCACACAACCCCTGGATTCTTCGGAGAATATGCCGTGAGGTGTTGCCAATTATTAGTTCTCTTGGCTAGCAGATGTTTA
GGGACTGGTtaaGCCTTTGGAGAAATTACCTTAGGAAAACGGGGAAATAAAAGCAAAGATTACCATGAATTGCAAGATTA
CCTAGCAATTGCAAGGtagGAGGAGAGAGGTGGAGGGCGGAGTAGACAGGAGGGAGGGAGAAAGtgaGAGGAAGCTAGGC
TGGTGGAAATAACCCTGCACTTGGAACAGCGGCAAAGAAGCGCGATTTTCCAGCTTtaaATGCCTGCCCGCGTTCTGCTT
GCCTACCCGGGAACGGAGATGTTGACCCAGGGCGAGTCTGAAGGGCTCCAGACCTTGGGGATAGTAGTGGTCCTGTGTTC
CTCTCTGAAACTACTGCACTACCTCGGGCTGATTGACTTGTCGGATGACAAGATCGAGGATGATCTGGAGATGACCATGG
TTTGCCATCGGCCTGAGGGACTGGAGCAGCTTGAGGCACAGACGAACTTCACCAAGAGAGAACTGCAAGTCCTTTACCGG
GGATTCAAAAACGAGTGCCCCAGTGGTGTGGTTAACGAAGAGACATTCAAGCAGATCTACGCTCAGTTTTTCCCTCATGG
AGATGCCAGCACATACGCACATTACCTCTTCAATGCCTTCGACACCACCCAGACAGGCTCTGTAAAGTTCGAGGACTTTG
TGACTGCTCTGTCGATTTTACTGAGAGGAACGGTCCATGAAAAACTGAGGTGGACGTTTAATTTGTACGACATCAATAAA
GACGGCTACATAAACAAAGAGGAGATGATGGACATAGTGAAAGCCATCTATGACATGATGGGGAAATACACCTATCCTGT
GCTCAAAGAGGACACTCCCAGGCAGCACGTGGACGTCTTCTTCCAGAAAATGGATAAAAATAAAGATGGCATTGTAACGT
TAGACGAATTTCTCGAGTCCTGTCAGGAGGATGACAACATCATGAGGTCTCTACAGCTGTTCCAAAATGTCATGTAACTG
AGGACACTGGCCATCCTGCTCTCAGAGACACTGACAAACACCTCAATGCCCTGATCTGCCCTTGTTCCAGTTTTACACAT
CAACTCTCGGGACAGAAATACCTTTTACACTTTGGAAGAATTCTCTGCTGAAGACTTTCTACAAAACCTGGCACCGAGTG
GCTCAGTCTCTGATTGCCAACTCTTCCTCCCTCCTCCTCTTGAGAGGGACGAGCTGAAATCCGAAGTTTGTTTTGGAAGC
ATGCCCATCTCTCCATGCTGCTGCTGCCCTGTGGAAGGCCCCTCTGCTTGAGCTTAAACAGTAGTGCACAGTTTTCTGCG
TATACAGATCCCCAACTCACTGCCTCTAAGTCAGGCAGACCCTGATCAATCTGAACCAAATGTGCACCATCCTCCGATGG
CCTCCCAAGCCAATGTGCCTGCTTCTCTTCCTCTGGTGGGAAGAAAGAACGCTCTACAGAGCACTTAGAGCTTACCATGA
AAATACTGGGAGAGGCAGCACCTAACACATGTAGAATAGGACTGAATTATTAAGCATGGTGGTATCAGATGATGCAAACA
GCCCATGTCATTTTTTTTTCCAGAGGTAGGGACTAATAATTCTCCCACACTAGCACCTACGATCATAGAACAAGTCTTTT
AACACATCCAGGAGGGAAACCGCTGCCCAGTGGTCTATCCCTTCTCTCCATCCCCTGCTCAAGCCCAGCACTGCATGTCT
CTCCCGGAAGGTCCAGAATGCCTGTGAAATGCTGTAACTTTTATACCCTGTTATAATCAATAAACAGAACTATTTCGTAC
AAAAAAAAAAAAAAAA

Fig. 2A

RAT 1vN (r1vN) PROTEIN

MLTQGESEGLQTLGIVVVLCSSLKLLHYLGLIDLSDDKIEDDLEMTMVCHRPEGLEQLEAQTNFTKRELQVLYRGFKNEC

PSGVVNEETFKQIYAQFFPHGDASTYAHYLFNAFDTTQTGSVKFEDFVTALSILLRGTVHEKLRWTFNLYDINKDGYINK

EEMMDIVKAIYDMMGKYTYPVLKEDTPRQHVDVFFQKMDKNKDGIVTLDEFLESCQEDDNIMRSLQLFQNVM.

Fig. 2B

MOUSE 1V (CD:477-1127)

CGGCCCCCTGAGATCCAGCCCGAGCGCGGGGCGGAGCGGCCGGGTGGCAGCAGGGGCGGGCGGGCGGAGCGCAGCTCCCG
CACCGCACGCGGCGCGGGCTCGGCAGCCTCGGCCGTGCGGGCACGCCGGCCCCGTGTCCAACATCAGGCAGGCTTTGGGG
CTCGGGGCTCGGGCCTCGGAGAAGCCAGTGGCCCGGCTGGGTGCCCGCACCGGGGGGCGCCTGTCAAGGCTCCCGCGAGC
CTCTGGCCCTGGGAGTCAGTGCATGTGCCTGGCTGAAGAAGGCAGCAGCCACGAGCTCCAGGCGCCCCGGCCCCACGTTT
TCTGAATACCAAGCTGCAGGCGAGCTGCTCGGGGCTTTTTTGCTTTCTCGCTTTTCCTCTCCTCCAATTCAAAGTGGGCA
ATCCACACCGATTTCTTTTCAGGGGAGGGAAGAGACAGGGCCTGGGGTCCCAAGACGCACACAAGTCTTCGCTGCCATGG
GGGCCGTCATGGGCACTTTCTCCTCCCTGCAGACCAAACAAAGGCGACCCTCTAAAGACAAGATTGAGGATGAGCTAGAG
ATGACCATGGTTTGCCACCGGCCTGAGGGACTGGAGCAGCTTGAGGCACAGACGAACTTCACCAAGAGAGAACTGCAAGT
CTTGTACCGGGGATTCAAAAACGAGTGCCCTAGCGGTGTGGTCAATGAAGAAACATTCAAGCAGATCTACGCTCAGTTTT
TCCCTCACGGAGATGCCAGCACATATGCACATTACCTCTTCAATGCCTTCGACACCACCCAGACAGGCTCTGTAAAGTTC
GAGGACTTTGTGACTGCTCTGTCGATTTTACTGAGAGGGACAGTCCATGAAAAACTAAGGTGGACGTTTAATTTGTATGA
CATCAATAAAGACGGCTACATAAACAAAGAGGAGATGATGGACATAGTCAAAGCCATCTATGACATGATGGGGAAATACA
CCTATCCTGTGCTCAAAGAGGACACTCCCAGGCAGCATGTGGATGTCTTCTTCCAGAAAATGGATAAAAATAAAGATGGC
ATTGTAACGTTAGATGAATTTCTTGAATCATGTCAGGAGGATGACAACATCATGAGATCTCTACAGCTGTTCCAAAATGT
CATGTAACTGAGGACACTGGCCATTCTGCTCTCAGAGACACTGACAAACACCTTAATGCCCTGATCTGCCCTTGTTCCAA
TTTTACACACCAACTCTTGGGACAGAAATACCTTTTACACTTTGGAAGAATTCTCTGCTGAAGACTTTCTACAAAACCTG
GCACCACGTGGCTCTGTCTCTGAGGGACGAGCGGAGATCCGACTTTGTTTTGGAAGCATGCCCATCTCTTCATGCTGCTG
CCCTGTGGAAGGCCCCTCTGCTTGAGCTTAATCAATAGTGCACAGTTTTATGCTTACACATATCCCCAACTCACTGCCTC
CAAGTCAGGCAGACTCTGATGAATCTGAGCCAAATGTGCACCATCCTCCGATGGCCTCCCAAGCCAATGTGCCTGCTTCT
CTTCCTCTGGTGGGAAGAAAGAGTGTTCTACGGAACAATTAGAGCTTACCATGAAAATATTGGGAGAGGCAGCACCTAAC
ACATGTAGAATAGGACTGAATTATTAAGCATGGTGATATCAGATGATGCAAATTGCCCATGTCATTTTTTTCAAAGGTAG
GGACAAATGATTCTCCCACACTAGCACCTGTGGTCATAGAGCAAGTCTCTTAACATGCCCAGAAGGGGAACCACTGTCCA
GTGGTCTATCCCTCCTCTCCATCCCCTGCTCAAACCCAGCACTGCATGTCCCTCCAAGAAGGTCCAGAATGCCTGCGAAA
CGCTGTACTTTTATACCCTGTTCTAATCAATAAACAGAACTATTTCGTAAAAAAAAAAAAAAAAAAA

MOUSE 1V PROTEIN

MGAVMGTFSSLQTKQRRPSKDKIEDELEMTMVCHRPEGLEQLEAQTNFTKRELQVLYRGFKNECPSGVVNEETFKQIYAQ
FFPHGDASTYAHYLFNAFDTTQTGSVKFEDFVTALSILLRGTVHEKLRWTFNLYDINKDGYINKEEMMDIVKAIYDMMGK
YTYPVLKEDTPRQHVDVFFQKMDKNKDGIVTLDEFLESCQEDDNIMRSLQLFQNVM.

Fig. 3

RAT 1VL DNA (CD: 31-714)

GTCCCAAGTCGCACACAAGTCTTCGCTGCCATGGGGGCCGTCATGGGTACCTTCTCGTCCCTGCAGACCAAACAAAGGCG
ACCCTCTAAAGACATCGCCTGGTGGTATTACCAGTATCAGAGAGACAAGATCGAGGATGATCTGGAGATGACCATGGTTT
GCCATCGGCCTGAGGGACTGGAGCAGCTTGAGGCACAGACGAACTTCACCAAGAGAGAACTGCAAGTCCTTTACCGGGGA
TTCAAAAACGAGTGCCCCAGTGGTGTGGTTAACGAAGAGACATTCAAGCAGATCTACGCTCAGTTTTTCCCTCATGGAGA
TGCCAGCACATACGCACATTACCTCTTCAATGCCTTCGACACCACCCAGACAGGCTCTGTAAAGTTCGAGGACTTTGTGA
CTGCTCTGTCGATTTTACTGAGAGGAACGGTCCATGAAAAACTGAGGTGGACGTTTAATTTGTACGACATCAATAAAGAC
GGCTACATAAACAAAGAGGAGATGATGGACATAGTGAAAGCCATCTATGACATGATGGGGAAATACACCTATCCTGTGCT
CAAAGAGGACACTCCCAGGCAGCACGTGGACGTCTTCTTCCAGAAAATGGATAAAAATAAAGATGGCATTGTAACGTTAG
ACGAATTTCTCGAGTCCTGTCAGGAGGATGACAACATCATGAGGTCTCTACAGCTGTTCCAAAATGTCATGTAACTGAGG
ACACTGGCCATCCTGCTCTCAGAGACACTGACAAACACCTCAATGCCCTGATCTGCCCTTGTTCCAGTTTTACACATCAA
CTCTCGGGACAGAAATACCTTTTACACTTTGGAAGAATTCTCTGCTGAAGACTTTCTACAAAACCTGGCACCGCGTGGCT
CAGTCTCTGATTGCCAACTCTTCCTCCCTCCTCCTCTTGAGAGGGACGAGCTGAAATCCGAAGTTTGTTTTGGAAGCATG
CCCATCTCTCCATGCTGCTGCTGCCCTGTGGAAGGCCCCTCTGCTTGAGCTTAAACAGTAGTGCACAGTTTTCTGCGTAT
ACAGATCCCCAACTCACTGCCTCTAAGTCAGGCAGACCCTGATCAATCTGAACCAAATGTGCACCATCCTCCGATGGCCT
CCCAAGCCAATGTGCCTGCTTCTCTTCCTCTGGTGGAAGAAAGAACGCTCTACAGAGCACTTAGAGCTTACCATGAAAA
TACTGGGAGAGGCAGCACCTAACACATGTAGAATAGGACTGAATTATTAAGCATGGTGGTATCAGATGATGCAAACAGCC
CATGTCATTTTTTTTCCAGAGGTAGGGACTAATAATTCTCCCACACTAGCACCTACGATCATAGAACAAGTCTTTTAACA
CATCCAGGAGGGAAACCGCTGCCCAGTGGTCTATCCCTTCTCTCCATCCCCTGCTCAAGCCCAGCACTGCATGTCTCTCC
CGGAAGGTCCAGAATGCCTGTGAAATGCTGTAACTTTTATACCCTGTTATAATCAATAAACAGAACTATTTCGTACAAAA
AAAAAAAAAAAAAA

RAT 1VL PROTEIN

MGAVMGTFSSLQTKQRRPSKDIAWWYYQYQRDKIEDDLEMTMVCHRPEGLEQLEAQTNFTKRELQVLYRGFKNECPSGVV
NEETFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM.

Fig. 4

MOUSE 1VL DNA (CD: 77-760)

ATCCACACCGATTTCTTTTCAGGGGAGGGAAGAGACAGGGCCTGGGGTCCCAAGACGCACACAAGTCTTCGCTGCCATGG
GGGCCGTCATGGGCACTTTCTCCTCCCTGCAGACCAAACAAAGGCGACCCTCTAAAGACATCGCCTGGTGGTATTACCAG
TATCAGAGAGACAAGATTGAGGATGAGCTAGAGATGACCATGGTTTGCCACCGGCCTGAGGGACTGGAGCAGCTTGAGGC
ACAGACGAACTTCACCAAGAGAGAACTGCAAGTCTTGTACCGGGGATTCAAAAACGAGTGCCCTAGCGGTGTGGTCAATG
AAGAAACATTCAAGCAGATCTACGCTCAGTTTTTCCCTCACGGAGATGCCAGCACATATGCACATTACCTCTTCAATGCC
TTCGACACCACCCAGACAGGCTCTGTAAAGTTCGAGGACTTTGTGACTGCTCTGTCGATTTTACTGAGAGGGACAGTCCA
TGAAAAACTAAGGTGGACGTTTAATTTGTATGACATCAATAAAGACGGCTACATAAACAAAGAGGAGATGATGGACATAG
TCAAAGCCATCTATGACATGATGGGGAAATACACCTATCCTGTGCTCAAAGAGGACACTCCCAGGCAGCATGTGGATGTC
TTCTTCCAGAAAATGGATAAAAATAAAGATGGCATTGTAACGTTAGATGAATTTCTTGAATCATGTCAGGAGGATGACAA
CATCATGAGATCTCTACAGCTGTTCCAAAATGTCATGTAACTGAGGACACTGGCCATTCTGCTCTCAGAGACACTGACAA
ACACCTTAATGCCCTGATCTGCCCTTGTTCCAATTTTACACACCAACTCTTGGGACAGAAATACCTTTTACACTTTGGAA
GAATTCTCTGCTGAAGACTTTCTACAAAACCTGGCACCACGTGGCTCTGTCTCTGAGGGACGAGCGGAGATCCGACTTTG
TTTTGGAAGCATGCCCATCTCTTCATGCTGCTGCCCTGTGGAAGGCCCCTCTGCTTGAGCTTAATCAATAGTGCACAGTT
TTATGCTTACACATATCCCCAACTCACTGCCTCCAAGTCAGGCAGACTCTGATGAATCTGAGCCAAATGTGCACCATCCT
CCGATGGCCTCCCAAGCCAATGTGCCTGCTTCTCTTCCTCTGGTGGGAAGAAAGAGTGTTCTACGGAACAATTAGAGCTT
ACCATGAAAATATTGGGAGAGGCAGCACCTAACACATGTAGAATAGGACTGAATTATTAAGCATGGTGATATCAGATGAT
GCAAATTGCCCATGTCATTTTTTTCAAAGGTAGGGACAAATGATTCTCCCACACTAGCACCTGTGGTCATAGAGCAAGTC
TCTTAACATGCCCAGAAGGGGAACCACTGTCCAGTGGTCTATCCCTCCTCTCCATCCCCTGCTCAAACCCAGCACTGCAT
GTCCCTCCAAGAAGGTCCAGAATGCCTGCGAAACGCTGTACTTTTATACCCTGTTCTAATCAATAAACAGAACTATTTCG
TACAAAAAAAAAAAAAAAAA

MOUSE 1VL PROTEIN

MGAVMGTFSSLQTKQRRPSKDIAWWYYQYQRDKIEDELEMTMVCHRPEGLEQLEAQTNFTKRELQVLYRGFKNECPSGVV
NEETFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM.

Fig. 5

RAT 1VN DNA (FIRST-PASS, PARTIAL; CD: 345-955)

GTCCGGGCACACAACCCCTGGATTCTTCGGAGAATATGCCGTGACGGTGTTGCCAATTATTAGTTCTCTTGGCTAGCAGA
TGTTTAGGGACTGGTTAAGCCTTTGGAGAAATTACCTTAGGAAAACGGGGAAATAAAAGCAAAGATTACCATGAATTGCA
AGATTACCTAGCAATTGCAAGGTAGGAGGAGAGAGGTGGAGGGCGGAGTAGACAGGAGGGAGGGAGAAAGTGAGAGGAAG
CTAGGCTGGTGGAAATAACCCTGCACTTGGAACAGCGGCAAAGAAGCGCGATTTTCCAGCTTTAAATGCCTGCCCGCGTT
CTGCTTGCCTACCCGGGAACGGAGATGTTGACCCAGGGCGAGTCTGAAGGGCTCCAGACCTTGGGGATAGTAGTGGTCCT
GTGTTCCTCTCTGAAACTACTGCACTACCTCGGGCTGATTGACTTGTCGGATGACAAGATCGAGGATGATCTGGAGATGA
CCATGGTTTGCCATCGGCCTGAGGGACTGGAGCAGCTTGAGGCACAGACGAACTTCACCAAGAGAGAACTGCAAGTCCTT
TACCGGGGATTCAAAAACGAGTGCCCCAGTGGTGTGGTTAACGAAGAGACATTCAAGCNGATCTACGCTCAGTTTTTCCC
TCATGGAGATGCCAGCACATACGCACATTACCTCTTCAATGCCTTCGACACCACCCAGACAGGCTCTGTAAAGTTCGAGG
ACTTTGTGACTGCTCTGTCGATTTTACTGAGAGGAACGGTCCATGAAAAACTGAAGTGGACGTTTAATTTGTACGACATC
AATAAAGACGGCTACATAAACAAAGAGGAGATGATGGACATAGTGAAAGCCATCTATGACATGATGGGGAAATACACCTA
TCTTGTGCTCAAAGAGGACACTTCCAGGCAGCACGTGGACGTCTTCTTCCAGAAAATGGATAAAAATAAAGATGG

RAT 1VN PROTEIN (PARTIAL)

MLTQGESEGLQTLGIVVVLCSSLKLLHYLGLIDLSDDKIEDDLEMTMVCHRPEGLEQLEAQTNFTKRELQVLYRGFKNEC
PSGVVNEETFKXIYAQFFPHGDASTYAHYLFNAFDTTQTGSVKFEDFVTALSILLRGTVHEKLKWTFNLYDINKDGYINK
EEMMDIVKAIYDMMGKYTYLVLKEDTSRQHVDVFFQKMDKNKD

Fig. 6

HUMAN 9QL DNA (CD:207-1019)

CTCACCTGCTGCCTAGTGTTCCCTCTCCTGCTCCAGGACCTCCGGGTAGACCTCAGACCCCGGGCCCATTCCCAGACTCA

GCCTCAGCCCGGACTTCCCCAGCCCCGACAGCACAGTAGGCCGCCAGGGGGCGCCGTGTGAGCGCCCTATCCCGGCCACC

CGGCGCCCCCTCCCACGGCCCGGGCGGGAGCGGGGCGCCGGGGGCCATGCGGGGCCAGGGCCGCAAGGAGAGTTTGTCCG

ATTCCCGAGACCTGGACGGCTCCTACGACCAGCTCACGGGCCACCCTCCAGGGCCCACTAAAAAAGCGCTGAAGCAGCGA

TTCCTCAAGCTGCTGCCGTGCTGCGGGCCCCAAGCCCTGCCCTCAGTCAGTGAAACATTAGCCGCCCCAGCCTCCCTCCG

CCCCCACAGACCCCGCCTGCTGGACCCAGACAGCGTGGACGATGAATTTGAATTGTCCACCGTGTGTCACCGGCCTGAGG

GTCTGGAGCAGCTGCAGGAGCAAACCAAATTCACGCGCAAGGAGTTGCAGGTCCTGTACCGGGGCTTCAAGAACGAATGT

CCCAGCGGAATTGTCAATGAGGAGAACTTCAAGCAGATTTACTCCCAGTTCTTTCCTCAAGGAGACTCCAGCACCTATGC

CACTTTTCTCTTCAATGCCTTTGACACCAACCATGATGGCTCGGTCAGTTTTGAGGACTTTGTGGCTGGTTTGTCCGTGA

TTCTTCGGGGAACTGTAGATGACAGGCTTAATTGGGCCTTCAACCTGTATGACCTTAACAAGGACGGCTGCATCACCAAG

GAGGAAATGCTTGACATCATGAAGTCCATCTATGACATGATGGGCAAGTACACGTACCCTGCACTCCGGGAGGAGGCCCC

AAGGGAACACGTGGAGAGCTTCTTCCAGAAGATGGACAGAAACAAGGATGGTGTGGTGACCATTGAGGAATTCATTGAGT

CTTGTCAAAAGGATGAGAACATCATGAGGTCCATGCAGCTCTTTGACAATGTCATCTAGCCCCCAGGAGAGGGGGTCAGT

GTTTCCTGGGGGGACCATGCTCTAACCCTAGTCCAGGCGGACCTCACCCTTCTCTTCCCAGGTCTATCCTCATCCTACGC

CTCCCTGGGGGCTGGAGGGATCCAAGAGCTTGGGGATTCAGTAGTCCAGATCTCTGGAGCTGAAGGGGCCAGAGAGTGGG

CAGAGTGCATCTCGGGGGGTGTTCCCAACTCCCACCAGCTCTCACCCCCTTCCTGCCTGACACCCAGTGTTGAGAGTGCC

CCTCCTGTAGGAATTGAGCGGTTCCCCAC CTCCTACCCTACTCTAGAAACACACTAGAGCGATGTCTCCTGCTATGGTGC

TTCCCCCATCCCTGACCTCATAAACATTTCCCCTAAGACTCCCCTCTCAGAGAGAATGCTCCATTCTTGGCACTGGCTGG

CTTCTCAGACCAGCCATTGAGAGCCCTGTGGGAGGGGGACAAGAATGTATAGGGAGAAATCTTGGGCCTGAGTCAATGGA

TAGGTCCTAGGAGGTGGGTGGGGTTGAGAATAGAAGGGCCTGGACAGATTATGATTGCTCAGGCATACCAGGTTATAGCT

CCAAGTTCCACAGGTCTGCTACCACAGGCCATCAAAATATAAGTTTCCAGGCTTTGCAGAAGACCTTGTCTCCTTAGAAA

TGCCCCAGAAATTTTCCACACCCTCCTCGGTATCCATGGAGAGCCTGGGGCCAGATATCTGGCTCATCTCTGGCATTGCT

TCCTCTCCTTCCTTCCTGCATGTGTTGGTGGTGGTTGTGGTGGGGGAATGTGGATGGGGGATGTCCTGGCTGATGCCTGC

CAAAATTTCATCCCACCCTCCTTGCTTATCGTCCCTGTTTTGAGGGCTATGACTTGAGTTTTTGTTTCCCATGTTCTCTA

TAGACTTGGGACCTTCCTGAACTTGGGGCCTATCACTCCCCACAGTGGATGCCTTAGAAGGGAGAGGGAAGGAGGGAGGC

AGGCATAGC

Fig. 7A

HUMAN 9QL PROTEIN

MRGQGRKESLSDSRDLDGSYDQLTGHPPGPTKKALKQRFLKLLPCCGPQALPSVSETLAAPASLRPHRPRLLDPDSVDDE

FELSTVCHRPEGLEQLQEQTKFTRKELQVLYRGFKNECPSGIVNEENFKQIYSQFFPQGDSSTYATFLFNAFDTNHDGSV

SFEDFVAGLSVILRGTVDDRLNWAFNLYDLNKDGCITKEEMLDIMKSIYDMMGKYTYPALREEAPREHVESFFQKMDRNK

DGVVTIEEFIESCQKDENIMRSMQLFDNVI.

Fig. 7B

RAT 9QL DNA (PARTIAL; CD: 2-775)

CCGAGATCTGGACGGCTCCTATGACCAGCTTACGGGCCACCCTCCAGGGCCCAGTAAAAAAGCCCTGAAGCAGCGTTTCC

TCAAGCTGCTGCCGTGCTGCGGGCCCCAAGCCCTGCCCTCAGTCAGTGAAACATTAGCTGCCCCAGCCTCCCTCCGCCCC

CACAGACCCCGCCCGCTGGACCCAGACAGCGTAGAGGATGAGTTTGAATTATCCACGGTGTGTCACCGACCTGAGGGCCT

GGAACAACTCCAGGAACAGACCAAGTTCACACGCAGAGAGCTGCAGGTCCTGTACCGAGGCTTCAAGAACGAATGCCCCA

GTGGGATTGTCAACGAGGAGAACTTCAAGCAGATTTATTCTCAGTTCTTTCCCCAAGGAGACTCCAGCAACTATGCTACT

TTTCTCTTCAATGCCTTTGACACCAACCACGATGGCTCTGTCAGTTTTGAGGACTTTGTGGCTGGTTTGTCGGTGATTCT

TCGGGGGACCATAGATGATAGACTGAGCTGGGCTTTCAACTTATATGACCCTCAACAAGGACGGCTGTATCACAAAGGAGG

AAATGCTTGACATTATGAAGTCCATCTATGACATGATGGGCAAGTACACATACCCTGCCCTCCGGGAGGAGGCCCCAAGA

GAACACGTGGAGAGCTTCTTCCAGAAGATGGACAGGAACAAGGACGGCGTGGTGACCATCGAGGAATTCATCGAGTCTTG

TCAACAGGACGAGAACATCATGAGGTCCATGCAGCTCTTTGATAATGTCATCTAGCTCCCCAGGGAGAGGGGTTAGTGTG

TCCTAGGGTGACCAGGCTGTAGTCCTAGTCCAGACGAACCTAACCCTCTCTCTCCAGGCCTGTCCTCATCTTACCTGTAC

CCTGGGGGCTGTAGGGATTCAATATCCTGGGGCTTCAGTAGTCCAGATCCCTGAGCTAAGTCACAAAAGTAGGCAAGAGT

AGGCAAGCTAAATCTGGGGGCTTCCCAACCCCCGACAGCTCTCACCCCTTCTCAACTGATACCTAGTGCTGAGGACACCC

CTGGTGTAGGGACCAAGTGGTTCTCCACCTTCTAGTCCCACTCTAGAAACCACATTAGACAGAAGGTCTGGTGCTATGGT

GCTTTCCCCATCCCTAATCTCTTAGATTTTCCTCAAGACTCCCTTCTCAGAGAACACGCTCTGTCCATGTCCCCAGCTGG

GGACATGGACAGAGCGTGTTCTCTAGTTCTAGATCGCGAGCGGCCGC

RAT 9QL PROTEIN (PARTIAL)

RDLDGSYDQLTGHPPGPSKKALKQRFLKLLPCCGPQALPSVSETLAAPASLRPHRPRPLDPDSVEDEFELSTVCHRPEGL

EQLQEQTKFTRRELQVLYRGFKNECPSGIVNEENFKQIYSQFFPQGDSSNYATFLFNAFDTNHDGSVSFEDFVAGLSVIL

RGTIDDRLSWAFNLYDLNKDGCITKEEMLDIMKSIYDMMGKYTYPALREEAPREHVESFFQKMDRNKDGVVTIEEFIESC

QQDENIMRSMQLFDNVI.

Fig. 8

MOUSE 9QL DNA (CD: 181-993)

CGGGACTCTGAGGTGGGCCCTAAAATCCAGCGCTCCCCAGAGAAAAGCCTTGCCAGCCCCTACTCCCGGCCCCCAGCCCC
AGCAGGTCGCTGCGCCGCCAGGGGGCACTGTGTGAGCGCCCTATCCTGGCCACCCGGCGCCCCCTCCCACCGCCCAGGCG
GGAGCGGGGCGCCGGGGGCCATGCGGGGCCAAGGCCGAAAGGAGAGTTTGTCCGAATCCCGAGATTTGGACGGCTCCTAT
GACCAGCTTACGGGCCACCCTCCAGGGCCCAGTAAAAAAGCCCTGAAGCAGCGTTTCCTCAAGCTGCTGCCGTGCTGCGG
GCCCCAAGCCCTGCCCTCAGTCAGTGAAACATTAGCTGCCCCAGCCTCCCTCCGCCCCCAGAGACCCCGCCCGCTGGACC
CAGACAGCGTGGAGGATGAGTTTGAACTATCCACGGTGTGCCACCGGCCTGAGGGTCTGGAACAACTCCAGGAACAAACC
AAGTTCACACGCAGAGAGTTGCAGGTCCTGTACAGAGGCTTCAAGAACGAATGTCCCAGCGGAATTGTCAACGAGGAGAA
CTTCAAGCAAATTTATTCTCAGTTCTTTCCCCAAGGAGACTCCAGCAACTACGCTACTTTTCTCTTCAATGCCTTTGACA
CCAACCATGATGGCTCTGTCAGTTTTGAGGACTTTGTGGCTGGTTTGTCAGTGATTCTTCGGGGAACCATAGATGATAGA
CTGAACTGGGCTTTCAACTTATATGACCTCAACAAGGATGGCTGTATCACGAAGGAGGAAATGCTCGACATCATGAAGTC
CATCTATGACATGATGGGCAAGTACACCTACCCTGCCCTCCGGGAGGAGGCCCCGAGGGAACACGTGGAGAGCTTCTTCC
AGAAGATGGACAGAAACAAGGACGGCGTGGTGACCATTGAGGAATTCATTGAGTCTTGTCAACAGGACGAGAACATCATG
AGGTCCATGCAACTCTTTGATAATGTCATCTAGCTCCCCAGGGAGAGGGGTTAGTGTGTCCCAGGGTAACCATGCTGTAG
CCCTAGTCCAGGCAAACCTAACCCTCCTCTCCCCGGGTCTGTCCTCATCCTACCTGTACCCTGGGGGCTGTAGGGATTCA
ACATCCTGGCGCTTCAGTAGTCCAGATCCCTGAGCTAAGTGGCGAGAGTAGGCAAGCTAAGTCTTTGGAGGGTGGGTGGG
GGCGCGCAGATTCCCAACCCCCGACGACTCTCACCCCTTTCTCGACTGATACCCAGTGCTGAGGCTACCCCTGGTGTCGG
GAACGACCAAAGTGGTTCTCTGCCTCCCCAGCCCACTCTAGAGACCCACACTAGACGGGAATATCTCCTGCTATGGTGCT
TTCCCCATCCCTGACCGCAGATTTTCCTCCTAAGACTCCCTTCTCAGAGAATATGCTTTTGTCCCTTGTCCCTGGCTGGC
TTTTCAGCCTAGCCTTTGAGGACCCTGTGGGAGGGGAGAATAAGAAAGCAGACAAAATCTTGGCCCTGAGCCAGTGGTTA
GGTCCTAGGAATCAGGCTGGAGTGGAGACCAGAAAGCCTGGGCAGGCTATGAGAGCCCCAGGTTGGCTTGTCACCGCCAG
GTTCCACAGGGCTGCTGCTCTGGGTCAGCAGAGTATGAGTTTCCAGACTTTCCAGAAGGCCTTATGTCCTTAGCAATGTC
CCAGAAATTCACCATACACTTCTCAGTGTCTTAGGATCCAGATGTCCGGTCCATCCCTGAAACCTCTCCCTCCTCCTTGC
TCCTATGGTGGGAGTGGTGGCCAGGGGACGATGAGTGAGCCGGTGTCCTGGATGATGCCTGTCAAGGTCCCACCTACCCT
CCGGCTGTCAAGCCGTTCTGGTGACCCTGTTTGATTCTCCATGACCCCTGTCTAGATGTAGAGGTGTGGAGTGAGTCTAG
TGGCAGCCTTAGGGGAATGGGAAGAACGAGAGGGGCACTCCATCTGAACCCAGTGTGGGGGCATCCATTCGAATCTTTGC
CTGGCTCCCCACAATGCCCTAGGATCCTCTAGGGTCCCCACCCCCACTCTTTAGTCTACCCAGAGATGCTCCAGAGCTCA
CCTAGAGGGCAGGGACCATAGGATCCAGGTCCAACCTGTCATCAGCATCCGGCCATGCTGCTGCTGCTTATTAATAAACC
TGCTTGTCGTTCAGCGCCCCTTCCCAGTCAGCCAGGGTCTGAGGGGAAGGCCCCCACTTTCCCGCCTCCTGTCAGACATT
GTTGACTGCTTTGCATTTTGGGCTCTTCTACCTATATTTGTATAATAAGAAAGACACCAGATCCAATAAAACACATGGC
TATGCACAAAAAAAAAAAAAAAAA

MOUSE 9QL PROTEIN

MRGQGRKESLSESRDLDGSYDQLTGHPPGPSKKALKQRFLKLLPCCGPQALPSVSETLAAPASLRPHRPRPLDPDSVEDE
FELSTVCHRPEGLEQLQEQTKFTRRELQVLYRGFKNECPSGIVNEENFKQIYSQFFPQGDSSNYATFLFNAFDTNHDGSV
SFEDFVAGLSVILRGTIDDRLNWAFNLYDLNKDGCITKEEMLDIMKSITDMMGKYTYPALREEAPREHVESFFQKMDRNK
DGVVTIEEFIESCQQDENIMRSMQLFDNVI

Fig. 9

HUMAN 9QM DNA (CD: 207-965)

CTCACCTGCTGCCTAGTGTTCCCTCTCCTGCTCCAGGACCTCCGGGTAGACCTCAGACCCCGGGCCCATTCCCAGACTCA

GCCTCAGCCCGGACTTCCCCAGCCCCGACAGCACAGTAGGCCGCCAGGGGGCGCCGTGTGAGCGCCCTATCCCGGCCACC

CGGCGCCCCCTCCCACGGCCCGGGCGGGAGCGGGGCGCCGGGGGCCATGCGGGGCCAGGGCCGCAAGGAGAGTTTGTCCG

ATTCCCGAGACCTGGACGGCTCCTACGACCAGCTCACGGGCCACCCTCCAGGGCCCACTAAAAAAGCGCTGAAGCAGCGA

TTCCTCAAGCTGCTGCCGTGCTGCGGGCCCCAAGCCCTGCCCTCAGTCAGTGAAAACAGCGTGGACGATGAATTTGAATT

GTCCACCGTGTGTCACCGGCCTGAGGGTCTGGAGCAGCTGCAGGAGCAAACCAAATTCACGCGCAAGGAGTTGCAGGTCC

TGTACCGGGGCTTCAAGAACGAATGTCCCAGCGGAATTGTCAATGAGGAGAACTTCAAGCAGATTTACTCCCAGTTCTTT

CCTCAAGGAGACTCCAGCACCTATGCCACTTTTCTCTTCAATGCCTTTGACACCAACCATGATGGCTCGGTCAGTTTTGA

GGACTTTGTGGCTGGTTTGTCCGTGATTCTTCGGGGAACTGTAGATGACAGGCTTAATTGGGCCTTCAACCTGTATGACC

TTAACAAGGACGGCTGCATCACCAAGGAGGAAATGCTTGACATCATGAAGTCCATCTATGACATGATGGGCAAGTACACG

TACCCTGCACTCCGGGAGGAGGCCCCAAGGGAACACGTGGAGAGCTTCTTCCAGAAGATGGACAGAAACAAGGATGGTGT

GGTGACCATTGAGGAATTCATTGAGTCTTGTGAAAAGGATGAGAACATCATGAGGTCCATGCAGCTCTTTGACAATGTCA

TCTAGCCCCCAGGAGAGGGGGTCAGTGTTTCCTGGGGGGACCATGCTCTAACCCTAGTCCAGGCGGACCTCACCCTTCTC

TTCCCAGGTCTATCCTCATCCTACGCCTCCCTGGGGGCTGGAGGGATCCAAGAGCTTGGGGATTCAGTAGTCCAGATCTC

TGGAGCTGAAGGGGCCAGAGAGTGGGCAGAGTGCATCTCGGGGGGTGTTCCCAACTCCCACCAGCTCTCACCCCCTTCCT

GCCTGACACCCAGTGTTGAGAGTGCCCCTCCTGTAGGAATTGAGCGGTTCCCCACCTCCTACCCTACTCTAGAAACACAC

TAGAGCGATGTCTCCTGCTATGGTGCTTCCCCCATCCCTGACCTCATAAACATTTCCCCTAAGACTCCCCTCTCAGAGAG

AATGCTCCATTCTTGGCACTGGCTGGCTTCTCAGACCAGCCATTGAGAGCCCTGTGGGAGGGGGACAAGAATGTATAGGG

AGAAATCTTGGGCCTGAGTCAATGGATAGGTCCTAGGAGGTGGGTGGGGTTGAGAATAGAAGGGCCTGGACAGATTATGA

TTGCTCAGGCATACCAGGTTATAGCTCCAAGTTCCACAGGTCTGCTACCACAGGCCATCAAAATATAAGTTTCCAGGCTT

TGCAGAAGACCTTGTCTCCTTAGAAATGCCCCAGAAATTTTCCACACCCTCCTCGGTATCCATGGAGAGCCTGGGGCCAG

ATATCTGGCTCATCTCTGGCATTGCTTCCTCTCCTTCCTTCCTGCATGTGTTGGTGGTGGTTGTGGTGGGGGAATGTGGA

TGGGGGATGTCCTGGCTGATGCCTGCCAAAATTTCATCCCACCCTCCTTGCTTATCGTCCCTGTTTTGAGGGCTATGACT

TGAGTTTTTGTTTCCCATGTTCTCTATAGACTTGGGACCTTCCTGAACTTGGGGCCTATCACTCCCCACAGTGGATGCCT

TAGAAGGGAGAGGGAAGGAGGGAGGCAGGCATAGC

Fig. 10A

HUMAN 9QM PROTEIN

MRGQGRKESLSDSRDLDGSYDQLTGHPPGPTKKALKQRFLKLLPCCGPQALPSVSENSVDDEFELSTVCHRPEGLEQLQE

QTKFTRKELQVLYRGFKNECPSGIVNEENFKQIYSQFFPQGDSSTYATFLFNAFDTNHDGSVSFEDFVAGLSVILRGTVD

DRLNWAFNLYDLNKDGCITKEEMLDIMKSIYDMMGKYTYPALREEAPREHVESFFQKMDRNKDGVVTIEEFIESCQKDEN

IMRSMQLFDNVI.

Fig. 10B

RAT 9QM DNA (CD: 214-972)

CTCACTTGCTGCCCAAGGCTCCTGCTCCTGCCCCAGGACTCTGAGGTGGGCCCTAAAACCCAGCGCTGTCTAAAGAAAAG
CCTTGCCAGCCCCTACTCCCGGCCCCCAACCCCAGCAGGTCGCTGCGCCGCCAGGGGGCGCTGTGTGAGCGCCCTATTCT
GGCCACCCGGCGCCCCCTCCCACGGCCCAGGCGGGAGCGGGGCGCCGGGGGCCATGCGGGGCCAAGGCAGAAAGGAGAGT
TTGTCCGAATCCCGAGATCTGGACGGCTCCTATGACCAGCTTACGGGCCACCCTCCAGGGCCCAGTAAAAAAGCCCTGAA
GCAGCGTTTCCTCAAGCTGCTGCCGTGCTGCGGGCCCCAAGCCCTGCCCTCAGTCAGTGAAAACAGCGTAGAGGATGAGT
TTGAATTATCCACGGTGTGTCACCGACCTGAGGGCCTGGAACAACTCCAGGAACAGACCAAGTTCACACGCAGAGAGCTG
CAGGTCCTGTACCGAGGCTTCAAGAACGAATGCCCCAGTGGGATTGTCAACGAGGAGAACTTCAAGCAGATTTATTCTCA
GTTCTTTCCCCAAGGAGACTCCAGCAACTATGCTACTTTTCTCTTCAATGCCTTTGACACCAACCACGATGGCTCTGTCA
GTTTTGAGGACTTTGTGGCTGGTTTGTCGGTGATTCTTCGGGGGACCATAGATGATAGACTGAGCTGGGCTTTCAACTTA
TATGACCTCAACAAGGACGGCTGTATCACAAAGGAGGAAATGCTTGACATTATGAAGTCCATCTATGACATGATGGGCAA
GTACACATACCCTGCCCTCCGGGAGGAGGCCCCAAGAGAACACGTGGAGAGCTTCTTCCAGAAGATGGACAGGAACAAGG
ACGGCGTGGTGACCATCGAGGAATTCATCGAGTCTTGTCAACAGGACGAGAACATCATGAGGTCCATGCAGCTCTTTGAT
AATGTCATCTAGCTCCCCAGGGAGAGGGGTTAGTGTGTCCTAGGGTGACCAGGCTGTAGTCCTAGTCCAGACGAACCTAA
CCCTCTCTCTCCAGGCCTGTCCTCATCTTACCTGTACCCTGGGGGCTGTAGGGATTCAATATCCTGGGGCTTCAGTAGTC
CAGATCCCTGAGCTAAGTCACAAAAGTAGGCAAGAGTAGGCAAGCTAAATCTGGGGGCTTCCCAACCCCCGACAGCTCTC
ACCCCTTCTCAACTGATACCTAGTGCTGAGGACACCCCTGGTGTAGGGACCAAGTGGTTCTCCACCTTCTAGTCCCACTC
TAGAAACCACATTAGACAGAAGGTCTCCTGCTATGGTGCTTTCCCCATCCCTAATCTCTTAGATTTTCCTCAAGACTCCC
TTCTCAGAGAACACGCTCTGTCCATGTCCCCAGCTGGCTTCTCAGCCTAGCCTTTGAGGGCCCTGTGGGGAGGCGGGGAC
AAGAAAGCAGAAAAGTCTTGGCCCCGAGCCAGTGGTTAGGTCCTAGGAATTGGCTGGAGTGGAGGCCAGAAAGCCTGGGC
AGATGATGAGAGCCCAGCTGGGCTGTCACTGCAGGTTCCGGGGCCTACAGCCCTGGGTCAGCAGAGTATGAGTTCCCAGA
CTTTCCAGAAGGTCCTTAGCAATGTCCCAGAAATTCACCGTACACTTCTCAGTGTCTTAGGAGGGCCCGGGATCCAGATG
TCTGGTTCATCCCTGAATCCTCTCCCTCCTTCTTGCTCGTATGGTGGGAGTGGTGGCCAGGGGAAGATGAGTGGTGTCCC
GGATGATGCCTGTCAAGGTCCCACCTCCCCTCCGGCTGTTCTCATGACAGCTGTTTGGTTCTCCATGACCCCTATCTAGA
TGTAGAGGCATGGAGTGAGTCAGGGATTTCCCGAACTTGAGTTTTACCACTCCTCCTAGTGGCTGCCTTAGGGGAATGGG
AAGAACCCAGTGTGGGGGCACCCATTAGAATCTTTGCCCGGCTCCTCACAATGCCCTAGGGTCCCCTAGGGTACCCGCTC
CCTCTGTTTAGTCTACCCAGAGATGCTCCTGAGCTCACCTAGAGGGTAGGGACGGTAGGCTCCAGGTCCAACCTCTCCAG
GTCAGCACCCTGCCATGCTGCTGCTCCTCATTAACAAACCTGCTTGTCTCCTCCTGCGCCCCTTCTCAGTCAGCCAGGGT
CTGAGGGGAAGGGCCTCCCGTTTCCCCATCCGTCAGACATGGTTGACTGCTTTGCATTTTGGGCTCTTCTATCTATTTTG
TAAAATAAGACATCAGATCCAATAAAACACACGGCTATGCACAAAAAAAAAAAAAAAAAA

RAT 9QM PROTEIN

MRGQGRKESLSESRDLDGSYDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLFDNVI.

Fig. 11

HUMAN 9QS DNA (CD: 207-869)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGACAGCGTGGACGATGAATTTGAATTGTCCACCGTGTGTCAC
CGGCCTGAGGGTCTGGAGCAGCTGCAGGAGCAAACCAAATTCACGCGCAAGGAGTTGCAGGTCCTGTACCGGGGCTTCAA
GAACGAATGTCCCAGCGGAATTGTCAATGAGGAGAACTTCAAGCAGATTTACTCCCAGTTCTTTCCTCAAGGAGACTCCA
GCACCTATGCCACTTTTCTCTTCAATGCCTTTGACACCAACCATGATGGCTCGGTCAGTTTTGAGGACTTTGTGGCTGGT
TTGTCCGTGATTCTTCGGGGAACTGTAGATGACAGGCTTAATTGGGCCTTCAACCTGTATGACCTTAACAAGGACGGCTG
CATCACCAAGGAGGAAATGCTTGACATCATGAAGTCCATCTATGACATGATGGGCAAGTACACGTACCCTGCACTCCGGG
AGGAGGCCCCAAGGGAACACGTGGAGAGCTTCTTCCAGAAGATGGACAGAAACAAGGATGGTGTGGTGACCATTGAGGAA
TTCATTGAGTCTTGTCAAAAGGATGAGAACATCATGAGGTCCATGCAGCTCTTTGACAATGTCATCTAGCCCCCAGGAGA
GGGGGTCAGTGTTTCCTGGGGGGACCATGCTCTAACCCTAGTCCAGGCGGACCTCACCCTTCTCTTCCCAGGTCTATCCT
CATCCTACGCCTCCCTGGGGGCTGGAGGGATCCAAGAGCTTGGGGATTCAGTAGTCCAGATCTCTGGAGCTGAAGGGGCC
AGAGAGTGGGCAGAGTGCATCTCGGGGGGTGTTCCCAACTCCCACCAGCTCTCACCCCCTTCCTGCCTGACACCCAGTGT
TGAGAGTGCCCCTCCTGTAGGAATTGAGCGGTTCCCCACCTCCTACCCTACTCTAGAAACACACTAGAGCGATGTCTCCT
GCTATGGTGCTTCCCCCATCCCTGACCTCATAAACATTTCCCCTAAGACTCCCCTCTCAGAGAGAATGCTCCATTCTTGG
CACTGGCTGGCTTCTCAGACCAGCCATTGAGAGCCCTGTGGAGGGGGACAAGAATGTATAGGGAGAAATCTTGGGCCTG
AGTCAATGGATAGGTCCTAGGAGGTGGGTGGGGTTGAGAATAGAAGGGCCTGGACAGATTATGATTGCTCAGGCATACCA
GGTTATAGCTCCAAGTTCCACAGGTCTGCTACCACAGGCCATCAAAATATAAGTTTCCAGGCTTTGCAGAAGACCTTGTC
TCCTTAGAAATGCCCCAGAAATTTTCCACACCCTCCTCGGTATCCATGGAGAGCCTGGGGCCAGATATCTGGCTCATCTC
TGGCATTGCTTCCTCTCCTTCCTTCCTGCATGTGTTGGTGGTGGTTGTGGTGGGGGAATGTGGATGGGGGATGTCCTGGC
TGATGCCTGCCAAAATTTCATCCCACCCTCCTTGCTTATCGTCCCTGTTTTGAGGGCTATGACTTGAGTTTTTGTTTCCC
ATGTTCTCTATAGACTTGGGACCTTCCTGAACTTGGGGCCTATCACTCCCCACAGTGGATGCCTTAGAAGGGAGAGGGAA
GGAGGGAGGCAGGCATAGC

Fig. 12

MONKEY 9QS DNA (CD: 133-795)

CCCACGCGTCCGCCCACGCGTCCGCGGACGCGTGGGGTGCACTAGGCCGCCAGGGGGCGCCGTGTGAGCGCCCTATCCCG
GCCACCCGGCGCCCCCTCCCACGGACCGGGCGGGAGCGGGGCGCCGGGGGCCATGCGGGGCCAGGGCCGCAAGGAGAGTT
TGTCCGATTCCCGAGACCTGGACGGATCCTACGACCAGCTCACGGACAGCGTGGAGGATGAATTTGAATTGTCCACCGTG
TGTCACCGGCCTGAGGGTCTGGAGCAGCTGCAGGAGCAAACCAAATTCACGCGCAAGGAGTTGCAGGTCCTGTACCGGGG
CTTCAAGAACGAATGTCCGAGCGGAATTGTCAATGAGGAGAACTTCAAGCAAATTTACTCCCAGTTCTTTCCTCAAGGAG
ACTCCAGCACCTATGCCACTTTTCTCTTCAATGCCTTTGACACCAACCATGATGGCTCGGTCAGTTTTGAGGACTTTGTG
GCTGGTTTGTCCGTGATTCTTCGGGAACTGTAGATGACAGGCTTAATTGGGCCTTCAACTTGTATGACCTCAACAAGGA
CGGCTGCATCACCAAGGAGGAAATGCTTGACATCATGAAGTCCATCTATGACATGATGGGCAAGTACACATACCCTGCAC
TCCGGGAGGAGGCCCCAAGGGAACATGTGGAGAACTTCTTCCAGAAGATGGACAGAAACAAGGATGGCGTGGTGACCATT
GAGGAATTCATTGAGTCTTGTCAAAAGGATGAGAACATCATGAGGTCCATGCAGCTCTTTGACAATGTCATCTAGCCCCC
AGGAGAGGGGGTCAGTGTTTCCTGGGGGGACCATGCTCTAACCCTAGTCCAGGTGGACCTCACCCTTCTCTTCCCAGGTC
TATCCTTGTCCTAGGCCTCCCTGGGGGCTGGAGGGATCCAAGAGCTTGGGGATTCAGTAGTCCAGATCTCTGGAGCTGAA
GGGGCCAGAGAGTGGGCAGAGTGCATCTTGGGGGGTGTTCCCAACTCCCACCAGCTTTCACCCGCTTCCTGCCTGACACC
CAGTGTTGAGAGTGCCCCTCCTGTAGGAACTGAGTGGTTCCCCACCTCCTACCCCCACTCTAGAAACACACTAGACAGAT
GTCTCCTGCTATGGTGCTTCCCCCATCCCTGACTTCATAAACATTTCCCCTAAAACTCCCTTCTCAGAGAGAATGCTCCA
TTCTTGGCACTGGCTGGCTTCTCAGACCAGCCTTTGAGAGCCCTGTGGAGGGGGACAAGAATGTATAGGGGAGAAATCT
TGGGCCTGAGTCAATGGATAGGTCCTAGGAGGTGGCTGGGGTTGAGAATAGAAAGGCCTGGACACAATGTGATTGCTCAG
GCATACCAAGTTATAGCTCCAAGTTCCACAGGTCTGCTACCACAGGCCATCAAAATATAAGTTTCCAGGCTTTGCAGAAG
ACCTTGTCTCCTTGGAAATGCCCCAGATATTTTCCATACCCTCCTCGATATCCATGGAGAGCCTGGGGCTAGATATCTGG
CATATCCCTGGCATTGCTTCCTCTCCTTCCTTCCTGCATGTGTTGGTGGTGGTTGTGGCAGGGGAATGTGGATAGGAGAT
GTCCTGGCAGATGCCTGCCAAAGTTTCATCCCACCCTCCCTGCTCATCGCCCCTGTTTTGAGGGCTGTGACTTGAGTTTT
TGTTTCCCATGTTCTCTATAGACTTGGGACCTTCCTGAACTTGGGGCCTATCACTCCCCACAGTGGATGCCTTAGAAGGG
AGAGGGAAGGAGGGAGGCAGGCATAGCATCTGAACCCAGTGTGGGGGCATTCACTAGGATCTTCAATCAACCCGGGCTCT
CCCCAACCCCCCAGATAACCTCCTCAGTTCCCTAGAGTCTCCTCTTGCTCTACTCAATCTACCCAGAGATGCCCCTTAGC
ACACTCAGAGGGCAGGACCATAGGACCCAGGTTCCAACCCCATTGTCAGCACCCCAGCCATGCTGCCATCCCTTAGCAC
ACCTGCTCGTCCCATTCAGCTTACCCTCCCAGTCAGCCAGAATCTGAGGGGAGGGCCCCCAGAGAGCCCCCTTCCCCATC
AGAAGACTGTTGACTGCTTTGCATTTTGGGCTCTTCTATATATTTTGTAAAATAAGAACTATACCAGATCTAATAAAACA
CAATGGCTATGCAAAAAAAAAAAAAAAAAAA

MONKEY 9QS PROTEIN

MRGQGRKESLSDSRDLDGSYDQLTDSVEDEFELSTVCHRPEGLEQLQEQTKFTRKELQVLYRGFKNECPSGIVNEENFKQ
IYSQFFPQGDSSTYATFLFNAFDTNHDGSVSFEDFVAGLSVILRGTVDDRLNWAFNLYDLNKDGCITKEEMLDIMKSIYD
MMGKYTYPALREEAPREHVENFFQKMDRNKDGVVTIEEFIESCQKDENIMRSMQLFDNVI

Fig. 13

RAT 9QC DNA (CD: 208-966)

TGCTGCCCAAGGCTCCTGCTCCTGCCCCAGGACTCTGAGGTGGGCCCTAAAACCCAGCGCTCTCTAAAGAAAAGCCTTGC
CAGCCCCTACTCCCGGCCCCCAACCCCAGCAGGTCGCTGCGCCGCCAGGGGGCGCTGTGTGAGCGCCCTATTCTGGCCAC
CCGGCGCCCCCTCCCACGGCCCAGGCGGGAGCGGGGCGCCGGGGGCCATGCGGGGCCAAGGCAGAAAGGAGAGTTTGTCC
GAATCCCGAGATCTGGACGGCTCCTATGACCAGCTTACGGGCCACCCTCCAGGGCCCAGTAAAAAAGCCCTGAAGCAGCG
TTTCCTCAAGCTGCTGCCGTGCTGCGGGCCCCAAGCCCTGCCCTCAGTCAGTGAAAACAGCGTAGAGGATGAGTTTGAAT
TATCCACGGTGTGTCACCGACCTGAGGGCCTGGAACAACTCCAGGAACAGACCAAGTTCACACGCAGAGAGCTGCAGGTC
CTGTACCGAGGCTTCAAGAACGAATGCCCCAGTGGGATTGTCAACGAGGAGAACTTCAAGCAGATTTATTCTCAGTTCTT
TCCCCAAGGAGACTCCAGCAACTATGCTACTTTTCTCTTCAATGCCTTTGACACCAACCACGATGGCTCTGTCAGTTTTG
AGGACTTTGTGGCTGGTTTGTCGGTGATTCTTCGGGGGACCATAGATGATAGACTGAGCTGGGCTTTCAACTTATATGAC
CTCAACAAGGACGGCTGTATCACAAAGGAGGAAATGCTTGACATTATGAAGTCCATCTATGACATGATGGGCAAGTACAC
ATACCCTGCCCTCCGGGAGGAGGCCCCAAGAGAACACGTGGAGAGCTTCTTCCAGAAGATGGACAGGAACAAGGACGGCG
TGGTGACCATCGAGGAATTCATCGAGTCTTGTCAACAGGACGAGAACATCATGAGGTCCATGCAGCTCTCACCCCTTCTC
AACTGATACCTAGTGCTGAGGACACCCCTGGTGTAGGGACCAAGTGGTTCTCCACCTTCTAGTCCCACTCTAGAAACCAC
ATTAGACAGAAGGTCTCCTGCTATGGTGCTTTCCCCATCCCTAATCTCTTAGATTTTCCTCAAGACTCCCTTCTCAGAGA
ACACGCTCTGTCCATGTCCCCAGCTGGCTTCTCAGCCTAGCCTTTGAGGGCCCTGTGGGGAGGCGGGGACAAGAAAGCAG
AAAAGTCTTGGCCCCGAGCCAGTGGTTAGGTCCTAGGAATTGGCTGGAGTGGAGGCCAGAAAGCCTGGGCAGATGATGAG
AGCCCAGCTGGGCTGTCACTGCAGGTTCCGGGGCCTACAGCCCTGGGTCAGCAGAGTATGAGTTCCCAGACTTTCCAGAA
GGTCCTTAGCAATGTCCCAGAAATTCACCGTACACTTCTCAGTGTCTTAGGAGGGCCCGGGATCCAGATGTCTGGTTCAT
CCCTGAATCCTCTCCCTCCTTCTTGCTCGTATGGTGGGAGTGGTGGCCAGGGGAAGATGAGTGGTGTCCCGGATGATGCC
TGTCAAGGTCCCACCTCCCCTCCGGCTGTTCTCATGACAGCTGTTTGGTTCTCCATGACCCCTATCTAGATGTAGAGGCA
TGGAGTGAGTCAGGGATTTCCCGAACTTGAGTTTTACCACTCCTCCTAGTGGCTGCCTTAGGGGAATGGAAGAACCCAG
TGTGGGGGCACCCATTAGAATCTTTGCCCGGCTCCTCACAATGCCCTAGGGTCCCCTAGGGTACCCGCTCCCTCTGTTTA
GTCTACCCAGAGATGCTCCTGAGCTCACCTAGAGGGTAGGGACGGTAGGCTCCAGGTCCAACCTCTCCAGGTCAGCACCC
TGCCATGCTGCTGCTCCTCATTAACAAACCTGCTTGTCTCCTCCTGCGCCCCTTCTCAGTCAGCCAGGGTCTGAGGGGAA
GGGCCTCCCGTTTCCCCATCCGTCAGACATGGTTGACTGCTTTGCATTTTGGGCTCTTCTATCTATTTTGTAAAATAAGA
CATCAGATCCAATAAAACACACGGCTATGCACAAAAAAAAAAAAAAAAAAAAAAAAA

RAT 9QC PROTEIN

MRGQGRKESLSESRDLDGSTDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLSPLLN.

Fig. 14

RAT 8T (9Q SPLICE VARAIANT) DNA (MAY NOT BE FULL LENGTH, CD: 1-678)

ATGAACCACTGCCCTCGCAGGTGCCGGAGCCCGTTGGGGCAGGCAGCTCGATCTCTCTACCAGTTGGTAACTGGGTCGCT
GTCGCCAGACAGCGTAGAGGATGAGTTTGAATTATCCACGGTGTGTCACCGACCTGAGGGCCTGGAACAACTCCAGGAAC
AGACCAAGTTCACACGCAGAGAGCTGCAGGTCCTGTACCGAGGCTTCAAGAACGAATGCCCCAGTGGGATTGTCAACGAG
GAGAACTTCAAGCAGATTTATTCTCAGTTCTTTCCCCAAGGAGACTCCAGCAACTATGCTACTTTTCTCTTCAATGCCTT
TGACACCAACCACGATGGCTCTGTCAGTTTTGAGGACTTTGTGGCTGGTTTGTCGGTGATTCTTCGGGGGACCATAGATG
ATAGACTGAGCTGGGCTTTCAACTTATATGACCTCAACAAGGACGGCTGTATCACAAAGGAGGAAATGCTTGACATTATG
AAGTCCATCTATGACATGATGGGCAAGTACACATACCCTGCCCTCCGGGAGGAGGCCCCAAGAGAACACGTGGAGAGCTT
CTTCCAGAAGATGGACAGGAACAAGGACGGCGTGGTGACCATCGAGGAATTCATCGAGTCTTGTCAACAGGACGAGAACA
TCATGAGGTCCATGCAGCTCTTTGATAATGTCATCTAGCTCCCCAGGGAGAGGGGTTAGTGTGTCCTAGGGTGACCAGGC
TGTAGTCCTAGTCCAGACGAACCTAACCCTCTCTCTCCAGGCCTGTCCTCATCTTACCTGTACCCTGGGGGCTGTAGGGA
TTCAATATCCTGGGGCTTCAGTAGTCCAGATCCCTGAGCTAAGTCACAAAAGTAGGCAAGAGTAGGCAAGCTAAATCTGG
GGGCTTCCCAACCCCCGACAGCTCTCACCCCTTCTCAACTGATACCTAGTGCTGAGGACACCCCTGGTGTAGGGACCAAG
TGGTTCTCCACCTTCTAGTCCCACTCTAGAAACCACATTAGACAGAAGGTCTCCTGCTATGGTGCTTTCCCCATCCCTAA
TCTCTTAGATTTTCCTCAAGACTCCCTTCTCAGAGAACACGCTCTGTCCATGTCCCCAGCTGGCTTCTCAGCCTAGCCTT
TGAGGGCCCTGTGGGGAGGCGGGGACAAGAAAGCAGAAAAGTCTTGGCCCCGAGCTAGTGGTTAGGTCCTAGGAATTGGC
TGGAGTGGAGGCCAGAAAGCCTGGGCAGATGATGAGAGCCCAGCTGGGCTGTCACTGCAGGTTCCAGGGCCTACAGCCCT
GGGTCAGCAGAGTATGAGTTCCCAGACTTTCCAGAAGGTCCTTAGCAATGTCCCAGAAATTCACCATACACTTCTCAGTG
TCCCGGATGATGCCTGTCAAGGTCCCACCTCCCCTCCGGCTGTTCTCATGACAGCTGTTTGGTTCTCCATGACCCCTATC
TAGATGTAGAGGCATGGAGTGAGTCAGGGATTTCCCGAACTTGAGTTTTACCACTCCTCCTAGTGGCTGCCTTAGGGGAA
TGGGAAGAACCCAGTGTGGGGGCACCCATTAGAATCTTTGCCCGGTTCCTCACAATGCCCTAGGGTCCCCTAGGGTACCC
GCTCCCTCTGTTTAGTCTACCCAGAGATGCTCCTGAGCTCACCTAGAGGGTAGGGACGGTAGGCTCCAGGTCCAACCTCT
CCAGGTCAGCACCCTGCCATGCTGCTGCTCCTCATTAACAAACCTGCTTGTCTCCTCCTGCGCCCCTTCTCAGTCAGCCA
GGGTCTGAGGGGAAGGGCCTCCCGTTTCCCCATCCGTCAGACATGGTTGACTGCTTTGCATTTTGGGCTCTTCTATCTAT
TTTGTAAAATAAGACATCAGATCCAATAAAACACACGGCTATGCACAAAAAAAAAAAAAAAAAA

RAT 8T (9Q SPLICE VARAIANT) PROTEIN (MAY NOT BE FULL LENGTH)

MNHCPRRCRSPLGQAARSLYQLVTGSLSPDSVEDEFELSTVCHRPEGLEQLQEQTKFTRRELQVLYRGFKNECPSGIVNE
ENFKQIYSQFFPQGDSSNYATFLFNAFDTNHDGSVSFEDFVAGLSVILRGTIDDRLSWAFNLYDLNKDGCITKEEMLDIM
KSIYDMMGKYTYPALREEAPREHVESFFQKMDRNKDGVVTIEEFIESCQQDENIMRSMQLFDNVI

Fig. 15

>human KChIP3 cds = 1-7

ATGCAGCCGGCTAAGGAAGTGACAAAGGCGTCGGACGGCAGCCTCCTGGGGGACCTCGGGC
ACACACCACTTAGCAAGAA
GGAGGGTATCAAGTGGCAGAGGCCGAGGCTCAGCCGCCAGGCTTTGATGAGATGCTGCCTG
GTCAAGTGGATCCTGTCCA
GCACAGCCCCACAGGGCTCAGATAGCAGCGACAGTGAGCTGGAGCTGTCCACGGTGCGCCA
CCAGCCAGAGGGGCTGGAC
CAGCTGCAGGCCCAGACCAAGTTCACCAAGAAGGAGCTGCAGTCTCTCTACAGGGGCTTTA
AGAATGAGTGTCCCACGGG
CCTGGTGGACGAAGACACCTTCAAACTCATTTACGCGCAGTTCTTCCCTCAGGGAGATGCCA
CCACCTATGCACACTTCC
TCTTCAACGCCTTTGATGCGGACGGGAACGGGGCCATCCACTTTGAGGACTTTGTGGTTGGC
CTCTCCATCCTGCTGCGG
GGCACAGTCCACGAGAAGCTCAAGTGGGCCTTTAATCTCTACGACATTAACAAGGATGGCT
ACATCACCAAAGAGGAGAT
GCTGGCCATCATGAAGTCCATCTATGACATGATGGGCCGCCACACCTACCCCATCCTGCGGG
AGGACGCGCCGGCGGAGC
ACGTGGAGAGGTTCTTCGAGAAAATGGACCGGAACCAGGATGGGGTAGTGACCATTGAAGA
GTTCCTGGAGGCCTGTCAG
AAGGATGAGAACATCATGAGCTCCATGCAGCTGTTTGAGAATGTCATCTAGgacacgtccaaaggagt
gcatggccacag
ccacctccacccccaagaaacctccatcctgccaggagcagcctccaagaaacttttaaaaaatagatttgcaaaaagtg
aacagattgctacacacacacacacacacacacacacacacacacacacagccattcatctgggctggcagaggggac
agagttcagggaggggctgagtctggctaggggccgagtccaggagccccagccagcccttcccaggccagcgaggcgag
gctgcctctgggtgagtggctgacagagcaggtctgcaggccaccagctgctggatgtcaccaagaaggggctcgagtgc
ccctgcaggggagggtccaatctccggtgtgagcccacctcgtcccgttctccattctgctttcttgccacacagtgggc
cggccccaggctcccctggtctcctccccgtagccactctctgcccactacctatgcttctagaaagcccctcacctcag
gaccccagagggaccagctgggggcagggggagaggggtaatggaggccaagcctgcagctttctggaaattcttcc
ctgggggtcccaggatcccctgctactccactgacctggaagagctgggtaccaggccacccactgtggggcaagcctga
gtggtgaggggccactgggccccattctccctccatggcaggaaggcgggggatttcaagtttagggattgggtcgtggt
ggagaatctgagggcactctctgccagctccacagggtgggatgagcctctccttgccccagtcctggttcagtgggaat
gcagtgggtggggctgtacacaccctccagcacagactgttccctccaaggtcctcttaggtcccgggaggaacgtggtt
cagagactggcagccagggagcccggggcagagctcagaggagtctgggaaggggcgtgtccctcctcttcctgtagtgc
ccctcccatggcccagcagcttggctgagcccccctctcctgaagcagtgtcgccgtccctctgccttgcacaaaaagcac
aagcattccttagcagctcaggcgcagccctagtgggagcccagcacactgcttctcggaggccaggccctcctgctggc
tgaggcttgggcccagtagccccaatatggtggccctggggaagaggccttgggggtctgctctgtgcctgggatcagtg
gggccccaaagcccagcccggctgaccaacattcaaaagcacaaaccctggggactctgcttggctgtcccctccatctg
gggatggagaatgccagcccaaagctggagccaatggtgagggctgagagggctgtggctgggtggtcagcagaaacccc
caggaggagagagatgctgctcccgcctgattggggcctcacccagaaggaacccggtcccaggccgcatggcccctcca
ggaacattcccacataatacattccatcacagccagcccagctccactcagggctggcccggggagtccccgtgtgcccc
aagaggctagccccagggtgagcagggccctcagaggaaaggcagtatggcggaggccatgggggcccctcggcattcac
acacagcctggcctcccctgcggagctgcatggacgcctggctccaggatccaggctgactgggggcctctgcctccagg
agggcatcagctttccctggctcagggatcttctccctcccctcacccgctgcccagccctcccagctggtgtcactctg
cctctaaggccaaggcctcaggagagcatcaccaccacacccctgccggccttggccttggggccagactggctgcacag
cccaaccaggaggggtctgcctcccacgctgggacacagaccggaagcatgtctgcatggcagaagcgtctcccttggcc
acggcctgggagggtggttcctgttctcagcatccactaatattcagtcctgtatattttaataaaataaacttgacaaa
ggaaaaaaaaaaaaaaaaaattcctgcggccgcgttctcca >human KChIP3

MQPAKEVTKASDGSLLGDLGHTPLSKKEGIKWQRPRLSRQALMRCCLVKWILSSTAPQGSDSSD
SELELSTVRHQPEGLD
QLQAQTKFTKKELQSLYRGFKNECPTGLVDEDTFKLIYAQFFPQGDATTYAHFLFNAFDADGNG
AIHFEDFVVGLSILLR
GTVHEKLKWAFNLYDINKDGYITKEEMLAIMKSIYDMMGRHTYPILREDAPAEHVERFFEKMD
RNQDGVVTIEEFLEACQ
KDENIMSSMQLFENVI

Fig. 16

RAT P19 DNA (FIRST-PASS, PARTIAL; CD: 1-330)

TTTGAGGACTTTGTGGTTGGGCTCTCCATCCTGCTTCGAGGGACCGTCCATGAGAAGCTCAAGTGGGCCTTCAATCTCTA

CGACATCAACAAGGACGGTTACATCACCAAAGAGGAGATGCTGGCCATCATGAAGTCCATCTACGACATGATGGGCCGCC

ACACCTACCCTATCCTGCGGGAGGACGCACCTCTGGAGCATGTGGAGAGGTTCTTCCAGAAAATGGACAGGAACCAGGAT

GGAGTAGTGACTATTGATGAATTTCTGGAGACTTGTCAGAAGGACGAGAACATCATGAGCTCCATGCAGCTGTTTGAGAA

CGTCATCTAGGACATGTAGGAGGGGACCCTGGGTGGCCATGGGTTCTCAACCCAGAGAAGCCTCAATCCTGACAGGAGAA

GCCTCTATGAGAAACATTTTTCTAATATATTTGCAAAAAGTG

RAT P19 PROTEIN (PARTIAL)

FEDFVVGLSILLRGTVHEKLKWAFNLYDINKDGYITKEEMLAIMKSIYDMMGRHTYPILREDAPLEHVERFFQKMDRNQD

GVVTIDEFLETCQKDENIMSSMQLFENVI

Fig. 17

MOUSE P19 DNA (CD: 49-819)

CGGGCTGCAAAGCGGGAAGATTAGTGACGGTCCCTTTCAGCAGCAGAGATGCAGAGGACCAAGGAAGCCGTGAAGGCATC
AGATGGCAACCTCCTGGGAGATCCTGGGCGCATACCACTGAGCAAGAGGGAAAGCATCAAGTGGCAAAGGCCACGGTTCA
CCCGCCAGGCCCTGATGCGTTGCTGCTTAATCAAGTGGATCCTGTCCAGTGCTGCCCCACAAGGCTCAGACAGCAGTGAC
AGTGAACTGGAGTTATCCACGGTGCGCCATCAGCCAGAGGGCTTGGACCAGCTACAAGCTCAGACCAAGTTCACCAAGAA
GGAGCTGCAGTCCCTTTACCGAGGCTTCAAGAATGAGTGTCCCACAGGCCTGGTGGATGAAGACACCTTCAAACTCATTT
ATTCCCAGTTCTTCCCTCAGGGAGATGCCACCACCTATGCACACTTCCTCTTCAATGCCTTTGATGCTGATGGGAACGGG
GCCATCCACTTTGAGGACTTTGTGGTTGGGCTCTCCATCCTGCTTCGAGGGACGGTCCATGAGAAGCTCAAGTGGGCCTT
CAATCTCTATGACATTAACAAGGATGGTTGCATCACCAAGGAGGAGATGCTGGCCATCATGAAGTCCATCTACGACATGA
TGGGCCGCCACACCTACCCCATCCTGCGGGAGGATGCACCCCTGGAGCATGTGGAGAGGTTCTTTCAGAAAATGGACAGG
AACCAGGATGGAGTGGTGACCATTGATGAATTTCTGGAGACTTGTCAGAAGGATGAGAACATCATGAACTCCATGCAGCT
GTTTGAGAACGTCATCTAGGACATGTGGGAGGGGACCCCAGTGGTCATTGCTTCTCAACCCAGAGAAGCCTCAATCCTGA
CAGGAGAAGCCTCTATGAGAAACATTTTTCTAATATATTTGCAAAAAGTGAGCAGTTTACTTCCAAGACACAGCCACCGT
CACACACAGACACAGACATACAGACACACACACACACACACACATGGTTCCTCTGGCTTGGCCAAGGAAGTGGCAGCC
AGAAGGCACCCCCGCCTATTCCTAGGTCAATAAAAAAGGCTGCCTCTGGGATGGCCAGCCCTGGCTAGATGTTACCCACA
AGGAACTCAGAGATCGAGAGGACCAGGTCTACAAAGCTAAGGTCCCTGTGTCTTTTCTACCACTCGGGAGATCAAACTAC
TCCCTGCCTATGGACCCATGCTCTTAGGAAGCTCCCAGAAACTCCAAGGGGACAAAGAGGGGAGAGGTCTATAGGAAGAA
ATGGTTTTGGAAGCTGGGCTTGCAGCCTTATGCTAATGATCACCTGGGGTCCTGGAACCCGAGTGCCAGGCTACCTACTA
TGCCGTGAGCTTAGATAGTGAGGGGCCATTGGACTAAGACCTCCTGTAAGAGTGGGGCAGGATTGAGGTTTTTGGAGAAA
CTGAGGAAACAATTTGTCCATACCACTGGGTGAAGACTGCTGGCCAGTGGGAATGTGGCTGGTGGAGATTTCCCAACTTC
CAGCACCAGGATGGCCTCTCCAAGGTCCTCTTTGATTCCCTGGGGAGATCACCTGGCTCATAGACTGACAACCAGGGAAC
TGGGCTGAAATGGGAGGTCTGGTAGGGGGCATCCCCCTCCTTTTCCCTGGCCACTTGCCACCCAGTTCCTTAACACAGTG
GATCGGCCACACCTCTGTGGCTGCCCTTGAACAGACTCATCCCGACCAAGACAAAAAAGCACAAACTCCTAGCAGCTCAG
GCCAAGCCCACAAGGGAAGGCCTGGGTCCCTGCAGCCCTGATTCAGTGGCCGAGGAAGACGCTCAGACATCCATCCTGTA
CCTCGGAGCCTTGGGGGTCTCACAGCCCTTTCCCAGCCCAGCTCGCCAACATTCTAAAGCACAAACCTGCGGATTCTGCT
TGCTTGGGCTGCGCCCTGGGGATTGAAGGCCACTGTTAACCCTAAGCTGGAGCTAGCCCTGAGGGCTGGGGACCTGTGAC
CAGGCAACAGGTCAGCAGACCCTCAGGAGGAGAGAGAGCTGTTCCTGCCTCCCCAGGCCTCGCCCAGAAGGAACAGTGTC
CCAAGAAGCATGTTTCCTGGAGGAACATCCCCACAAAAGTACATTCCATCATCTGAAGCCCGGTCTCTGCTCAGGCCTGC
CTCTGAAAGTCCACGTGTGTTCCCCAGAAGGCCAGCCCCAAGATAAGGGAGGTCCTTAGAGGAAGGACAGGGTGACAACA
CCCCTATACACAGGTGGACCCCCCCTCTGAGGACTGTACTGACCCCATCTCCATCCTGACCGGGGCCTTCCTTTACCCGA
TCTACAGACCACCAGTTCTCCCTGGCTCAGGGACCCCCTGTCCCCCAGTCTGACTCTTCCCATCGAGGTCCCTGTCTTGT
GAAAAGCCAAGGCCACGGGAAAAGGCCACCACTCTAACCTGCTGCATCCCTTAGCCTCTGGCTGCACGCCCAACCTGGAG
GGGTCTGTCCCCTTTGCAGGGACACAGACTGGCCGCATGTCCGCATGGCAGAAGCGTCTCCCTTGGGTGCAGCCTGGAAG
GGTGGTTTCTGTCTCAGCGCCCACCAATATTCAGTCCTATATATTTTAATAAAAGAAACTTGACAAAGGAAAAAAAAAAA
AAAA

Fig. 18

>AI 352454 (partial) cds = 1-339
CACGAGGTGGAAAGCATTTCGGCTCAGCTGGAGGAGGCCAGCTCTACAGGCGGTTTCCTGT
ACGCTCAGAACAGCACCAA
GCGCAGCATTAAAGAGCGGCTCATGAAGCTCTTGCCCTGCTCAGCTGCCAAAACGTCGTCTC
CTGCTATTCAAAACAGCG
TGGAAGATGAACTGGAGATGGCCACCGTCAGGCATCGGCCCGAAGCCCTTGAGCTTCTGGA
AGCCCAGAGCAAATTTACC
AAGAAAGAGCTTCAGATCCTTTACAGAGGATTTAAGAACGTAAGAACTTTCTTTTTGACTTT
ACCTTCACACAATTCCCA
GAGGAGCATTGAGAAATGAgaggaaaagggggaaaatatcccattctatgagaagccccatcatatgtatatttcatact
gatccttcccagataggaatataatcagtatctgtggactttgaatctctgtggcacacccatgctggcatactgtaatt
gcccattaaacaaanagttttgagaaaaaaaaaaaaaaaaaaaaaaaa >AI 352454
HEVESISAQLEEASSTGGFLYAQNSTKRSIKERLMKLLPCSAAKTSSPAIQNSVEDELEMATVRHR
PEALELLEAQSKFT
KKELQILYRGFKNVRTFFLTLPSHNSQRSIEK

Fig. 19

P193 (AA349365) DNA (CD: 2-127, partial)

TGAAAGGTTCTTCGAGAAAATGGACCGGAACCAGGATGGGGTAGTGACCATTGAAGAGTTCCTGGAGGC
CTGTCAGAAGGATGAGAACATCATGAGCTCCATGCAGCTGTTTGAGAATGTCATCTAGGACACGTCCAAA
GGAGTGCATGGCCACAGCCACCTCCACCCCCAAGAAACCTCCATCCTGCCAGGAGCAGCCTCCAAGAAA
CTTTTAAAAAATAGATTTGCAAAAAGTGAACAGATTGCTACACACACACACACACACACACACACACAC
ACACACACACAGCCATTCATCTGGGCTGGCAGAGGGGACAGAGTTCAGGGAGGGGCTGAGTCTGGCTAG
GGGCCGAGTCCAGGAGCCCCAGCCAGCCCTTCCCAGGCCAGCGAGGCGAGGCTGCCTCTGGGTGAGTGG
CTGACAGAGCAGGTCTGCAGGCCACCAGCTGCTGGATGTCACCAAGAAGGGGCTCGAGTGCCCCTGCAG
GGGAGGGTCCAATCTCCGGTGTGAGCCCACCTCGTCCCGTTCTCCATTCTGCTTTCTTGCCACACAGTGGG
CCGGCCCCAGGCTCCCCTGGTCTCCTCCCCGTAGCCACTCTCTGCCCACTACCTATGCTTCTAGAAAGCCC
CTCACCTCAGGACCCCAGAGGGACCAGCTGGGGGGCAGGGGGGAGAGGGGGTAATGGAGGCCAAGCCT
GCAGCTTTCTGGAAATTCTTCCCTGGGGGTCCCAGGATCCCCTGCTACTCCACTGACCTGGAAGAGCTGG
GTACCAGGCCACCCACTGTGGGGCAAGCCTGAGTGGTGAGGGGCCACTGGGCCCCATTCTCCCTCCATGG
CAGGAAGGCGGGGGATTTCAAGTTTAGGGATTGGGTCGTGGTGGAGAATCTGAGGGCACTCTCTGCCAG
CTCCACAGGGTGGGATGAGCCTCTCCTTGCCCCAGTCCTGGTTCAGTGGGAATGCAGTGGGTGGGGCTGT
ACACACCCTCCAGCACAGACTGTTCCCTCCAAGGTCCTCTTAGGTCCCGGGAGGAACGTGGTTCAGAGAC
TGGCAGCCAGGGAGCCCGGGGCAGAGCTCAGAGGAGTCTGGGAAGGGGCGTGTCCCTCCTCTTCCTGTA
GTGCCCCTCCCATGGCCCAGCAGCTTGGCTGAGCCCCCTCTCCTGAAGCAGTGTCGCCGTCCCTCTGCCTT
GCACAAAAAGCACAAGCATTCCTTAGCAGCTCAGGCGCAGCCCTAGTGGGAGCCCAGCACACTGCTTCT
CGGAGGCCAGGCCCTCCTGCTGGCTGAGGCTTGGGCCCAGTAGCCCCAATATGGTGGCCCTGGGGAAGA
GGCCTTGGGGGTCTGCTCTGTGCCTGGGATCAGTGGGGCCCCAAAGCCCAGCCCGGCTGACCAACATTCA
AAAGCACAAACCCTGGGGACTCTGCTTGGCTGTCCCCTCCATCTGGGGATGGAGAATGCCAGCCCAAAG
CTGGAGCCAATGGTGAGGGCTGAGAGGGCTGTGGCTGGGTGGTCAGCAGAAACCCCCAGGAGGAGAGA
GATGCTGCTCCCGCCTGATTGGGGCCTCACCCAGAAGGAACCCGGTCCCAGGCCGCATGGCCCCTCCAGG
AACATTCCCACATAATACATTCCATCACAGCCAGCCCAGCTCCACTCAGGGCTGGCCCGGGGAGTCCCCG
TGTGCCCCAAGAGGCTAGCCCCAGGGTGAGCAGGGCCCTCAGAGGAAAGGCAGTATGGCGGAGGCCATG
GGGGCCCCTCGGCATTCACACACAGCCTGGCCTCCCCTGCGGAGCTGCATGGACGCCTGGCTCCAGGCTC
CAGGCTGACTGGGGGCCTCTGCCTCCAGGAGGGCATCAGCTTTCCCTGGCTCAGGGATCTTCTCCCTCCC
CTCACCCGCTGCCCAGCCCTCCCAGCTGGTGTCACTCTGCCTCTAAGGCCAAGGCCTCAGGAGAGCATCA
CCACCACACCCCTGCCGGCCTTGGCCTTGGGGCCAGACTGGCTGCACAGCCCAACCAGGAGGGGTCTGC
CTCCCACGCTGGGACACAGACCGGCCGCATGTCTGCATGGCAGAAGCGTCTCCCTTGGCCACGGCCTGGG
AGGGTGGTTCCTGTTCTCAGCATCCACTAATATTCAGTCCTGTATATTTTAATAAAATAAACTTGACAAAG
GAAAAAAAAAAAAAAAAA

P193 PROTEIN (PARTIAL)

ERFFEKMDRNQDGVVTIEEFLEACQKDENIMSSMQLFENVI

Fig. 20 exon1 SEQUENCE (WITH INTRONS INCLUDED):

CGGGAGGAGAGAGGCAGCTCGGCTCGGCTCCGCGCTCAGCTCCGCTCTGCCTCCGGCTCTGCGCTCACCTGCTGCCT
AGTGTTCCCTCTCCTGCTCCAGGACCTCCGGGTAGACCTCAGACCCCGGGCCCATTCCCAGACTCAGCCTCAGCCCG
GACTTCCCCAGCCCCGACAGCACAGTAGGCCGCCAGGGGGCGCCGTGTGAGCGCCCTATCCCGGCCACCCGGCGCCC
CCTCCCACGGCCCGGGCGGGAGCGGGGCGCCGGGGGCCATGCGGGGCCAGGGCCGCAAGGAGAGTTTGTCCGATTCC
CGAGACCTGGACGGCTCCTACGACCAGCTCACGGGTGAGTCAGTGACGTGGGGGTCGCGGGAGGGAGGGTGGATTCC
ATTCCTCCAGACCCTTCCGCCTCTCCGACCCCGGCCTGGCCCGCACCAACACTCTGCCCCATTCCCAGGCACTCTTA
TGGCCGGTCTGGGCGGCAGGACACTGGGGGTTCAAAGCCTTGGGTCCCGCAGGGGTTGGGGAGGAACAGAAGAGGCA
GGTGTGGAGAGGCAGCAGGTGTGGGCGTATGTGACACAGGGCTGAGAGGGTGTCTGGAGTGGGAGGTGTTACCGTGC
GTGAGCACCTGTCATTCTGTGTGTGTGTGTGTGTGTGCGCGCGCACCTCCCACAGCTGGTTGCCATGTGCCCTGGGC
TTGGTGACAGCTAGGGTGAGTGTGATTGTATGTGGCAGTGCAATTGTATGGTCTCGTCAGATGTTTGAGTTTGCGTA
GGACCCTGGTTGTACTGATGAAGTTGTTTTGACCATGTGTCTYTATGTGCAACGATGTGTTGTGAGTGTGTAATTCT
GTATGAAAGTGGTGTGTAACTACCAGAATGTGTCAGGGCTCTACTTTAGGGTGGCTTGTCTCTTTG

Fig. 22A exon 2-11 SEQUENCE (WITH INTRONS INCLUDED):

AGCCNANTGGGTCNCCATGTGTATGCATCCTGTTTACTTAGGTCACATTTGTATATGTTGTGTAAGGAGTACCAGGT
CAATGTGTGTGTGTGTGTGAGCATGNATAAACGCCANCAGGTGTGAGTTANTGAATATCAAGCTGTCACTGGCACCC
ATCACTGTGATGTATTGTTCATACATGTCACNAACACGGCCTGTCACTGTAGGTGTGTGTATRAGAGAGGTGTTCTT
ACCCAGGCAATCCTTGGGTTGGACATCATCNTGAGAGGTCCAGCCATGGCACTTGAGCCAAGGGTACTAGGTCAGCA
AAGACATTGAGGCCACTGCCACCTCATCCTTGCCGCCTCGCTGTCACCGGCCACGTCCCATTAAACCAAGTGCNTGA
GCCTCACCTCTATGGACTCACTGGGCTCCCCTAACCCGATTCCAACCACCCTTGCCATTCCTTTCCTCCCCTTAATT
CCTCCCCCAGCCCGGTCCCCAGATGGGGTTGATTTGTGACTGGCGGGGAGGGGACAGGGAACAGAGGGACCCCGGGA
GTTAATGTGCCTTCCTGGGGTCTTCTCTCTTCNCAGGCCACCCTCCAGGGCCCACTAAAAAAGCGCTGAAGCAGCGA
TTCCTCAAGCTGCTGCCGAGCTGCGGGCCCCAAGCCCTGCCCTCAGTCAGTGAAAGCAAGTGCCTCTCATGTGCTTC
CCGGGGCGGGGCTCGATGTGTGCGTGCGTGTCTGTGCATGANTGTGTGCGCGTGTGCCCCAGGCCTGCRAGTGTKCS
CATGYTCCAGGCTTGCATGTGTGGGGGGGCGTGCCCCAAGCCTKSGTGTTTGGGGGTGGGGCCTGCCCCAVGCCTGT
GCGTGTGTATGTGTGTGCATGTGCGCRCGAGCGTRCCCCAGACCGGCGTGTGTGTGTGTGGGGGCGTGCCCTACCCC
TGCATGTGTGTGGAGGGCGTGCCCCAKGCCCKCGGCGNGTTGTTTGTTGTGTATGGGAAGGCGTACCGCACGCCTGC
GTGTGGGGGAGGGGCGTGCCCCAGAGCCTGCGTGCGTGTGTGTGTGTGTGTGTGTGTGTGTGTGGGCGTGACCAGCG
TGGCGAGGGCGGGTGCTGGCAAGGCTGGAGCATAAGNGGGCGNGGCTACATGTGTGNGTGTACGNCTGAAGCCAGCG
TGTGTGGGCGTGGTCAGTTGGNAGCGGGTGTGTGTCACCGCTCCCGCAAAACTGTGGACCCGAGAGTGTGGGTGTG
ACCATTGTGACCAGGNTGAGGCCTGAGCCTGTGTAGCTGTGGCGGCCTGTGTAGACCAGGCGGCCGTGAGGGTCTGT
ATGTGGCTTAGCTGGGTTAGTGTCTTCAACTCCGTGCGGCCGCCCCCTTCCCCACCGTGTTTTGGACCCCTGATGTG
TGTTGCCTATGCCCCGACAGGATGGTGACAGGTGTAGAGGATGGCGCCTGCCCTCCTCCAGACGCCAGGGTATTTGG
GTTTTCTGTGCCAGCCTGGTCCCCTGCTGAAGTGATCTCCAGTTGAGTGACCTCGCTTTGTCTCTAGGTCTCCATTT
CCTCAGTTGGGCCTTGCCCACCTCATAGGATCATACTGCATTTTGCAAACCATAAAGGCCCGCTTTGTAGTTATTTG
AGCATGCTGTTGTGTTGGACTTAGATGGGTCCCACACGGGGGTGGATTCGGARAAGGACAGGCGTGAGTCCCGCAAG
CTTGTGTGCATGGGGTCCGTTTCGTGTGTGTCTGTGCTGGTTGGGTGTGCCTTTGCACGGGCTGGGTTGTCAGGTTT
GCTCTGAGTGTGAGGGGCCAGGTGTGTGTATGCAGTTGGCCGGGTCTTCCGCTTTCTCGGTGWCAGTTCGCTCCCTT
CAGCATTAGCCGCCCCAGCCTCCCTCCGCCCCCACAGACCCCGCCTGCTGGACCCAGGTGACTTACGCTCCTGGTGG
GGGCGGGGCGGGGCAGGGCGGCTTTGCCATCTTGGGGTGGGGGGCACTTGCCTGGGGGCTGGACGTTGGGGGCGGGG
CAGGATTGAGATGGGGCCGGGGGTGGGGTCTGGATGGAGGTTGGCTGAGCTGGGCGGGGCATGGCTCAGGCATGGCT
GGGATAGATGGGGCTGGGCGGGGCGAGGGGAGGGGCTGGGTGGGACGAGGGGAGGGTTTGGGCGGGGCAAGGCTGGG
GCTGGGCGGATCTGAGTTGGTCCCCGAAGGCCCGGAGCTCTGACCCTCAGACGCCCCCTCTTGAACTGGCTTTTCCC
ACTCCTCCCTTTCTAAAACGAAGATGCGGCTGGGGGCCTTCCCCTCCAACGAGGGATCGAGGGCCGCGGGGCGAGCA
CTGAGTCGGATCCCTGGCTCTGGGGCCAGGCCAGGCCTTGGCCCGCTGATAGACCTCGAAGATGGCCATCATCTTTT
CTCCTTACCTCAGTGTCCTTGGCTCGGGGCCCAGGGAACTGGCAGCCTGGTCTCCGGCATCGGATGGGACCGGGGGG
CGGGGAGGGGGTGAATGGGGCAGTGATTTGAAGAGGGGTCGCGGAGGCTGGGCATGAGGCGCGGCTGTCCTCACCGC
TCCCGCAGACAGCGTGGACGATGAATTTGAATTGTCCACCGTGTGTCACCGGCCTGAGGGTCTGGAGCAGCTGCAGG
AGCAAACCAAATTCACGCGCAAGGAGTTGCAGGTCCTGTACCGGGGCTTCAAGAACGTGAGTGCNGGGCGAGGCCAA

Fig. 22B

ACTCAGCGNGGGTGGACAGGAGGACCCAANCCGGTCCANATTTTTCCCANAAAGCATGGCTTNGATGCTTGAGGNG
CGGGCGGAAGGGAGGCAAGGCCCTGAGACTGAACTTCTAGCTGGAGGTTCTGGGGCGGGGCCAGAACGRAAGTGGCG
CCTGTAGACTGTCAGTTTCGTTCCATGTTTTTATTTGTGCACTGGGAAAGAAGTCTTCCCTCCCATCACATGAGCC
ACGTGGTGAGTCCTCTGGAGGCTTGAAGATTATCCCCCTCCCTGGGAGTCTTGGGCCATGGAGGGTGGGGGCGGTGA
ACGGAAGGGGATTTTGTCTCTGCCCTCAGCCTGGTGCCCTCTCCTTCCAGGAATGTCCCAGCGGAATTGTCAATGAG
GAGAACTTCAAGCAGATTTACTCCCAGTTCTTTCCTCAAGGAGGTGAGGGGACAAGGCCCAAGGGGAAGCAGTTGTC
CTTCTCTAGGCTGAGGGAGGGAGGGATTCTGGAGGAGCTGGGAATGCCAAGGTGATGGGGGGTATGGGGAGCTCCTT
AGAGGGAGGAAGTCCTCTCCTGTGTGGAAGCCAACTTCTCCACACTCACCCTGCAGACTCCAGCACCTATGCCACTT
TTCTCTTCAATGCCTTTGACACCAACCATGATGGCTCGGTCAGTTTTGAGGTGAGCTGGGCGAGGTGGGCCAGGGAA
GCCTGTTTCCTGGAGTTCAGGGCCAGGATCTCCAGGCCAAACCCAGAGAAGGAGTTGGGTGAAGAGKACCCGAGGAC
ACAGCTCCCTNCTGCCTTCTTCCCAGGACTTTGTGGCTGGTTTGYCCGTGATTCTTCGGGGAACTGTAGATGACAGG
CTTAATTGGGCCTTCAACCTGTATGACCTTAACAAGGACGGCTGCATCACCAAGGAGGTGCAGGGCAACTGAAGGGC
TGGGGGTCTGTGGCGGTGATGGGGGTGGCGTGCAKAGGGTGATGGGAGGGAAATATGACCCACATATGCCCACAAGC
AATGGGATCAAGGGAGGCTGGAGGCTCTGAGGAAGGATCCTCTTCTCTCTTGGCCTAACAGGAAATGCTTGACATCA
TGAAGTCCATCTATGACATGATGGGCAAGTACACGTACCCTGCACTCCGGGAGGAGGCCCCAAGGGAACACGTGGAG
AGCTTCTTCCAGGTACTTGGGAGTGGGTATGGCTGGAGGGCCCTGGAGTGAAGGGAAGAAGGCCAAGAACCAGCAGG
GAACTCACCTGACTTCTGTCTGCCTCTCTCTTGCCATCCCTCCTGTTCTCCCTGCCTGACCACCTTCTTGCAGAAGA
TGGACAGAAACAAGGATGGTGTGGTGACCATTGAGGAATTCATTGAGTCTTGTCAAAAGGTACAGCTCCCTGCCCTC
TACATTACCCTGACCTGGACTCAGGCCTGATTTAGTAATGCAGGGAAAAGCTTCTTTGGGAAGAATACCACCTTCCC
ACCTCACCCCCATATTTCAATCCTATTCCTTTGTGGGAGGCTTACCCCTTCCCTACCTCAGGTCTCTCTGGGCATCT
CCTTCCTCTGTGCTTTTGAATGTCCCCGTCTGTGACTCAAGTGTCCCTCTCACTGTCTCTGATAAAGCTCCTTCTCT
TTCTCTCTCTTCAATCTGCCTCGCTCACATCATGGCCACAGGATGAGAACATCATGAGGTCCATGCAGCTCTTTGAC
AATGTCATCTAGCCCCCAGGAGAGGGGGTCAGTGTTTCCTGGGGGGACCATGCTCTAACCCTAGTCCAGGCGGACCT
CACCCTTCTCTTCCCAGGTCTATCCTCATCCTACGCCTCCCTGGGGGCTGGAGGGATCCAAGAGCTTGGGGATTCAG
TAGTCCAGATCTCTGGAGCTGAAGGGGCCAGAGAGTGGGCAGAGTGCATCTCGGGGGGTGTTCCCAACTCCCACCAG
CTCTCACCCCCTTCCTGCCTGACACCCAGTGTTGAGAGTGCCCCTCCTGTAGGAATTGAGCGGTTCCCCACCTCCTA
CCCCTACTCTAGAAACACACTAGACAGATGTCTCCTGCTATGGTGCTTCCCCCATCCCTGACCTCATAAACATTTCC
CCTAAGACTCCCCTCTCAGAGAGAATGCTCCATTCTTGGCACTGGCTGGCTTCTCAGACCAGCCATTGAGAGCCCTG
TGGGAGGGGGACAAGAATGTATAGGGAGAAATCTTGGGCCTGAGTCAATGGATAGGTCCTAGRAGGTGGCTGGGGTT
GAGAATAGAAGGGCCTGGACAGATTATGATTGCTCAGGCATACCAGGTTATAGCTCCAAGTTCCACAGGTCTGCTAC
CACAGGCCATCAAAATATAAGTTTCCAGGCTTTGCAGAAGACCTTGTCTCCTTAGAAATGCCCCAGAAATTTTCCAC
ACCCTCCTCGGTATCCATGGAGAGCCTGGGGCCAGATATCTGGCTCATCTCTGGCATTGCTTCCTCTCCTTCTTTCC
TGCATGTGTTGGTGGTGGTTGTGGTGGGGGAATGTGGATGGGGGATGTCCTGGCTGATGCCTGCCAAAATTTCATCC
CACCCTCCTTGCTTATCGTCCCTGTTTTGAGGGCTATGACTTGAGTTTTTGTTTCCCATGTTCTCTATAGACTTGGG
ACCTTCCTGAACTTGGGGCCTATCACTCCCCACAGTGGATGCCTTAGAAGGGAGAGGGAAGGAGGGAGGCAGGCATA
GCATCTGAACCCAGTGTGGGGGCATTCACTAGAATCTTCAATCAACCTGGGCTCTCCCCACCCCACCCCAGATAACC
TCCTCAGKTCCCTAGGGTCTCTTCTYGCTTGACTCAATCTACCCAGAGATGCCCCTTAGCACACCTAGAGGGCAGGG
ACCATAGGACCCAGGTTCCAACCCCATTGTCAGCACCCCAGCCATGCGGCCACCCCTTAGCACACCTGCTCGTCCCA
TTTAGCTTACCCTCCCAGTTGGCCAGAATCTGAGGGGAGAGCCCCCAGAGAGCCCCCTTCCCCATCAGAAGACTGTT
GACTGCTTTGCATTTTGGGCTCTTCTATATATTTTGTAAAGTAAGAAATATACCAGATC:TAATAAAACACAATGGC
TATGCACAGGCTGCCGTCTCTGCCTTTTGTCCCTCCCACCTACAAATACTACACAACCCCTAACGAATGCACCTGCA
GCCTTTTAGATCCCCAAGAAAGTGGCTTTCTTTTCCATAGTTGGCCATACCTTGGCATGAGACTGAGACACAGGCTC
TGGAATGGTTGGAAACCCACCCAACCTCAGGCCCCCACATGAATCTCCCTCCCACACAGCCTGAGAGGAGACAAGGA
AGGAAGGACAGGACACTGATGTCCCGAAGACTGTGCCAAGCAAGCTGTTTTTTAGCTGACATTCTTACAAGTTGAAT
CACAGATTTCTAATTTACAGACTTTTTAGTTAATCTCAAAGTGCTTTCTTTTGAGGGGCCTCCTTTAAGTTCYTTCT
TTTTTTTTTTTTTTT

Fig. 22C

>monkey KChIP4 cds = 265 gtcgacccacgcgtccggtgcgctgtggttgcgggggggagccccgccagccaaatgccaggatcagcatgagaggctgg
actttagtccaggtctgtcctcaccccgggggaccgccggctttgcagggtgcagctgcgaggaactgctcactttttc
cccttgcaagtctttgttccaagcctgacgttgctacgattctgtaattaactccctccactccaaaggggtctggaggc
tgggatgctctgccagctcagaggATGTTGACTCTGGAGTGGGAGTCCGAAGGACTGCAAACAGTGGGTA
TTGTTGTGAT
TATATGTGCATCTCTGAAGCTGCTTCATTTGCTGGGACTGATTGATTTTTCGGAAGACAGCGT
GGAAGATGAACTGGAGA
TGGCCACTGTCAGGCATCGGCCTGAGGCCCTTGAGCTTCTGGAAGCCCAGAGCAAATTTACC
AAGAAAGAGCTTCAGATC
CTTTACAGAGGATTTAAGAACGAATGCCCCAGTGGTGTTGTTAATGAAGAAACCTTCAAAGA
GATTTACTCGCAGTTCTT
TCCACAGGGAGACTCTACAACATATGCACATTTTCTGTTCAATGCGTTTGATACGGACCACA
ATGGAGCTGTGAGTTTCG
AGGATTTCATCAAAGGTCTTTCCATTTTGCTCCGGGGGACAGTACAAGAAAAACTCAATTGG
GCATTTAATCTGTATGAT
ATAAATAAAGATGGCTACATCACTAAAGAGGAAATGCTTGATATAATGAAAGCAATATACG
ACATGATGGGTAAATGTAC
ATATCCTGTCCTCAAAGAAGATGCACCCAGACAACACGTCGAAACATTTTTTCAGAAAATGG
ACAAAAATAAAGATGGGG
TTGTTACCATAGATGAGTTCATTGAAAGCTGCCAAAAAGATGAAAACATAATGCGCTCCATG
CAGCTCTTTGAAAATGTG
ATTTAActtgtcaactagatcctgaatccaacagacaaatgtgaactattctaccacccttaaagtcggagctaccactt
ttagcatagattgctcagcttgacactgaagcatattatgcaaacaagctttgttttaatataaagcaatccccaaaaga
tttgagtttctcagttataaatttgcatcctttccataatgccactgagttcatgggatgttctaactcatttcatactc
tgtgaatattcaaaagtaatagaatctggcatatagttttattgattccttagccatgggattattgaggctttcacata
tcagtgattttaaaataccagtgtttttgctctcatttgtatgtattcagtcctaggattttgaatggttttctaatat
actgacatctgcatttaatttccagaaattaaattaattttcatgtctgaatgctgtaattccatttatatactttaagt
aaacaaataagattactacaattaaacacatagttccagtttctatggccttcccttcccaccttctattataaattaat
tttatctggtattttaaacatttaaaaatttatcatcagatatcagcatatgcctaattatgcctaatgaaacttaata
agcatttaattttccatcatacattatagccaaggcctatatactatatataattttggatttgtttaatcttacaggct
gttttccattgtatcatcaagtggaagttcaagacggcatcaaacaaaacaaggatgtttacagacatatgcaaagggtc
aggatatctatcctccagtatatgttaatgcttaataacaagtaatcctaacagcattaaaggccaaatctgtcctcttt
cccctgacttccttacagcatgtttatattacaagccattcagggacaaagaaaccttgactaccccactgtctactagg
aacaaacaaacagcaagcaaaattcactttgaaagcaccagtggttccattacattgacaactactaccaagattcagta
gaaaataagtgctcaacaactaatccagattacaatatgatttagtgcatcataaaattccaacaattcagattatttt
aatcatctcagccacaactgtaaagttgccacattactaaagacacacacatcgtccctgttttgtagaaatatcacaaa
gaccaagaggctacagaaggaggaaatttgcaactgtctttgcaacaataaatcaggtatctattctggtgtagagatag
gatgttgaaagctgccctgctatcaccagtgtagaaattaagagtagtacaatacatgtacactgaaatttgccatcgcg
tgtttgtgtaaactcaatgtgcacattttgtatttcaaaagaaaaaataaaagcaaaataaaatgttwawaamwmwaaa
aaaaaaaaaaaaa >monkey KChIP4

MLTLEWESEGLQTVGIVVIICASLKLLHLLGLIDFSEDSVEDELEMATVRHRPEALELLEAQSKFT
KKELQILYRGFKNE
CPSGVVNEETFKEIYSQFFPQGDSTTYAHFLFNAFDTDHNGAVSFEDFIKGLSILLRGTVQEKLNW
AFNLYDINKDGYIT
KEEMLDIMKAIYDMMGKCTYPVLKEDAPRQHVETFFQKMDKNKDGVVTIDEFIESCQKDENIM
RSMQLFENVI

Fig. 23

>monkey KChIP4 C terminal splice variant cds = 265-966 gtcgacccacgcgtccggtgcgctgtggttgcggggggagccccgccagccaaatgccaggatcagcatgagaggctgg
actttagtccaggtctgtcctcaccccgggggaccgccggctttgcagggtgcagctgcgaggaactgctcactttttc
cccttgcaagtctttgttccaagcctgacgttgctacgattctgtaattaactccctccactccaaaggggtctggaggc
tgggatgctctgccagctcagaggATGTTGACTCTGGAGTGGGAGTCCGAAGGACTGCAAACAGTGGGTA
TTGTTGTGAT
TATATGTGCATCTCTGAAGCTGCTTCATTTGCTGGGACTGATTGATTTTTCGGAAGACAGCGT
GGAAGATGAACTGGAGA
TGGCCACTGTCAGGCATCGGCCTGAGGCCCTTGAGCTTCTGGAAGCCCAGAGCAAATTTACC
AAGAAAGAGCTTCAGATC
CTTTACAGAGGATTTAAGAACGAATGCCCCAGTGGTGTTGTTAATGAAGAAACCTTCAAAGA
GATTTACTCGCAGTTCTT
TCCACAGGGAGACTCTACAACATATGCACATTTTCTGTTCAATGCGTTTGATACGGACCACA
ATGGAGCTGTGAGTTTCG
AGGATTTCATCAAAGGTCTTTCCATTTTGCTCCGGGGGACAGTACAAGAAAAACTCAATTGG
GCATTTAATCTGTATGAT
ATAAATAAAGATGGCTACATCACTAAAGAGGAAATGCTTGATATAATGAAAGCAATATACG
ACATGATGGGTAAATGTAC
ATATCCTGTCCTCAAAGAAGATGCACCCAGACAACACGTCGAAACATTTTTTCAGGCTGTTT
TCCATTGTATCATCAAGT
GGAAGTTCAAGACGGCATCAAACAAAACAAGGATGTTTACAGACATATGCAAAGGGTCAGG
ATATCTATCCTCCAGTATA
TGTTAAtgcttaataacaagtaatcctaacagcattaaaggccaaatctgtcctctttcccctgacttccttacagcatg
tttatattacaagccattcagggacaaagaaaccttgactaccccactgtctactaggaacaaacaaacagcaagcaaaa
ttcactttgaaagcaccagtggttccattacattgacaactactaccaagattcagtagaaaataagtgctcaacaacta
atccagattacaatatgatttagtgcatcataaaattccaacaattcagattatttttaatcatctcagccacaactgta
aagttgccacattactaaagacacacacatcgtccctgttttgtagaaatatcacaaagaccaagaggctacagaaggag
gaaatttgcaactgtctttgcaacaataaatcaggtatctattctggtgtagagataggatgttgaaagctgccctgcta
tcaccagtgtagaaattaagagtagtacaatacatgtacactgaaatttgccatcgcgtgtttgtgtaaactcaatgtgc
acatttgtatttcaaaaagaaaaaataaaagcaaaataaaatgttwawaamwmwaaaaaaaaaaaaaaa >monkey KChIP4 C terminal splice variant MLTLEWESEGLQTVGIVVIICASLKLLHLLGLIDFSEDSVEDELEMATVRHRPEALELLEAQSKFT
KKELQILYRGFKNE
CPSGVVNEETFKEIYSQFFPQGDSTTYAHFLFNAFDTDHNGAVSFEDFIKGLSILLRGTVQEKLNW
AFNLYDINKDGYIT
KEEMLDIMKAIYDMMGKCTYPVLKEDAPRQHVETFFQAVFHCIIKWKFKTASNKTRMFTDICK
GSGYLSSSIC

Fig. 24

```
KChIP1_1v   ----------------MGAVMGTF------SSLQTKQ----RRP----------------
KChIP2_9ql  MRGQGRKESLSDSRDLDGSYDQLTGHPPGPTKKALKQRFLKLLPCCGPQALPSVSETLAA
KChIP3_p19  --MQPAKEVTKAS---DGSLLGDLGH----TPLSKKEGIKWQRPRLSRQALMRCCLVKWI
KChIP4_352  ---MLTLEWESEGLQTVGIVVIICAS----LKLLHLLGLIDFSE----------------
KChIP4_231  ---MLTLEWESEGLQTVGIVVIICAS----LKLLHLLGLIDFSE----------------
hsncspara   ----HEVESISAQLEEASSTGGFLYAQN-STKRSIKERLMKLLPCS--------------

KChIP1_1v   ------------SKDKIEDELEMTMVCHRPEGLEQLEAQTNFTKRELQVLYRGFKNECPS
KChIP2_9ql  PASLRPHRPRLLDPDSVDDEFELSTVCHRPEGLEQLQEQTKFTRKELQVLYRGFKNECPS
KChIP3_p19  LSSTAPQ-----GSDSSDSELELSTVRHQPEGLDQLQAQTKFTKKELQSLYRGFKNECPT
KChIP4_352  --------------DSVEDELEMATVRHRPEALELLEAQSKFTKKELQILYRGFKNECPS
KChIP4_231  --------------DSVEDELEMATVRHRPEALELLEAQSKFTKKELQILYRGFKNECPS
hsncspara   -AAKTSSP---AIQNSVEDELEMATVRHRPEALELLEAQSKFTKKELQILYRGFKNVRTF

KChIP1_1v   GVVNEDTFKQIYAQFFPHGDASTYAHYLFNAFDTTQTGSVKFEDFVTALSILLRGTVHEK
KChIP2_9ql  GIVNEENFKQIYSQFFPQGDSSTYATFLFNAFDTNHDGSVSFEDFVAGLSVILRGTVDDR
KChIP3_p19  GLVDEDTFKLIYAQFFPQGDATTYAHFLFNAFDA GNGAIHFEDFVVGLSILLRGTVHEK
KChIP4_352  GVVNEETFKEIYSQFFPQGDSTTYAHFLFNAFDTDHNGAVSFEDFIKGLSILLRGTVQEK
KChIP4_231  GVVNEETFKEIYSQFFPQGDSTTYAHFLFNAFDTDHNGAVSFEDFIKGLSILLRGTVQEK
hsncspara   FLTLPSHNSQRSIEK---------------------------------------------

KChIP1_1v   LRWTFNLYDINKDGYINKEEMNDIVKAIYDMMGKYTYPVLKEDTPRQHVDVFFQKMD---
KChIP2_9ql  LNWAFNLYDLNKDGCITKEEMLDIMKSIYDMMGKYTYPALREEAPREHVESFFQKMD---
KChIP3_p19  LKWAFNLYDINKDGYITKEEMLAIMKSIYDMMGRHTYPILREDAPAEHVERFFEKMD---
KChIP4_352  LNWAFNLYDINKDGYITKEEMLDIMKAIYDMMGKCTYPVLKEDAPRQHVETFFQKMD---
KChIP4_231  LNWAFNLYDINKDGYITKEEMLDIMKAIYDMMGKCTYPVLKEDAPRQHVETFFQAVFHCI
hsncspara   ------------------------------------------------------------

KChIP1_1v   ---KNKDGIVTLDEFLESCQEDDNIMRSLQLFQNVM
KChIP2_9ql  ---RNKDGVVTIEEFIESCQKDENIMRSMQLFDNVI
KChIP3_p19  ---RNQDGVVTIEEFLEACQKDENIMSSMQLFENVI
KChIP4_352  ---KNKDGVVTIDEFIESCQKDENIMRSMQLFENVI
KChIP4_231  IKWKFKTASNKTRMFTDICKGSGYLSSSIC------
hsncspara   ------------------------------------
```

Fig. 25

Rat 33b07 protein

MNGVEGNNELPLANTSTSALVPEDLDLKQDQPLSEETDTVREMEAAGEAGAEGGASPDSEHCDPQLCLRVAENGCAAAAG
EGLEDGLSSSKCGDAPLASVAANDANKNGCQLAGPLSPAKPKTLEASGAVGLGSQMMPGPKKTKVMTTKGAISATTGKEG
EAGAAMQEKKGVQKEKKAAGGGKDETRPRAPKINNCMDSLEAIDQELSNVNAQADRAFLQLERKFGRMRRLHMQRRSFII
QNIPGFWVTAFRNHPQLSPMISGQDEDMMRYMINLEVEELKHPRAGCKFKFIFQSNPYFRNEGLVKEYERRSSGRVVSLS
TPIRWHRGQEPQAHIHRNREGNTIPSFFNWFSDHSLLEFDRIAEIIKGELWSNPLQYYLMGDGPRRGVRVPPRQPVESPR
SFRFQSG.

Rat 33b07 DNA (coding: 85-1308)

GGTGGAGCTAAGCACTCACTGCGGTGCTGCCCTGCGTCTGCAGAGAACAAGGAAAGCTTCTCTGCAGGGCTGTCAGCTGC
CAAAATGAACGGCGTGGAAGGGAACAACGAGCTCCCTCTCGCTAACACCTCGACCTCCGCCCTTGTCCCGGAAGATCTGG
ATCTGAAGCAAGACCAGCCGCTCAGCGAGGAAACTGACACGGTGCGGGAGATGGAGGCTGCAGGTGAGGCCGGTGCGGAG
GGAGGCGCGTCCCCCGATTCGGAGCACTGCGACCCCCAGCTCTGCCTCCGAGTGGCTGAGAATGGCTGTGCTGCCGCAGC
GGGAGAGGGGCTGGAGGATGGTCTGTCTTCATCAAAGTGTGGGGACGCACCCTTGGCGTCTGTGGCAGCCAACGACAGCA
ATAAAAATGGCTGTCAGCTTGCAGGGCCGCTCAGCCCTGCTAAGCCAAAAACTCTGGAAGCCAGTGGTGCAGTGGGCCTG
GGGTCGCAGATGATGCCAGGGAAGAAGAAGACCAAGGTAATGACTACCAAGGGCGCCATCTCTGCGACTACAGGCAAGGA
AGGAGAAGCAGGGGCGGCAATGCAGGAAAAGAAGGGGGTGCAGAAAGAAAAAAAGGCAGCTGGAGGAGGGAAAGACGAGA
CTCGTCCTAGAGCCCCTAAGATCAATAACTGCATGGACTCCCTGGAAGCCATCGATCAAGAGCTGTCAAATGTAAATGCG
CAAGCTGACAGGGCCTTCCTCCAGCTGGAACGCAAATTTGGGCGGATGAGAAGGCTCCACATGCAGCGCCGAAGTTTCAT
CATCCAAAACATCCCAGGTTTCTGGGTCACAGCGTTTCGGAACCACCCGCAACTGTCACCGATGATCAGTGGCCAAGATG
AAGACATGATGAGGTACATGATCAATTTAGAGGTGGAGGAGCTTAAGCACCCAAGAGCAGGGTGCAAATTTAAGTTCATC
TTCCAAAGCAACCCCTACTTCCGAAATGAGGGGCTGGTCAAAGAGTACGAGCGCAGATCCTCAGGTCGAGTGGTGTCGCT
CTCTACGCCAATCCGCTGGCACCGGGGTCAAGAACCCCAGGCCCATATCCACAGGAATAGAGAGGGGAACACGATTCCCA
GTTTCTTCAATTGGTTGTCAGACCACAGCCTCCTAGAATTCGACAGAATAGCTGAAATTATCAAAGGGGAGCTTTGGTCC
AATCCCCTACAATACTACCTGATGGGCGATGGGCCACGCAGAGGAGTTCGAGTCCCACCAAGGCAGCCAGTGGAGAGTCC
CAGGTCCTTCAGGTTCCAGTCTGGCTAAGCTCTGCCCTCGTGAGAAGCTCTTACAGAAGAGTCCTTACCACCTTCTCAGC
TTGGCTAGCAGCATGCAGCCTTCTGTCTGCTTTCTCTTCCTTGGATTGTGTCCTTTGGTTCTTCTAAGTCTCCGGTAGTT
TCAAGGTTGTGGCTTCCAAGTCTTTGCTCTTCTTTCTCTTGGCCATCACGATGTCCTGCATAGTGTTAATGGTGTTCCAA
GTGCATGGCCTCCAAACTGCTTCTATGCCAAGCTCACGTGCTGTAGTTTGTACTGCTTTTCTTTGCATGGCTTGGTTCCT
GTCTGTGATCTTCTAGGTTTTTTGTTTTCTTTTTTAAAAGTGGTTCTCTATCAAAAGAAAGCTTGACATATCCTTACCAA
GAACTAGCCAGATTTCATACTGTGTTCCCGATATCTATGTACTGTGAAGAACTGTGAGTTTCGCCACTGCAAGATGGGAC
TGTATCCCAATCCAGCCATCAGCCCAACAGGACATTCCAAGCTGTCACCAACTGATCCTAGCTGTCTTCCTGGGCCTTTG
CCATTTACCCTGCTTTTTATCTATAGAATGAGCAGGTGGCTGGTAGGTGACTACTAGGTAAGAGTGAAGTATTAGGTGAG
GAGTGTTTTCTGTCACCACATTGTTCTTGTACCAATGCATCATGATCAGCTTGGATCAGCTACTGACTGTCTGATATTTC
TAACCCCAACACAAAAAAAAAAAAAAAAAAAAAAAAAAAAAAAAAAAAAAA

Fig. 26

Human 33b7 (106d5) DNA (coding: 88-1332)

GGGGTGGTGCTAGACGTTTCGGGCAGAGCTCGGCCGCTGCGGAGGACAAGGAACTCTCCCTCTCCCACTAGTCTGACTTC
TTCCAAAATGAGCGGCCTGGATGGGGGCAACAAGCTCCCTCTCGCCCAAACCGGCGGCCTGGCTGCTCCCGACCATGCCT
CAGGAGATCCGGACCTAGACCAGTGCCAAGGGCTCCGTGAAGAAACCGAGGCGACACAGGTGATGGCGAACACAGGTGGG
GGCAGCCTGGAGACCGTTGCGGAGGGGGGTGCATCCCAGGATCCTGTCGACTGTGGCCCCGCGCTCCGCGTCCCAGTTGC
CGGGAGTCGCGGCGGTGCAGCGACCAAAGCCGGGCAGGAGGATGCTCCACCTTCTACGAAAGGTCTGGAAGCAGCCTCTG
CCGCCGAGGCTGCTGACAGCAGCCAGAAAAATGGCTGTCAGCTTGGAGAGCCCCGTGGCCCTGCTGGGCAGAAGGCTCTA
GAAGCCTGTGGCGCAGGGGGCTTGGGGTCTCAGATGATACCGGGGAAGAAGGCCAAGGAAGTGACGACTAAAAAACGCGC
CATCTCGGCAGCAGTGGAAAAGGAGGGAGAAGCAGGGGCGGCGATGGAGGAAAAGAAGGTAGTGCAGAAGGAAAAAAAGG
TGGCAGGAGGGGTGAAAGAGGAGACACGGCCCAGGGCCCCGAAGATCAATAACTGCATGGACTCACTGGAGGCCATCGAT
CAAGAGTTGTCAAACGTAAATGCCCAGGCTGACAGGGCCTTCCTTCAGCTTGAGCGCAAGTTTGGCCGCATGCGAAGGCT
CCACATGCAGCGCAGAAGTTTCATTATCCAGAATATCCCAGGTTTCTGGGTTACTGCCTTTCGAAACCACCCCCAGCTGT
CACCTATGATCAGTGGCCAAGATGAAGACATGCTGAGGTACATGATCAATTTGGAGGTGGAGGAGCTTAAACACCCCAGA
GCAGGCTGCAAATTCAAGTTCATCTTTCAGGGCAACCCCTACTTCCGAAATGAGGGGCTTGTCAAGGAATATGAACGCAG
ATCCTCTGGCCGGGTGGTGTCTCTTTCCACTCCAATCCGCTGGCACCGAGGCCAAGACCCCCAGGCTCATATCCACAGAA
ACCGGGAAGGGAACACTATCCCTAGTTTCTTCAACTGGTTTTCAGACCACAGCCTTCTAGAATTCGACAGAATTGCAGAG
ATTATCAAAGGAGAACTGTGGCCCAATCCCCTACAATACTACCTGATGGGTGAAGGGCCCCGTAGAGGAATTCGAGGCCC
ACCAAGGCAGCCAGTGGAGAGCGCCAGATCCTTCAGGTTCCAGTCTGGCTAATCTCTGTCCTGTGAGAAGCTTCTGCACA
AGTTTCCTTACCACCTCCTCTTGGACCTATGCTTGGCCAACAGCATGCAGTCTTCCATCTGCTTTCTCTTCATACTGTGG
ATTATCTTTTCCTTTGGTTCTAAATCTTCAGTAATCGGTTGCAAGATTGTTGGCTTACCTGCCTGTGCCATTCTTCCTCT
GGGCCTTCATGCTTTTCTGCATTGTGTTAACATGTTTCAAGTGCATGGCCTTCTACGGCTTCTATGCCAAGCGTATGATA
CTATAGATATAGTGTACCATACTGCCTTTCTTTGCATGGCTTGGACCCTATCTGTGACCATGCTCTTCTCCCAATTTAAG
TGGTTCTGTACCACAAAGAATCTTGATACATTTTCACAAATAACTGATTGGGCTTCATACTTTATGCTGGCTGTGTCCTG
ATACCCATGTACTTATGGTAAGCTATTTGGGTATTACCACTGCAAGACAAAACTGATATCTTAACCCGGCCATCAACCCA
AATTGGACATTCCAGACTACCACCAACTGGATCCCAGCTGCCTTCCTGGGCTTGTGCCATCCACCCTACTGGTTATCTGA
TAGAACAAGCTGGTGGCTGATGGGTGACTGCTAGGCGTGACTGAGGTAATAGATGAAAAGTGTTCTATGTTATCACATTG
GTTTTCCTGTACCTTTGGTTACTCTACGTCATGACCAGCTGCTGGTGAGTATGAAGCCTGTGCTATAGCCCACCCCTACT
CACTCTCACCTTCTGGTTGAACTTTGCTTAGGCCACCATTGTCTGCCTCATCAGGAACTATCTGTAGACGTAGCTCCCAG
GGAGCTCACAGCAACACCCCCTACCACCAGGATGGGCAGTAATATGTGACAGAGCCCAAAGCAAGGCTGGAACGCAGTCC
CTTCCAGCTTAGTCTTTCTGACTCCTAGCCAACAAACCATCCTTAATGTGAGCAACTTCTTTAGGCATTTCCTCTTTTCC
CCGCCTGCACCCACTCTGAACATGACAAAAGTTGCCAGAGTTGGGGCATTGAGGAAGAGATATTTCTGGAATGTGAGACT
TGTTATGCCTCTGTCTCTTTCTCTCCCTCCCCCTCCCCTCTCCCTCCCCCTCTCCCTCCCATCCCTTTTCTTCCCTTTCA
CTCTGAAGCAGTTTTAGCTTATTAACAGAAAACAAAACTGGCAAAGCAGGCTTTTTGTTTAATTTGCTCTTTCCCTGATT
GTGTTCAGAGAGAAAGGTTATGATTAAATGGGCTCCAGATCTCTTATTGCCCTTATTCCTCCACCCCACTTCTTTTAGCA
AGGTCTGAAAGTTTCAAAGGGAGACCTATAGGTTAATTGTTTAGTTATAGGCAGTGTTAAATTAGGCAGATTTTGACATA
TTTATCTTTTTACCCCATCCATTCTACCAAAACCTGTGTATTTCTTGAGTTTTTAGTTTGAGAAGCTGGAAAGAGAGAGA
AGGGCCTCACAGTGATGGGTTCAGGACGGGTCAAAGGCAAAGGCCTTTGTGATGTGAGCAAAGGCAACCAAAACTTAGCC
TCACTCCACTTTTCTAAAGATGGAAATTCTTTTTTGGGCCTTGGACTGCTTCTAGGGTAGCATTTTGTAGGTCACTCTTC
TCCTTTGTACTATTTTGTTTCTGCCCTGATGTCCCTTGGGTCTCCATCCTACTGCCTGGCTTTCTTGGCCCTCATTTCTC
AGCTTCTGCATTTCCTTCCCTGCTCCTAACAAATGAAGAAGCAGGCTGCAGCCTGCATTGTGGAAGATCTCCAGCCTCCT
TGTAGGGGATAAGGGGATGTGTAGCATCTGTGTGGATTTTCACGGACAAGTTCCAGTAGGTGGGACAGTGATGCCGTCAA
GGCTTAGTTATGATCATGTGTGGTGATAAAGACCATCCACCATCACCCTTTTCCCCTTTGGTTTTGAAGGCCTTGCCCTA
AGCTACCTGAGGGTTTAGGAGGTCTGAACACACACAGTGGAGAGGTTAATCTAGGTTGGGAAACTGAGTAAAAGTCCAGA
GCAGGAATGAGCCTGCTGTGGCGTGGGTTTGGAAAGGCTCACAGGAAAGAACCTGCAGGATCAGGGGTGGAGGGGAGGC
CCCTGAGGTGCTCTCCAGGGAAGAGGGGCTGGGGTTTAAATAGCATGCTTGGAGGAAGATTTTCCTTCAATTTTTCCTAA
GTCCTTGAATTCACCAGTAGATTTTTGTAAACAAAATGTAAGTCGATGTTTTCTCTCAATTATCCTAGGAGTGACCTTTA
TATGTGTGGAAGATTAATGGTATATGCTCCTTATGTCACTGTTTTTGAGTAAAATCCATTTCCTTTCTCTGTTTCAGCCT
ATGACAAAATTGATGTTTACAGGCCTGCTTTTTGCTTATAATTGACAACATGTGCAAAAATACCAAATTTGTGTCCTGTG
CAGTATGAAGAATTCAGTGAATATTCATTAATGTATTAGCTTGTTTTGCTCTCTGTTCATATATGGCTCTATTCTTAGAA
ATATAATTTGAATGTGATCTTTCAATAGTCTGAATATTTTACAAATTATAGCTATGTCTTGTGAAAATAACCTCAAAAAG
AAAAATACGACTCTGTTGTCTTACTTGATATTTCTTGCCCTAGTAATGTACTTGACATTTATGTTCCTAAGCAGTGTAAG
TACCAGTAGAATTTCTCTGTCAAACTCAATGATCATTTAGTACTTTTGTCTTCTCCCATGTGCTTGAAGGAAAAATAAAG
TGTCACTACCGTATTTCTTGTTTTCATCAAAAAATAAAAATAATTTAAAAACAAAAAAAAAAAAAAA

Fig. 27A

Human 33b7 (106d5) protein

MSGLDGGNKLPLAQTGGLAAPDHASGDPDLDQCQGLREETEATQVWANTGGGSLETVAEGGASQDPVDCGPALRVPVAGS
RGGAATKAGQEDAPPSTKGLEAASAAEAADSSQKNGCQLGEPRGPAGQKALEACGAGGLGSQMIPGKKAKEVTTKKRAIS
AAVEKEGEAGAAMEEKKVVQKEKKVAGGVKEETRPRAPKINNCMDSLEAIDQELSNVNAQADRAFLQLERKFGRMRRLHM
QRRSFIIQNIPGFWVTAFRNHPQLSPMISGQDEDMLRYMINLEVEELKHPRAGCKFKFIFQGNPYFRNEGLVKEYERRSS
GRVVSLSTPIRWHRGQDPQAHIHRNREGNTIPSFFNWFSDHSLLEFDRIAEIIKGELWPNPLQYYLMGEGPRRGIRGPPR
QPVESARSFRFQSG

Fig. 27B

Rat 1p protein (partial)

LKGARPRVVNSTCSDFNHGSALHIAASNLCLGAAKCLLEHGANPALRNRKGQVPAEVVPDPMDMSLDKAEAALVAKELRT
LLEEAVPLSCTLPKVTKPNYDNVPGNLMLSALGLRLGDRVLLDGQKTGTLRFCGTTEFASGQWVGVELDEPEGKNDGSVG
GVRYFICPPKQGLFASVSKVSKAVDAPPSSVTSTPRTPRMDFSRVTGKGRREHKGKKKSPSSPSLGSLQQREGAKAEVGD
QVLVAGQNRDCAFLWEDRLCSRLLVWH

Rat 1p DNA (partial, coding: 1-804)

CTGAAAGGGGCGAGGCCCAGGGTGGTGAACTCCACCTGCAGTGACTTCAACCATGGCTCAGCTCTGCACATCGCTGCCTC
GAATCTGTGCCTGGGCGCCGCCAAATGTTTACTGGAGCATGGTGCCAACCCAGCGCTGAGGAATCGAAAAGGACAGGTAC
CAGCGGAAGTGGTCCCAGACCCCATGGACATGTCCCTTGACAAGGCAGAGGCAGCCCTGGTGGCCAAGGAATTGCGGACG
CTGCTAGAAGAGGCTGTGCCACTGTCCTGCACCCTTCCTAAAGTCACACTACCCAACTATGACAACGTCCCAGGCAATCT
CATGCTCAGCGCGCTGGGCCTGCGTCTAGGAGACCGAGTGCTCCTCGATGGCCAGAAGACGGGCACGCTGAGGTTCTGCG
GGACCACCGAGTTCGCCAGTGGCCAGTGGGTGGGCGTGGAGCTAGATGAACCGGAAGGCAAGAACGACGGCAGCGTTGGG
GGTGTCCGGTACTTCATCTGCCCTCCCAAGCAGGGTCTCTTTGCATCTGTGTCCAAGGTCTCCAAGGCAGTGGATGCACC
CCCCTCATCTGTTACCTCCACGCCCCGCACTCCCCGGATGGACTTCTCCCGTGTAACGGGCAAAGGCCGGAGGGAACACA
AAGGGAAGAAGAAGTCCCCATCTTCCCCATCTCTGGGCAGCCTGCAGCAGCGTGAAGGGGCCAAAGCTGAAGTTGGAGAC
CAAGTCCTTGTGGCAGGCCAGAACAGGGATTGTGCGTTTCTATGGGAAGACAGACTTTGCTCCAGGTTACTGGTATGGCA
TTGAACTGGACCAGCCCACGGGCAAGCATGACGGCTCTGTGTTCGGTGTCCGGTACTTTACCTGTGCCCCGAGGCACGGG
GTCTTTGCACCAGCATCTCGTATCCAGAGGATTGGTGGATCCACTGATCCCCCTGGAGACAGTGTTGGAGCAAAAAAAGT
GCATCAAGTGACAATGACACAGCCCAAACGCACCTTCACAACAGTCCGGACCCCAAAGGACATTGCATCAGAGAACTCTA
TCTCCAGGTTACTCTTCTGCTGCTGGTTTCCTTGGATGCTGAGGGCGGAGATGCAGTCTTAGAGACCTGGATACCTGACA
CAGAGACAGAGTCCCCTCTAGCATCTCCTGACACAAGGAGACCCCAGTCACCCTAAGATAGAGATTCCCAGTGACACCTC
CAGAATAGAAACCCCGTTAGCCAGCCCTCGATTACTGAGGTCCCATTATTAACAGATCTCCCATGACGACTCCCCCAAAT
ACAGACCTCATGTTACCCCAAAAGAGATTCCCTGAGTAGCACCTTCAGGCTAGTCCCTGTCCCCTACCCCTCAGAGCAGA
TTTCCCCCAATAAACATTTTCCACATCACCCAAGGGATGCTGACCCTCTCCACGACAGGACGTTCTTGAGTTACCAGTGG
ATTAGAGTCCCATGAATGAAGACCCCCCCCACCCCGGTTCTCCTTAAGCATAGGTCATACCTCCAGAATAGCCAGCCACA
TCACTATCCCCATGTAACATCAGTCTCCTCAAAATGGCGTGAGGTCACTAGAAAGACCTTATACTCTCCTCTCCTTCTCA
GAGATGCCCTCCATTCACTTAAGTCCCTGTTCTCACCCCTGAACAAGACACCTAATTAACCGGCCCACTCACCTCAATTA
CAAACACCAAAATCGTCCTGGAAGCATGAATTACAGGACAGCAAGTCTTCCTGCCCTCTGCACCCTTGAGAAACCCCCAG
TGCCTTGTATGAAGCCCACCCCACATGGCCCACAGTCCCTGTGCTGGCCAAGGCTCCCAGAAAATTCTCTATTTTTTAAA
GTAATAACTTCCCCCCCTTTGGGGGGATCCCCAAATTTGGAGACCCCATTCTAGAACACTGGGGAGTTCAAATTCCAGAG
AGAATATATATTATATATAATCCCCAATTCCCCATGCTTCCAAGCCCTACAATCTCTAGAAGACCCCAAATTTCTAATTC
CCAGGACTTCCCCTACCCAAGTCACAGAATCTTCAAATCCCCAGGGAATCCCAAACTTAAGATACCAATCCCAAACCCTC
AGGAAATCCCCCAACACAAGGTCCTTAGGACCGGGAGGAAGGAACCTGTTGCCAGGAGAACATCCCAGGCTCTCAGGGCA
TCTCAAACCTGACTCCCAGGCACCAGGAGACCCCAAACAGAAAGTCCCATCTTTGGAACAAGGATAGGACTCTAATACCC
TTAGTCCATGGATCTTTAATTTCCCAACCTCCAAACTCCATGGGCCCCACCCTCAAGGGAACCCCCAAGATCCAAATCTC
TGATAACTAATATGTGCAGGGCCCCAGGGCTCTAACAGGACCCCAAATCATGGAGTCCCTACTTCAATCTACCTTCTGGT
CACAGGTCCAAGACACTAAATCTGAGTCATTGGCCCCAAAGGACTTCACAGCACCTGGGCCAGACTAACAGCCTGAGGGA
GAACCTGAGGGCCCCGTGGGTCCAGAGCAGACCTGGGGCCCTGACCACCAAGGACAGCTCACGACTGCCCCTTCACTGCA
TGTCCCTAAACTCAGCATGACTCCTGTCCTCTTCAATAAAGACGTTTCTATGGCAAAAAAAAAAAAAAAAAAAAAAAAAA
AAA

Fig. 28

Rat 7s protein (partial)

ADSTSRWAEALREISGRLAEMPADSGYPAYLGARLASFYERAGRVKCLGNPEREGSVSIVGAVSPPGGDFSDPVTSATLG
IVQVFWGLDKKLAQRKHFPSVNWLISYSKYMRALDEYYDKHFTEFVPLRTKAKEILQEEEDLAEIVQLVGKASLAETDKI
TLEVAKLIKDDFLQQNGYTPYDRFCPFYKTVGMLSNMISFYDMARRAVETTAQSDNKITWSIIREHMGEILYKLSSMKFK
DPVKDGEAKIKADYAQLLEDMQNAFRSLED

Rat 7s DNA (partial, coding: 1-813)

GCTGACTCTACCTCTAGATGGGCTGAGGCCCTCAGAGAAATCTCTGGTCGCTTAGCTGAAATGCCTGCAGATAGTGGATA
CCCTGCATACCTTGGTGCCCGACTGGCTTCTTTCTATGAGCGAGCAGGCAGAGTGAAATGTCTTGGAAACCCTGAGAGAG
AAGGGAGTGTCAGCATTGTAGGAGCAGTTTCTCCACCTGGTGGTGATTTTTCTGATCCAGTCACATCTGCTACTCTGGGT
ATTGTTCAGGTGTTCTGGGGCTTGGATAAGAAGCTAGCTCAGCGCAAGCACTTCCCGTCCGTCAACTGGCTCATTAGCTA
CAGCAAGTACATGCGCGCCCTGGACGAGTACTATGACAAACACTTCACAGAGTTCGTGCCTCTGAGGACCAAAGCTAAGG
AGATTCTGCAGGAAGAGGAGGATCTGGCGGAAATCGTGCAGCTCGTGGGAAAGGCGTCTTTAGCAGAGACAGATAAAATC
ACCCTGGAGGTAGCAAAACTTATCAAAGATGACTTCCTACAACAAAATGGGTACACTCCTTATGACAGGTTCTGTCCATT
CTATAAGACGGTGGGGATGCTGTCCAACATGATTTCATTCTATGATATGGCCCGCCGGGCTGTGGAGACCACCGCCCAGA
GTGACAATAAGATCACATGGTCCATTATCCGTGAGCACATGGGGGAGATTCTCTATAAACTTTCCTCCATGAAATTCAAG
GATCCAGTGAAGGATGGCGAGGCAAAGATCAAGGCCGACTACGCACAGCTTCTTGAAGATATGCAGAACGCATTCCGTAG
CCTGGAAGATTAGAACTGTGACTTCTCTCCTCCTCTTCCGCAGCTCATATGTGTATATTTTCCTGAATTTCTCATCTCCA
ACCCTTTGCTTCCATATTGTGCAGCTTTGAGACTAGTGCCTCGTGCGTTCTCGTTCATTTTGCTGTTTCTTTGGTAGGTC
TTATAAAACACACATTCCTGTGCTCCGCTGTCTGAAGGAGCTCCTGACCTTTGTCTGAAGTGGTGAATGTAGTGCATATG
ATACACAGTGTAACATACACATTGTAACATATACGTTCTGTAAACTTGTATGTAAGGTGACTACCCCTTCCCTCCTCTCC
AGTAAACTGTAAACAGGACTACTGCATGTGCTCTATTGGGGATGGAAGGCCAGATCTCCATACCGTGGACAGGTACATAA
GGAAACTAGACCACTTGCAACTTAGTGTTTGTTGAGTAACCATTTTGCAGGAAGTATTTCCATTTAAAAAACAAAAGATT
AATGTTCCAATTATTTGTAGCTTCCCCAGTATCAATCAGGACTGTTTGTGGCGCACTTGGGAACTATTTTGTTTTCCTAA
CAGACGTTTGCAAGGCTGAACGTAATAGATAAATCAGTTCCCTCTGAAAGTGTGAAAGTAAAAAGAGAGCTAGGTGGTCA
GACTTAAATTGACATCGTCTTGTTTAAGCATATTTTATTTCACTGAGAGATTTAATATCAAGGACTTTTATATACTCAAT
TACTAGGAAATCTTTTTTTAAGTACAATTTAAAAATCATTGAAAATGTGATCCACATCATAGCCATTTTCCTTATATTTA
GTCAGATGAGCTCAGAGTGGGGAGGGTGTGGGTTAGAATACCACAAGGACACGCAGCAGTGCCTGCAGGCAGTGTGGCCG
GGGGCCAGAGCGGCATTGTTTTCACGAGGTACGTGTGTGGCGTGTGTGTTTGCTTGTTGACACTCTGAAAACAGCAAGCT
TACCAGTTCCAGGAAATATTTTGTTTTCTTTCACTGGCTCAGAAAGCTCCTCAAAGTACCTGGTCCCTGAAGCTTCCTAT
CTGTTAATAGAGACGAGAGAGGTTCTTAAATTTAACTGGTGACAAAACAAAAAGAAAAAAAAGATCGATTTTTGTCTTGC
TGTTTTGGTGTGTTTAAATAATAATTCCATATTTGCATAACGAGGCTCGCTTCTGAGAGCTTGGAGATCGTGCTCCCTCT
TCACTCTCCGGGGTGATAATGCTGGCGCCATGCTACCTCTTCAGGAGGGGAAGGGGATTGAACATGGCTAACACTCTCAA
GTACACAAGCGTAACGACAAAGTATTTATTTTAAGCCTTGGTATGTTGTTTAAATTATTAGGTGGTGCATTTCTTATGGT
CTTTTGGGTAGACATAGTATACACTTCAGATGTAATGTGTAAATCCTTGCTAGTGCATGTCTACACGATAGACTGCTATT
CAAGAAGGATATTCTTCCACATAACAATTTAAAAACTATTAAATCAGATATGGATTATGCAATGACTTGTTGAGAGGTGG
ATTAACGGTGCTGCTTAATCAGTTTGCTTCCAATATGGCTTCGTATCCAGAAGCCCTGACTAGTGGAGATGAGAAAGATT
TCAAAACCTGTCTGCCTACACCTACCAGCAACCTAGGCTTGTGATCAGAATGAATGATCCCAAGAAACTACTTGACCAAG
TGTGTTTTGTTGTCCTGGATTTGAGATGTGCGTTCTTCCTCCCTCTGAGACTGTTGATGTATGAGTGTGAAGAAGTTACA
GAAACAACGCTCAGATTTTCACGGTAACTTTCCCTCTGCCCACACTGTAGAGTTTCAGATTGTTCACTGATAGTGCTTCT
TTCGTAAGGATGTGTTAAAATATAGCAGTCTTTTTAAAAGATTATGCAGTTCTCTATTTATTGTGCTGTGCCTGGTCCTA
AGTGCAGCCGGTTAAACAAGTTTCATATGTATTTTTCCAGTGTTAAATCTCATACCTATGCCCTTTGGAAAGCTCCATCC
TGAACAATGAATAGAAGAGGCTATATAAATTGCCTCCTTATCCTTAAGATTTCACTATCTTTATGTTAAGAGTAATGTAT
AATTATTAAAATCTATGAAAAATAAAAAGTGGATTTAAATTAAGAGATC

Fig. 29

Rat 29x protein

ARLPAPEHARQQPLLSGPEPGSSARVPVPGVASRRQPRGGKPPSGDGLESGPSPRPLLHARGEAGLHRQSGRVPHTGTAY
FADEPTEAQAPGGFCVSPSLLGVRWPACATRTPGSLPLSPPSAQPRTLWPTPPAGPSSRMVARNQVAADNAISPASEPRR
RPEPSSSSSSSSPAAPARPRPCPVVPAPAPGDTHFRTFRSHSDYRRITRTSALLDACGFYWGPLSVHGAHERLRAEPVGT
FLVRDSRQRNCFFALSVKMASGPTSIRVHFQAGRFHLDGSRETFDCLFELLEHYVAAPRRMLGAPLRQRRVRPLQELCRQ
RIVAAVGRENLARIPLNPVLRDYLSSFPFQI

Rat 29x DNA (coding: 433-1071)

GCACGGCTCCCGGCCCCGGAGCATGCGCGACAGCAGCCCCTCCTCtCCGGCCCTGAGCCCGGATCGTCCGCCCGGGTTCC
AGTTCCCGGCGTGGCCAGTAGGCGGCAGCCGCGAGGCGGCAAGCCACCCAGCGGGGACGGCCTGGAGTCGGGCCCCTCTC
CACGCCCCCTTCTCCACGCGCGCGGGGAGGCAGGGCTCCACCGCCAGTCTGGAAGGGTTCCACATACAGGAACGGCCTAC
TTCGCAGATGAGCCCACCGAGGCTCAGGCTCCGGGCGGATTCTGCGTGTCACCCTCGCTCCTTGGGGTCCGCTGGCCGGC
CTGTGCCACCCGGACGCCCGGCTCACTGCCTCTGTCTCCCCCATCAGCGCAGCCCCGGACGCTATGGCCCACCCCTCCAG
CTGGCCCCTCGAGTAGGATGGTAGCACGTAACCAGGTGGCAGCCGACAATGCGATCTCCCCGGCATCAGAGCCCCGACGG
CGGCCAGAGCCATCCTCGTCCTCGTCTTCGTCCTCGCCGGCGGCCCCGGCGCGTCCCCGGCCCTGCCCGGTGGTCCCGGC
CCCGGCTCCGGGCGACACTCACTTCCGCACCTTCCGCTCCCACTCTGATTACCGGCGCATCACGCGGACCAGCGCTCTCC
TGGACGCCTGCGGCTTCTACTGGGGACCCCTGAGCGTGCATGGGGCGCACGAACGGCTGCGTGCCGAGCCCGTGGGCACC
TTCTTGGTGCGCGACAGTCGCCAGCGGAACTGCTTCTTCGCGCTCAGCGTGAAGATGGCTTCGGGCCCCACGAGCATTCG
TGTGCACTTCCAGGCCGGCCGCTTCCACCTGGACGGCAGCCGCGAGACCTTCGACTGCCTCTTCGAGCTGCTGGAGCACT
ACGTGGCGGCGCCGCGCCGCATGTTGGGGGCCCCACTGCGCCAGCGCCGCGTGCGGCCGCTGCAGGAGCTGTGTCGCCAG
CGCATCGTGGCCGCCGTGGGTCGCGAGAACCTGGCACGCATCCCTCTTAACCCGGTACTCCGTGACTACCTGAGTTCCTT
CCCCTTCCAGATCTGACCGGCTGCCGCCGTGCCCGCAGCATTAAGTGGAGCGCCTTATTATTTCTTATTATTAATTATT
ATTATTTTTcTGGAACCACGTGGGAGCCCTCCCCGCCTAGGTCGGAGGGAGTGGGTGTGGAGGGTGAGATGCCTCCCACT
TCTGGCTGGAGACCTTATCCCGCCTCTCGGGGGGCCTCCCCTCCTGGTGCTCCCTCCCGGTCCCCCTGGTTGTAGCAGCT
TGTGTCTGGGGCCAGGACCTGAACTCCACGCCTACCTCTCCATGTTTACATGTTCCCAGTATCTTTGCACAAACCAGGGG
TGGGGGAGGGTCTCTGGCTTCATTTTTCTGCTGTGCAGAATATTCTATTTTATATTTTTACATCCAGTTTAGATAATAAA
CTTTATTATGAAAGTTTTTTTTTTAAAGAAAAAAAAAAAAAAAAAAAA

Fig. 30

Rat 25r DNA (coding 130-768)

GGCACGGCTCCCGGCCCCGGAGCATGCGCGACAGCAGCCCCGGAACCCCCAGCCGCGGCGCCCCGCGTCCCGCCGCCAGC
GCAGCCCCGGACGCTATGGCCCACCCCTCCAGCTGGCCCCTCGAGTAGGATGGTAGCACGTAACCAGGTGGCAGCCGACA
ATGCGATCTCCCCGGCATCAGAGCCCCGACGGCGGCCAGAGCCATCCTCGTCCTCGTCTTCGTCCTCGCCGGCGGCCCCG
GCGCGTCCCCGGCCCTGCCCGGTGGTCCCGGCCCCGGCTCCGGGCGACACTCACTTCCGCACCTTCCGCTCCCACTCTGA
TTACCGGCGCATCACGCGGACCAGCGCTCTCCTGGACGCCTGCGGCTTCTACTGGGGACCCCTGAGCGTGCATGGGGCGC
ACGAACGGCTGCGTGCCGAGCCCGTGGGCACCTTCTTGGTGCGCGACAGTCGCCAGCGGAACTGCTTCTTCGCGCTCAGC
GTGAAGATGGCTTCGGGCCCCACGAGCATTCGTGTGCACTTCCAGGCCGGCCGCTTCCACCTGGACGGCAGCCGCGAGAC
CTTCGACTGCCTCTTCGAGCTGCTGGAGCACTACGTGGCGGCGCCGCGCCGCATGTTGGGGGCCCCACTGCGCCAGCGCC
GCGTGCGGCCGCTGCAGGAGCTGTGTCGCCAGCGCATCGTGGCCGCCGTGGGTCGCGAGAACCTGGCACGCATCCCTCTT
AACCCGGTACTCCGTGACTACCTGAGTTCCTTCCCCTTCCAGATCTGACCGGCTGCCGCCGTGCCCGCAGCATTAAGTGG
GAGCGCCTTATTATTTCTTATTATTAATTATTATTATTTTTCTGGAACCACGTGGGAGCCCTCCCCGCCTAGGTCGGAGG
GAGTGGGTGTGGAGGGTGAGATGCCTCCCACTTCTGGCTGGAGACCTTATCCCGCCTCTCGGGGGGCCTCCCCTCCTGGT
GCTCCCTCCCGGTCCCCCTGGTTGTAGCAGCTTGTGTCTGGGGCCAGGACCTGAACTCCACGCCTACCTCTCCATGTTTA
CATGTTCCCAGTATCTTTGCACAAACCAGGGGTGGGGAGGGTCTCTGGCTTCATTTTTCTGCTGTGCAGAATATTCTAT
TTTATATTTTTACATCCAGTTTAGATAATAAACTTTATTATGAAAGTTTTTTTTTTAAAAAAAAAAAAAAAAA

Fig. 31

Rat 5p protein

MPSQMEHAMETMMLTFHRFAGEKNYLTKEDLRVLMEREFPGFLENQKDPLAVDKIMKDLDQCRDGKVGFQSFLSLVAGLI
IACNDYFVVHMKQKK

Rat 5p DNA (coding: 52-339)

CTTCCAAAGACTGCAGCGCCTCAGGGCCCAGGTTTCAACAGATTCTTCAAAATGCCATCCCAAATGGAGCATGCCATGGA
AACCATGATGCTTACATTTCACAGGTTTGCAGGGGAAAAAAACTACTTGACAAAGGAGGACCTGAGAGTGCTCATGGAAA
GGGAGTTCCCTGGGTTTTTGGAAAATCAAAAGGACCCTCTGGCTGTGGACAAAATAATGAAAGACCTGGACCAGTGCCGA
GATGGAAAAGTGGGCTTCCAGAGCTTTCTATCACTAGTGGCGGGGCTCATCATTGCATGCAATGACTATTTTGTAGTACA
CATGAAGCAGAAGAAGTAGGCCAACTGGAGCCCTGGTACCCACACCTTGATGCGTCCTCTCCCATGGGGTCAACTGAGGA
ATCTGCCCCACTGCTTCCTGTGAGCAGATCAGGACCCTTAGGAAATGTGCAAATAACATCCAACTCCAATTCGACAAGCA
GAGAAAGAAAAGTTAATCCAATGACAGAGGAGCTTTCGAGTTTTATATTGTTTGCATCCGGTTGCCCTCAATAAAGAAAG
TCTTTTTTTTTAAGTTCCGAAAAAAAAAAAAAAAAAAAAA

Fig. 32

Rat 7q protein

MAYAYLFKYIIIGDTGVGKSCLLLQFTDKRFQPVHDLTIGVEFGARMITIDGKQIKLQIWDTAGQESFRSITRSYYRGAA
GALLVYDITRRDTFNHLTTWLEDARQHSNSNMVIMLIGNKSDLESRREVKKEEGEAFAREHGLIFMETSAKTASNVEEAF
INTAKEIYEKIQEGVFDINNEANGIKIGPQHAATNASHGGNQGGQQAGGGCC

Rat 7q DNA (coding: 1-639)

ATGGCGTACGCCTATCTCTTCAAGTACATCATCATCGGCGACACAGGTGTTGGTAAATCGTGCTTATTGCTACAGTTTAC
AGACAAGAGGTTTCAGCCGGTGCATGACCTCACAATTGGTGTAGAGTTTGGTGCTCGAATGATAACCATTGATGGGAAAC
AGATAAAACTCCAGATCTGGGATACAGCAGGGCAGGAGTCCTTTCGTTCTATCACAAGGTCATATTACAGAGGTGCAGCG
GGGGCTTTACTAGTGTATGATATTACAAGGAGAGACACGTTCAACCACTTGACAACCTGGTTAGAAGACGCCCGTCAGCA
TTCCAATTCCAACATGGTCATCATGCTTATTGGAAATAAAAGTGACTTAGAATCTAGGAGAGAAGTGAAAAAGGAAGAAG
GTGAAGCTTTTGCACGAGAGCATGGACTTATCTTCATGGAAACTTCTGCCAAGACTGCTTCTAATGTAGAGGAGGCATTT
ATTAACACAGCAAAAGAAATTTATGAAAAAATCCAAGAAGGGGTCTTTGACATTAATAATGAGGCAAACGGCATCAAAAT
TGGCCCTCAGCATGCTGCTACCAATGCATCTCACGGAGGCAACCAAGGAGGGCAGCAGGCAGGGGGAGGCTGCTGCTGA

Fig. 33

Rat 19r protein

MVLLKEYRVILPVSVDEYQVGQLYSVAEASKNETGGGEGVEVLVNEPYEKDDGEKGQYTHKIYHLQSKVPTFVRMLAPEG
ALNIHEKAWNAYPYCRTVITNEYMKEDFLIKIETWHKPDLGTQENVHKLEPEAWKHVEAIYIDIADRSQVLSKDYKAEED
PAKFKSIKTGRGPLGPNWKQELVNQKDCPYMCAYKLVTVKFKWWGLQNKVENFIHKQEKRLFTNFHRQLFCWLDKWVDLT
MDDIRRMEEETKRQKDEMRQKDPVKGMTADD

Rat 19r DNA (coding: 1-816)

ATGGTGCTGCTCAAGGAATATCGGGTCATCCTGCCTGTGTCTGTAGATGAGTATCAAGTGGGGCAGCTGTACTCTGTGGC
TGAAGCCAGTAAAAATGAAACTGGTGGTGGGGAAGGTGTGGAGGTCCTGGTGAACGAGCCCTACGAGAAGGATGATGGCG
AGAAAGGCCAGTACACACACAAGATCTACCACTTACAGAGCAAAGTTCCCACGTTTGTTCGAATGCTGGCCCCAGAAGGC
GCCCTGAATATACATGAGAAAGCCTGGAATGCCTACCCTTACTGCAGAACCGTTATTACAAATGAGTACATGAAGGAAGA
CTTTCTCATTAAAATTGAAACCTGGCACAAGCCAGACCTTGGCACCCAGGAGAATGTGCATAAACTGGAGCCTGAGGCAT
GGAAACATGTGGAAGCTATATATATAGACATCGCTGATCGAAGCCAAGTACTTAGCAAGGATTACAAGGCAGAGGAAGAC
CCAGCAAAATTTAAATCTATCAAAACAGGACGAGGACCATTGGGCCCGAATTGGAAGCAAGAACTTGTCAATCAGAAGGA
CTGCCCATATATGTGTGCATACAAACTGGTTACTGTCAAGTTCAAGTGGTGGGGCTTGCAGAACAAAGTGGAAAACTTTA
TACATAAGCAAGAGAAGCGTCTGTTTACAAACTTTCACAGGCAGCTGTTCTGTTGGCTTGATAAATGGGTTGATCTGACT
ATGGATGACATTCGGAGGATGGAAGAAGAGACGAAGAGACAGCTGGATGAGATGAGACAAAAGGACCCCGTGAAAGGAAT
GACAGCAGATGACTAG

Fig. 34

Monkey KChIP4c (jlkxa053c02) DNA sequence (CD: 122-811)

CGCTCTCCTCCTCCCCTTTCTCTAGCAGTAGCCTTCTTAATGTAGTTTAATGGCTTTACAAAGAAAGCCAGGCAGAGGAG
CACTTCTCAGTGGCTGTGGTCGGACCATGACCTAGCTGACCATGAACTTGGAAGGGCTTGAAATGATAGCAGTTCTGATC
GTCATTGTGCTTTTTGTTAAATTATTGGAACAGTTTGGGCTGATTGAAGCAGGTTTAGAAGACAGCGTGGAAGATGAACT
GGAGATGGCCACTGTCAGGCATCGGCCTGAGGCCCTTGAGCTTCTGGAAGCCCAGAGCAAATTTACCAAGAAAGAGCTTC
AGATCCTTTACAGAGGATTTAAGAACGAATGCCCCAGTGGTGTTGTTAATGAAGAAACCTTCAAAGAGATTTACTCGCAG
TTCTTTCCACAGGGAGACTCTACAACATATGCACATTTTCTGTTCAATGCGTTTGATACGGACCACAATGGAGCTGTGAG
TTTCGAGGATTTCATCAAAGGTCTTTCCATTTTGCTCCGGGGGACAGTACAAGAAAAACTCAATTGGGCATTTAATCTGT
ATGATATAAATAAAGATGGCTACATCACTAAAGAGGAAATGCTTGATATAATGAAAGCAATATACGACATGATGGGTAAA
TGTACATATCCTGTCCTCAAAGAAGATGCACCCAGACAACACGTCGAAACATTTTTTCAGAAAATGGACAAAAATAAAGA
TGGGGTTGTTACCATAGATGAGTTCATTGAAAGCTGCCAAAAAGATGAAAACATAATGCGCTCCATGCAGCTCTTTGAAA
ATGTGATTTAACTTGTCAACTAGATCCTGAATCCAACAGACAAATGTGAACTATTCTACCACCCTTAAAGTCGGAGCTAC
CACTTTTAGCATAGATTGCTCAGCTTGACACTGAAGCATATTATGCAAACAAGCTTTGTTTTAATATAAAGCAATCCCCA
AAAGATTTGAGTTTCTCAGTTATAAATTTGCATCCTTTCCATAATGCCACTGAGTTCATGGGATGTTCTAACTCATTTCA
TACTCTGTGAATATTCAAAAGTAATAGAATCTGGCATATAGTTTTATTGATTCCTTAGCCATGGGATTATTGAGGCTTTC
ACATATCAGTGATTTTAAAATACCAGTGTTTTTTGCTACTCATTTGTATGTATTCAGTCCTAGGATTTTGAATGGTTTTC
TAATATACTGACATCTGCATTTAATTTCCAGAAATTAAATTAATTTTCATGTCTGAATGCTGTAATTCCATTTATATACT
TTAAGTAAACAAATAAGATTACTACAATTAAACACATAGTTCCAGTTTCTATGGCCTTCACTTCCCACCTTCTATTAGAA
ATTAATTTTATCTGGTATTTTTAAACATTTAAAAATTTATCATCAGATATCAGCATATGCCTAATTATGCCTAATGAAAC
TTAATAAGCATTTAATTTTCCATCATACATTATAGTCAAGGCCTATATACTATATATAATTTTGGATTTGTTTAATCTTA
CAGGCTGTTTTCCATTGTATCATCAAGTGGAAGTTCAAGACGGCATCAAACAAAACAAGGATGTTTACAGACATATGCAA
AGGGTCAGGATATCTATCCTCCAGTATATGTTAATGCTTAATAACAAGTAATCCTAACAGCATTAAAGGCCAAATCTGTC
CTCTTTCCCCTGACTTCCTTACAGCATGTTTATATTACAAGCCATTCAGGGACAAAGAAACCTTGACTACCCCACTGTCT
ACTAGGAACAAACAAACAGCAAGCAAAATTCACTTTGAAAGCACCAGTGGTTCCATTACATTGACAACTACTACCAAGAT
TCAGTAGAAAATAAGTGCTCAACAACTAATCCAGATTACAATATGATTTAGTGCATCATAAAATTCCAACAATTCAGATT
ATTTTTAATCACCTCAGCCACAACTGTAAAGTTGCCACATTACTAAAGACACACACATCGTCCCTGTTTTGTAGAAATAT
CACAAAGACCAAGAGGCTACAGAAGGAGGAAATTTGCAACTGTCTTTGCAACAATAAATCAGGTATCTATTCTGGTGTAG
AGATAGGATGTTGAAAGCTGCCCTGCTATCACCAGTGTAGAAATTAAGAGTAGTACAATACATGTACACTGAAATTTGCC
ATCGCGTGTTTGTGTAAACTCAATGTGCACATTTTGTATTTCAAAAAGAAAAAATAAAAGCAAAATAAAATGTTTATAAC
TCTAAAAAAAAAAAAAAAAAAAA

Monkey KChIP4c protein sequence

MNLEGLEMIAVLIVIVLFVKLLEQFGLIEAGLEDSVEDELEMAYVRHRPEALELLEAQSKFTKKELQILYRGFKNECPSG
VVNEETFKEIYSQFFPQGDSTTYAHFLFNAFDTDHNGAVSFEDFIKGLSILLRGTVQEKLNWAFNLYDINKDGYITKEEM
LDIMKAIYDMMGKCTYPVLKEDAPRQHVETFFQKMDKNKDGVVTIDEFIESCQKDENIMRSMQLFENVI.

Fig. 35

Monkey KChIP4d (jlkx015b10) DNA sequence (CD: 64-816)

GTCGACAGACGCCCCTGGCCGGTGGACTCCTGAGTCTTACTCCTGCACCCTGCGTCCCCAGACATGAATGTGAGGAGAGT
GGAAAGCATTTCGGCTCAGCTGGAGGAGGCCAGCTCCACAGGCGGTTTCCTGTATGCTCAGAACAGCACCAAGCGCAGCA
TTAAAGAGCGGCTCATGAAGCTCTTGCCCTGCTCAGCTGCCAAAACATCGTCTCCTGCTATTCAAAACAGCGTGGAAGAT
GAACTGGAGATGGCCACTGTCAGGCATCGGCCTGAGGCCCTTGAGCTTCTGGAAGCCCAGAGCAAATTTACCAAGAAAGA
GCTTCAGATCCTTTACAGAGGATTTAAGAACGAATGCCCCAGTGGTGTTGTTAATGAAGAAACCTTCAAAGAGATTTACT
CGCAGTTCTTTCCACAGGGAGACTCTACAACATATGCACATTTTCTGTTCAATGCGTTTGATACGGACCACAATGGAGCT
GTGAGTTTCGAGGATTTCATCAAAGGTCTTTCCATTTTGCTCCGGGGGACAGTACAAGAAAAACTCAATTGGGCATTTAA
TCTGTATGATATAAATAAAGATGGCTACATCACTAAAGAGGAAATGCTTGATATAATGAAAGCAATATACGACATGATGG
GTAAATGTACATATCCTGTCCTCAAAGAAGATGCACCCAGACAACACGTCGAAACATTTTTTCAGAAAATGGACAAAAAT
AAAGATGGGGTTGTTACCATAGATGAGTTCATTGAAAGCTGCCAAAAAGATGAAAACATAATGCGCTCCATGCAGCTCTT
TGAAAATGTGATTTAACTTGTCAACTAGATCCTGAATCCAACAGACAAATGTGAACTATTCTACCACCCTTAAAGTCGGA
GCTACCACTTTTAGCATAGATTGCTCAGCTTGACACTGAAGCATATTATGCAAACAAGCTTTGTTTTAATATAAAGCAAT
CCCCAAAAGATTTGAGTTTCTCAGTTATAAATTTGCATCCTTTCCATAATGCCACTGAGTTCATGGGATGTTCTGACTCA
TTTCATACTCTGTGAATATTCAAAAGTAATAGAATCTGGCATATAGTTTTATTGATTCCTTAGCCATGGGATTATTGAGG
CTTTCACATATCAGTGATTTTAAAATACCAGTGTTTTTTGCTACTCATTTGTATGTATTCAGTCCTAGGATTTTGAATGG
TTTTCTAATATACTGACATCTGCATTTAATTTCCAGAAATTAAATTAATTTTCATGTCTGAATGCTGTAATTCCATTTAT
ATACTTTAAGTAAACAAATAAGATTACTACAATTAAACACATAGTTCCAGTTTCTATGGCCTTCACTTCCCACCTTCTAT
TAGAAATTAATTTTATCTGGTATTTTTAAACATTTAAAAATTTATCATCAGATATCAGCATATGCCTAATTATGCCTAAT
GAAACTTAATAAGCATTTAATTTTCCATCATACATTATAGTCAAGGCCTATATACTATATATAATTTTGGATTTGTTTAA
TCTTACAGGCTGTTTTCCATTGTATCATCAAGTGGAAGTTCAAGACGGCATCAAACAAAACAAGGATGTTTACAGACATA
TGCAAAGGGTCAGGATATCTATCCTCCAGTATATGTTAATGCTTAATAACAAGTAATCCTAACAGCATTAAAGGCCAAAT
CTGTCCTCTTTCCCCTGACTTCCTTACAGCATGTTTATATTACAAGCCATTCAGGGACAAAGAAACCTTGACTACCCCAC
TGTCTACTAGGAACAAACAAACAGCAAGCAAAATTCACTTTGAAAGCACCAGTGGTTCCATTACATTGACAACTACTACC
AAGATTCAGTAGAAAATAAGTGCTCAACAACTAATCCAGATTACAATATGATTTAGTGCATCATAAAATTCCAACAATTC
AGATTATTTTTAATCACCTCAGCCACAACTGTAAAGTTGCCACATTACTAAAGACACACACATCGTCCCTGTTTTGTAGA
AATATCACAAAGACCAAGAGGCTACAGAAGGAGGAAATTTGCAACTGTCTTTGCAACAATAAATCAGGTATCTATTCTGG
TGTAGAGATAGGATGTTGAAAGCTGCCCTGCTATCACCAGTGTAGAAATTAAGAGTAGTACAATACATGTACACTGAAAT
TTGCCATCGCGTGTTTGTGTAAACTCAATGTGCACATTTTGTATTTCAAAAAGAAAAAATAAAAGCAAAATAAAATGTTA
AAAAAAAAAAAAAAAAAAA

Monkey KChIP4d protein sequence

MNVRRVESISAQLEEASSTGGFLYAQNSTKRSIKERLMKLLPCSAAKTSSPAIQNSVEDELEMATVRHRPEALELLEAQS
KFTKKELQILYRGFKNECPSGVVNEETFKEIYSQFFPQGDSTTYAHFLFNAFDTDHNGAVSFEDFIKGLSILLRGTVQEK
LNWAFNLYDINKDGYITKEEMLDIMKAIYDMMGKCTYPVLKEDAPRQHVETFFQKMDKNKDGVVTIDEFIESCQKDENIM
RSMQLFENVI.

Fig. 36

ALIGNMENT OF MONKEY KChIP4

```
                       10                  20                  30                          40
  1 M. . . . . . . . . . .LTLEWESEGLQTVGIVVIICASLKLLHLLG. . . . .LIDFS.EDSVEDE   KChIP4N1
  1 M. . . . . . . . . . .LTLEWESEGLQTVGIVVIICASLKLLHLLG. . . . .LIDFS.EDSVEDE   KChIP4C
  1 M. . . . . . . . . . . . . . . .NLEGLEMIAVLIVIVLFVKLLEFFG. . . . .LIEAGLEDSVEDE   KChIP4N2
  1 MNVRRVESISANLEEASSTGGFLYAQNSTKRSIKERLMKLLPCSAAKTSSPAIQNSVEDE   KChIP4N3

        50        60        70        80        90        100
 44 LEMATVRHRPEALELLEAQSKFTKKELQILYRGFKNECPSGVVNEETFKKIYSQFFPQGD   KChIP4N1
 44 LEMATVRHRPEALELLEAQSKFTKKELQILYRGFKNECPSGVVNEETFKKIYSQFFPQGD   KChIP4C
 40 LEMATVRHRPEALELLEAQSKFTKKELQILYRGFKNECPSGVVNEETFKKIYSQFFPQGD   KChIP4N2
 61 LEMATVRHRPEALELLEAQSKFTKKELQILYRGFKNECPSGVVNEETFKKIYSQFFPQGD   KChIP4N3

        110       120       130       140       150       160
104 STTYAHFLFHAFDTDHNGAVSFEDFIKGLSILLRGTVQEKLNWAFNLYDINKDGYITKEE   KChIP4N1
104 STTYAHFLFHAFDTDHNGAVSFEDFIKGLSILLRGTVQEKLNWAFNLYDINKDGYITKEE   KChIP4C
101 STTYAHFLFHAFDTDHNGAVSFEDFIKGLSILLRGTVQEKLNWAFNLYDINKDGYITKEE   KChIP4N2
121 STTYAHFLFHAFDTDHNGAVSFEDFIKGLSILLRGTVQEKLNWAFNLYDINKDGYITKEE   KChIP4N3

        170       180       190       200             210
164 MLDIMKAIYDMNGKCTYPVLKEDAPRQNVETFFQKMD. . . . . .KNKDGVVTIDEFIESCQ   KChIP4N1
164 MLDIMKAIYDMNGKCTYPVLKEDAPRQNVETFFQAVFHCIIKWKFKTASNKTRMFTDIC.   KChIP4C
160 MLDIMKAIYDMNGKCTYPVLKEDAPRQNVETFFQKMD. . . . . .KNKDGVVTIDEFIESCQ   KChIP4N2
181 MLDIMKAIYDMNGKCTYPVLKEDAPRQNVETFFQKMD. . . . . .KNKDGVVTIDEFIESCQ   KChIP4N3

      220       230
218 KDENIMRSMQLFENVI.   KChIP4N1
223 KGSGYLSS. . . . .SIC.   KChIP4C
214 KDENIMRSMQLFENVI.   KChIP4N2
235 KDENIMRSMQLFENVI.   KChIP4N3
```

Fig. 37

| CURRENT PARAMETER | CHO | |
|---|---|---|
| | rKv4.2 | rKv4.2 +KChIP2 |
| PEAK-CURRENT (nA/cell, at 50 mV) | 0.51 ±0.098 | 3.3 ±0.45 |
| PEAK-CURRENT DENSITY (pA/pF, at 50 mV) | 18.6 ±2.8 | 196.6 ±26.6 |
| INACTIVATION TIME CONSTANT (ms, at 50 mV) | 28.47 ±3.5 | 195.14 ±8.3 |
| RECOVERY FROM INACTIVATION TIME CONSTANT (ms, at -80 mV) | 257.9 | 49.5 |
| ACTIVATION $V_{1/2}$ (mV) | 20.5 | -2.2 |
| STEADY-STATE INACTIVATION $V_{1/2}$ (mV) | -47.1 | -45.7 |

| CURRENT PARAMETER | CHO | |
|---|---|---|
| | rKv4.2 +RBG4 | rKv4.2 KChIP3 |
| PEAK-CURRENT (nA/cell, at 50 mV) | 0.46 ±0.084 | 3.5 ±0.99 |
| PEAK-CURRENT DENSITY (pA/pF, at 50 mV) | 29.7 ±11.2 | 161.7 ±21.8 |
| INACTIVATION TIME CONSTANT (ms, at 50 mV) | 29.5 ±9.5 | 67.2 ±14.1 |
| RECOVERY FROM INACTIVATION TIME CONSTANT (ms, at -80 mV) | 435.9 | 130.8 |
| ACTIVATION $V_{1/2}$ (mV) | 4.1 | 6.1 |

SEQUENCE LISTING

```
<160> NUMBER OF SEQ ID NOS: 72

<210> SEQ ID NO 1
<211> LENGTH: 1463
<212> TYPE: DNA
<213> ORGANISM: Homo sapiens
<220> FEATURE:
<221> NAME/KEY: CDS
<222> LOCATION: (225)..(872)

<400> SEQUENCE: 1

gaatagcccc ctttcacttc tgagtccctg catgtgcggg gctgaagaag gaagccagaa     60

gcctcctagc ctcgcctcca cgtttgctga ataccaagct gcaggcgagc tgccgggcgc    120

ttttctctcc tccaattcag agtagacaaa ccacggggat ttctttccag ggtaggggag    180
```

-continued

```
gggccgggcc cggggtccca actcgcactc aagtcttcgc tgcc atg ggg gcc gtc      236
                                                 Met Gly Ala Val
                                                   1

atg ggc acc ttc tca tct ctg caa acc aaa caa agg cga ccc tcg aaa      284
Met Gly Thr Phe Ser Ser Leu Gln Thr Lys Gln Arg Arg Pro Ser Lys
  5                  10                  15                  20

gat aag att gaa gat gag ctg gag atg acc atg gtt tgc cat cgg ccc      332
Asp Lys Ile Glu Asp Glu Leu Glu Met Thr Met Val Cys His Arg Pro
                 25                  30                  35

gag gga ctg gag cag ctc gag gcc cag acc aac ttc acc aag agg gag      380
Glu Gly Leu Glu Gln Leu Glu Ala Gln Thr Asn Phe Thr Lys Arg Glu
             40                  45                  50

ctg cag gtc ctt tat cga ggc ttc aaa aat gag tgc ccc agt ggt gtg      428
Leu Gln Val Leu Tyr Arg Gly Phe Lys Asn Glu Cys Pro Ser Gly Val
         55                  60                  65

gtc aac gaa gac aca ttc aag cag atc tat gct cag ttt ttc cct cat      476
Val Asn Glu Asp Thr Phe Lys Gln Ile Tyr Ala Gln Phe Phe Pro His
     70                  75                  80

gga gat gcc agc acg tat gcc cat tac ctc ttc aat gcc ttc gac acc      524
Gly Asp Ala Ser Thr Tyr Ala His Tyr Leu Phe Asn Ala Phe Asp Thr
 85                  90                  95                 100

act cag aca ggc tcc gtg aag ttc gag gac ttt gta acc gct ctg tcg      572
Thr Gln Thr Gly Ser Val Lys Phe Glu Asp Phe Val Thr Ala Leu Ser
                105                 110                 115

att tta ttg aga gga act gtc cac gag aaa cta agg tgg aca ttt aat      620
Ile Leu Leu Arg Gly Thr Val His Glu Lys Leu Arg Trp Thr Phe Asn
            120                 125                 130

ttg tat gac atc aac aag gac gga tac ata aac aaa gag gag atg atg      668
Leu Tyr Asp Ile Asn Lys Asp Gly Tyr Ile Asn Lys Glu Glu Met Met
        135                 140                 145

gac att gtc aaa gcc atc tat gac atg atg ggg aaa tac aca tat cct      716
Asp Ile Val Lys Ala Ile Tyr Asp Met Met Gly Lys Tyr Thr Tyr Pro
    150                 155                 160

gtg ctc aaa gag gac act cca agg cag cat gtg gac gtc ttc ttc cag      764
Val Leu Lys Glu Asp Thr Pro Arg Gln His Val Asp Val Phe Phe Gln
165                 170                 175                 180

aaa atg gac aaa aat aaa gat ggc atc gta act tta gat gaa ttt ctt      812
Lys Met Asp Lys Asn Lys Asp Gly Ile Val Thr Leu Asp Glu Phe Leu
                185                 190                 195

gaa tca tgt cag gag gac gac aac atc atg agg tct ctc cag ctg ttt      860
Glu Ser Cys Gln Glu Asp Asp Asn Ile Met Arg Ser Leu Gln Leu Phe
            200                 205                 210

caa aat gtc atg taactggtga cactcagcca ttcagctctc agagacattg          912
Gln Asn Val Met
        215

tactaaacaa ccaccttaac accctgatct gcccttgttc tgattttaca caccaactct     972

tgggacagaa acacctttta cactttggaa gaattctctg ctgaagactt tcttatggaa    1032

cccagcatca tgtggctcag tctctgattg ccaactcttc ctctttcttc ttcttgagag    1092

agacaagatg aaatttgagt ttgttttgga agcatgctca tctcctcaca ctgctgccct    1152

atggaaggtc cctctgctta agcttaaaca gtagtgcaca aaatatgctg cttacgtgcc    1212

cccagcccac tgcctccaag tcaggcagac cttggtgaat ctggaagcaa gaggacctga    1272

gccagatgca caccatctct gatggcctcc caaaccaatg tgcctgtttc tcttcctttg    1332

gtgggaagaa tgagagttat ccagaacaat taggatctgt catgaccaga ttgggagagc    1392

cagcacctaa catatgtggg ataggactga attattaagc atgacattgt ctgatgaccc    1452

aaactgcccc g                                                         1463
```

-continued

<210> SEQ ID NO 2
<211> LENGTH: 216
<212> TYPE: PRT
<213> ORGANISM: Homo sapiens

<400> SEQUENCE: 2

```
Met Gly Ala Val Met Gly Thr Phe Ser Ser Leu Gln Thr Lys Gln Arg
  1               5                  10                  15

Arg Pro Ser Lys Asp Lys Ile Glu Asp Glu Leu Glu Met Thr Met Val
             20                  25                  30

Cys His Arg Pro Glu Gly Leu Glu Gln Leu Glu Ala Gln Thr Asn Phe
         35                  40                  45

Thr Lys Arg Glu Leu Gln Val Leu Tyr Arg Gly Phe Lys Asn Glu Cys
     50                  55                  60

Pro Ser Gly Val Val Asn Glu Asp Thr Phe Lys Gln Ile Tyr Ala Gln
 65                  70                  75                  80

Phe Phe Pro His Gly Asp Ala Ser Thr Tyr Ala His Tyr Leu Phe Asn
                 85                  90                  95

Ala Phe Asp Thr Thr Gln Thr Gly Ser Val Lys Phe Glu Asp Phe Val
            100                 105                 110

Thr Ala Leu Ser Ile Leu Leu Arg Gly Thr Val His Glu Lys Leu Arg
        115                 120                 125

Trp Thr Phe Asn Leu Tyr Asp Ile Asn Lys Asp Gly Tyr Ile Asn Lys
    130                 135                 140

Glu Glu Met Met Asp Ile Val Lys Ala Ile Tyr Asp Met Met Gly Lys
145                 150                 155                 160

Tyr Thr Tyr Pro Val Leu Lys Glu Asp Thr Pro Arg Gln His Val Asp
                165                 170                 175

Val Phe Phe Gln Lys Met Asp Lys Asn Lys Asp Gly Ile Val Thr Leu
            180                 185                 190

Asp Glu Phe Leu Glu Ser Cys Gln Glu Asp Asp Asn Ile Met Arg Ser
        195                 200                 205

Leu Gln Leu Phe Gln Asn Val Met
    210                 215
```

<210> SEQ ID NO 3
<211> LENGTH: 1856
<212> TYPE: DNA
<213> ORGANISM: Rattus sp.
<220> FEATURE:
<221> NAME/KEY: CDS
<222> LOCATION: (300)..(1034)

<400> SEQUENCE: 3

```
ggcacacaac ccctggattc ttcggagaat atgccgtgag gtgttgccaa ttattagttc     60

tcttggctag cagatgttta gggactggtt aagcctttgg agaaattacc ttaggaaaac    120

ggggaaataa aagcaaagat taccatgaat tgcaagatta cctagcaatt gcaaggtagg    180

aggagagagg tggagggcgg agtagacagg agggagggag aaagtgagag gaagctaggc    240

tggtggaaat aaccctgcac ttggaacagc ggcaaagaag cgcgattttc cagctttaa     299

atg cct gcc cgc gtt ctg ctt gcc tac ccg gga acg gag atg ttg acc      347
Met Pro Ala Arg Val Leu Leu Ala Tyr Pro Gly Thr Glu Met Leu Thr
  1               5                  10                  15

cag ggc gag tct gaa ggg ctc cag acc ttg ggg ata gta gtg gtc ctg      395
Gln Gly Glu Ser Glu Gly Leu Gln Thr Leu Gly Ile Val Val Val Leu
             20                  25                  30
```

-continued

```
tgt tcc tct ctg aaa cta ctg cac tac ctc ggg ctg att gac ttg tcg      443
Cys Ser Ser Leu Lys Leu Leu His Tyr Leu Gly Leu Ile Asp Leu Ser
        35                  40                  45

gat gac aag atc gag gat gat ctg gag atg acc atg gtt tgc cat cgg      491
Asp Asp Lys Ile Glu Asp Asp Leu Glu Met Thr Met Val Cys His Arg
    50                  55                  60

cct gag gga ctg gag cag ctt gag gca cag acg aac ttc acc aag aga      539
Pro Glu Gly Leu Glu Gln Leu Glu Ala Gln Thr Asn Phe Thr Lys Arg
 65                  70                  75                  80

gaa ctg caa gtc ctt tac cgg gga ttc aaa aac gag tgc ccc agt ggt      587
Glu Leu Gln Val Leu Tyr Arg Gly Phe Lys Asn Glu Cys Pro Ser Gly
                 85                  90                  95

gtg gtt aac gaa gag aca ttc aag cag atc tac gct cag ttt ttc cct      635
Val Val Asn Glu Glu Thr Phe Lys Gln Ile Tyr Ala Gln Phe Phe Pro
            100                 105                 110

cat gga gat gcc agc aca tac gca cat tac ctc ttc aat gcc ttc gac      683
His Gly Asp Ala Ser Thr Tyr Ala His Tyr Leu Phe Asn Ala Phe Asp
        115                 120                 125

acc acc cag aca ggc tct gta aag ttc gag gac ttt gtg act gct ctg      731
Thr Thr Gln Thr Gly Ser Val Lys Phe Glu Asp Phe Val Thr Ala Leu
    130                 135                 140

tcg att tta ctg aga gga acg gtc cat gaa aaa ctg agg tgg acg ttt      779
Ser Ile Leu Leu Arg Gly Thr Val His Glu Lys Leu Arg Trp Thr Phe
145                 150                 155                 160

aat ttg tac gac atc aat aaa gac ggc tac ata aac aaa gag gag atg      827
Asn Leu Tyr Asp Ile Asn Lys Asp Gly Tyr Ile Asn Lys Glu Glu Met
                165                 170                 175

atg gac ata gtg aaa gcc atc tat gac atg atg ggg aaa tac acc tat      875
Met Asp Ile Val Lys Ala Ile Tyr Asp Met Met Gly Lys Tyr Thr Tyr
            180                 185                 190

cct gtg ctc aaa gag gac act ccc agg cag cac gtg gac gtc ttc ttc      923
Pro Val Leu Lys Glu Asp Thr Pro Arg Gln His Val Asp Val Phe Phe
        195                 200                 205

cag aaa atg gat aaa aat aaa gat ggc att gta acg tta gac gaa ttt      971
Gln Lys Met Asp Lys Asn Lys Asp Gly Ile Val Thr Leu Asp Glu Phe
    210                 215                 220

ctc gag tcc tgt cag gag gat gac aac atc atg agg tct cta cag ctg     1019
Leu Glu Ser Cys Gln Glu Asp Asp Asn Ile Met Arg Ser Leu Gln Leu
225                 230                 235                 240

ttc caa aat gtc atg taactgagga cactggccat cctgctctca gagacactga     1074
Phe Gln Asn Val Met
                245

caaacacctc aatgccctga tctgcccttg ttccagtttt acacatcaac tctcgggaca   1134

gaaatacctt ttacactttg gaagaattct ctgctgaaga ctttctacaa aacctggcac   1194

cgagtggctc agtctctgat tgccaactct tcctccctcc tcctcttgag agggacgagc   1254

tgaaatccga agtttgtttt ggaagcatgc ccatctctcc atgctgctgc tgccctgtgg   1314

aaggcccctc tgcttgagct taaacagtag tgcacagttt tctgcgtata cagatcccca   1374

actcactgcc tctaagtcag gcagaccctg atcaatctga accaaatgtg caccatcctc   1434

cgatggcctc ccaagccaat gtgcctgctt ctcttcctct ggtgggaaga aagaacgctc   1494

tacagagcac ttagagctta ccatgaaaat actgggagag gcagcaccta acacatgtag   1554

aataggactg aattattaag catggtggta tcagatgatg caaacagccc atgtcatttt   1614

tttttccaga ggtagggact aataattctc ccacactagc acctacgatc atagaacaag   1674

tcttttaaca catccaggag ggaaaccgct gcccagtggt ctatcccttc tctccatccc   1734
```

-continued

```
ctgctcaagc ccagcactgc atgtctctcc cggaaggtcc agaatgcctg tgaaatgctg   1794

taacttttat accctgttat aatcaataaa cagaactatt tcgtacaaaa aaaaaaaaaa   1854

aa                                                                  1856


<210> SEQ ID NO 4
<211> LENGTH: 245
<212> TYPE: PRT
<213> ORGANISM: Rattus sp.

<400> SEQUENCE: 4

Met Pro Ala Arg Val Leu Leu Ala Tyr Pro Gly Thr Glu Met Leu Thr
  1               5                  10                  15

Gln Gly Glu Ser Glu Gly Leu Gln Thr Leu Gly Ile Val Val Val Leu
             20                  25                  30

Cys Ser Ser Leu Lys Leu Leu His Tyr Leu Gly Leu Ile Asp Leu Ser
         35                  40                  45

Asp Asp Lys Ile Glu Asp Asp Leu Glu Met Thr Met Val Cys His Arg
     50                  55                  60

Pro Glu Gly Leu Glu Gln Leu Glu Ala Gln Thr Asn Phe Thr Lys Arg
 65                  70                  75                  80

Glu Leu Gln Val Leu Tyr Arg Gly Phe Lys Asn Glu Cys Pro Ser Gly
                 85                  90                  95

Val Val Asn Glu Glu Thr Phe Lys Gln Ile Tyr Ala Gln Phe Phe Pro
            100                 105                 110

His Gly Asp Ala Ser Thr Tyr Ala His Tyr Leu Phe Asn Ala Phe Asp
        115                 120                 125

Thr Thr Gln Thr Gly Ser Val Lys Phe Glu Asp Phe Val Thr Ala Leu
    130                 135                 140

Ser Ile Leu Leu Arg Gly Thr Val His Glu Lys Leu Arg Trp Thr Phe
145                 150                 155                 160

Asn Leu Tyr Asp Ile Asn Lys Asp Gly Tyr Ile Asn Lys Glu Glu Met
                165                 170                 175

Met Asp Ile Val Lys Ala Ile Tyr Asp Met Met Gly Lys Tyr Thr Tyr
            180                 185                 190

Pro Val Leu Lys Glu Asp Thr Pro Arg Gln His Val Asp Val Phe Phe
        195                 200                 205

Gln Lys Met Asp Lys Asn Lys Asp Gly Ile Val Thr Leu Asp Glu Phe
    210                 215                 220

Leu Glu Ser Cys Gln Glu Asp Asp Asn Ile Met Arg Ser Leu Gln Leu
225                 230                 235                 240

Phe Gln Asn Val Met
                245


<210> SEQ ID NO 5
<211> LENGTH: 1907
<212> TYPE: DNA
<213> ORGANISM: Mus musculus
<220> FEATURE:
<221> NAME/KEY: CDS
<222> LOCATION: (477)..(1124)

<400> SEQUENCE: 5

cggccccctg agatccagcc cgagcgcggg gcggagcggc cgggtggcag caggggcggg     60

cgggcggagc gcagctcccg caccgcacgc ggcgcgggct cggcagcctc ggccgtgcgg    120

gcacgccggc cccgtgtcca acatcaggca ggctttgggg ctcggggctc gggcctcgga    180
```

-continued

```
gaagccagtg gcccggctgg gtgcccgcac cggggggcgc ctgtgaaggc tcccgcgagc    240

ctctggccct gggagtcagt gcatgtgcct ggctgaagaa ggcagcagcc acgagctcca    300

ggcgccccgg ccccacgttt tctgaatacc aagctgcagg cgagctgctc ggggcttttt    360

tgctttctcg cttttcctct cctccaattc aaagtgggca atccacaccg atttcttttc    420

aggggaggga agagacaggg cctggggtcc caagacgcac acaagtcttc gctgcc atg    479
                                                              Met
                                                                1

ggg gcc gtc atg ggc act ttc tcc tcc ctg cag acc aaa caa agg cga      527
Gly Ala Val Met Gly Thr Phe Ser Ser Leu Gln Thr Lys Gln Arg Arg
            5                  10                  15

ccc tct aaa gac aag att gag gat gag cta gag atg acc atg gtt tgc      575
Pro Ser Lys Asp Lys Ile Glu Asp Glu Leu Glu Met Thr Met Val Cys
        20                  25                  30

cac cgg cct gag gga ctg gag cag ctt gag gca cag acg aac ttc acc      623
His Arg Pro Glu Gly Leu Glu Gln Leu Glu Ala Gln Thr Asn Phe Thr
    35                  40                  45

aag aga gaa ctg caa gtc ttg tac cgg gga ttc aaa aac gag tgc cct      671
Lys Arg Glu Leu Gln Val Leu Tyr Arg Gly Phe Lys Asn Glu Cys Pro
 50                  55                  60                  65

agc ggt gtg gtc aat gaa gaa aca ttc aag cag atc tac gct cag ttt      719
Ser Gly Val Val Asn Glu Glu Thr Phe Lys Gln Ile Tyr Ala Gln Phe
                70                  75                  80

ttc cct cac gga gat gcc agc aca tat gca cat tac ctc ttc aat gcc      767
Phe Pro His Gly Asp Ala Ser Thr Tyr Ala His Tyr Leu Phe Asn Ala
            85                  90                  95

ttc gac acc acc cag aca ggc tct gta aag ttc gag gac ttt gtg act      815
Phe Asp Thr Thr Gln Thr Gly Ser Val Lys Phe Glu Asp Phe Val Thr
        100                 105                 110

gct ctg tcg att tta ctg aga ggg aca gtc cat gaa aaa cta agg tgg      863
Ala Leu Ser Ile Leu Leu Arg Gly Thr Val His Glu Lys Leu Arg Trp
    115                 120                 125

acg ttt aat ttg tat gac atc aat aaa gac ggc tac ata aac aaa gag      911
Thr Phe Asn Leu Tyr Asp Ile Asn Lys Asp Gly Tyr Ile Asn Lys Glu
130                 135                 140                 145

gag atg atg gac ata gtc aaa gcc atc tat gac atg atg ggg aaa tac      959
Glu Met Met Asp Ile Val Lys Ala Ile Tyr Asp Met Met Gly Lys Tyr
                150                 155                 160

acc tat cct gtg ctc aaa gag gac act ccc agg cag cat gtg gat gtc     1007
Thr Tyr Pro Val Leu Lys Glu Asp Thr Pro Arg Gln His Val Asp Val
            165                 170                 175

ttc ttc cag aaa atg gat aaa aat aaa gat ggc att gta acg tta gat     1055
Phe Phe Gln Lys Met Asp Lys Asn Lys Asp Gly Ile Val Thr Leu Asp
        180                 185                 190

gaa ttt ctt gaa tca tgt cag gag gat gac aac atc atg aga tct cta     1103
Glu Phe Leu Glu Ser Cys Gln Glu Asp Asp Asn Ile Met Arg Ser Leu
    195                 200                 205

cag ctg ttc caa aat gtc atg taactgagga cactggccat tctgctctca        1154
Gln Leu Phe Gln Asn Val Met
210                 215

gagacactga caaacacctt aatgccctga tctgcccttg ttccaatttt acacaccaac   1214

tcttgggaca gaaatacctt ttacactttg gaagaattct ctgctgaaga ctttctacaa   1274

aacctggcac cacgtggctc tgtctctgag ggacgagcgg agatccgact ttgttttgga   1334

agcatgccca tctcttcatg ctgctgccct gtggaaggcc cctctgcttg agcttaatca   1394

atagtgcaca gttttatgct tacacatatc cccaactcac tgcctccaag tcaggcagac   1454

tctgatgaat ctgagccaaa tgtgcaccat cctccgatgg cctcccaagc caatgtgcct   1514
```

```
gcttctcttc ctctggtggg aagaaagagt gttctacgga acaattagag cttaccatga    1574

aaatattggg agaggcagca cctaacacat gtagaatagg actgaattat taagcatggt    1634

gatatcagat gatgcaaatt gcccatgtca tttttttcaa aggtagggac aaatgattct    1694

cccacactag cacctgtggt catagagcaa gtctcttaac atgcccagaa ggggaaccac    1754

tgtccagtgg tctatccctc ctctccatcc cctgctcaaa cccagcactg catgtccctc    1814

caagaaggtc cagaatgcct gcgaaacgct gtacttttat accctgttct aatcaataaa    1874

cagaactatt tcgtaaaaaa aaaaaaaaaa aaa                                  1907

<210> SEQ ID NO 6
<211> LENGTH: 216
<212> TYPE: PRT
<213> ORGANISM: Mus musculus

<400> SEQUENCE: 6

Met Gly Ala Val Met Gly Thr Phe Ser Ser Leu Gln Thr Lys Gln Arg
  1               5                  10                  15

Arg Pro Ser Lys Asp Lys Ile Glu Asp Glu Leu Glu Met Thr Met Val
                 20                  25                  30

Cys His Arg Pro Glu Gly Leu Glu Gln Leu Glu Ala Gln Thr Asn Phe
             35                  40                  45

Thr Lys Arg Glu Leu Gln Val Leu Tyr Arg Gly Phe Lys Asn Glu Cys
         50                  55                  60

Pro Ser Gly Val Val Asn Glu Glu Thr Phe Lys Gln Ile Tyr Ala Gln
 65                  70                  75                  80

Phe Phe Pro His Gly Asp Ala Ser Thr Tyr Ala His Tyr Leu Phe Asn
                 85                  90                  95

Ala Phe Asp Thr Thr Gln Thr Gly Ser Val Lys Phe Glu Asp Phe Val
            100                 105                 110

Thr Ala Leu Ser Ile Leu Leu Arg Gly Thr Val His Glu Lys Leu Arg
        115                 120                 125

Trp Thr Phe Asn Leu Tyr Asp Ile Asn Lys Asp Gly Tyr Ile Asn Lys
    130                 135                 140

Glu Glu Met Met Asp Ile Val Lys Ala Ile Tyr Asp Met Met Gly Lys
145                 150                 155                 160

Tyr Thr Tyr Pro Val Leu Lys Glu Asp Thr Pro Arg Gln His Val Asp
                165                 170                 175

Val Phe Phe Gln Lys Met Asp Lys Asn Lys Asp Gly Ile Val Thr Leu
            180                 185                 190

Asp Glu Phe Leu Glu Ser Cys Gln Glu Asp Asp Asn Ile Met Arg Ser
        195                 200                 205

Leu Gln Leu Phe Gln Asn Val Met
    210                 215

<210> SEQ ID NO 7
<211> LENGTH: 1534
<212> TYPE: DNA
<213> ORGANISM: Rattus sp.
<220> FEATURE:
<221> NAME/KEY: CDS
<222> LOCATION: (31)..(711)

<400> SEQUENCE: 7

gtcccaagtc gcacacaagt cttcgctgcc atg ggg gcc gtc atg ggt acc ttc    54
                                 Met Gly Ala Val Met Gly Thr Phe
                                  1               5
```

-continued

```
tcg tcc ctg cag acc aaa caa agg cga ccc tct aaa gac atc gcc tgg      102
Ser Ser Leu Gln Thr Lys Gln Arg Arg Pro Ser Lys Asp Ile Ala Trp
     10                  15                  20

tgg tat tac cag tat cag aga gac aag atc gag gat gat ctg gag atg      150
Trp Tyr Tyr Gln Tyr Gln Arg Asp Lys Ile Glu Asp Asp Leu Glu Met
 25                  30                  35                  40

acc atg gtt tgc cat cgg cct gag gga ctg gag cag ctt gag gca cag      198
Thr Met Val Cys His Arg Pro Glu Gly Leu Glu Gln Leu Glu Ala Gln
                 45                  50                  55

acg aac ttc acc aag aga gaa ctg caa gtc ctt tac cgg gga ttc aaa      246
Thr Asn Phe Thr Lys Arg Glu Leu Gln Val Leu Tyr Arg Gly Phe Lys
             60                  65                  70

aac gag tgc ccc agt ggt gtg gtt aac gaa gag aca ttc aag cag atc      294
Asn Glu Cys Pro Ser Gly Val Val Asn Glu Glu Thr Phe Lys Gln Ile
         75                  80                  85

tac gct cag ttt ttc cct cat gga gat gcc agc aca tac gca cat tac      342
Tyr Ala Gln Phe Phe Pro His Gly Asp Ala Ser Thr Tyr Ala His Tyr
     90                  95                 100

ctc ttc aat gcc ttc gac acc acc cag aca ggc tct gta aag ttc gag      390
Leu Phe Asn Ala Phe Asp Thr Thr Gln Thr Gly Ser Val Lys Phe Glu
105                 110                 115                 120

gac ttt gtg act gct ctg tcg att tta ctg aga gga acg gtc cat gaa      438
Asp Phe Val Thr Ala Leu Ser Ile Leu Leu Arg Gly Thr Val His Glu
                125                 130                 135

aaa ctg agg tgg acg ttt aat ttg tac gac atc aat aaa gac ggc tac      486
Lys Leu Arg Trp Thr Phe Asn Leu Tyr Asp Ile Asn Lys Asp Gly Tyr
            140                 145                 150

ata aac aaa gag gag atg atg gac ata gtg aaa gcc atc tat gac atg      534
Ile Asn Lys Glu Glu Met Met Asp Ile Val Lys Ala Ile Tyr Asp Met
        155                 160                 165

atg ggg aaa tac acc tat cct gtg ctc aaa gag gac act ccc agg cag      582
Met Gly Lys Tyr Thr Tyr Pro Val Leu Lys Glu Asp Thr Pro Arg Gln
    170                 175                 180

cac gtg gac gtc ttc ttc cag aaa atg gat aaa aat aaa gat ggc att      630
His Val Asp Val Phe Phe Gln Lys Met Asp Lys Asn Lys Asp Gly Ile
185                 190                 195                 200

gta acg tta gac gaa ttt ctc gag tcc tgt cag gag gat gac aac atc      678
Val Thr Leu Asp Glu Phe Leu Glu Ser Cys Gln Glu Asp Asp Asn Ile
                205                 210                 215

atg agg tct cta cag ctg ttc caa aat gtc atg taactgagga cactggccat    731
Met Arg Ser Leu Gln Leu Phe Gln Asn Val Met
            220                 225

cctgctctca gagacactga caaacacctc aatgccctga tctgcccttg ttccagtttt    791

acacatcaac tctcgggaca gaaatacctt ttacactttg gaagaattct ctgctgaaga    851

ctttctacaa aacctggcac cgcgtggctc agtctctgat tgccaactct tcctccctcc    911

tcctcttgag agggacgagc tgaaatccga agtttgtttt ggaagcatgc ccatctctcc    971

atgctgctgc tgccctgtgg aaggcccctc tgcttgagct taaacagtag tgcacagttt   1031

tctgcgtata cagatcccca actcactgcc tctaagtcag gcagaccctg atcaatctga   1091

accaaatgtg caccatcctc cgatggcctc ccaagccaat gtgcctgctt ctcttcctct   1151

ggtgggaaga aagaacgctc tacagagcac ttagagctta ccatgaaaat actgggagag   1211

gcagcaccta acacatgtag aataggactg aattattaag catggtggta tcagatgatg   1271

caaacagccc atgtcatttt ttttccagag gtagggacta ataattctcc cacactagca   1331

cctacgatca tagaacaagt cttttaacac atccaggagg gaaaccgctg cccagtggtc   1391
```

-continued tatcccttct ctccatcccc tgctcaagcc cagcactgca tgtctctccc ggaaggtcca 1451 gaatgcctgt gaaatgctgt aacttttata ccctgttata atcaataaac agaactattt 1511 cgtacaaaaa aaaaaaaaaa aaa 1534

<210> SEQ ID NO 8
<211> LENGTH: 227
<212> TYPE: PRT
<213> ORGANISM: Rattus sp.

<400> SEQUENCE: 8

```
Met Gly Ala Val Met Gly Thr Phe Ser Ser Leu Gln Thr Lys Gln Arg
  1               5                  10                  15

Arg Pro Ser Lys Asp Ile Ala Trp Trp Tyr Tyr Gln Tyr Gln Arg Asp
             20                  25                  30

Lys Ile Glu Asp Asp Leu Glu Met Thr Met Val Cys His Arg Pro Glu
         35                  40                  45

Gly Leu Glu Gln Leu Glu Ala Gln Thr Asn Phe Thr Lys Arg Glu Leu
     50                  55                  60

Gln Val Leu Tyr Arg Gly Phe Lys Asn Glu Cys Pro Ser Gly Val Val
 65                  70                  75                  80

Asn Glu Glu Thr Phe Lys Gln Ile Tyr Ala Gln Phe Phe Pro His Gly
                 85                  90                  95

Asp Ala Ser Thr Tyr Ala His Tyr Leu Phe Asn Ala Phe Asp Thr Thr
            100                 105                 110

Gln Thr Gly Ser Val Lys Phe Glu Asp Phe Val Thr Ala Leu Ser Ile
        115                 120                 125

Leu Leu Arg Gly Thr Val His Glu Lys Leu Arg Trp Thr Phe Asn Leu
    130                 135                 140

Tyr Asp Ile Asn Lys Asp Gly Tyr Ile Asn Lys Glu Glu Met Met Asp
145                 150                 155                 160

Ile Val Lys Ala Ile Tyr Asp Met Met Gly Lys Tyr Thr Tyr Pro Val
                165                 170                 175

Leu Lys Glu Asp Thr Pro Arg Gln His Val Asp Val Phe Phe Gln Lys
            180                 185                 190

Met Asp Lys Asn Lys Asp Gly Ile Val Thr Leu Asp Glu Phe Leu Glu
        195                 200                 205

Ser Cys Gln Glu Asp Asp Asn Ile Met Arg Ser Leu Gln Leu Phe Gln
    210                 215                 220

Asn Val Met
225
```

<210> SEQ ID NO 9
<211> LENGTH: 1540
<212> TYPE: DNA
<213> ORGANISM: Mus musculus
<220> FEATURE:
<221> NAME/KEY: CDS
<222> LOCATION: (77)..(757)

<400> SEQUENCE: 9

```
atccacaccg atttcttttc aggggaggga agagacaggg cctggggtcc caagacgcac     60

acaagtcttc gctgcc atg ggg gcc gtc atg ggc act ttc tcc tcc ctg cag    112
                  Met Gly Ala Val Met Gly Thr Phe Ser Ser Leu Gln
                    1               5                  10

acc aaa caa agg cga ccc tct aaa gac atc gcc tgg tgg tat tac cag      160
Thr Lys Gln Arg Arg Pro Ser Lys Asp Ile Ala Trp Trp Tyr Tyr Gln
         15                  20                  25
```

-continued

```
tat cag aga gac aag att gag gat gag cta gag atg acc atg gtt tgc      208
Tyr Gln Arg Asp Lys Ile Glu Asp Glu Leu Glu Met Thr Met Val Cys
     30                  35                  40

cac cgg cct gag gga ctg gag cag ctt gag gca cag acg aac ttc acc      256
His Arg Pro Glu Gly Leu Glu Gln Leu Glu Ala Gln Thr Asn Phe Thr
 45                  50                  55                  60

aag aga gaa ctg caa gtc ttg tac cgg gga ttc aaa aac gag tgc cct      304
Lys Arg Glu Leu Gln Val Leu Tyr Arg Gly Phe Lys Asn Glu Cys Pro
                 65                  70                  75

agc ggt gtg gtc aat gaa gaa aca ttc aag cag atc tac gct cag ttt      352
Ser Gly Val Val Asn Glu Glu Thr Phe Lys Gln Ile Tyr Ala Gln Phe
             80                  85                  90

ttc cct cac gga gat gcc agc aca tat gca cat tac ctc ttc aat gcc      400
Phe Pro His Gly Asp Ala Ser Thr Tyr Ala His Tyr Leu Phe Asn Ala
         95                 100                 105

ttc gac acc acc cag aca ggc tct gta aag ttc gag gac ttt gtg act      448
Phe Asp Thr Thr Gln Thr Gly Ser Val Lys Phe Glu Asp Phe Val Thr
    110                 115                 120

gct ctg tcg att tta ctg aga ggg aca gtc cat gaa aaa cta agg tgg      496
Ala Leu Ser Ile Leu Leu Arg Gly Thr Val His Glu Lys Leu Arg Trp
125                 130                 135                 140

acg ttt aat ttg tat gac atc aat aaa gac ggc tac ata aac aaa gag      544
Thr Phe Asn Leu Tyr Asp Ile Asn Lys Asp Gly Tyr Ile Asn Lys Glu
                145                 150                 155

gag atg atg gac ata gtc aaa gcc atc tat gac atg atg ggg aaa tac      592
Glu Met Met Asp Ile Val Lys Ala Ile Tyr Asp Met Met Gly Lys Tyr
            160                 165                 170

acc tat cct gtg ctc aaa gag gac act ccc agg cag cat gtg gat gtc      640
Thr Tyr Pro Val Leu Lys Glu Asp Thr Pro Arg Gln His Val Asp Val
        175                 180                 185

ttc ttc cag aaa atg gat aaa aat aaa gat ggc att gta acg tta gat      688
Phe Phe Gln Lys Met Asp Lys Asn Lys Asp Gly Ile Val Thr Leu Asp
    190                 195                 200

gaa ttt ctt gaa tca tgt cag gag gat gac aac atc atg aga tct cta      736
Glu Phe Leu Glu Ser Cys Gln Glu Asp Asp Asn Ile Met Arg Ser Leu
205                 210                 215                 220

cag ctg ttc caa aat gtc atg taactgagga cactggccat tctgctctca         787
Gln Leu Phe Gln Asn Val Met
                225
gagacactga caaacacctt aatgccctga tctgcccttg ttccaatttt acacaccaac   847

tcttgggaca gaaatacctt ttacactttg gaagaattct ctgctgaaga ctttctacaa   907

aacctggcac cacgtggctc tgtctctgag ggacgagcgg agatccgact ttgttttgga   967

agcatgccca tctcttcatg ctgctgccct gtggaaggcc cctctgcttg agcttaatca   1027

atagtgcaca gttttatgct tacacatatc cccaactcac tgcctccaag tcaggcagac   1087

tctgatgaat ctgagccaaa tgtgcaccat cctccgatgg cctcccaagc caatgtgcct   1147

gcttctcttc ctctggtggg aagaaagagt gttctacgga acaattagag cttaccatga   1207

aaatattggg agaggcagca cctaacacat gtagaatagg actgaattat taagcatggt   1267

gatatcagat gatgcaaatt gcccatgtca ttttttttcaa aggtagggac aaatgattct   1327

cccacactag cacctgtggt catagagcaa gtctcttaac atgcccagaa ggggaaccac   1387

tgtccagtgg tctatccctc ctctccatcc cctgctcaaa cccagcactg catgtccctc   1447

caagaaggtc cagaatgcct gcgaaacgct gtacttttat accctgttct aatcaataaa   1507

cagaactatt tcgtacaaaa aaaaaaaaaa aaa                                1540
```

-continued

```
<210> SEQ ID NO 10
<211> LENGTH: 227
<212> TYPE: PRT
<213> ORGANISM: Mus musculus

<400> SEQUENCE: 10

Met Gly Ala Val Met Gly Thr Phe Ser Ser Leu Gln Thr Lys Gln Arg
  1               5                  10                  15

Arg Pro Ser Lys Asp Ile Ala Trp Trp Tyr Tyr Gln Tyr Gln Arg Asp
             20                  25                  30

Lys Ile Glu Asp Glu Leu Glu Met Thr Met Val Cys His Arg Pro Glu
         35                  40                  45

Gly Leu Glu Gln Leu Glu Ala Gln Thr Asn Phe Thr Lys Arg Glu Leu
     50                  55                  60

Gln Val Leu Tyr Arg Gly Phe Lys Asn Glu Cys Pro Ser Gly Val Val
 65                  70                  75                  80

Asn Glu Glu Thr Phe Lys Gln Ile Tyr Ala Gln Phe Phe Pro His Gly
                 85                  90                  95

Asp Ala Ser Thr Tyr Ala His Tyr Leu Phe Asn Ala Phe Asp Thr Thr
            100                 105                 110

Gln Thr Gly Ser Val Lys Phe Glu Asp Phe Val Thr Ala Leu Ser Ile
        115                 120                 125

Leu Leu Arg Gly Thr Val His Glu Lys Leu Arg Trp Thr Phe Asn Leu
    130                 135                 140

Tyr Asp Ile Asn Lys Asp Gly Tyr Ile Asn Lys Glu Glu Met Met Asp
145                 150                 155                 160

Ile Val Lys Ala Ile Tyr Asp Met Met Gly Lys Tyr Thr Tyr Pro Val
                165                 170                 175

Leu Lys Glu Asp Thr Pro Arg Gln His Val Asp Val Phe Phe Gln Lys
            180                 185                 190

Met Asp Lys Asn Lys Asp Gly Ile Val Thr Leu Asp Glu Phe Leu Glu
        195                 200                 205

Ser Cys Gln Glu Asp Asp Asn Ile Met Arg Ser Leu Gln Leu Phe Gln
    210                 215                 220

Asn Val Met
225


<210> SEQ ID NO 11
<211> LENGTH: 955
<212> TYPE: DNA
<213> ORGANISM: Rattus sp.
<220> FEATURE:
<221> NAME/KEY: CDS
<222> LOCATION: (345)..(953)
<220> FEATURE:
<223> OTHER INFORMATION: Xaa at position 92 of the corresponding amino
      acid sequence may be any amino acid

<400> SEQUENCE: 11

gtccgggcac acaacccctg gattcttcgg agaatatgcc gtgacggtgt tgccaattat      60

tagttctctt ggctagcaga tgtttaggga ctggttaagc ctttggagaa attaccttag     120

gaaaacgggg aaataaaagc aaagattacc atgaattgca agattaccta gcaattgcaa     180

ggtaggagga gagaggtgga gggcggagta gacaggaggg agggagaaag tgagaggaag     240

ctaggctggt ggaaataacc ctgcacttgg aacagcggca aagaagcgcg attttccagc     300

tttaaatgcc tgcccgcgtt ctgcttgcct acccgggaac ggag atg ttg acc cag      356
                                                 Met Leu Thr Gln
                                                   1
```

-continued

```
ggc gag tct gaa ggg ctc cag acc ttg ggg ata gta gtg gtc ctg tgt      404
Gly Glu Ser Glu Gly Leu Gln Thr Leu Gly Ile Val Val Val Leu Cys
  5               10                  15                  20

tcc tct ctg aaa cta ctg cac tac ctc ggg ctg att gac ttg tcg gat      452
Ser Ser Leu Lys Leu Leu His Tyr Leu Gly Leu Ile Asp Leu Ser Asp
                25                  30                  35

gac aag atc gag gat gat ctg gag atg acc atg gtt tgc cat cgg cct      500
Asp Lys Ile Glu Asp Asp Leu Glu Met Thr Met Val Cys His Arg Pro
            40                  45                  50

gag gga ctg gag cag ctt gag gca cag acg aac ttc acc aag aga gaa      548
Glu Gly Leu Glu Gln Leu Glu Ala Gln Thr Asn Phe Thr Lys Arg Glu
        55                  60                  65

ctg caa gtc ctt tac cgg gga ttc aaa aac gag tgc ccc agt ggt gtg      596
Leu Gln Val Leu Tyr Arg Gly Phe Lys Asn Glu Cys Pro Ser Gly Val
    70                  75                  80

gtt aac gaa gag aca ttc aag cng atc tac gct cag ttt ttc cct cat      644
Val Asn Glu Glu Thr Phe Lys Xaa Ile Tyr Ala Gln Phe Phe Pro His
 85                  90                  95                 100

gga gat gcc agc aca tac gca cat tac ctc ttc aat gcc ttc gac acc      692
Gly Asp Ala Ser Thr Tyr Ala His Tyr Leu Phe Asn Ala Phe Asp Thr
                105                 110                 115

acc cag aca ggc tct gta aag ttc gag gac ttt gtg act gct ctg tcg      740
Thr Gln Thr Gly Ser Val Lys Phe Glu Asp Phe Val Thr Ala Leu Ser
            120                 125                 130

att tta ctg aga gga acg gtc cat gaa aaa ctg aag tgg acg ttt aat      788
Ile Leu Leu Arg Gly Thr Val His Glu Lys Leu Lys Trp Thr Phe Asn
        135                 140                 145

ttg tac gac atc aat aaa gac ggc tac ata aac aaa gag gag atg atg      836
Leu Tyr Asp Ile Asn Lys Asp Gly Tyr Ile Asn Lys Glu Glu Met Met
    150                 155                 160

gac ata gtg aaa gcc atc tat gac atg atg ggg aaa tac acc tat ctt      884
Asp Ile Val Lys Ala Ile Tyr Asp Met Met Gly Lys Tyr Thr Tyr Leu
165                 170                 175                 180

gtg ctc aaa gag gac act tcc agg cag cac gtg gac gtc ttc ttc cag      932
Val Leu Lys Glu Asp Thr Ser Arg Gln His Val Asp Val Phe Phe Gln
                185                 190                 195

aaa atg gat aaa aat aaa gat gg                                       955
Lys Met Asp Lys Asn Lys Asp
            200


<210> SEQ ID NO 12
<211> LENGTH: 203
<212> TYPE: PRT
<213> ORGANISM: Rattus sp.

<400> SEQUENCE: 12

Met Leu Thr Gln Gly Glu Ser Glu Gly Leu Gln Thr Leu Gly Ile Val
  1               5                  10                  15

Val Val Leu Cys Ser Ser Leu Lys Leu Leu His Tyr Leu Gly Leu Ile
            20                  25                  30

Asp Leu Ser Asp Asp Lys Ile Glu Asp Asp Leu Glu Met Thr Met Val
        35                  40                  45

Cys His Arg Pro Glu Gly Leu Glu Gln Leu Glu Ala Gln Thr Asn Phe
    50                  55                  60

Thr Lys Arg Glu Leu Gln Val Leu Tyr Arg Gly Phe Lys Asn Glu Cys
 65                  70                  75                  80

Pro Ser Gly Val Val Asn Glu Glu Thr Phe Lys Xaa Ile Tyr Ala Gln
                85                  90                  95
```

-continued

```
Phe Phe Pro His Gly Asp Ala Ser Thr Tyr Ala His Tyr Leu Phe Asn
            100                 105                 110

Ala Phe Asp Thr Thr Gln Thr Gly Ser Val Lys Phe Glu Asp Phe Val
        115                 120                 125

Thr Ala Leu Ser Ile Leu Leu Arg Gly Thr Val His Glu Lys Leu Lys
    130                 135                 140

Trp Thr Phe Asn Leu Tyr Asp Ile Asn Lys Asp Gly Tyr Ile Asn Lys
145                 150                 155                 160

Glu Glu Met Met Asp Ile Val Lys Ala Ile Tyr Asp Met Met Gly Lys
                165                 170                 175

Tyr Thr Tyr Leu Val Leu Lys Glu Asp Thr Ser Arg Gln His Val Asp
            180                 185                 190

Val Phe Phe Gln Lys Met Asp Lys Asn Lys Asp
        195                 200


<210> SEQ ID NO 13
<211> LENGTH: 2009
<212> TYPE: DNA
<213> ORGANISM: Homo sapiens
<220> FEATURE:
<221> NAME/KEY: CDS
<222> LOCATION: (207)..(1016)

<400> SEQUENCE: 13

ctcacctgct gcctagtgtt ccctctcctg ctccaggacc tccgggtaga cctcagaccc      60

cgggcccatt cccagactca gcctcagccc ggacttcccc agccccgaca gcacagtagg     120

ccgccagggg gcgccgtgtg agcgccctat cccggccacc cggcgccccc tcccacggcc     180

cgggcgggag cggggcgccg ggggcc atg cgg ggc cag ggc cgc aag gag agt      233
                             Met Arg Gly Gln Gly Arg Lys Glu Ser
                             1               5

ttg tcc gat tcc cga gac ctg gac ggc tcc tac gac cag ctc acg ggc       281
Leu Ser Asp Ser Arg Asp Leu Asp Gly Ser Tyr Asp Gln Leu Thr Gly
 10                  15                  20                  25

cac cct cca ggg ccc act aaa aaa gcg ctg aag cag cga ttc ctc aag       329
His Pro Pro Gly Pro Thr Lys Lys Ala Leu Lys Gln Arg Phe Leu Lys
                 30                  35                  40

ctg ctg ccg tgc tgc ggg ccc caa gcc ctg ccc tca gtc agt gaa aca       377
Leu Leu Pro Cys Cys Gly Pro Gln Ala Leu Pro Ser Val Ser Glu Thr
             45                  50                  55

tta gcc gcc cca gcc tcc ctc cgc ccc cac aga ccc cgc ctg ctg gac       425
Leu Ala Ala Pro Ala Ser Leu Arg Pro His Arg Pro Arg Leu Leu Asp
         60                  65                  70

cca gac agc gtg gac gat gaa ttt gaa ttg tcc acc gtg tgt cac cgg       473
Pro Asp Ser Val Asp Asp Glu Phe Glu Leu Ser Thr Val Cys His Arg
     75                  80                  85

cct gag ggt ctg gag cag ctg cag gag caa acc aaa ttc acg cgc aag       521
Pro Glu Gly Leu Glu Gln Leu Gln Glu Gln Thr Lys Phe Thr Arg Lys
 90                  95                 100                 105

gag ttg cag gtc ctg tac cgg ggc ttc aag aac gaa tgt ccc agc gga       569
Glu Leu Gln Val Leu Tyr Arg Gly Phe Lys Asn Glu Cys Pro Ser Gly
                110                 115                 120

att gtc aat gag gag aac ttc aag cag att tac tcc cag ttc ttt cct       617
Ile Val Asn Glu Glu Asn Phe Lys Gln Ile Tyr Ser Gln Phe Phe Pro
            125                 130                 135

caa gga gac tcc agc acc tat gcc act ttt ctc ttc aat gcc ttt gac       665
Gln Gly Asp Ser Ser Thr Tyr Ala Thr Phe Leu Phe Asn Ala Phe Asp
        140                 145                 150

acc aac cat gat ggc tcg gtc agt ttt gag gac ttt gtg gct ggt ttg       713
```

-continued

```
Thr Asn His Asp Gly Ser Val Ser Phe Glu Asp Phe Val Ala Gly Leu
    155                 160                 165

tcc gtg att ctt cgg gga act gta gat gac agg ctt aat tgg gcc ttc      761
Ser Val Ile Leu Arg Gly Thr Val Asp Asp Arg Leu Asn Trp Ala Phe
170                 175                 180                 185

aac ctg tat gac ctt aac aag gac ggc tgc atc acc aag gag gaa atg      809
Asn Leu Tyr Asp Leu Asn Lys Asp Gly Cys Ile Thr Lys Glu Glu Met
                190                 195                 200

ctt gac atc atg aag tcc atc tat gac atg atg ggc aag tac acg tac      857
Leu Asp Ile Met Lys Ser Ile Tyr Asp Met Met Gly Lys Tyr Thr Tyr
            205                 210                 215

cct gca ctc cgg gag gag gcc cca agg gaa cac gtg gag agc ttc ttc      905
Pro Ala Leu Arg Glu Glu Ala Pro Arg Glu His Val Glu Ser Phe Phe
        220                 225                 230

cag aag atg gac aga aac aag gat ggt gtg gtg acc att gag gaa ttc      953
Gln Lys Met Asp Arg Asn Lys Asp Gly Val Val Thr Ile Glu Glu Phe
    235                 240                 245

att gag tct tgt caa aag gat gag aac atc atg agg tcc atg cag ctc     1001
Ile Glu Ser Cys Gln Lys Asp Glu Asn Ile Met Arg Ser Met Gln Leu
250                 255                 260                 265

ttt gac aat gtc atc tagcccccag gagagggggt cagtgtttcc tgggggggacc     1056
Phe Asp Asn Val Ile
                270

atgctctaac cctagtccag gcggacctca cccttctctt cccaggtcta tcctcatcct   1116

acgcctccct gggggctgga gggatccaag agcttgggga ttcagtagtc cagatctctg   1176

gagctgaagg ggccagagag tgggcagagt gcatctcggg gggtgttccc aactcccacc   1236

agctctcacc cccttcctgc ctgacaccca gtgttgagag tgcccctcct gtaggaattg   1296

agcggttccc cacctcctac cctactctag aaacacacta gagcgatgtc tcctgctatg   1356

gtgcttcccc catccctgac ctcataaaca tttcccctaa gactcccctc tcagagagaa   1416

tgctccattc ttggcactgg ctggcttctc agaccagcca ttgagagccc tgtgggaggg   1476

ggacaagaat gtatagggag aaatcttggg cctgagtcaa tggataggtc ctaggaggtg   1536

ggtggggttg agaatagaag ggcctggaca gattatgatt gctcaggcat accaggttat   1596

agctccaagt tccacaggtc tgctaccaca ggccatcaaa atataagttt ccaggctttg   1656

cagaagacct tgtctcctta gaaatgcccc agaaatttc cacaccctcc tcggtatcca   1716

tggagagcct ggggccagat atctggctca tctctggcat tgcttcctct ccttccttcc   1776

tgcatgtgtt ggtggtggtt gtggtggggg aatgtggatg ggggatgtcc tggctgatgc   1836

ctgccaaaat ttcatcccac cctccttgct tatcgtccct gttttgaggg ctatgacttg   1896

agtttttgtt tcccatgttc tctatagact tgggaccttc ctgaacttgg ggcctatcac   1956

tccccacagt ggatgcctta gaagggagag ggaaggaggg aggcaggcat agc          2009


<210> SEQ ID NO 14
<211> LENGTH: 270
<212> TYPE: PRT
<213> ORGANISM: Homo sapiens

<400> SEQUENCE: 14

Met Arg Gly Gln Gly Arg Lys Glu Ser Leu Ser Asp Ser Arg Asp Leu
  1               5                  10                  15

Asp Gly Ser Tyr Asp Gln Leu Thr Gly His Pro Pro Gly Pro Thr Lys
             20                  25                  30

Lys Ala Leu Lys Gln Arg Phe Leu Lys Leu Leu Pro Cys Cys Gly Pro
         35                  40                  45
```

-continued

```
Gln Ala Leu Pro Ser Val Ser Glu Thr Leu Ala Ala Pro Ala Ser Leu
     50                  55                  60

Arg Pro His Arg Pro Arg Leu Leu Asp Pro Asp Ser Val Asp Asp Glu
 65                  70                  75                  80

Phe Glu Leu Ser Thr Val Cys His Arg Pro Glu Gly Leu Glu Gln Leu
                 85                  90                  95

Gln Glu Gln Thr Lys Phe Thr Arg Lys Glu Leu Gln Val Leu Tyr Arg
            100                 105                 110

Gly Phe Lys Asn Glu Cys Pro Ser Gly Ile Val Asn Glu Glu Asn Phe
        115                 120                 125

Lys Gln Ile Tyr Ser Gln Phe Phe Pro Gln Gly Asp Ser Ser Thr Tyr
    130                 135                 140

Ala Thr Phe Leu Phe Asn Ala Phe Asp Thr Asn His Asp Gly Ser Val
145                 150                 155                 160

Ser Phe Glu Asp Phe Val Ala Gly Leu Ser Val Ile Leu Arg Gly Thr
                165                 170                 175

Val Asp Asp Arg Leu Asn Trp Ala Phe Asn Leu Tyr Asp Leu Asn Lys
            180                 185                 190

Asp Gly Cys Ile Thr Lys Glu Glu Met Leu Asp Ile Met Lys Ser Ile
        195                 200                 205

Tyr Asp Met Met Gly Lys Tyr Thr Tyr Pro Ala Leu Arg Glu Glu Ala
    210                 215                 220

Pro Arg Glu His Val Glu Ser Phe Phe Gln Lys Met Asp Arg Asn Lys
225                 230                 235                 240

Asp Gly Val Val Thr Ile Glu Glu Phe Ile Glu Ser Cys Gln Lys Asp
                245                 250                 255

Glu Asn Ile Met Arg Ser Met Gln Leu Phe Asp Asn Val Ile
            260                 265                 270


<210> SEQ ID NO 15
<211> LENGTH: 1247
<212> TYPE: DNA
<213> ORGANISM: Rattus sp.
<220> FEATURE:
<221> NAME/KEY: CDS
<222> LOCATION: (2)..(772)

<400> SEQUENCE: 15

c cga gat ctg gac ggc tcc tat gac cag ctt acg ggc cac cct cca ggg      49
  Arg Asp Leu Asp Gly Ser Tyr Asp Gln Leu Thr Gly His Pro Pro Gly
    1               5                  10                  15

ccc agt aaa aaa gcc ctg aag cag cgt ttc ctc aag ctg ctg ccg tgc       97
Pro Ser Lys Lys Ala Leu Lys Gln Arg Phe Leu Lys Leu Leu Pro Cys
             20                  25                  30

tgc ggg ccc caa gcc ctg ccc tca gtc agt gaa aca tta gct gcc cca      145
Cys Gly Pro Gln Ala Leu Pro Ser Val Ser Glu Thr Leu Ala Ala Pro
         35                  40                  45

gcc tcc ctc cgc ccc cac aga ccc cgc ccg ctg gac cca gac agc gta      193
Ala Ser Leu Arg Pro His Arg Pro Arg Pro Leu Asp Pro Asp Ser Val
     50                  55                  60

gag gat gag ttt gaa tta tcc acg gtg tgt cac cga cct gag ggc ctg      241
Glu Asp Glu Phe Glu Leu Ser Thr Val Cys His Arg Pro Glu Gly Leu
 65                  70                  75                  80

gaa caa ctc cag gaa cag acc aag ttc aca cgc aga gag ctg cag gtc      289
Glu Gln Leu Gln Glu Gln Thr Lys Phe Thr Arg Arg Glu Leu Gln Val
                 85                  90                  95
ctg tac cga ggc ttc aag aac gaa tgc ccc agt ggg att gtc aac gag      337
Leu Tyr Arg Gly Phe Lys Asn Glu Cys Pro Ser Gly Ile Val Asn Glu
```

-continued

```
            100                 105                 110

gag aac ttc aag cag att tat tct cag ttc ttt ccc caa gga gac tcc      385
Glu Asn Phe Lys Gln Ile Tyr Ser Gln Phe Phe Pro Gln Gly Asp Ser
        115                 120                 125

agc aac tat gct act ttt ctc ttc aat gcc ttt gac acc aac cac gat      433
Ser Asn Tyr Ala Thr Phe Leu Phe Asn Ala Phe Asp Thr Asn His Asp
    130                 135                 140

ggc tct gtc agt ttt gag gac ttt gtg gct ggt ttg tcg gtg att ctt      481
Gly Ser Val Ser Phe Glu Asp Phe Val Ala Gly Leu Ser Val Ile Leu
145                 150                 155                 160

cgg ggg acc ata gat gat aga ctg agc tgg gct ttc aac tta tat gac      529
Arg Gly Thr Ile Asp Asp Arg Leu Ser Trp Ala Phe Asn Leu Tyr Asp
                165                 170                 175

ctc aac aag gac ggc tgt atc aca aag gag gaa atg ctt gac att atg      577
Leu Asn Lys Asp Gly Cys Ile Thr Lys Glu Glu Met Leu Asp Ile Met
            180                 185                 190

aag tcc atc tat gac atg atg ggc aag tac aca tac cct gcc ctc cgg      625
Lys Ser Ile Tyr Asp Met Met Gly Lys Tyr Thr Tyr Pro Ala Leu Arg
        195                 200                 205

gag gag gcc cca aga gaa cac gtg gag agc ttc ttc cag aag atg gac      673
Glu Glu Ala Pro Arg Glu His Val Glu Ser Phe Phe Gln Lys Met Asp
    210                 215                 220

agg aac aag gac ggc gtg gtg acc atc gag gaa ttc atc gag tct tgt      721
Arg Asn Lys Asp Gly Val Val Thr Ile Glu Glu Phe Ile Glu Ser Cys
225                 230                 235                 240

caa cag gac gag aac atc atg agg tcc atg cag ctc ttt gat aat gtc      769
Gln Gln Asp Glu Asn Ile Met Arg Ser Met Gln Leu Phe Asp Asn Val
                245                 250                 255

atc tagctcccca gggagagggg ttagtgtgtc ctagggtgac caggctgtag           822
Ile

tcctagtcca gacgaaccta accctctctc tccaggcctg tcctcatctt acctgtaccc    882

tgggggctgt agggattcaa tatcctgggg cttcagtagt ccagatccct gagctaagtc    942

acaaaagtag gcaagagtag gcaagctaaa tctgggggct tcccaacccc cgacagctct   1002

caccccttct caactgatac ctagtgctga ggacacccct ggtgtaggga ccaagtggtt   1062

ctccaccttc tagtcccact ctagaaacca cattagacag aaggtctcct gctatggtgc   1122

tttccccatc cctaatctct tagattttcc tcaagactcc cttctcagag aacacgctct   1182

gtccatgtcc ccagctgggg acatggacag agcgtgttct ctagttctag atcgcgagcg   1242

gccgc                                                                 1247


<210> SEQ ID NO 16
<211> LENGTH: 257
<212> TYPE: PRT
<213> ORGANISM: Rattus sp.

<400> SEQUENCE: 16

Arg Asp Leu Asp Gly Ser Tyr Asp Gln Leu Thr Gly His Pro Pro Gly
  1               5                  10                  15

Pro Ser Lys Lys Ala Leu Lys Gln Arg Phe Leu Lys Leu Leu Pro Cys
            20                  25                  30

Cys Gly Pro Gln Ala Leu Pro Ser Val Ser Glu Thr Leu Ala Ala Pro
        35                  40                  45

Ala Ser Leu Arg Pro His Arg Pro Arg Pro Leu Asp Pro Asp Ser Val
    50                  55                  60

Glu Asp Glu Phe Glu Leu Ser Thr Val Cys His Arg Pro Glu Gly Leu
 65                  70                  75                  80
```

-continued

```
Glu Gln Leu Gln Glu Gln Thr Lys Phe Thr Arg Arg Glu Leu Gln Val
                85                  90                  95

Leu Tyr Arg Gly Phe Lys Asn Glu Cys Pro Ser Gly Ile Val Asn Glu
            100                 105                 110

Glu Asn Phe Lys Gln Ile Tyr Ser Gln Phe Phe Pro Gln Gly Asp Ser
        115                 120                 125

Ser Asn Tyr Ala Thr Phe Leu Phe Asn Ala Phe Asp Thr Asn His Asp
    130                 135                 140

Gly Ser Val Ser Phe Glu Asp Phe Val Ala Gly Leu Ser Val Ile Leu
145                 150                 155                 160

Arg Gly Thr Ile Asp Asp Arg Leu Ser Trp Ala Phe Asn Leu Tyr Asp
                165                 170                 175

Leu Asn Lys Asp Gly Cys Ile Thr Lys Glu Glu Met Leu Asp Ile Met
            180                 185                 190

Lys Ser Ile Tyr Asp Met Met Gly Lys Tyr Thr Tyr Pro Ala Leu Arg
        195                 200                 205

Glu Glu Ala Pro Arg Glu His Val Glu Ser Phe Phe Gln Lys Met Asp
    210                 215                 220

Arg Asn Lys Asp Gly Val Val Thr Ile Glu Glu Phe Ile Glu Ser Cys
225                 230                 235                 240

Gln Gln Asp Glu Asn Ile Met Arg Ser Met Gln Leu Phe Asp Asn Val
                245                 250                 255

Ile


<210> SEQ ID NO 17
<211> LENGTH: 2343
<212> TYPE: DNA
<213> ORGANISM: Mus musculus
<220> FEATURE:
<221> NAME/KEY: CDS
<222> LOCATION: (181)..(990)

<400> SEQUENCE: 17

cgggactctg aggtgggccc taaaatccag cgctccccag agaaaagcct tgccagcccc      60

tactcccggc ccccagcccc agcaggtcgc tgcgccgcca gggggcactg tgtgagcgcc     120

ctatcctggc cacccggcgc cccctcccac ggcccaggcg ggagcggggc gccgggggcc     180

atg cgg ggc caa ggc cga aag gag agt ttg tcc gaa tcc cga gat ttg       228
Met Arg Gly Gln Gly Arg Lys Glu Ser Leu Ser Glu Ser Arg Asp Leu
  1               5                  10                  15

gac ggc tcc tat gac cag ctt acg ggc cac cct cca ggg ccc agt aaa       276
Asp Gly Ser Tyr Asp Gln Leu Thr Gly His Pro Pro Gly Pro Ser Lys
             20                  25                  30

aaa gcc ctg aag cag cgt ttc ctc aag ctg ctg ccg tgc tgc ggg ccc       324
Lys Ala Leu Lys Gln Arg Phe Leu Lys Leu Leu Pro Cys Cys Gly Pro
         35                  40                  45

caa gcc ctg ccc tca gtc agt gaa aca tta gct gcc cca gcc tcc ctc       372
Gln Ala Leu Pro Ser Val Ser Glu Thr Leu Ala Ala Pro Ala Ser Leu
     50                  55                  60

cgc ccc cac aga ccc cgc ccg ctg gac cca gac agc gtg gag gat gag       420
Arg Pro His Arg Pro Arg Pro Leu Asp Pro Asp Ser Val Glu Asp Glu
 65                  70                  75                  80

ttt gaa cta tcc acg gtg tgc cac cgg cct gag ggt ctg gaa caa ctc       468
Phe Glu Leu Ser Thr Val Cys His Arg Pro Glu Gly Leu Glu Gln Leu
                 85                  90                  95

cag gaa caa acc aag ttc aca cgc aga gag ttg cag gtc ctg tac aga       516
Gln Glu Gln Thr Lys Phe Thr Arg Arg Glu Leu Gln Val Leu Tyr Arg
```

-continued

```
            100                 105                 110

ggc ttc aag aac gaa tgt ccc agc gga att gtc aac gag gag aac ttc      564
Gly Phe Lys Asn Glu Cys Pro Ser Gly Ile Val Asn Glu Glu Asn Phe
        115                 120                 125

aag caa att tat tct cag ttc ttt ccc caa gga gac tcc agc aac tac      612
Lys Gln Ile Tyr Ser Gln Phe Phe Pro Gln Gly Asp Ser Ser Asn Tyr
    130                 135                 140

gct act ttt ctc ttc aat gcc ttt gac acc aac cat gat ggc tct gtc      660
Ala Thr Phe Leu Phe Asn Ala Phe Asp Thr Asn His Asp Gly Ser Val
145                 150                 155                 160

agt ttt gag gac ttt gtg gct ggt ttg tca gtg att ctt cgg gga acc      708
Ser Phe Glu Asp Phe Val Ala Gly Leu Ser Val Ile Leu Arg Gly Thr
                165                 170                 175

ata gat gat aga ctg aac tgg gct ttc aac tta tat gac ctc aac aag      756
Ile Asp Asp Arg Leu Asn Trp Ala Phe Asn Leu Tyr Asp Leu Asn Lys
            180                 185                 190

gat ggc tgt atc acg aag gag gaa atg ctc gac atc atg aag tcc atc      804
Asp Gly Cys Ile Thr Lys Glu Glu Met Leu Asp Ile Met Lys Ser Ile
        195                 200                 205

tat gac atg atg ggc aag tac acc tac cct gcc ctc cgg gag gag gcc      852
Tyr Asp Met Met Gly Lys Tyr Thr Tyr Pro Ala Leu Arg Glu Glu Ala
    210                 215                 220

ccg agg gaa cac gtg gag agc ttc ttc cag aag atg gac aga aac aag      900
Pro Arg Glu His Val Glu Ser Phe Phe Gln Lys Met Asp Arg Asn Lys
225                 230                 235                 240

gac ggc gtg gtg acc att gag gaa ttc att gag tct tgt caa cag gac      948
Asp Gly Val Val Thr Ile Glu Glu Phe Ile Glu Ser Cys Gln Gln Asp
                245                 250                 255

gag aac atc atg agg tcc atg caa ctc ttt gat aat gtc atc              990
Glu Asn Ile Met Arg Ser Met Gln Leu Phe Asp Asn Val Ile
            260                 265                 270

tagctcccca gggagagggg ttagtgtgtc ccagggtaac catgctgtag ccctagtcca   1050

ggcaaaccta accctcctct ccccgggtct gtcctcatcc tacctgtacc ctgggggctg   1110

tagggattca acatcctggc gcttcagtag tccagatccc tgagctaagt ggcgagagta   1170

ggcaagctaa gtctttggag ggtgggtggg ggcgcgcaga ttcccaaccc ccgacgactc   1230

tcaccccttt ctcgactgat acccagtgct gaggctaccc ctggtgtcgg gaacgaccaa   1290

agtggttctc tgcctcccca gcccactcta gagacccaca ctagacggga atatctcctg   1350

ctatggtgct ttccccatcc ctgaccgcag attttcctcc taagactccc ttctcagaga   1410

atatgctttt gtcccttgtc cctggctggc ttttcagcct agcctttgag gaccctgtgg   1470

gaggggagaa taagaaagca gacaaaatct tggccctgag ccagtggtta ggtcctagga   1530

atcaggctgg agtggagacc agaaagcctg ggcaggctat gagagcccca ggttggcttg   1590

tcaccgccag gttccacagg gctgctgctc tgggtcagca gagtatgagt ttccagactt   1650

tccagaaggc cttatgtcct tagcaatgtc ccagaaattc accatacact tctcagtgtc   1710

ttaggatcca gatgtccggt ccatccctga aacctctccc tcctccttgc tcctatggtg   1770

ggagtggtgg ccaggggacg atgagtgagc cggtgtcctg gatgatgcct gtcaaggtcc   1830

cacctaccct ccggctgtca agccgttctg gtgaccctgt ttgattctcc atgacccctg   1890

tctagatgta gaggtgtgga gtgagtctag tggcagcctt aggggaatgg gaagaacgag   1950

aggggcactc catctgaacc cagtgtgggg gcatccattc gaatctttgc ctggctcccc   2010

acaatgccct aggatcctct agggtcccca cccccactct ttagtctacc cagagatgct   2070

ccagagctca cctagagggc agggaccata ggatccaggt ccaacctgtc atcagcatcc   2130
```

-continued ggccatgctg ctgctgctta ttaataaacc tgcttgtcgt tcagcgcccc ttcccagtca 2190
gccagggtct gaggggaagg cccccacttt cccgcctcct gtcagacatt gttgactgct 2250
ttgcattttg ggctcttcta cctatatttt gtataataag aaagacacca gatccaataa 2310
aacacatggc tatgcacaaa aaaaaaaaaa aaa 2343

<210> SEQ ID NO 18
<211> LENGTH: 270
<212> TYPE: PRT
<213> ORGANISM: Mus musculus

<400> SEQUENCE: 18

```
Met Arg Gly Gln Gly Arg Lys Glu Ser Leu Ser Glu Ser Arg Asp Leu
  1               5                  10                  15

Asp Gly Ser Tyr Asp Gln Leu Thr Gly His Pro Pro Gly Pro Ser Lys
             20                  25                  30

Lys Ala Leu Lys Gln Arg Phe Leu Lys Leu Leu Pro Cys Cys Gly Pro
         35                  40                  45

Gln Ala Leu Pro Ser Val Ser Glu Thr Leu Ala Ala Pro Ala Ser Leu
     50                  55                  60

Arg Pro His Arg Pro Arg Pro Leu Asp Pro Asp Ser Val Glu Asp Glu
 65                  70                  75                  80

Phe Glu Leu Ser Thr Val Cys His Arg Pro Glu Gly Leu Glu Gln Leu
                 85                  90                  95

Gln Glu Gln Thr Lys Phe Thr Arg Arg Glu Leu Gln Val Leu Tyr Arg
            100                 105                 110

Gly Phe Lys Asn Glu Cys Pro Ser Gly Ile Val Asn Glu Glu Asn Phe
        115                 120                 125

Lys Gln Ile Tyr Ser Gln Phe Phe Pro Gln Gly Asp Ser Ser Asn Tyr
    130                 135                 140

Ala Thr Phe Leu Phe Asn Ala Phe Asp Thr Asn His Asp Gly Ser Val
145                 150                 155                 160

Ser Phe Glu Asp Phe Val Ala Gly Leu Ser Val Ile Leu Arg Gly Thr
                165                 170                 175

Ile Asp Asp Arg Leu Asn Trp Ala Phe Asn Leu Tyr Asp Leu Asn Lys
            180                 185                 190

Asp Gly Cys Ile Thr Lys Glu Glu Met Leu Asp Ile Met Lys Ser Ile
        195                 200                 205

Tyr Asp Met Met Gly Lys Tyr Thr Tyr Pro Ala Leu Arg Glu Glu Ala
    210                 215                 220

Pro Arg Glu His Val Glu Ser Phe Phe Gln Lys Met Asp Arg Asn Lys
225                 230                 235                 240

Asp Gly Val Val Thr Ile Glu Glu Phe Ile Glu Ser Cys Gln Gln Asp
                245                 250                 255

Glu Asn Ile Met Arg Ser Met Gln Leu Phe Asp Asn Val Ile
            260                 265                 270
```

<210> SEQ ID NO 19
<211> LENGTH: 1955
<212> TYPE: DNA
<213> ORGANISM: Homo sapiens
<220> FEATURE:
<221> NAME/KEY: CDS
<222> LOCATION: (207)..(962)

<400> SEQUENCE: 19

-continued

```
ctcacctgct gcctagtgtt ccctctcctg ctccaggacc tccgggtaga cctcagaccc     60

cgggcccatt cccagactca gcctcagccc ggacttcccc agccccgaca gcacagtagg    120

ccgccagggg gcgccgtgtg agcgccctat cccggccacc cggcgccccc tcccacggcc    180

cgggcgggag cggggcgccg ggggcc atg cgg ggc cag ggc cgc aag gag agt     233
                             Met Arg Gly Gln Gly Arg Lys Glu Ser
                                         1               5

ttg tcc gat tcc cga gac ctg gac ggc tcc tac gac cag ctc acg ggc      281
Leu Ser Asp Ser Arg Asp Leu Asp Gly Ser Tyr Asp Gln Leu Thr Gly
 10                  15                  20                  25

cac cct cca ggg ccc act aaa aaa gcg ctg aag cag cga ttc ctc aag      329
His Pro Pro Gly Pro Thr Lys Lys Ala Leu Lys Gln Arg Phe Leu Lys
                 30                  35                  40

ctg ctg ccg tgc tgc ggg ccc caa gcc ctg ccc tca gtc agt gaa aac      377
Leu Leu Pro Cys Cys Gly Pro Gln Ala Leu Pro Ser Val Ser Glu Asn
             45                  50                  55

agc gtg gac gat gaa ttt gaa ttg tcc acc gtg tgt cac cgg cct gag      425
Ser Val Asp Asp Glu Phe Glu Leu Ser Thr Val Cys His Arg Pro Glu
         60                  65                  70

ggt ctg gag cag ctg cag gag caa acc aaa ttc acg cgc aag gag ttg      473
Gly Leu Glu Gln Leu Gln Glu Gln Thr Lys Phe Thr Arg Lys Glu Leu
     75                  80                  85

cag gtc ctg tac cgg ggc ttc aag aac gaa tgt ccc agc gga att gtc      521
Gln Val Leu Tyr Arg Gly Phe Lys Asn Glu Cys Pro Ser Gly Ile Val
 90                  95                 100                 105

aat gag gag aac ttc aag cag att tac tcc cag ttc ttt cct caa gga      569
Asn Glu Glu Asn Phe Lys Gln Ile Tyr Ser Gln Phe Phe Pro Gln Gly
                110                 115                 120

gac tcc agc acc tat gcc act ttt ctc ttc aat gcc ttt gac acc aac      617
Asp Ser Ser Thr Tyr Ala Thr Phe Leu Phe Asn Ala Phe Asp Thr Asn
            125                 130                 135

cat gat ggc tcg gtc agt ttt gag gac ttt gtg gct ggt ttg tcc gtg      665
His Asp Gly Ser Val Ser Phe Glu Asp Phe Val Ala Gly Leu Ser Val
        140                 145                 150

att ctt cgg gga act gta gat gac agg ctt aat tgg gcc ttc aac ctg      713
Ile Leu Arg Gly Thr Val Asp Asp Arg Leu Asn Trp Ala Phe Asn Leu
    155                 160                 165

tat gac ctt aac aag gac ggc tgc atc acc aag gag gaa atg ctt gac      761
Tyr Asp Leu Asn Lys Asp Gly Cys Ile Thr Lys Glu Glu Met Leu Asp
170                 175                 180                 185

atc atg aag tcc atc tat gac atg atg ggc aag tac acg tac cct gca      809
Ile Met Lys Ser Ile Tyr Asp Met Met Gly Lys Tyr Thr Tyr Pro Ala
                190                 195                 200

ctc cgg gag gag gcc cca agg gaa cac gtg gag agc ttc ttc cag aag      857
Leu Arg Glu Glu Ala Pro Arg Glu His Val Glu Ser Phe Phe Gln Lys
            205                 210                 215

atg gac aga aac aag gat ggt gtg gtg acc att gag gaa ttc att gag      905
Met Asp Arg Asn Lys Asp Gly Val Val Thr Ile Glu Glu Phe Ile Glu
        220                 225                 230

tct tgt caa aag gat gag aac atc atg agg tcc atg cag ctc ttt gac      953
Ser Cys Gln Lys Asp Glu Asn Ile Met Arg Ser Met Gln Leu Phe Asp
    235                 240                 245

aat gtc atc tagcccccag gagagggggt cagtgtttcc tggggggacc             1002
Asn Val Ile
250

atgctctaac cctagtccag gcggacctca cccttctctt cccaggtcta tcctcatcct   1062

acgcctccct gggggctgga gggatccaag agcttgggga ttcagtagtc cagatctctg   1122

gagctgaagg ggccagagag tgggcagagt gcatctcggg ggtgttccc aactcccacc    1182
```

-continued agctctcacc cccttcctgc ctgacaccca gtgttgagag tgcccctcct gtaggaattg 1242 agcggttccc cacctcctac cctactctag aaacacacta gagcgatgtc tcctgctatg 1302 gtgcttcccc catccctgac ctcataaaca tttcccctaa gactcccctc tcagagagaa 1362 tgctccattc ttggcactgg ctggcttctc agaccagcca ttgagagccc tgtgggaggg 1422 ggacaagaat gtatagggag aaatcttggg cctgagtcaa tggataggtc ctaggaggtg 1482 ggtggggttg agaatagaag ggcctggaca gattatgatt gctcaggcat accaggttat 1542 agctccaagt tccacaggtc tgctaccaca ggccatcaaa atataagttt ccaggctttg 1602 cagaagacct tgtctcctta gaaatgcccc agaaattttc cacaccctcc tcggtatcca 1662 tggagagcct ggggccagat atctggctca tctctggcat tgcttcctct ccttccttcc 1722 tgcatgtgtt ggtggtggtt gtggtggggg aatgtggatg ggggatgtcc tggctgatgc 1782 ctgccaaaat ttcatcccac cctccttgct tatcgtccct gttttgaggg ctatgacttg 1842 agtttttgtt tcccatgttc tctatagact tgggaccttc ctgaacttgg ggcctatcac 1902 tccccacagt ggatgcctta gaagggagag ggaaggaggg aggcaggcat agc 1955

<210> SEQ ID NO 20
<211> LENGTH: 252
<212> TYPE: PRT
<213> ORGANISM: Homo sapiens

<400> SEQUENCE: 20

Met Arg Gly Gln Gly Arg Lys Glu Ser Leu Ser Asp Ser Arg Asp Leu
1 5 10 15

Asp Gly Ser Tyr Asp Gln Leu Thr Gly His Pro Pro Gly Pro Thr Lys
20 25 30

Lys Ala Leu Lys Gln Arg Phe Leu Lys Leu Leu Pro Cys Cys Gly Pro
35 40 45

Gln Ala Leu Pro Ser Val Ser Glu Asn Ser Val Asp Asp Glu Phe Glu
50 55 60

Leu Ser Thr Val Cys His Arg Pro Glu Gly Leu Glu Gln Leu Gln Glu
65 70 75 80

Gln Thr Lys Phe Thr Arg Lys Glu Leu Gln Val Leu Tyr Arg Gly Phe
85 90 95

Lys Asn Glu Cys Pro Ser Gly Ile Val Asn Glu Glu Asn Phe Lys Gln
100 105 110

Ile Tyr Ser Gln Phe Phe Pro Gln Gly Asp Ser Ser Thr Tyr Ala Thr
115 120 125

Phe Leu Phe Asn Ala Phe Asp Thr Asn His Asp Gly Ser Val Ser Phe
130 135 140

Glu Asp Phe Val Ala Gly Leu Ser Val Ile Leu Arg Gly Thr Val Asp
145 150 155 160

Asp Arg Leu Asn Trp Ala Phe Asn Leu Tyr Asp Leu Asn Lys Asp Gly
165 170 175

Cys Ile Thr Lys Glu Glu Met Leu Asp Ile Met Lys Ser Ile Tyr Asp
180 185 190

Met Met Gly Lys Tyr Thr Tyr Pro Ala Leu Arg Glu Glu Ala Pro Arg
195 200 205

Glu His Val Glu Ser Phe Phe Gln Lys Met Asp Arg Asn Lys Asp Gly
210 215 220

Val Val Thr Ile Glu Glu Phe Ile Glu Ser Cys Gln Lys Asp Glu Asn
225 230 235 240

-continued

```
Ile Met Arg Ser Met Gln Leu Phe Asp Asn Val Ile
            245                 250


<210> SEQ ID NO 21
<211> LENGTH: 2300
<212> TYPE: DNA
<213> ORGANISM: Rattus sp.
<220> FEATURE:
<221> NAME/KEY: CDS
<222> LOCATION: (214)..(969)

<400> SEQUENCE: 21

ctcacttgct gcccaaggct cctgctcctg ccccaggact ctgaggtggg ccctaaaacc      60

cagcgctctc taaagaaaag ccttgccagc ccctactccc ggcccccaac cccagcaggt     120

cgctgcgccg ccagggggcg ctgtgtgagc gccctattct ggccacccgg cgccccctcc     180

cacggcccag gcgggagcgg ggcgccgggg gcc atg cgg ggc caa ggc aga aag      234
                                     Met Arg Gly Gln Gly Arg Lys
                                       1               5

gag agt ttg tcc gaa tcc cga gat ctg gac ggc tcc tat gac cag ctt      282
Glu Ser Leu Ser Glu Ser Arg Asp Leu Asp Gly Ser Tyr Asp Gln Leu
        10                  15                  20

acg ggc cac cct cca ggg ccc agt aaa aaa gcc ctg aag cag cgt ttc      330
Thr Gly His Pro Pro Gly Pro Ser Lys Lys Ala Leu Lys Gln Arg Phe
    25                  30                  35

ctc aag ctg ctg ccg tgc tgc ggg ccc caa gcc ctg ccc tca gtc agt      378
Leu Lys Leu Leu Pro Cys Cys Gly Pro Gln Ala Leu Pro Ser Val Ser
 40                  45                  50                  55

gaa aac agc gta gag gat gag ttt gaa tta tcc acg gtg tgt cac cga      426
Glu Asn Ser Val Glu Asp Glu Phe Glu Leu Ser Thr Val Cys His Arg
                60                  65                  70

cct gag ggc ctg gaa caa ctc cag gaa cag acc aag ttc aca cgc aga      474
Pro Glu Gly Leu Glu Gln Leu Gln Glu Gln Thr Lys Phe Thr Arg Arg
            75                  80                  85

gag ctg cag gtc ctg tac cga ggc ttc aag aac gaa tgc ccc agt ggg      522
Glu Leu Gln Val Leu Tyr Arg Gly Phe Lys Asn Glu Cys Pro Ser Gly
        90                  95                 100

att gtc aac gag gag aac ttc aag cag att tat tct cag ttc ttt ccc      570
Ile Val Asn Glu Glu Asn Phe Lys Gln Ile Tyr Ser Gln Phe Phe Pro
    105                 110                 115

caa gga gac tcc agc aac tat gct act ttt ctc ttc aat gcc ttt gac      618
Gln Gly Asp Ser Ser Asn Tyr Ala Thr Phe Leu Phe Asn Ala Phe Asp
120                 125                 130                 135

acc aac cac gat ggc tct gtc agt ttt gag gac ttt gtg gct ggt ttg      666
Thr Asn His Asp Gly Ser Val Ser Phe Glu Asp Phe Val Ala Gly Leu
                140                 145                 150

tcg gtg att ctt cgg ggg acc ata gat gat aga ctg agc tgg gct ttc      714
Ser Val Ile Leu Arg Gly Thr Ile Asp Asp Arg Leu Ser Trp Ala Phe
            155                 160                 165

aac tta tat gac ctc aac aag gac ggc tgt atc aca aag gag gaa atg      762
Asn Leu Tyr Asp Leu Asn Lys Asp Gly Cys Ile Thr Lys Glu Glu Met
        170                 175                 180

ctt gac att atg aag tcc atc tat gac atg atg ggc aag tac aca tac      810
Leu Asp Ile Met Lys Ser Ile Tyr Asp Met Met Gly Lys Tyr Thr Tyr
    185                 190                 195

cct gcc ctc cgg gag gag gcc cca aga gaa cac gtg gag agc ttc ttc      858
Pro Ala Leu Arg Glu Glu Ala Pro Arg Glu His Val Glu Ser Phe Phe
200                 205                 210                 215

cag aag atg gac agg aac aag gac ggc gtg gtg acc atc gag gaa ttc      906
Gln Lys Met Asp Arg Asn Lys Asp Gly Val Val Thr Ile Glu Glu Phe
```

-continued

```
            220                 225                 230

atc gag tct tgt caa cag gac gag aac atc atg agg tcc atg cag ctc      954
Ile Glu Ser Cys Gln Gln Asp Glu Asn Ile Met Arg Ser Met Gln Leu
            235                 240                 245

ttt gat aat gtc atc tagctcccca gggagagggg ttagtgtgtc ctagggtgac     1009
Phe Asp Asn Val Ile
        250

caggctgtag tcctagtcca gacgaaccta accctctctc tccaggcctg tcctcatctt   1069

acctgtaccc tgggggctgt agggattcaa tatcctgggg cttcagtagt ccagatccct   1129

gagctaagtc acaaaagtag gcaagagtag gcaagctaaa tctgggggct tcccaacccc   1189

cgacagctct caccccttct caactgatac ctagtgctga ggacacccct ggtgtaggga   1249

ccaagtggtt ctccaccttc tagtcccact ctagaaacca cattagacag aaggtctcct   1309

gctatggtgc tttccccatc cctaatctct tagattttcc tcaagactcc cttctcagag   1369

aacacgctct gtccatgtcc ccagctggct tctcagccta gcctttgagg gccctgtggg   1429

gaggcgggga caagaaagca gaaaagtctt ggccccgagc cagtggttag gtcctaggaa   1489

ttggctggag tggaggccag aaagcctggg cagatgatga gagcccagct gggctgtcac   1549

tgcaggttcc ggggcctaca gccctgggtc agcagagtat gagttcccag actttccaga   1609

aggtccttag caatgtccca gaaattcacc gtacacttct cagtgtctta ggagggcccg   1669

ggatccagat gtctggttca tccctgaatc ctctccctcc ttcttgctcg tatggtggga   1729

gtggtggcca ggggaagatg agtggtgtcc cggatgatgc ctgtcaaggt cccacctccc   1789

ctccggctgt tctcatgaca gctgtttggt tctccatgac ccctatctag atgtagaggc   1849

atggagtgag tcagggattt cccgaacttg agttttacca ctcctcctag tggctgcctt   1909

aggggaatgg gaagaaccca gtgtgggggc acccattaga atctttgccc ggctcctcac   1969

aatgccctag ggtcccctag ggtacccgct ccctctgttt agtctaccca gagatgctcc   2029

tgagctcacc tagagggtag ggacggtagg ctccaggtcc aacctctcca ggtcagcacc   2089

ctgccatgct gctgctcctc attaacaaac ctgcttgtct cctcctgcgc cccttctcag   2149

tcagccaggg tctgagggga agggcctccc gtttccccat ccgtcagaca tggttgactg   2209

ctttgcattt tgggctcttc tatctatttt gtaaaataag acatcagatc caataaaaca   2269

cacggctatg cacaaaaaaa aaaaaaaaaa a                                  2300


<210> SEQ ID NO 22
<211> LENGTH: 252
<212> TYPE: PRT
<213> ORGANISM: Rattus sp.

<400> SEQUENCE: 22

Met Arg Gly Gln Gly Arg Lys Glu Ser Leu Ser Glu Ser Arg Asp Leu
  1               5                  10                  15

Asp Gly Ser Tyr Asp Gln Leu Thr Gly His Pro Pro Gly Pro Ser Lys
             20                  25                  30

Lys Ala Leu Lys Gln Arg Phe Leu Lys Leu Leu Pro Cys Cys Gly Pro
         35                  40                  45

Gln Ala Leu Pro Ser Val Ser Glu Asn Ser Val Glu Asp Glu Phe Glu
     50                  55                  60

Leu Ser Thr Val Cys His Arg Pro Glu Gly Leu Glu Gln Leu Gln Glu
 65                  70                  75                  80

Gln Thr Lys Phe Thr Arg Arg Glu Leu Gln Val Leu Tyr Arg Gly Phe
                 85                  90                  95
```

-continued

```
Lys Asn Glu Cys Pro Ser Gly Ile Val Asn Glu Glu Asn Phe Lys Gln
            100                 105                 110

Ile Tyr Ser Gln Phe Phe Pro Gln Gly Asp Ser Ser Asn Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220

Val Val Thr Ile Glu Glu Phe Ile Glu Ser Cys Gln Gln Asp Glu Asn
225                 230                 235                 240

Ile Met Arg Ser Met Gln Leu Phe Asp Asn Val Ile
                245                 250


<210> SEQ ID NO 23
<211> LENGTH: 1859
<212> TYPE: DNA
<213> ORGANISM: Homo sapiens
<220> FEATURE:
<221> NAME/KEY: CDS
<222> LOCATION: (207)..(866)

<400> SEQUENCE: 23

ctcacctgct gcctagtgtt ccctctcctg ctccaggacc tccgggtaga cctcagaccc    60

cgggcccatt cccagactca gcctcagccc ggacttcccc agccccgaca gcacagtagg   120

ccgccagggg gcgccgtgtg agcgccctat cccggccacc cggcgccccc tcccacggcc   180

cgggcgggag cggggcgccg ggggcc atg cgg ggc cag ggc cgc aag gag agt    233
                             Met Arg Gly Gln Gly Arg Lys Glu Ser
                               1               5

ttg tcc gat tcc cga gac ctg gac ggc tcc tac gac cag ctc acg gac     281
Leu Ser Asp Ser Arg Asp Leu Asp Gly Ser Tyr Asp Gln Leu Thr Asp
 10                  15                  20                  25

agc gtg gac gat gaa ttt gaa ttg tcc acc gtg tgt cac cgg cct gag     329
Ser Val Asp Asp Glu Phe Glu Leu Ser Thr Val Cys His Arg Pro Glu
                 30                  35                  40

ggt ctg gag cag ctg cag gag caa acc aaa ttc acg cgc aag gag ttg     377
Gly Leu Glu Gln Leu Gln Glu Gln Thr Lys Phe Thr Arg Lys Glu Leu
             45                  50                  55

cag gtc ctg tac cgg ggc ttc aag aac gaa tgt ccc agc gga att gtc     425
Gln Val Leu Tyr Arg Gly Phe Lys Asn Glu Cys Pro Ser Gly Ile Val
         60                  65                  70

aat gag gag aac ttc aag cag att tac tcc cag ttc ttt cct caa gga     473
Asn Glu Glu Asn Phe Lys Gln Ile Tyr Ser Gln Phe Phe Pro Gln Gly
     75                  80                  85

gac tcc agc acc tat gcc act ttt ctc ttc aat gcc ttt gac acc aac     521
Asp Ser Ser Thr Tyr Ala Thr Phe Leu Phe Asn Ala Phe Asp Thr Asn
90                  95                 100                 105

cat gat ggc tcg gtc agt ttt gag gac ttt gtg gct ggt ttg tcc gtg     569
His Asp Gly Ser Val Ser Phe Glu Asp Phe Val Ala Gly Leu Ser Val
                110                 115                 120
```

-continued

```
att ctt cgg gga act gta gat gac agg ctt aat tgg gcc ttc aac ctg      617
Ile Leu Arg Gly Thr Val Asp Asp Arg Leu Asn Trp Ala Phe Asn Leu
            125                 130                 135

tat gac ctt aac aag gac ggc tgc atc acc aag gag gaa atg ctt gac      665
Tyr Asp Leu Asn Lys Asp Gly Cys Ile Thr Lys Glu Glu Met Leu Asp
        140                 145                 150

atc atg aag tcc atc tat gac atg atg ggc aag tac acg tac cct gca      713
Ile Met Lys Ser Ile Tyr Asp Met Met Gly Lys Tyr Thr Tyr Pro Ala
    155                 160                 165

ctc cgg gag gag gcc cca agg gaa cac gtg gag agc ttc ttc cag aag      761
Leu Arg Glu Glu Ala Pro Arg Glu His Val Glu Ser Phe Phe Gln Lys
170                 175                 180                 185

atg gac aga aac aag gat ggt gtg gtg acc att gag gaa ttc att gag      809
Met Asp Arg Asn Lys Asp Gly Val Val Thr Ile Glu Glu Phe Ile Glu
                190                 195                 200

tct tgt caa aag gat gag aac atc atg agg tcc atg cag ctc ttt gac      857
Ser Cys Gln Lys Asp Glu Asn Ile Met Arg Ser Met Gln Leu Phe Asp
            205                 210                 215

aat gtc atc tagcccccag gagagggggt cagtgtttcc tgggggggacc             906
Asn Val Ile
        220

atgctctaac cctagtccag gcggacctca cccttctctt cccaggtcta tcctcatcct    966

acgcctccct gggggctgga gggatccaag agcttgggga ttcagtagtc cagatctctg   1026

gagctgaagg ggccagagag tgggcagagt gcatctcggg gggtgttccc aactcccacc   1086

agctctcacc cccttcctgc ctgacaccca gtgttgagag tgcccctcct gtaggaattg   1146

agcggttccc cacctcctac cctactctag aaacacacta gagcgatgtc tcctgctatg   1206

gtgcttcccc catccctgac ctcataaaca tttccccta a gactcccctc tcagagagaa  1266

tgctccattc ttggcactgg ctggcttctc agaccagcca ttgagagccc tgtgggaggg   1326

ggacaagaat gtatagggag aaatcttggg cctgagtcaa tggataggtc ctaggaggtg   1386

ggtggggttg agaatagaag ggcctggaca gattatgatt gctcaggcat accaggttat   1446

agctccaagt tccacaggtc tgctaccaca ggccatcaaa atataagttt ccaggctttg   1506

cagaagacct tgtctcctta gaaatgcccc agaaatttc cacaccctcc tcggtatcca   1566

tggagagcct ggggccagat atctggctca tctctggcat tgcttcctct ccttccttcc   1626

tgcatgtgtt ggtggtggtt gtggtggggg aatgtggatg ggggatgtcc tggctgatgc   1686

ctgccaaaat ttcatcccac cctccttgct tatcgtccct gttttgaggg ctatgacttg   1746

agtttttgtt tcccatgttc tctatagact tgggaccttc ctgaacttgg ggcctatcac   1806

tccccacagt ggatgcctta gaagggagag ggaaggaggg aggcaggcat agc          1859


<210> SEQ ID NO 24
<211> LENGTH: 220
<212> TYPE: PRT
<213> ORGANISM: Homo sapiens

<400> SEQUENCE: 24

Met Arg Gly Gln Gly Arg Lys Glu Ser Leu Ser Asp Ser Arg Asp Leu
  1               5                  10                  15

Asp Gly Ser Tyr Asp Gln Leu Thr Asp Ser Val Asp Asp Glu Phe Glu
             20                  25                  30

Leu Ser Thr Val Cys His Arg Pro Glu Gly Leu Glu Gln Leu Gln Glu
         35                  40                  45

Gln Thr Lys Phe Thr Arg Lys Glu Leu Gln Val Leu Tyr Arg Gly Phe
```

-continued

```
    50                  55                  60

Lys Asn Glu Cys Pro Ser Gly Ile Val Asn Glu Glu Asn Phe Lys Gln
 65                 70                  75                  80

Ile Tyr Ser Gln Phe Phe Pro Gln Gly Asp Ser Ser Thr Tyr Ala Thr
                85                  90                  95

Phe Leu Phe Asn Ala Phe Asp Thr Asn His Asp Gly Ser Val Ser Phe
            100                 105                 110

Glu Asp Phe Val Ala Gly Leu Ser Val Ile Leu Arg Gly Thr Val Asp
        115                 120                 125

Asp Arg Leu Asn Trp Ala Phe Asn Leu Tyr Asp Leu Asn Lys Asp Gly
    130                 135                 140

Cys Ile Thr Lys Glu Glu Met Leu Asp Ile Met Lys Ser Ile Tyr Asp
145                 150                 155                 160

Met Met Gly Lys Tyr Thr Tyr Pro Ala Leu Arg Glu Glu Ala Pro Arg
                165                 170                 175

Glu His Val Glu Ser Phe Phe Gln Lys Met Asp Arg Asn Lys Asp Gly
            180                 185                 190

Val Val Thr Ile Glu Glu Phe Ile Glu Ser Cys Gln Lys Asp Glu Asn
        195                 200                 205

Ile Met Arg Ser Met Gln Leu Phe Asp Asn Val Ile
    210                 215                 220


<210> SEQ ID NO 25
<211> LENGTH: 2191
<212> TYPE: DNA
<213> ORGANISM: Simian sp.
<220> FEATURE:
<221> NAME/KEY: CDS
<222> LOCATION: (133)..(792)

<400> SEQUENCE: 25

cccacgcgtc cgcccacgcg tccgcggacg cgtggggtgc actaggccgc caggggggcgc     60

cgtgtgagcg ccctatcccg gccacccggc gccccctccc acggaccggg cgggagcggg    120

gcgccggggg cc atg cgg ggc cag ggc cgc aag gag agt ttg tcc gat tcc    171
              Met Arg Gly Gln Gly Arg Lys Glu Ser Leu Ser Asp Ser
                1               5                   10

cga gac ctg gac gga tcc tac gac cag ctc acg gac agc gtg gag gat      219
Arg Asp Leu Asp Gly Ser Tyr Asp Gln Leu Thr Asp Ser Val Glu Asp
     15                  20                  25

gaa ttt gaa ttg tcc acc gtg tgt cac cgg cct gag ggt ctg gag cag      267
Glu Phe Glu Leu Ser Thr Val Cys His Arg Pro Glu Gly Leu Glu Gln
 30                 35                  40                  45

ctg cag gag caa acc aaa ttc acg cgc aag gag ttg cag gtc ctg tac      315
Leu Gln Glu Gln Thr Lys Phe Thr Arg Lys Glu Leu Gln Val Leu Tyr
                50                  55                  60

cgg ggc ttc aag aac gaa tgt ccg agc gga att gtc aat gag gag aac      363
Arg Gly Phe Lys Asn Glu Cys Pro Ser Gly Ile Val Asn Glu Glu Asn
            65                  70                  75

ttc aag caa att tac tcc cag ttc ttt cct caa gga gac tcc agc acc      411
Phe Lys Gln Ile Tyr Ser Gln Phe Phe Pro Gln Gly Asp Ser Ser Thr
        80                  85                  90

tat gcc act ttt ctc ttc aat gcc ttt gac acc aac cat gat ggc tcg      459
Tyr Ala Thr Phe Leu Phe Asn Ala Phe Asp Thr Asn His Asp Gly Ser
     95                 100                 105

gtc agt ttt gag gac ttt gtg gct ggt ttg tcc gtg att ctt cgg gga      507
Val Ser Phe Glu Asp Phe Val Ala Gly Leu Ser Val Ile Leu Arg Gly
110                 115                 120                 125
act gta gat gac agg ctt aat tgg gcc ttc aac ttg tat gac ctc aac      555
```

-continued

```
Thr Val Asp Asp Arg Leu Asn Trp Ala Phe Asn Leu Tyr Asp Leu Asn
                130                 135                 140

aag gac ggc tgc atc acc aag gag gaa atg ctt gac atc atg aag tcc      603
Lys Asp Gly Cys Ile Thr Lys Glu Glu Met Leu Asp Ile Met Lys Ser
            145                 150                 155

atc tat gac atg atg ggc aag tac aca tac cct gca ctc cgg gag gag      651
Ile Tyr Asp Met Met Gly Lys Tyr Thr Tyr Pro Ala Leu Arg Glu Glu
        160                 165                 170

gcc cca agg gaa cat gtg gag aac ttc ttc cag aag atg gac aga aac      699
Ala Pro Arg Glu His Val Glu Asn Phe Phe Gln Lys Met Asp Arg Asn
    175                 180                 185

aag gat ggc gtg gtg acc att gag gaa ttc att gag tct tgt caa aag      747
Lys Asp Gly Val Val Thr Ile Glu Glu Phe Ile Glu Ser Cys Gln Lys
190                 195                 200                 205

gat gag aac atc atg agg tcc atg cag ctc ttt gac aat gtc atc          792
Asp Glu Asn Ile Met Arg Ser Met Gln Leu Phe Asp Asn Val Ile
                210                 215                 220

tagcccccag gagagggggt cagtgtttcc tgggggggacc atgctctaac cctagtccag    852

gtggacctca cccttctctt cccaggtcta tccttgtcct aggcctccct gggggctgga    912

gggatccaag agcttgggga ttcagtagtc cagatctctg gagctgaagg ggccagagag    972

tgggcagagt gcatcttggg gggtgttccc aactcccacc agctttcacc cgcttcctgc   1032

ctgacaccca gtgttgagag tgcccctcct gtaggaactg agtggttccc cacctcctac   1092

ccccactcta gaaacacact agacagatgt ctcctgctat ggtgcttccc ccatccctga   1152

cttcataaac atttccccta aaactccctt ctcagagaga atgctccatt cttggcactg   1212

gctggcttct cagaccagcc tttgagagcc ctgtgggagg gggacaagaa tgtatagggg   1272

agaaatcttg ggcctgagtc aatggatagg tcctaggagg tggctggggt tgagaataga   1332

aaggcctgga cacaatgtga ttgctcaggc ataccaagtt atagctccaa gttccacagg   1392

tctgctacca caggccatca aaatataagt ttccaggctt tgcagaagac cttgtctcct   1452

tggaaatgcc ccagatattt tccataccct cctcgatatc catggagagc ctggggctag   1512

atatctggca tatccctggc attgcttcct ctccttcctt cctgcatgtg ttggtggtgg   1572

ttgtggcagg ggaatgtgga taggagatgt cctggcagat gcctgccaaa gtttcatccc   1632

accctccctg ctcatcgccc ctgttttgag ggctgtgact tgagtttttg tttcccatgt   1692

tctctataga cttgggacct tcctgaactt ggggcctatc actccccaca gtggatgcct   1752

tagaagggag agggaaggag ggaggcaggc atagcatctg aacccagtgt gggggcattc   1812

actaggatct tcaatcaacc cgggctctcc ccaacccccc agataacctc ctcagttccc   1872

tagagtctcc tcttgctcta ctcaatctac ccagagatgc cccttagcac actcagaggg   1932

cagggaccat aggacccagg ttccaacccc attgtcagca ccccagccat gctgccatcc   1992

cttagcacac ctgctcgtcc cattcagctt accctcccag tcagccagaa tctgagggga   2052

gggcccccag agagcccccct tccccatcag aagactgttg actgctttgc attttgggct   2112

cttctatata ttttgtaaaa taagaactat accagatcta ataaaacaca atggctatgc   2172

aaaaaaaaaa aaaaaaaaa                                                2191

<210> SEQ ID NO 26
<211> LENGTH: 220
<212> TYPE: PRT
<213> ORGANISM: Simian sp.

<400> SEQUENCE: 26
```

-continued

```
Met Arg Gly Gln Gly Arg Lys Glu Ser Leu Ser Asp Ser Arg Asp Leu
  1               5                  10                  15

Asp Gly Ser Tyr Asp Gln Leu Thr Asp Ser Val Glu Asp Glu Phe Glu
             20                  25                  30

Leu Ser Thr Val Cys His Arg Pro Glu Gly Leu Glu Gln Leu Gln Glu
         35                  40                  45

Gln Thr Lys Phe Thr Arg Lys Glu Leu Gln Val Leu Tyr Arg Gly Phe
     50                  55                  60

Lys Asn Glu Cys Pro Ser Gly Ile Val Asn Glu Glu Asn Phe Lys Gln
 65                  70                  75                  80

Ile Tyr Ser Gln Phe Phe Pro Gln Gly Asp Ser Ser Thr Tyr Ala Thr
                 85                  90                  95

Phe Leu Phe Asn Ala Phe Asp Thr Asn His Asp Gly Ser Val Ser Phe
            100                 105                 110

Glu Asp Phe Val Ala Gly Leu Ser Val Ile Leu Arg Gly Thr Val Asp
        115                 120                 125

Asp Arg Leu Asn Trp Ala Phe Asn Leu Tyr Asp Leu Asn Lys Asp Gly
    130                 135                 140

Cys Ile Thr Lys Glu Glu Met Leu Asp Ile Met Lys Ser Ile Tyr Asp
145                 150                 155                 160

Met Met Gly Lys Tyr Thr Tyr Pro Ala Leu Arg Glu Glu Ala Pro Arg
                165                 170                 175

Glu His Val Glu Asn Phe Phe Gln Lys Met Asp Arg Asn Lys Asp Gly
            180                 185                 190

Val Val Thr Ile Glu Glu Phe Ile Glu Ser Cys Gln Lys Asp Glu Asn
        195                 200                 205

Ile Met Arg Ser Met Gln Leu Phe Asp Asn Val Ile
    210                 215                 220


<210> SEQ ID NO 27
<211> LENGTH: 2057
<212> TYPE: DNA
<213> ORGANISM: Simian sp.
<220> FEATURE:
<221> NAME/KEY: CDS
<222> LOCATION: (208)..(963)

<400> SEQUENCE: 27

tgctgcccaa ggctcctgct cctgccccag gactctgagg tgggccctaa aacccagcgc      60

tctctaaaga aaagccttgc cagcccctac tcccggcccc caaccccagc aggtcgctgc     120

gccgccaggg ggcgctgtgt gagcgcccta ttctggccac ccggcgcccc ctcccacggc     180

ccaggcggga gcggggcgcc gggggcc atg cgg ggc caa ggc aga aag gag agt     234
                              Met Arg Gly Gln Gly Arg Lys Glu Ser
                                1               5

ttg tcc gaa tcc cga gat ctg gac ggc tcc tat gac cag ctt acg ggc       282
Leu Ser Glu Ser Arg Asp Leu Asp Gly Ser Tyr Asp Gln Leu Thr Gly
 10                  15                  20                  25

cac cct cca ggg ccc agt aaa aaa gcc ctg aag cag cgt ttc ctc aag       330
His Pro Pro Gly Pro Ser Lys Lys Ala Leu Lys Gln Arg Phe Leu Lys
                 30                  35                  40

ctg ctg ccg tgc tgc ggg ccc caa gcc ctg ccc tca gtc agt gaa aac       378
Leu Leu Pro Cys Cys Gly Pro Gln Ala Leu Pro Ser Val Ser Glu Asn
             45                  50                  55

agc gta gag gat gag ttt gaa tta tcc acg gtg tgt cac cga cct gag       426
Ser Val Glu Asp Glu Phe Glu Leu Ser Thr Val Cys His Arg Pro Glu
         60                  65                  70
```

-continued

```
ggc ctg gaa caa ctc cag gaa cag acc aag ttc aca cgc aga gag ctg      474
Gly Leu Glu Gln Leu Gln Glu Gln Thr Lys Phe Thr Arg Arg Glu Leu
     75                  80                  85

cag gtc ctg tac cga ggc ttc aag aac gaa tgc ccc agt ggg att gtc      522
Gln Val Leu Tyr Arg Gly Phe Lys Asn Glu Cys Pro Ser Gly Ile Val
 90                  95                 100                 105

aac gag gag aac ttc aag cag att tat tct cag ttc ttt ccc caa gga      570
Asn Glu Glu Asn Phe Lys Gln Ile Tyr Ser Gln Phe Phe Pro Gln Gly
                110                 115                 120

gac tcc agc aac tat gct act ttt ctc ttc aat gcc ttt gac acc aac      618
Asp Ser Ser Asn Tyr Ala Thr Phe Leu Phe Asn Ala Phe Asp Thr Asn
            125                 130                 135

cac gat ggc tct gtc agt ttt gag gac ttt gtg gct ggt ttg tcg gtg      666
His Asp Gly Ser Val Ser Phe Glu Asp Phe Val Ala Gly Leu Ser Val
        140                 145                 150

att ctt cgg ggg acc ata gat gat aga ctg agc tgg gct ttc aac tta      714
Ile Leu Arg Gly Thr Ile Asp Asp Arg Leu Ser Trp Ala Phe Asn Leu
    155                 160                 165

tat gac ctc aac aag gac ggc tgt atc aca aag gag gaa atg ctt gac      762
Tyr Asp Leu Asn Lys Asp Gly Cys Ile Thr Lys Glu Glu Met Leu Asp
170                 175                 180                 185

att atg aag tcc atc tat gac atg atg ggc aag tac aca tac cct gcc      810
Ile Met Lys Ser Ile Tyr Asp Met Met Gly Lys Tyr Thr Tyr Pro Ala
                190                 195                 200

ctc cgg gag gag gcc cca aga gaa cac gtg gag agc ttc ttc cag aag      858
Leu Arg Glu Glu Ala Pro Arg Glu His Val Glu Ser Phe Phe Gln Lys
            205                 210                 215

atg gac agg aac aag gac ggc gtg gtg acc atc gag gaa ttc atc gag      906
Met Asp Arg Asn Lys Asp Gly Val Val Thr Ile Glu Glu Phe Ile Glu
        220                 225                 230

tct tgt caa cag gac gag aac atc atg agg tcc atg cag ctc tca ccc      954
Ser Cys Gln Gln Asp Glu Asn Ile Met Arg Ser Met Gln Leu Ser Pro
    235                 240                 245

ctt ctc aac tgatacctag tgctgaggac acccctggtg tagggaccaa             1003
Leu Leu Asn
250

gtggttctcc accttctagt cccactctag aaaccacatt agacagaagg tctcctgcta   1063

tggtgctttc cccatcccta atctcttaga ttttcctcaa gactcccttc tcagagaaca   1123

cgctctgtcc atgtccccag ctggcttctc agcctagcct ttgagggccc tgtggggagg   1183

cggggacaag aaagcagaaa agtcttggcc ccgagccagt ggttaggtcc taggaattgg   1243

ctggagtgga ggccagaaag cctgggcaga tgatgagagc ccagctgggc tgtcactgca   1303

ggttccgggg cctacagccc tgggtcagca gagtatgagt tcccagactt tccagaaggt   1363

ccttagcaat gtcccagaaa ttcaccgtac acttctcagt gtcttaggag ggcccgggat   1423

ccagatgtct ggttcatccc tgaatcctct ccctccttct tgctcgtatg gtgggagtgg   1483

tggccagggg aagatgagtg gtgtcccgga tgatgcctgt caaggtccca cctcccctcc   1543

ggctgttctc atgacagctg tttggttctc catgacccct atctagatgt agaggcatgg   1603

agtgagtcag ggatttcccg aacttgagtt ttaccactcc tcctagtggc tgccttaggg   1663

gaatgggaag aacccagtgt gggggcaccc attagaatct ttgcccggct cctcacaatg   1723

ccctagggtc ccctagggta cccgctccct ctgtttagtc tacccagaga tgctcctgag   1783

ctcacctaga gggtagggac ggtaggctcc aggtccaacc tctccaggtc agcaccctgc   1843

catgctgctg ctcctcatta acaaacctgc ttgtctcctc ctgcgcccct tctcagtcag   1903

ccagggtctg aggggaaggg cctcccgttt ccccatccgt cagacatggt tgactgcttt   1963
```

-continued gcattttggg ctcttctatc tattttgtaa aataagacat cagatccaat aaaacacacg 2023 gctatgcaca aaaaaaaaaa aaaaaaaaaa aaaa 2057

<210> SEQ ID NO 28
<211> LENGTH: 252
<212> TYPE: PRT
<213> ORGANISM: Simian sp.

<400> SEQUENCE: 28

```
Met Arg Gly Gln Gly Arg Lys Glu Ser Leu Ser Glu Ser Arg Asp Leu
  1               5                  10                  15

Asp Gly Ser Tyr Asp Gln Leu Thr Gly His Pro Pro Gly Pro Ser Lys
             20                  25                  30

Lys Ala Leu Lys Gln Arg Phe Leu Lys Leu Leu Pro Cys Cys Gly Pro
         35                  40                  45

Gln Ala Leu Pro Ser Val Ser Glu Asn Ser Val Glu Asp Glu Phe Glu
     50                  55                  60

Leu Ser Thr Val Cys His Arg Pro Glu Gly Leu Glu Gln Leu Gln Glu
 65                  70                  75                  80

Gln Thr Lys Phe Thr Arg Arg Glu Leu Gln Val Leu Tyr Arg Gly Phe
                 85                  90                  95

Lys Asn Glu Cys Pro Ser Gly Ile Val Asn Glu Glu Asn Phe Lys Gln
            100                 105                 110

Ile Tyr Ser Gln Phe Phe Pro Gln Gly Asp Ser Ser Asn Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220

Val Val Thr Ile Glu Glu Phe Ile Glu Ser Cys Gln Gln Asp Glu Asn
225                 230                 235                 240

Ile Met Arg Ser Met Gln Leu Ser Pro Leu Leu Asn
                245                 250
```

<210> SEQ ID NO 29
<211> LENGTH: 1904
<212> TYPE: DNA
<213> ORGANISM: Rattus sp.
<220> FEATURE:
<221> NAME/KEY: CDS
<222> LOCATION: (1)..(675)

<400> SEQUENCE: 29

```
atg aac cac tgc cct cgc agg tgc cgg agc ccg ttg ggg cag gca gct      48
Met Asn His Cys Pro Arg Arg Cys Arg Ser Pro Leu Gly Gln Ala Ala
  1               5                  10                  15

cga tct ctc tac cag ttg gta act ggg tcg ctg tcg cca gac agc gta      96
Arg Ser Leu Tyr Gln Leu Val Thr Gly Ser Leu Ser Pro Asp Ser Val
             20                  25                  30
```

-continued

```
gag gat gag ttt gaa tta tcc acg gtg tgt cac cga cct gag ggc ctg        144
Glu Asp Glu Phe Glu Leu Ser Thr Val Cys His Arg Pro Glu Gly Leu
         35                  40                  45

gaa caa ctc cag gaa cag acc aag ttc aca cgc aga gag ctg cag gtc        192
Glu Gln Leu Gln Glu Gln Thr Lys Phe Thr Arg Arg Glu Leu Gln Val
 50                  55                  60

ctg tac cga ggc ttc aag aac gaa tgc ccc agt ggg att gtc aac gag        240
Leu Tyr Arg Gly Phe Lys Asn Glu Cys Pro Ser Gly Ile Val Asn Glu
 65                  70                  75                  80

gag aac ttc aag cag att tat tct cag ttc ttt ccc caa gga gac tcc        288
Glu Asn Phe Lys Gln Ile Tyr Ser Gln Phe Phe Pro Gln Gly Asp Ser
                 85                  90                  95

agc aac tat gct act ttt ctc ttc aat gcc ttt gac acc aac cac gat        336
Ser Asn Tyr Ala Thr Phe Leu Phe Asn Ala Phe Asp Thr Asn His Asp
            100                 105                 110

ggc tct gtc agt ttt gag gac ttt gtg gct ggt ttg tcg gtg att ctt        384
Gly Ser Val Ser Phe Glu Asp Phe Val Ala Gly Leu Ser Val Ile Leu
        115                 120                 125

cgg ggg acc ata gat gat aga ctg agc tgg gct ttc aac tta tat gac        432
Arg Gly Thr Ile Asp Asp Arg Leu Ser Trp Ala Phe Asn Leu Tyr Asp
130                 135                 140

ctc aac aag gac ggc tgt atc aca aag gag gaa atg ctt gac att atg        480
Leu Asn Lys Asp Gly Cys Ile Thr Lys Glu Glu Met Leu Asp Ile Met
145                 150                 155                 160

aag tcc atc tat gac atg atg ggc aag tac aca tac cct gcc ctc cgg        528
Lys Ser Ile Tyr Asp Met Met Gly Lys Tyr Thr Tyr Pro Ala Leu Arg
                165                 170                 175

gag gag gcc cca aga gaa cac gtg gag agc ttc ttc cag aag atg gac        576
Glu Glu Ala Pro Arg Glu His Val Glu Ser Phe Phe Gln Lys Met Asp
            180                 185                 190

agg aac aag gac ggc gtg gtg acc atc gag gaa ttc atc gag tct tgt        624
Arg Asn Lys Asp Gly Val Val Thr Ile Glu Glu Phe Ile Glu Ser Cys
        195                 200                 205

caa cag gac gag aac atc atg agg tcc atg cag ctc ttt gat aat gtc        672
Gln Gln Asp Glu Asn Ile Met Arg Ser Met Gln Leu Phe Asp Asn Val
    210                 215                 220

atc tagctcccca gggagagggg ttagtgtgtc ctagggtgac caggctgtag             725
Ile
225

tcctagtcca gacgaaccta accctctctc tccaggcctg tcctcatctt acctgtaccc      785

tgggggctgt agggattcaa tatcctgggg cttcagtagt ccagatccct gagctaagtc      845

acaaaagtag gcaagagtag gcaagctaaa tctgggggct tcccaacccc cgacagctct      905

caccccttct caactgatac ctagtgctga ggacacccct ggtgtaggga ccaagtggtt      965

ctccaccttc tagtcccact ctagaaacca cattagacag aaggtctcct gctatggtgc     1025

tttccccatc cctaatctct tagattttcc tcaagactcc cttctcagag aacacgctct     1085

gtccatgtcc ccagctggct tctcagccta gcctttgagg gccctgtggg gaggcgggga     1145

caagaaagca gaaaagtctt ggccccgagc tagtggttag gtcctaggaa ttggctggag     1205

tggaggccag aaagcctggg cagatgatga gagcccagct gggctgtcac tgcaggttcc     1265

agggcctaca gccctgggtc agcagagtat gagttcccag actttccaga aggtccttag     1325

caatgtccca gaaattcacc atacacttct cagtgtcccg gatgatgcct gtcaaggtcc     1385

cacctcccct ccggctgttc tcatgacagc tgtttggttc tccatgaccc ctatctagat     1445

gtagaggcat ggagtgagtc agggatttcc cgaacttgag ttttaccact cctcctagtg     1505

gctgccttag gggaatggga agaacccagt gtgggggcac ccattagaat ctttgcccgg     1565
```

-continued ttcctcacaa tgccctaggg tcccctaggg tacccgctcc ctctgtttag tctacccaga 1625 gatgctcctg agctcaccta gagggtaggg acggtaggct ccaggtccaa cctctccagg 1685 tcagcaccct gccatgctgc tgctcctcat taacaaacct gcttgtctcc tcctgcgccc 1745 cttctcagtc agccagggtc tgaggggaag ggcctcccgt ttccccatcc gtcagacatg 1805 gttgactgct ttgcattttg ggctcttcta tctattttgt aaaataagac atcagatcca 1865 ataaaacaca cggctatgca caaaaaaaaa aaaaaaaaa 1904

<210> SEQ ID NO 30
<211> LENGTH: 225
<212> TYPE: PRT
<213> ORGANISM: Rattus sp.

<400> SEQUENCE: 30

Met Asn His Cys Pro Arg Arg Cys Arg Ser Pro Leu Gly Gln Ala Ala
1 5 10 15

Arg Ser Leu Tyr Gln Leu Val Thr Gly Ser Leu Ser Pro Asp Ser Val
20 25 30

Glu Asp Glu Phe Glu Leu Ser Thr Val Cys His Arg Pro Glu Gly Leu
35 40 45

Glu Gln Leu Gln Glu Gln Thr Lys Phe Thr Arg Arg Glu Leu Gln Val
50 55 60

Leu Tyr Arg Gly Phe Lys Asn Glu Cys Pro Ser Gly Ile Val Asn Glu
65 70 75 80

Glu Asn Phe Lys Gln Ile Tyr Ser Gln Phe Phe Pro Gln Gly Asp Ser
85 90 95

Ser Asn Tyr Ala Thr Phe Leu Phe Asn Ala Phe Asp Thr Asn His Asp
100 105 110

Gly Ser Val Ser Phe Glu Asp Phe Val Ala Gly Leu Ser Val Ile Leu
115 120 125

Arg Gly Thr Ile Asp Asp Arg Leu Ser Trp Ala Phe Asn Leu Tyr Asp
130 135 140

Leu Asn Lys Asp Gly Cys Ile Thr Lys Glu Glu Met Leu Asp Ile Met
145 150 155 160

Lys Ser Ile Tyr Asp Met Met Gly Lys Tyr Thr Tyr Pro Ala Leu Arg
165 170 175

Glu Glu Ala Pro Arg Glu His Val Glu Ser Phe Phe Gln Lys Met Asp
180 185 190

Arg Asn Lys Asp Gly Val Val Thr Ile Glu Glu Phe Ile Glu Ser Cys
195 200 205

Gln Gln Asp Glu Asn Ile Met Arg Ser Met Gln Leu Phe Asp Asn Val
210 215 220

Ile
225

<210> SEQ ID NO 31
<211> LENGTH: 2841
<212> TYPE: DNA
<213> ORGANISM: Homo sapiens
<220> FEATURE:
<221> NAME/KEY: CDS
<222> LOCATION: (1)..(768)

<400> SEQUENCE: 31 atg cag ccg gct aag gaa gtg aca aag gcg tcg gac ggc agc ctc ctg 48
Met Gln Pro Ala Lys Glu Val Thr Lys Ala Ser Asp Gly Ser Leu Leu -continued

```
 1               5                  10                  15

ggg gac ctc ggg cac aca cca ctt agc aag aag gag ggt atc aag tgg      96
Gly Asp Leu Gly His Thr Pro Leu Ser Lys Lys Glu Gly Ile Lys Trp
             20                  25                  30

cag agg ccg agg ctc agc cgc cag gct ttg atg aga tgc tgc ctg gtc     144
Gln Arg Pro Arg Leu Ser Arg Gln Ala Leu Met Arg Cys Cys Leu Val
         35                  40                  45

aag tgg atc ctg tcc agc aca gcc cca cag ggc tca gat agc agc gac     192
Lys Trp Ile Leu Ser Ser Thr Ala Pro Gln Gly Ser Asp Ser Ser Asp
     50                  55                  60

agt gag ctg gag ctg tcc acg gtg cgc cac cag cca gag ggg ctg gac     240
Ser Glu Leu Glu Leu Ser Thr Val Arg His Gln Pro Glu Gly Leu Asp
 65                  70                  75                  80

cag ctg cag gcc cag acc aag ttc acc aag aag gag ctg cag tct ctc     288
Gln Leu Gln Ala Gln Thr Lys Phe Thr Lys Lys Glu Leu Gln Ser Leu
                 85                  90                  95

tac agg ggc ttt aag aat gag tgt ccc acg ggc ctg gtg gac gaa gac     336
Tyr Arg Gly Phe Lys Asn Glu Cys Pro Thr Gly Leu Val Asp Glu Asp
            100                 105                 110

acc ttc aaa ctc att tac gcg cag ttc ttc cct cag gga gat gcc acc     384
Thr Phe Lys Leu Ile Tyr Ala Gln Phe Phe Pro Gln Gly Asp Ala Thr
        115                 120                 125

acc tat gca cac ttc ctc ttc aac gcc ttt gat gcg gac ggg aac ggg     432
Thr Tyr Ala His Phe Leu Phe Asn Ala Phe Asp Ala Asp Gly Asn Gly
    130                 135                 140

gcc atc cac ttt gag gac ttt gtg gtt ggc ctc tcc atc ctg ctg cgg     480
Ala Ile His Phe Glu Asp Phe Val Val Gly Leu Ser Ile Leu Leu Arg
145                 150                 155                 160

ggc aca gtc cac gag aag ctc aag tgg gcc ttt aat ctc tac gac att     528
Gly Thr Val His Glu Lys Leu Lys Trp Ala Phe Asn Leu Tyr Asp Ile
                165                 170                 175

aac aag gat ggc tac atc acc aaa gag gag atg ctg gcc atc atg aag     576
Asn Lys Asp Gly Tyr Ile Thr Lys Glu Glu Met Leu Ala Ile Met Lys
            180                 185                 190

tcc atc tat gac atg atg ggc cgc cac acc tac ccc atc ctg cgg gag     624
Ser Ile Tyr Asp Met Met Gly Arg His Thr Tyr Pro Ile Leu Arg Glu
        195                 200                 205

gac gcg ccg gcg gag cac gtg gag agg ttc ttc gag aaa atg gac cgg     672
Asp Ala Pro Ala Glu His Val Glu Arg Phe Phe Glu Lys Met Asp Arg
    210                 215                 220

aac cag gat ggg gta gtg acc att gaa gag ttc ctg gag gcc tgt cag     720
Asn Gln Asp Gly Val Val Thr Ile Glu Glu Phe Leu Glu Ala Cys Gln
225                 230                 235                 240

aag gat gag aac atc atg agc tcc atg cag ctg ttt gag aat gtc atc     768
Lys Asp Glu Asn Ile Met Ser Ser Met Gln Leu Phe Glu Asn Val Ile
                245                 250                 255

taggacacgt ccaaaggagt gcatggccac agccacctcc acccccaaga aacctccatc    828

ctgccaggag cagcctccaa gaaactttta aaaaatagat ttgcaaaaag tgaacagatt    888

gctacacaca cacacacaca cacacacaca cacacacaca cacagccatt catctgggct    948

ggcagagggg acagagttca gggaggggct gagtctggct aggggccgag tccaggagcc   1008

ccagccagcc cttcccaggc cagcgaggcg aggctgcctc tgggtgagtg gctgacagag   1068

caggtctgca ggccaccagc tgctggatgt caccaagaag ggctcgagt gcccctgcag   1128

gggagggtcc aatctccggt gtgagcccac ctcgtcccgt tctccattct gctttcttgc   1188

cacacagtgg gccggcccca ggctcccctg gtctcctccc cgtagccact ctctgcccac   1248

tacctatgct tctagaaagc ccctcacctc aggaccccag agggaccagc tggggggcag   1308
```

-continued

```
gggggagagg gggtaatgga ggccaagcct gcagctttct ggaaattctt ccctgggggt   1368
cccaggatcc cctgctactc cactgacctg gaagagctgg gtaccaggcc acccactgtg   1428
gggcaagcct gagtggtgag gggccactgg gccccattct ccctccatgg caggaaggcg   1488
ggggatttca agtttaggga ttgggtcgtg gtggagaatc tgagggcact ctctgccagc   1548
tccacagggt gggatgagcc tctccttgcc ccagtcctgg ttcagtggga atgcagtggg   1608
tggggctgta cacaccctcc agcacagact gttccctcca aggtcctctt aggtcccggg   1668
aggaacgtgg ttcagagact ggcagccagg gagcccgggg cagagctcag aggagtctgg   1728
gaaggggcgt gtccctcctc ttcctgtagt gcccctccca tggcccagca gcttggctga   1788
gccccctctc ctgaagcagt gtcgccgtcc ctctgccttg cacaaaaagc acaagcattc   1848
cttagcagct caggcgcagc cctagtggga gcccagcaca ctgcttctcg gaggccaggc   1908
cctcctgctg gctgaggctt gggcccagta gccccaatat ggtggccctg ggaagaggc    1968
cttgggggtc tgctctgtgc ctgggatcag tggggcccca aagcccagcc cggctgacca   2028
acattcaaaa gcacaaaccc tggggactct gcttggctgt cccctccatc tggggatgga   2088
gaatgccagc ccaaagctgg agccaatggt gagggctgag agggctgtgg ctgggtggtc   2148
agcagaaacc cccaggagga gagagatgct gctcccgcct gattggggcc tcacccagaa   2208
ggaacccggt cccaggccgc atggcccctc caggaacatt cccacataat acattccatc   2268
acagccagcc cagctccact cagggctggc ccggggagtc cccgtgtgcc ccaagaggct   2328
agccccaggg tgagcagggc cctcagagga aaggcagtat ggcggaggcc atgggggccc   2388
ctcggcattc acacacagcc tggcctcccc tgcggagctg catggacgcc tggctccagg   2448
ctccaggctg actggggggcc tctgcctcca ggagggcatc agctttccct ggctcaggga   2508
tcttctccct cccctcaccc gctgcccagc cctcccagct ggtgtcactc tgcctctaag   2568
gccaaggcct caggagagca tcaccaccac accccctgccg gccttggcct tggggccaga   2628
ctggctgcac agcccaacca ggaggggtct gcctcccacg ctgggacaca gaccggccgc   2688
atgtctgcat ggcagaagcg tctcccttgg ccacggcctg ggagggtggt tcctgttctc   2748
agcatccact aatattcagt cctgtatatt ttaataaaat aaacttgaca aaggaaaaaa   2808
aaaaaaaaaa aattcctgcg gccgcgttct cca                                2841
```

<210> SEQ ID NO 32
<211> LENGTH: 256
<212> TYPE: PRT
<213> ORGANISM: Homo sapiens

<400> SEQUENCE: 32

```
Met Gln Pro Ala Lys Glu Val Thr Lys Ala Ser Asp Gly Ser Leu Leu
  1               5                  10                  15

Gly Asp Leu Gly His Thr Pro Leu Ser Lys Lys Glu Gly Ile Lys Trp
             20                  25                  30

Gln Arg Pro Arg Leu Ser Arg Gln Ala Leu Met Arg Cys Cys Leu Val
         35                  40                  45

Lys Trp Ile Leu Ser Ser Thr Ala Pro Gln Gly Ser Asp Ser Ser Asp
     50                  55                  60

Ser Glu Leu Glu Leu Ser Thr Val Arg His Gln Pro Glu Gly Leu Asp
 65                  70                  75                  80

Gln Leu Gln Ala Gln Thr Lys Phe Thr Lys Lys Glu Leu Gln Ser Leu
                 85                  90                  95
```

-continued

```
Tyr Arg Gly Phe Lys Asn Glu Cys Pro Thr Gly Leu Val Asp Glu Asp
            100                 105                 110

Thr Phe Lys Leu Ile Tyr Ala Gln Phe Phe Pro Gln Gly Asp Ala Thr
        115                 120                 125

Thr Tyr Ala His Phe Leu Phe Asn Ala Phe Asp Ala Asp Gly Asn Gly
    130                 135                 140

Ala Ile His Phe Glu Asp Phe Val Val Gly Leu Ser Ile Leu Leu Arg
145                 150                 155                 160

Gly Thr Val His Glu Lys Leu Lys Trp Ala Phe Asn Leu Tyr Asp Ile
                165                 170                 175

Asn Lys Asp Gly Tyr Ile Thr Lys Glu Glu Met Leu Ala Ile Met Lys
            180                 185                 190

Ser Ile Tyr Asp Met Met Gly Arg His Thr Tyr Pro Ile Leu Arg Glu
        195                 200                 205

Asp Ala Pro Ala Glu His Val Glu Arg Phe Phe Glu Lys Met Asp Arg
    210                 215                 220

Asn Gln Asp Gly Val Val Thr Ile Glu Glu Phe Leu Glu Ala Cys Gln
225                 230                 235                 240

Lys Asp Glu Asn Ile Met Ser Ser Met Gln Leu Phe Glu Asn Val Ile
                245                 250                 255


<210> SEQ ID NO 33
<211> LENGTH: 442
<212> TYPE: DNA
<213> ORGANISM: Rattus sp.
<220> FEATURE:
<221> NAME/KEY: CDS
<222> LOCATION: (1)..(327)

<400> SEQUENCE: 33

ttt gag gac ttt gtg gtt ggg ctc tcc atc ctg ctt cga ggg acc gtc       48
Phe Glu Asp Phe Val Val Gly Leu Ser Ile Leu Leu Arg Gly Thr Val
  1               5                  10                  15

cat gag aag ctc aag tgg gcc ttc aat ctc tac gac atc aac aag gac       96
His Glu Lys Leu Lys Trp Ala Phe Asn Leu Tyr Asp Ile Asn Lys Asp
             20                  25                  30

ggt tac atc acc aaa gag gag atg ctg gcc atc atg aag tcc atc tac      144
Gly Tyr Ile Thr Lys Glu Glu Met Leu Ala Ile Met Lys Ser Ile Tyr
         35                  40                  45

gac atg atg ggc cgc cac acc tac cct atc ctg cgg gag gac gca cct      192
Asp Met Met Gly Arg His Thr Tyr Pro Ile Leu Arg Glu Asp Ala Pro
     50                  55                  60

ctg gag cat gtg gag agg ttc ttc cag aaa atg gac agg aac cag gat      240
Leu Glu His Val Glu Arg Phe Phe Gln Lys Met Asp Arg Asn Gln Asp
 65                  70                  75                  80

gga gta gtg act att gat gaa ttt ctg gag act tgt cag aag gac gag      288
Gly Val Val Thr Ile Asp Glu Phe Leu Glu Thr Cys Gln Lys Asp Glu
                 85                  90                  95

aac atc atg agc tcc atg cag ctg ttt gag aac gtc atc taggacatgt       337
Asn Ile Met Ser Ser Met Gln Leu Phe Glu Asn Val Ile
            100                 105

aggaggggac cctgggtggc catgggttct caacccagag aagcctcaat cctgacagga    397

gaagcctcta tgagaaacat ttttctaata tatttgcaaa aagtg                    442


<210> SEQ ID NO 34
<211> LENGTH: 109
<212> TYPE: PRT
<213> ORGANISM: Rattus sp.
```

-continued

<400> SEQUENCE: 34

```
Phe Glu Asp Phe Val Val Gly Leu Ser Ile Leu Leu Arg Gly Thr Val
  1               5                  10                  15

His Glu Lys Leu Lys Trp Ala Phe Asn Leu Tyr Asp Ile Asn Lys Asp
             20                  25                  30

Gly Tyr Ile Thr Lys Glu Glu Met Leu Ala Ile Met Lys Ser Ile Tyr
         35                  40                  45

Asp Met Met Gly Arg His Thr Tyr Pro Ile Leu Arg Glu Asp Ala Pro
     50                  55                  60

Leu Glu His Val Glu Arg Phe Phe Gln Lys Met Asp Arg Asn Gln Asp
 65                  70                  75                  80

Gly Val Val Thr Ile Asp Glu Phe Leu Glu Thr Cys Gln Lys Asp Glu
                 85                  90                  95

Asn Ile Met Ser Ser Met Gln Leu Phe Glu Asn Val Ile
            100                 105
```

<210> SEQ ID NO 35
<211> LENGTH: 2644
<212> TYPE: DNA
<213> ORGANISM: Mus musculus
<220> FEATURE:
<221> NAME/KEY: CDS
<222> LOCATION: (49)..(816)

<400> SEQUENCE: 35

```
cgggctgcaa agcgggaaga ttagtgacgg tccctttcag cagcagag atg cag agg      57
                                                     Met Gln Arg
                                                       1

acc aag gaa gcc gtg aag gca tca gat ggc aac ctc ctg gga gat cct      105
Thr Lys Glu Ala Val Lys Ala Ser Asp Gly Asn Leu Leu Gly Asp Pro
      5                  10                  15

ggg cgc ata cca ctg agc aag agg gaa agc atc aag tgg caa agg cca      153
Gly Arg Ile Pro Leu Ser Lys Arg Glu Ser Ile Lys Trp Gln Arg Pro
 20                  25                  30                  35

cgg ttc acc cgc cag gcc ctg atg cgt tgc tgc tta atc aag tgg atc      201
Arg Phe Thr Arg Gln Ala Leu Met Arg Cys Cys Leu Ile Lys Trp Ile
                 40                  45                  50

ctg tcc agt gct gcc cca caa ggc tca gac agc agt gac agt gaa ctg      249
Leu Ser Ser Ala Ala Pro Gln Gly Ser Asp Ser Ser Asp Ser Glu Leu
             55                  60                  65

gag tta tcc acg gtg cgc cat cag cca gag ggc ttg gac cag cta caa      297
Glu Leu Ser Thr Val Arg His Gln Pro Glu Gly Leu Asp Gln Leu Gln
         70                  75                  80

gct cag acc aag ttc acc aag aag gag ctg cag tcc ctt tac cga ggc      345
Ala Gln Thr Lys Phe Thr Lys Lys Glu Leu Gln Ser Leu Tyr Arg Gly
     85                  90                  95

ttc aag aat gag tgt ccc aca ggc ctg gtg gat gaa gac acc ttc aaa      393
Phe Lys Asn Glu Cys Pro Thr Gly Leu Val Asp Glu Asp Thr Phe Lys
100                 105                 110                 115

ctc att tat tcc cag ttc ttc cct cag gga gat gcc acc acc tat gca      441
Leu Ile Tyr Ser Gln Phe Phe Pro Gln Gly Asp Ala Thr Thr Tyr Ala
                120                 125                 130

cac ttc ctc ttc aat gcc ttt gat gct gat ggg aac ggg gcc atc cac      489
His Phe Leu Phe Asn Ala Phe Asp Ala Asp Gly Asn Gly Ala Ile His
            135                 140                 145

ttt gag gac ttt gtg gtt ggg ctc tcc atc ctg ctt cga ggg acg gtc      537
Phe Glu Asp Phe Val Val Gly Leu Ser Ile Leu Leu Arg Gly Thr Val
        150                 155                 160

cat gag aag ctc aag tgg gcc ttc aat ctc tat gac att aac aag gat      585
His Glu Lys Leu Lys Trp Ala Phe Asn Leu Tyr Asp Ile Asn Lys Asp
```

-continued

```
    165                 170                 175

ggt tgc atc acc aag gag gag atg ctg gcc atc atg aag tcc atc tac      633
Gly Cys Ile Thr Lys Glu Glu Met Leu Ala Ile Met Lys Ser Ile Tyr
180                 185                 190                 195

gac atg atg ggc cgc cac acc tac ccc atc ctg cgg gag gat gca ccc      681
Asp Met Met Gly Arg His Thr Tyr Pro Ile Leu Arg Glu Asp Ala Pro
                200                 205                 210

ctg gag cat gtg gag agg ttc ttt cag aaa atg gac agg aac cag gat      729
Leu Glu His Val Glu Arg Phe Phe Gln Lys Met Asp Arg Asn Gln Asp
            215                 220                 225

gga gtg gtg acc att gat gaa ttt ctg gag act tgt cag aag gat gag      777
Gly Val Val Thr Ile Asp Glu Phe Leu Glu Thr Cys Gln Lys Asp Glu
        230                 235                 240

aac atc atg aac tcc atg cag ctg ttt gag aac gtc atc taggacatgt       826
Asn Ile Met Asn Ser Met Gln Leu Phe Glu Asn Val Ile
    245                 250                 255

gggaggggac cccagtggtc attgcttctc aacccagaga agcctcaatc ctgacaggag    886

aagcctctat gagaaacatt tttctaatat atttgcaaaa agtgagcagt ttacttccaa    946

gacacagcca ccgtcacaca cagacacaga catacagaca cacacacaca cacacacaca   1006

tggttcctct ggcttggcca aggaagtggc agccagaagg cacccccgcc tattcctagg   1066

tcaataaaaa aggctgcctc tgggatggcc agccctggct agatgttacc cacaaggaac   1126

tcagagatcg agaggaccag gtctacaaag ctaaggtccc tgtgtctttt ctaccactcg   1186

ggagatcaaa ctactccctg cctatggacc catgctctta ggaagctccc agaaactcca   1246

aggggacaaa gaggggagag gtctatagga agaaatggtt ttggaagctg ggcttgcagc   1306

cttatgctaa tgatcacctg ggtcctggga acccgagtgc caggctacct actatgccgt   1366

gagcttagat agtgaggggc cattggacta agacctcctg taagagtggg gcaggattga   1426

ggtttttgga gaaactgagg aaacaatttg tccataccac tgggtgaaga ctgctggcca   1486

gtgggaatgt ggctggtgga gatttcccaa cttccagcac caggatggcc tctccaaggt   1546

cctctttgat tccctgggga gatcacctgg ctcatagact gacaaccagg gaactgggct   1606

gaaatgggag gtctggtagg gggcatcccc ctccttttcc ctggccactt gccacccagt   1666

tccttaacac agtggatcgg ccacacctct gtggctgccc ttgaacagac tcatcccgac   1726

caagacaaaa aagcacaaac tcctagcagc tcaggccaag cccacaaggg aaggcctggg   1786

tccctgcagc cctgattcag tggccgagga agacgctcag acatccatcc tgtacctcgg   1846

agccttgggg gtctcacagc cctttcccag cccagctcgc caacattcta aagcacaaac   1906

ctgcggattc tgcttgcttg ggctgcgccc tggggattga aggccactgt taaccctaag   1966

ctggagctag ccctgagggc tggggacctg tgaccaggca acaggtcagc agaccctcag   2026

gaggagagag agctgttcct gcctccccag gcctcgccca gaaggaacag tgtcccaaga   2086

agcatgtttc ctggaggaac atccccacaa aagtacattc catcatctga agcccggtct   2146

ctgctcaggc ctgcctctga aagtccacgt gtgttcccca gaaggccagc cccaagataa   2206

gggaggtcct tagaggaagg acagggtgac aacaccccta tacacaggtg gacccccccct  2266

ctgaggactg tactgacccc atctccatcc tgaccggggc cttcctttac ccgatctaca   2326

gaccaccagt tctccctggc tcagggaccc cctgtccccc agtctgactc ttcccatcga   2386

ggtccctgtc ttgtgaaaag ccaaggccac gggaaaaggc caccactcta acctgctgca   2446

tcccttagcc tctggctgca cgcccaacct ggaggggtct gtccccttttg cagggacaca  2506

gactggccgc atgtccgcat ggcagaagcg tctcccttgg gtgcagcctg gaagggtggt   2566
```

-continued

```
ttctgtctca gcgcccacca atattcagtc ctatatattt taataaaaga aacttgacaa   2626

aggaaaaaaa aaaaaaaa                                                 2644


<210> SEQ ID NO 36
<211> LENGTH: 256
<212> TYPE: PRT
<213> ORGANISM: Mus musculus

<400> SEQUENCE: 36

Met Gln Arg Thr Lys Glu Ala Val Lys Ala Ser Asp Gly Asn Leu Leu
  1               5                  10                  15

Gly Asp Pro Gly Arg Ile Pro Leu Ser Lys Arg Glu Ser Ile Lys Trp
             20                  25                  30

Gln Arg Pro Arg Phe Thr Arg Gln Ala Leu Met Arg Cys Cys Leu Ile
         35                  40                  45

Lys Trp Ile Leu Ser Ser Ala Ala Pro Gln Gly Ser Asp Ser Ser Asp
     50                  55                  60

Ser Glu Leu Glu Leu Ser Thr Val Arg His Gln Pro Glu Gly Leu Asp
 65                  70                  75                  80

Gln Leu Gln Ala Gln Thr Lys Phe Thr Lys Lys Glu Leu Gln Ser Leu
                 85                  90                  95

Tyr Arg Gly Phe Lys Asn Glu Cys Pro Thr Gly Leu Val Asp Glu Asp
            100                 105                 110

Thr Phe Lys Leu Ile Tyr Ser Gln Phe Phe Pro Gln Gly Asp Ala Thr
        115                 120                 125

Thr Tyr Ala His Phe Leu Phe Asn Ala Phe Asp Ala Asp Gly Asn Gly
    130                 135                 140

Ala Ile His Phe Glu Asp Phe Val Val Gly Leu Ser Ile Leu Leu Arg
145                 150                 155                 160

Gly Thr Val His Glu Lys Leu Lys Trp Ala Phe Asn Leu Tyr Asp Ile
                165                 170                 175

Asn Lys Asp Gly Cys Ile Thr Lys Glu Glu Met Leu Ala Ile Met Lys
            180                 185                 190

Ser Ile Tyr Asp Met Met Gly Arg His Thr Tyr Pro Ile Leu Arg Glu
        195                 200                 205

Asp Ala Pro Leu Glu His Val Glu Arg Phe Phe Gln Lys Met Asp Arg
    210                 215                 220

Asn Gln Asp Gly Val Val Thr Ile Asp Glu Phe Leu Glu Thr Cys Gln
225                 230                 235                 240

Lys Asp Glu Asn Ile Met Asn Ser Met Gln Leu Phe Glu Asn Val Ile
                245                 250                 255


<210> SEQ ID NO 37
<211> LENGTH: 531
<212> TYPE: DNA
<213> ORGANISM: Homo sapiens
<220> FEATURE:
<221> NAME/KEY: CDS
<222> LOCATION: (1)..(336)
<220> FEATURE:
<223> OTHER INFORMATION: At position 495, n=any amino acid

<400> SEQUENCE: 37

cac gag gtg gaa agc att tcg gct cag ctg gag gag gcc agc tct aca      48
His Glu Val Glu Ser Ile Ser Ala Gln Leu Glu Glu Ala Ser Ser Thr
  1               5                  10                  15

ggc ggt ttc ctg tac gct cag aac agc acc aag cgc agc att aaa gag      96
```

-continued

```
Gly Gly Phe Leu Tyr Ala Gln Asn Ser Thr Lys Arg Ser Ile Lys Glu
            20                  25                  30

cgg ctc atg aag ctc ttg ccc tgc tca gct gcc aaa acg tcg tct cct      144
Arg Leu Met Lys Leu Leu Pro Cys Ser Ala Ala Lys Thr Ser Ser Pro
        35                  40                  45

gct att caa aac agc gtg gaa gat gaa ctg gag atg gcc acc gtc agg      192
Ala Ile Gln Asn Ser Val Glu Asp Glu Leu Glu Met Ala Thr Val Arg
    50                  55                  60

cat cgg ccc gaa gcc ctt gag ctt ctg gaa gcc cag agc aaa ttt acc      240
His Arg Pro Glu Ala Leu Glu Leu Leu Glu Ala Gln Ser Lys Phe Thr
 65                  70                  75                  80

aag aaa gag ctt cag atc ctt tac aga gga ttt aag aac gta aga act      288
Lys Lys Glu Leu Gln Ile Leu Tyr Arg Gly Phe Lys Asn Val Arg Thr
                85                  90                  95

ttc ttt ttg act tta cct tca cac aat tcc cag agg agc att gag aaa      336
Phe Phe Leu Thr Leu Pro Ser His Asn Ser Gln Arg Ser Ile Glu Lys
            100                 105                 110

tgagaggaaa agggggaaaa tatcccattc tatgagaagc cccatcatat gtatatttca    396

tactgatcct tcccagatag gaatataatc agtatctgtg gactttgaat ctctgtggca    456

cacccatgct ggcatactgt aattgcccat taaacaaana gtttttgaga aaaaaaaaaa    516

aaaaaaaaaa aaaaa                                                      531


<210> SEQ ID NO 38
<211> LENGTH: 112
<212> TYPE: PRT
<213> ORGANISM: Homo sapiens

<400> SEQUENCE: 38

His Glu Val Glu Ser Ile Ser Ala Gln Leu Glu Glu Ala Ser Ser Thr
  1               5                  10                  15

Gly Gly Phe Leu Tyr Ala Gln Asn Ser Thr Lys Arg Ser Ile Lys Glu
            20                  25                  30

Arg Leu Met Lys Leu Leu Pro Cys Ser Ala Ala Lys Thr Ser Ser Pro
        35                  40                  45

Ala Ile Gln Asn Ser Val Glu Asp Glu Leu Glu Met Ala Thr Val Arg
    50                  55                  60

His Arg Pro Glu Ala Leu Glu Leu Leu Glu Ala Gln Ser Lys Phe Thr
 65                  70                  75                  80

Lys Lys Glu Leu Gln Ile Leu Tyr Arg Gly Phe Lys Asn Val Arg Thr
                85                  90                  95

Phe Phe Leu Thr Leu Pro Ser His Asn Ser Gln Arg Ser Ile Glu Lys
            100                 105                 110


<210> SEQ ID NO 39
<211> LENGTH: 2176
<212> TYPE: DNA
<213> ORGANISM: Homo sapiens
<220> FEATURE:
<221> NAME/KEY: CDS
<222> LOCATION: (2)..(124)

<400> SEQUENCE: 39

t gaa agg ttc ttc gag aaa atg gac cgg aac cag gat ggg gta gtg acc     49
  Glu Arg Phe Phe Glu Lys Met Asp Arg Asn Gln Asp Gly Val Val Thr
    1               5                  10                  15

att gaa gag ttc ctg gag gcc tgt cag aag gat gag aac atc atg agc       97
Ile Glu Glu Phe Leu Glu Ala Cys Gln Lys Asp Glu Asn Ile Met Ser
            20                  25                  30
```

-continued

```
tcc atg cag ctg ttt gag aat gtc atc taggacacgt ccaaaggagt          144
Ser Met Gln Leu Phe Glu Asn Val Ile
        35                  40

gcatggccac agccacctcc acccccaaga aacctccatc ctgccaggag cagcctccaa    204

gaaactttta aaaaatagat ttgcaaaaag tgaacagatt gctacacaca cacacacaca    264

cacacacaca cacacacaca cacagccatt catctgggct ggcagagggg acagagttca    324

gggaggggct gagtctggct aggggccgag tccaggagcc ccagccagcc cttcccaggc    384

cagcgaggcg aggctgcctc tgggtgagtg gctgacagag caggtctgca ggccaccagc    444

tgctggatgt caccaagaag gggctcgagt gcccctgcag gggagggtcc aatctccggt    504

gtgagcccac ctcgtcccgt tctccattct gctttcttgc cacacagtgg gccggcccca    564

ggctcccctg gtctcctccc cgtagccact ctctgcccac tacctatgct tctagaaagc    624

ccctcacctc aggaccccag agggaccagc tggggggcag gggggagagg gggtaatgga    684

ggccaagcct gcagctttct ggaaattctt ccctggggt cccaggatcc cctgctactc     744

cactgacctg gaagagctgg gtaccaggcc acccactgtg gggcaagcct gagtggtgag    804

gggccactgg gccccattct ccctccatgg caggaaggcg ggggatttca agtttaggga    864

ttgggtcgtg gtggagaatc tgagggcact ctctgccagc tccacagggt gggatgagcc    924

tctccttgcc ccagtcctgg ttcagtggga atgcagtggg tggggctgta cacaccctcc    984

agcacagact gttccctcca aggtcctctt aggtcccggg aggaacgtgg ttcagagact   1044

ggcagccagg gagcccgggg cagagctcag aggagtctgg gaaggggcgt gtccctcctc   1104

ttcctgtagt gcccctccca tggcccagca gcttggctga gccccctctc ctgaagcagt   1164

gtcgccgtcc ctctgccttg cacaaaaagc acaagcattc cttagcagct caggcgcagc   1224

cctagtggga gcccagcaca ctgcttctcg gaggccaggc cctcctgctg gctgaggctt   1284

gggcccagta gccccaatat ggtggccctg gggaagaggc cttgggggtc tgctctgtgc   1344

ctgggatcag tggggcccca aagcccagcc cggctgacca acattcaaaa gcacaaaccc   1404

tggggactct gcttggctgt cccctccatc tggggatgga gaatgccagc ccaaagctgg   1464

agccaatggt gagggctgag agggctgtgg ctgggtggtc agcagaaacc cccaggagga   1524

gagagatgct gctcccgcct gattggggcc tcacccagaa ggaacccggt cccaggccgc   1584

atggcccctc caggaacatt cccacataat acattccatc acagccagcc cagctccact   1644

cagggctggc ccggggagtc cccgtgtgcc ccaagaggct agccccaggg tgagcagggc   1704

cctcagagga aaggcagtat ggcggaggcc atgggggccc ctcggcattc acacacagcc   1764

tggcctcccc tgcggagctg catggacgcc tggctccagg ctccaggctg actgggggcc   1824

tctgcctcca ggagggcatc agctttccct ggctcaggga tcttctccct cccctcaccc   1884

gctgcccagc cctcccagct ggtgtcactc tgcctctaag gccaaggcct caggagagca   1944

tcaccaccac acccctgccg gccttggcct tggggccaga ctggctgcac agcccaacca   2004

ggaggggtct gcctcccacg ctgggacaca gaccggccgc atgtctgcat ggcagaagcg   2064

tctcccttgg ccacggcctg ggagggtggt tcctgttctc agcatccact aatattcagt   2124

cctgtatatt ttaataaaat aaacttgaca aaggaaaaaa aaaaaaaaaa aa           2176
```

<210> SEQ ID NO 40
<211> LENGTH: 41
<212> TYPE: PRT
<213> ORGANISM: Homo sapiens

<400> SEQUENCE: 40

-continued

```
Glu Arg Phe Phe Glu Lys Met Asp Arg Asn Gln Asp Gly Val Val Thr
  1               5                  10                  15

Ile Glu Glu Phe Leu Glu Ala Cys Gln Lys Asp Glu Asn Ile Met Ser
             20                  25                  30

Ser Met Gln Leu Phe Glu Asn Val Ile
         35                  40


<210> SEQ ID NO 41
<211> LENGTH: 2057
<212> TYPE: DNA
<213> ORGANISM: Rattus sp.
<220> FEATURE:
<221> NAME/KEY: CDS
<222> LOCATION: (208)..(963)

<400> SEQUENCE: 41

tgctgcccaa ggctcctgct cctgccccag gactctgagg tgggccctaa aacccagcgc     60

tctctaaaga aaagccttgc cagcccctac tcccggcccc caaccccagc aggtcgctgc    120

gccgccaggg ggcgctgtgt gagcgcccta ttctggccac ccggcgcccc ctcccacggc    180

ccaggcggga gcggggcgcc gggggcc atg cgg ggc caa ggc aga aag gag agt    234
                              Met Arg Gly Gln Gly Arg Lys Glu Ser
                               1               5

ttg tcc gaa tcc cga gat ctg gac ggc tcc tat gac cag ctt acg ggc      282
Leu Ser Glu Ser Arg Asp Leu Asp Gly Ser Tyr Asp Gln Leu Thr Gly
 10                  15                  20                  25

cac cct cca ggg ccc agt aaa aaa gcc ctg aag cag cgt ttc ctc aag      330
His Pro Pro Gly Pro Ser Lys Lys Ala Leu Lys Gln Arg Phe Leu Lys
                 30                  35                  40

ctg ctg ccg tgc tgc ggg ccc caa gcc ctg ccc tca gtc agt gaa aac      378
Leu Leu Pro Cys Cys Gly Pro Gln Ala Leu Pro Ser Val Ser Glu Asn
             45                  50                  55

agc gta gag gat gag ttt gaa tta tcc acg gtg tgt cac cga cct gag      426
Ser Val Glu Asp Glu Phe Glu Leu Ser Thr Val Cys His Arg Pro Glu
         60                  65                  70

ggc ctg gaa caa ctc cag gaa cag acc aag ttc aca cgc aga gag ctg      474
Gly Leu Glu Gln Leu Gln Glu Gln Thr Lys Phe Thr Arg Arg Glu Leu
     75                  80                  85

cag gtc ctg tac cga ggc ttc aag aac gaa tgc ccc agt ggg att gtc      522
Gln Val Leu Tyr Arg Gly Phe Lys Asn Glu Cys Pro Ser Gly Ile Val
 90                  95                 100                 105

aac gag gag aac ttc aag cag att tat tct cag ttc ttt ccc caa gga      570
Asn Glu Glu Asn Phe Lys Gln Ile Tyr Ser Gln Phe Phe Pro Gln Gly
                110                 115                 120

gac tcc agc aac tat gct act ttt ctc ttc aat gcc ttt gac acc aac      618
Asp Ser Ser Asn Tyr Ala Thr Phe Leu Phe Asn Ala Phe Asp Thr Asn
            125                 130                 135

cac gat ggc tct gtc agt ttt gag gac ttt gtg gct ggt ttg tcg gtg      666
His Asp Gly Ser Val Ser Phe Glu Asp Phe Val Ala Gly Leu Ser Val
        140                 145                 150

att ctt cgg ggg acc ata gat gat aga ctg agc tgg gct ttc aac tta      714
Ile Leu Arg Gly Thr Ile Asp Asp Arg Leu Ser Trp Ala Phe Asn Leu
    155                 160                 165

tat gac ctc aac aag gac ggc tgt atc aca aag gag gaa atg ctt gac      762
Tyr Asp Leu Asn Lys Asp Gly Cys Ile Thr Lys Glu Glu Met Leu Asp
170                 175                 180                 185

att atg aag tcc atc tat gac atg atg ggc aag tac aca tac cct gcc      810
Ile Met Lys Ser Ile Tyr Asp Met Met Gly Lys Tyr Thr Tyr Pro Ala
                190                 195                 200
```

-continued

```
ctc cgg gag gag gcc cca aga gaa cac gtg gag agc ttc ttc cag aag      858
Leu Arg Glu Glu Ala Pro Arg Glu His Val Glu Ser Phe Phe Gln Lys
            205                 210                 215

atg gac agg aac aag gac ggc gtg gtg acc atc gag gaa ttc atc gag      906
Met Asp Arg Asn Lys Asp Gly Val Val Thr Ile Glu Glu Phe Ile Glu
        220                 225                 230

tct tgt caa cag gac gag aac atc atg agg tcc atg cag ctc tca ccc      954
Ser Cys Gln Gln Asp Glu Asn Ile Met Arg Ser Met Gln Leu Ser Pro
    235                 240                 245

ctt ctc aac tgatacctag tgctgaggac acccctggtg tagggaccaa             1003
Leu Leu Asn
250

gtggttctcc accttctagt cccactctag aaaccacatt agacagaagg tctcctgcta   1063

tggtgctttc cccatcccta atctcttaga ttttcctcaa gactcccttc tcagagaaca   1123

cgctctgtcc atgtccccag ctggcttctc agcctagcct ttgagggccc tgtggggagg   1183

cggggacaag aaagcagaaa agtcttggcc ccgagccagt ggttaggtcc taggaattgg   1243

ctggagtgga ggccagaaag cctgggcaga tgatgagagc ccagctgggc tgtcactgca   1303

ggttccgggg cctacagccc tgggtcagca gagtatgagt tcccagactt tccagaaggt   1363

ccttagcaat gtcccagaaa ttcaccgtac acttctcagt gtcttaggag ggcccgggat   1423

ccagatgtct ggttcatccc tgaatcctct ccctccttct tgctcgtatg gtgggagtgg   1483

tggccagggg aagatgagtg gtgtcccgga tgatgcctgt caaggtccca cctcccctcc   1543

ggctgttctc atgacagctg tttggttctc catgacccct atctagatgt agaggcatgg   1603

agtgagtcag ggatttcccg aacttgagtt ttaccactcc tcctagtggc tgccttaggg   1663

gaatgggaag aacccagtgt gggggcaccc attagaatct ttgcccggct cctcacaatg   1723

ccctagggtc ccctagggta cccgctccct ctgtttagtc tacccagaga tgctcctgag   1783

ctcacctaga gggtagggac ggtaggctcc aggtccaacc tctccaggtc agcaccctgc   1843

catgctgctg ctcctcatta acaaacctgc ttgtctcctc ctgcgcccct tctcagtcag   1903

ccagggtctg aggggaaggg cctcccgttt ccccatccgt cagacatggt tgactgcttt   1963

gcattttggg ctcttctatc tattttgtaa aataagacat cagatccaat aaaacacacg   2023

gctatgcaca aaaaaaaaaa aaaaaaaaaa aaaa                                2057


<210> SEQ ID NO 42
<211> LENGTH: 252
<212> TYPE: PRT
<213> ORGANISM: Rattus sp.

<400> SEQUENCE: 42

Met Arg Gly Gln Gly Arg Lys Glu Ser Leu Ser Glu Ser Arg Asp Leu
  1               5                  10                  15

Asp Gly Ser Tyr Asp Gln Leu Thr Gly His Pro Pro Gly Pro Ser Lys
             20                  25                  30

Lys Ala Leu Lys Gln Arg Phe Leu Lys Leu Leu Pro Cys Cys Gly Pro
         35                  40                  45

Gln Ala Leu Pro Ser Val Ser Glu Asn Ser Val Glu Asp Glu Phe Glu
     50                  55                  60

Leu Ser Thr Val Cys His Arg Pro Glu Gly Leu Glu Gln Leu Gln Glu
 65                  70                  75                  80

Gln Thr Lys Phe Thr Arg Arg Glu Leu Gln Val Leu Tyr Arg Gly Phe
                 85                  90                  95

Lys Asn Glu Cys Pro Ser Gly Ile Val Asn Glu Glu Asn Phe Lys Gln
```

-continued

```
        100                 105                 110

Ile Tyr Ser Gln Phe Phe Pro Gln Gly Asp Ser Ser Asn Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220

Val Val Thr Ile Glu Glu Phe Ile Glu Ser Cys Gln Gln Asp Glu Asn
225                 230                 235                 240

Ile Met Arg Ser Met Gln Leu Ser Pro Leu Leu Asn
                245                 250


<210> SEQ ID NO 43
<211> LENGTH: 26
<212> TYPE: PRT
<213> ORGANISM: Artificial Sequence
<220> FEATURE:
<223> OTHER INFORMATION: Xaas at positions 2,5,6,9,17,25 and 26 may be
      Ile, Leu, Val or Met
<220> FEATURE:
<223> OTHER INFORMATION: Xaas at positions 3,4,7,8,16,18-20,23 and 24
      may be any amino acid
<220> FEATURE:
<223> OTHER INFORMATION: Description of Artificial Sequence: consensus
      motif

<400> SEQUENCE: 43

Glu Xaa Xaa Xaa Xaa Xaa Xaa Xaa Xaa Asp Lys Asp Gly Asp Gly Xaa
  1               5                  10                  15

Xaa Xaa Xaa Xaa Glu Phe Xaa Xaa Xaa Xaa
             20                  25


<210> SEQ ID NO 44
<211> LENGTH: 40
<212> TYPE: DNA
<213> ORGANISM: Rattus sp.

<400> SEQUENCE: 44

taatacgact cactataggg actggccatc ctgctctcag                          40


<210> SEQ ID NO 45
<211> LENGTH: 40
<212> TYPE: DNA
<213> ORGANISM: Rattus sp.

<400> SEQUENCE: 45

attaaccctc actaaaggga cactactgtt taagctcaag                          40


<210> SEQ ID NO 46
<211> LENGTH: 40
<212> TYPE: DNA
<213> ORGANISM: Rattus sp.

<400> SEQUENCE: 46
```

```
taatacgact cactataggg cacctcccct ccggctgttc                              40
```

<210> SEQ ID NO 47
<211> LENGTH: 40
<212> TYPE: DNA
<213> ORGANISM: Rattus sp.

<400> SEQUENCE: 47

```
attaaccctc actaaggga gagcagcagc atggcagggt                              40
```

<210> SEQ ID NO 48
<211> LENGTH: 2413
<212> TYPE: DNA
<213> ORGANISM: Simian sp.
<220> FEATURE:
<221> NAME/KEY: CDS
<222> LOCATION: (265)..(963)

<400> SEQUENCE: 48

```
gtcgacccac gcgtccggtg cgctgtggtt gcggggggga gccccgccag ccaaatgcca       60

ggatcagcat gagaggctgg actttagtcc aggtctgtcc tcaccccggg ggaccgccgg      120

ctttgcaggg tgcagctgcg aggaactgct cacttttttc cccttgcaag tctttgttcc      180

aagcctgacg ttgctacgat tctgtaatta actccctcca ctccaaaggg gtctggaggc      240

tgggatgctc tgccagctca gagg atg ttg act ctg gag tgg gag tcc gaa        291
                          Met Leu Thr Leu Glu Trp Glu Ser Glu
                            1               5

gga ctg caa aca gtg ggt att gtt gtg att ata tgt gca tct ctg aag        339
Gly Leu Gln Thr Val Gly Ile Val Val Ile Ile Cys Ala Ser Leu Lys
 10                  15                  20                  25

ctg ctt cat ttg ctg gga ctg att gat ttt tcg gaa gac agc gtg gaa        387
Leu Leu His Leu Leu Gly Leu Ile Asp Phe Ser Glu Asp Ser Val Glu
                 30                  35                  40

gat gaa ctg gag atg gcc act gtc agg cat cgg cct gag gcc ctt gag        435
Asp Glu Leu Glu Met Ala Thr Val Arg His Arg Pro Glu Ala Leu Glu
             45                  50                  55

ctt ctg gaa gcc cag agc aaa ttt acc aag aaa gag ctt cag atc ctt        483
Leu Leu Glu Ala Gln Ser Lys Phe Thr Lys Lys Glu Leu Gln Ile Leu
         60                  65                  70

tac aga gga ttt aag aac gaa tgc ccc agt ggt gtt gtt aat gaa gaa        531
Tyr Arg Gly Phe Lys Asn Glu Cys Pro Ser Gly Val Val Asn Glu Glu
     75                  80                  85

acc ttc aaa gag att tac tcg cag ttc ttt cca cag gga gac tct aca        579
Thr Phe Lys Glu Ile Tyr Ser Gln Phe Phe Pro Gln Gly Asp Ser Thr
 90                  95                 100                 105

aca tat gca cat ttt ctg ttc aat gcg ttt gat acg gac cac aat gga        627
Thr Tyr Ala His Phe Leu Phe Asn Ala Phe Asp Thr Asp His Asn Gly
                110                 115                 120

gct gtg agt ttc gag gat ttc atc aaa ggt ctt tcc att ttg ctc cgg        675
Ala Val Ser Phe Glu Asp Phe Ile Lys Gly Leu Ser Ile Leu Leu Arg
            125                 130                 135

ggg aca gta caa gaa aaa ctc aat tgg gca ttt aat ctg tat gat ata        723
Gly Thr Val Gln Glu Lys Leu Asn Trp Ala Phe Asn Leu Tyr Asp Ile
        140                 145                 150

aat aaa gat ggc tac atc act aaa gag gaa atg ctt gat ata atg aaa        771
Asn Lys Asp Gly Tyr Ile Thr Lys Glu Glu Met Leu Asp Ile Met Lys
155                 160                 165

gca ata tac gac atg atg ggt aaa tgt aca tat cct gtc ctc aaa gaa        819
Ala Ile Tyr Asp Met Met Gly Lys Cys Thr Tyr Pro Val Leu Lys Glu
170                 175                 180                 185
```

-continued

```
gat gca ccc aga caa cac gtc gaa aca ttt ttt cag aaa atg gac aaa      867
Asp Ala Pro Arg Gln His Val Glu Thr Phe Phe Gln Lys Met Asp Lys
            190                 195                 200

aat aaa gat ggg gtt gtt acc ata gat gag ttc att gaa agc tgc caa      915
Asn Lys Asp Gly Val Val Thr Ile Asp Glu Phe Ile Glu Ser Cys Gln
        205                 210                 215

aaa gat gaa aac ata atg cgc tcc atg cag ctc ttt gaa aat gtg att      963
Lys Asp Glu Asn Ile Met Arg Ser Met Gln Leu Phe Glu Asn Val Ile
    220                 225                 230

taacttgtca actagatcct gaatccaaca gacaaatgtg aactattcta ccacccttaa   1023

agtcggagct accactttta gcatagattg ctcagcttga cactgaagca tattatgcaa   1083

acaagctttg ttttaatata aagcaatccc caaaagattt gagtttctca gttataaatt   1143

tgcatccttt ccataatgcc actgagttca tgggatgttc taactcattt catactctgt   1203

gaatattcaa aagtaataga atctggcata tagttttatt gattccttag ccatgggatt   1263

attgaggctt tcacatatca gtgattttaa aataccagtg ttttttgctc tcatttgtat   1323

gtattcagtc ctaggatttt gaatggtttt ctaatatact gacatctgca tttaatttcc   1383

agaaattaaa ttaattttca tgtctgaatg ctgtaattcc atttatatac tttaagtaaa   1443

caaataagat tactacaatt aaacacatag ttccagtttc tatggccttc ccttcccacc   1503

ttctattata aattaatttt atctggtatt tttaaacatt taaaaattta tcatcagata   1563

tcagcatatg cctaattatg cctaatgaaa cttaataagc atttaatttt ccatcataca   1623

ttatagccaa ggcctatata ctatatataa ttttggattt gtttaatctt acaggctgtt   1683

ttccattgta tcatcaagtg gaagttcaag acggcatcaa acaaaacaag gatgtttaca   1743

gacatatgca aagggtcagg atatctatcc tccagtatat gttaatgctt aataacaagt   1803

aatcctaaca gcattaaagg ccaaatctgt cctctttccc ctgacttcct tacagcatgt   1863

ttatattaca agccattcag ggacaaagaa accttgacta ccccactgtc tactaggaac   1923

aaacaaacag caagcaaaat tcactttgaa agcaccagtg gttccattac attgacaact   1983

actaccaaga ttcagtagaa aataagtgct caacaactaa tccagattac aatatgattt   2043

agtgcatcat aaaattccaa caattcagat tatttttaat catctcagcc acaactgtaa   2103

agttgccaca ttactaaaga cacacacatc gtccctgttt tgtagaaata tcacaaagac   2163

caagaggcta cagaaggagg aaatttgcaa ctgtctttgc aacaataaat caggtatcta   2223

ttctggtgta gagataggat gttgaaagct gccctgctat caccagtgta gaaattaaga   2283

gtagtacaat acatgtacac tgaaatttgc catcgcgtgt ttgtgtaaac tcaatgtgca   2343

cattttgtat ttcaaaaaga aaaaataaaa gcaaaataaa atgttwawaa mwmwaaaaaa   2403

aaaaaaaaaa                                                          2413
```

```
<210> SEQ ID NO 49
<211> LENGTH: 233
<212> TYPE: PRT
<213> ORGANISM: Simian sp.

<400> SEQUENCE: 49

Met Leu Thr Leu Glu Trp Glu Ser Glu Gly Leu Gln Thr Val Gly Ile
  1               5                  10                  15

Val Val Ile Ile Cys Ala Ser Leu Lys Leu Leu His Leu Leu Gly Leu
             20                  25                  30

Ile Asp Phe Ser Glu Asp Ser Val Glu Asp Glu Leu Glu Met Ala Thr
         35                  40                  45
```

-continued

```
Val Arg His Arg Pro Glu Ala Leu Glu Leu Leu Glu Ala Gln Ser Lys
     50                  55                  60

Phe Thr Lys Lys Glu Leu Gln Ile Leu Tyr Arg Gly Phe Lys Asn Glu
 65                  70                  75                  80

Cys Pro Ser Gly Val Val Asn Glu Glu Thr Phe Lys Glu Ile Tyr Ser
                 85                  90                  95

Gln Phe Phe Pro Gln Gly Asp Ser Thr Thr Tyr Ala His Phe Leu Phe
            100                 105                 110

Asn Ala Phe Asp Thr Asp His Asn Gly Ala Val Ser Phe Glu Asp Phe
        115                 120                 125

Ile Lys Gly Leu Ser Ile Leu Leu Arg Gly Thr Val Gln Glu Lys Leu
    130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
                165                 170                 175

Lys Cys Thr Tyr Pro Val Leu Lys Glu Asp Ala Pro Arg Gln His Val
            180                 185                 190

Glu Thr Phe Phe Gln Lys Met Asp Lys Asn Lys Asp Gly Val Val Thr
        195                 200                 205

Ile Asp Glu Phe Ile Glu Ser Cys Gln Lys Asp Glu Asn Ile Met Arg
    210                 215                 220

Ser Met Gln Leu Phe Glu Asn Val Ile
225                 230


<210> SEQ ID NO 50
<211> LENGTH: 1591
<212> TYPE: DNA
<213> ORGANISM: Simian sp.
<220> FEATURE:
<221> NAME/KEY: CDS
<222> LOCATION: (265)..(963)

<400> SEQUENCE: 50

gtcgacccac gcgtccggtg cgctgtggtt gcgggggga gccccgccag ccaaatgcca      60

ggatcagcat gagaggctgg actttagtcc aggtctgtcc tcaccccggg ggaccgccgg    120

ctttgcaggg tgcagctgcg aggaactgct cactttttc cccttgcaag tctttgttcc    180

aagcctgacg ttgctacgat tctgtaatta actccctcca ctccaaaggg gtctggaggc    240

tgggatgctc tgccagctca gagg atg ttg act ctg gag tgg gag tcc gaa       291
                           Met Leu Thr Leu Glu Trp Glu Ser Glu
                             1               5

gga ctg caa aca gtg ggt att gtt gtg att ata tgt gca tct ctg aag      339
Gly Leu Gln Thr Val Gly Ile Val Val Ile Ile Cys Ala Ser Leu Lys
 10                  15                  20                  25

ctg ctt cat ttg ctg gga ctg att gat ttt tcg gaa gac agc gtg gaa      387
Leu Leu His Leu Leu Gly Leu Ile Asp Phe Ser Glu Asp Ser Val Glu
                 30                  35                  40

gat gaa ctg gag atg gcc act gtc agg cat cgg cct gag gcc ctt gag      435
Asp Glu Leu Glu Met Ala Thr Val Arg His Arg Pro Glu Ala Leu Glu
             45                  50                  55

ctt ctg gaa gcc cag agc aaa ttt acc aag aaa gag ctt cag atc ctt      483
Leu Leu Glu Ala Gln Ser Lys Phe Thr Lys Lys Glu Leu Gln Ile Leu
         60                  65                  70

tac aga gga ttt aag aac gaa tgc ccc agt ggt gtt gtt aat gaa gaa      531
Tyr Arg Gly Phe Lys Asn Glu Cys Pro Ser Gly Val Val Asn Glu Glu
     75                  80                  85
```

-continued

```
acc ttc aaa gag att tac tcg cag ttc ttt cca cag gga gac tct aca      579
Thr Phe Lys Glu Ile Tyr Ser Gln Phe Phe Pro Gln Gly Asp Ser Thr
 90                 95                 100                 105

aca tat gca cat ttt ctg ttc aat gcg ttt gat acg gac cac aat gga      627
Thr Tyr Ala His Phe Leu Phe Asn Ala Phe Asp Thr Asp His Asn Gly
                110                 115                 120

gct gtg agt ttc gag gat ttc atc aaa ggt ctt tcc att ttg ctc cgg      675
Ala Val Ser Phe Glu Asp Phe Ile Lys Gly Leu Ser Ile Leu Leu Arg
            125                 130                 135

ggg aca gta caa gaa aaa ctc aat tgg gca ttt aat ctg tat gat ata      723
Gly Thr Val Gln Glu Lys Leu Asn Trp Ala Phe Asn Leu Tyr Asp Ile
        140                 145                 150

aat aaa gat ggc tac atc act aaa gag gaa atg ctt gat ata atg aaa      771
Asn Lys Asp Gly Tyr Ile Thr Lys Glu Glu Met Leu Asp Ile Met Lys
    155                 160                 165

gca ata tac gac atg atg ggt aaa tgt aca tat cct gtc ctc aaa gaa      819
Ala Ile Tyr Asp Met Met Gly Lys Cys Thr Tyr Pro Val Leu Lys Glu
170                 175                 180                 185

gat gca ccc aga caa cac gtc gaa aca ttt ttt cag gct gtt ttc cat      867
Asp Ala Pro Arg Gln His Val Glu Thr Phe Phe Gln Ala Val Phe His
                190                 195                 200

tgt atc atc aag tgg aag ttc aag acg gca tca aac aaa aca agg atg      915
Cys Ile Ile Lys Trp Lys Phe Lys Thr Ala Ser Asn Lys Thr Arg Met
            205                 210                 215

ttt aca gac ata tgc aaa ggg tca gga tat cta tcc tcc agt ata tgt      963
Phe Thr Asp Ile Cys Lys Gly Ser Gly Tyr Leu Ser Ser Ser Ile Cys
        220                 225                 230

taatgcttaa taacaagtaa tcctaacagc attaaaggcc aaatctgtcc tctttcccct   1023

gacttcctta cagcatgttt atattacaag ccattcaggg acaaagaaac cttgactacc   1083

ccactgtcta ctaggaacaa acaaacagca agcaaaattc actttgaaag caccagtggt   1143

tccattacat tgacaactac taccaagatt cagtagaaaa taagtgctca acaactaatc   1203

cagattacaa tatgatttag tgcatcataa aattccaaca attcagatta tttttaatca   1263

tctcagccac aactgtaaag ttgccacatt actaaagaca cacacatcgt ccctgttttg   1323

tagaaatatc acaaagacca agaggctaca gaaggaggaa atttgcaact gtctttgcaa   1383

caataaatca ggtatctatt ctggtgtaga gataggatgt tgaaagctgc cctgctatca   1443

ccagtgtaga aattaagagt agtacaatac atgtacactg aaatttgcca tcgcgtgttt   1503

gtgtaaactc aatgtgcaca ttttgtattt caaaaagaaa aaataaaagc aaaataaaat   1563

gttwawaamw mwaaaaaaaa aaaaaaaa                                      1591


<210> SEQ ID NO 51
<211> LENGTH: 233
<212> TYPE: PRT
<213> ORGANISM: Simian sp.

<400> SEQUENCE: 51

Met Leu Thr Leu Glu Trp Glu Ser Glu Gly Leu Gln Thr Val Gly Ile
  1               5                  10                  15

Val Val Ile Ile Cys Ala Ser Leu Lys Leu Leu His Leu Leu Gly Leu
             20                  25                  30

Ile Asp Phe Ser Glu Asp Ser Val Glu Asp Glu Leu Glu Met Ala Thr
         35                  40                  45

Val Arg His Arg Pro Glu Ala Leu Glu Leu Leu Glu Ala Gln Ser Lys
     50                  55                  60
```

-continued

```
Phe Thr Lys Lys Glu Leu Gln Ile Leu Tyr Arg Gly Phe Lys Asn Glu
 65                  70                  75                  80

Cys Pro Ser Gly Val Val Asn Glu Glu Thr Phe Lys Glu Ile Tyr Ser
                 85                  90                  95

Gln Phe Phe Pro Gln Gly Asp Ser Thr Thr Tyr Ala His Phe Leu Phe
            100                 105                 110

Asn Ala Phe Asp Thr Asp His Asn Gly Ala Val Ser Phe Glu Asp Phe
        115                 120                 125

Ile Lys Gly Leu Ser Ile Leu Leu Arg Gly Thr Val Gln Glu Lys Leu
    130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
                165                 170                 175

Lys Cys Thr Tyr Pro Val Leu Lys Glu Asp Ala Pro Arg Gln His Val
            180                 185                 190

Glu Thr Phe Phe Gln Ala Val Phe His Cys Ile Ile Lys Trp Lys Phe
        195                 200                 205

Lys Thr Ala Ser Asn Lys Thr Arg Met Phe Thr Asp Ile Cys Lys Gly
    210                 215                 220

Ser Gly Tyr Leu Ser Ser Ser Ile Cys
225                 230


<210> SEQ ID NO 52
<211> LENGTH: 2051
<212> TYPE: DNA
<213> ORGANISM: Rattus sp.
<220> FEATURE:
<221> NAME/KEY: CDS
<222> LOCATION: (85)..(1305)

<400> SEQUENCE: 52

ggtggagcta agcactcact gcggtgctgc cctgcgtctg cagagaacaa ggaaagcttc      60

tctgcagggc tgtcagctgc caaa atg aac ggc gtg gaa ggg aac aac gag       111
                           Met Asn Gly Val Glu Gly Asn Asn Glu
                             1               5

ctc cct ctc gct aac acc tcg acc tcc gcc ctt gtc ccg gaa gat ctg      159
Leu Pro Leu Ala Asn Thr Ser Thr Ser Ala Leu Val Pro Glu Asp Leu
 10                  15                  20                  25

gat ctg aag caa gac cag ccg ctc agc gag gaa act gac acg gtg cgg      207
Asp Leu Lys Gln Asp Gln Pro Leu Ser Glu Glu Thr Asp Thr Val Arg
                 30                  35                  40

gag atg gag gct gca ggt gag gcc ggt gcg gag gga ggc gcg tcc ccc      255
Glu Met Glu Ala Ala Gly Glu Ala Gly Ala Glu Gly Gly Ala Ser Pro
             45                  50                  55

gat tcg gag cac tgc gac ccc cag ctc tgc ctc cga gtg gct gag aat      303
Asp Ser Glu His Cys Asp Pro Gln Leu Cys Leu Arg Val Ala Glu Asn
         60                  65                  70

ggc tgt gct gcc gca gcg gga gag ggg ctg gag gat ggt ctg tct tca      351
Gly Cys Ala Ala Ala Ala Gly Glu Gly Leu Glu Asp Gly Leu Ser Ser
     75                  80                  85

tca aag tgt ggg gac gca ccc ttg gcg tct gtg gca gcc aac gac agc      399
Ser Lys Cys Gly Asp Ala Pro Leu Ala Ser Val Ala Ala Asn Asp Ser
 90                  95                 100                 105

aat aaa aat ggc tgt cag ctt gca ggg ccg ctc agc cct gct aag cca      447
Asn Lys Asn Gly Cys Gln Leu Ala Gly Pro Leu Ser Pro Ala Lys Pro
                110                 115                 120

aaa act ctg gaa gcc agt ggt gca gtg ggc ctg ggg tcg cag atg atg      495
```

-continued

```
Lys Thr Leu Glu Ala Ser Gly Ala Val Gly Leu Gly Ser Gln Met Met
            125                 130                 135

cca ggg ccg aag aag acc aag gta atg act acc aag ggc gcc atc tct      543
Pro Gly Pro Lys Lys Thr Lys Val Met Thr Thr Lys Gly Ala Ile Ser
        140                 145                 150

gcg act aca ggc aag gaa gga gaa gca ggg gcg gca atg cag gaa aag      591
Ala Thr Thr Gly Lys Glu Gly Glu Ala Gly Ala Ala Met Gln Glu Lys
    155                 160                 165

aag ggg gtg cag aaa gaa aaa aag gca gct gga gga ggg aaa gac gag      639
Lys Gly Val Gln Lys Glu Lys Lys Ala Ala Gly Gly Gly Lys Asp Glu
170                 175                 180                 185

act cgt cct aga gcc cct aag atc aat aac tgc atg gac tcc ctg gaa      687
Thr Arg Pro Arg Ala Pro Lys Ile Asn Asn Cys Met Asp Ser Leu Glu
                190                 195                 200

gcc atc gat caa gag ctg tca aat gta aat gcg caa gct gac agg gcc      735
Ala Ile Asp Gln Glu Leu Ser Asn Val Asn Ala Gln Ala Asp Arg Ala
            205                 210                 215

ttc ctc cag ctg gaa cgc aaa ttt ggg cgg atg aga agg ctc cac atg      783
Phe Leu Gln Leu Glu Arg Lys Phe Gly Arg Met Arg Arg Leu His Met
        220                 225                 230

cag cgc cga agt ttc atc atc caa aac atc cca ggt ttc tgg gtc aca      831
Gln Arg Arg Ser Phe Ile Ile Gln Asn Ile Pro Gly Phe Trp Val Thr
    235                 240                 245

gcg ttt cgg aac cac ccg caa ctg tca ccg atg atc agt ggc caa gat      879
Ala Phe Arg Asn His Pro Gln Leu Ser Pro Met Ile Ser Gly Gln Asp
250                 255                 260                 265

gaa gac atg atg agg tac atg atc aat tta gag gtg gag gag ctt aag      927
Glu Asp Met Met Arg Tyr Met Ile Asn Leu Glu Val Glu Glu Leu Lys
                270                 275                 280

cac cca aga gca ggg tgc aaa ttt aag ttc atc ttc caa agc aac ccc      975
His Pro Arg Ala Gly Cys Lys Phe Lys Phe Ile Phe Gln Ser Asn Pro
            285                 290                 295

tac ttc cga aat gag ggg ctg gtc aaa gag tac gag cgc aga tcc tca      1023
Tyr Phe Arg Asn Glu Gly Leu Val Lys Glu Tyr Glu Arg Arg Ser Ser
        300                 305                 310

ggt cga gtg gtg tcg ctc tct acg cca atc cgc tgg cac cgg ggt caa      1071
Gly Arg Val Val Ser Leu Ser Thr Pro Ile Arg Trp His Arg Gly Gln
    315                 320                 325

gaa ccc cag gcc cat atc cac agg aat aga gag ggg aac acg att ccc      1119
Glu Pro Gln Ala His Ile His Arg Asn Arg Glu Gly Asn Thr Ile Pro
330                 335                 340                 345

agt ttc ttc aat tgg ttc tca gac cac agc ctc cta gaa ttc gac aga      1167
Ser Phe Phe Asn Trp Phe Ser Asp His Ser Leu Leu Glu Phe Asp Arg
                350                 355                 360

ata gct gaa att atc aaa ggg gag ctt tgg tcc aat ccc cta caa tac      1215
Ile Ala Glu Ile Ile Lys Gly Glu Leu Trp Ser Asn Pro Leu Gln Tyr
            365                 370                 375

tac ctg atg ggc gat ggg cca cgc aga gga gtt cga gtc cca cca agg      1263
Tyr Leu Met Gly Asp Gly Pro Arg Arg Gly Val Arg Val Pro Pro Arg
        380                 385                 390

cag cca gtg gag agt ccc agg tcc ttc agg ttc cag tct ggc              1305
Gln Pro Val Glu Ser Pro Arg Ser Phe Arg Phe Gln Ser Gly
    395                 400                 405

taagctctgc cctcgtgaga agctcttaca gaagagtcct taccaccttc tcagcttggc   1365

tagcagcatg cagccttctg tctgctttct cttccttgga ttgtgtcctt tggttcttct   1425

aagtctccgg tagtttcaag gttgtggctt ccaagtcttt gctcttcttt ctcttggcca   1485

tcacgatgtc ctgcatagtg ttaatggtgt tccaagtgca tggcctccaa actgcttcta   1545
```

-continued

```
tgccaagctc acgtgctgta gtttgtactg cttttctttg catggcttgg ttcctgtctg   1605

tgatcttcta ggttttttgt tttctttttt aaaagtggtt ctctatcaaa agaaagcttg   1665

acatatcctt accaagaact agccagattt catactgtgt tcccgatatc tatgtactgt   1725

gaagaactgt gagtttcgcc actgcaagat gggactgtat cccaatccag ccatcagccc   1785

aacaggacat tccaagctgt caccaactga tcctagctgt cttcctgggc ctttgccatt   1845

taccctgctt tttatctata gaatgagcag gtggctggta ggtgactact aggtaagagt   1905

gaagtattag gtgaggagtg ttttctgtca ccacattgtt cttgtaccaa tgcatcatga   1965

tcagcttgga tcagctactg actgtctgat atttctaacc cccaacacaa aaaaaaaaaa   2025

aaaaaaaaaa aaaaaaaaaa aaaaaa                                        2051
```

```
<210> SEQ ID NO 53
<211> LENGTH: 407
<212> TYPE: PRT
<213> ORGANISM: Rattus sp.

<400> SEQUENCE: 53

Met Asn Gly Val Glu Gly Asn Asn Glu Leu Pro Leu Ala Asn Thr Ser
  1               5                  10                  15

Thr Ser Ala Leu Val Pro Glu Asp Leu Asp Leu Lys Gln Asp Gln Pro
             20                  25                  30

Leu Ser Glu Glu Thr Asp Thr Val Arg Glu Met Glu Ala Ala Gly Glu
         35                  40                  45

Ala Gly Ala Glu Gly Gly Ala Ser Pro Asp Ser Glu His Cys Asp Pro
     50                  55                  60

Gln Leu Cys Leu Arg Val Ala Glu Asn Gly Cys Ala Ala Ala Ala Gly
 65                  70                  75                  80

Glu Gly Leu Glu Asp Gly Leu Ser Ser Ser Lys Cys Gly Asp Ala Pro
                 85                  90                  95

Leu Ala Ser Val Ala Ala Asn Asp Ser Asn Lys Asn Gly Cys Gln Leu
            100                 105                 110

Ala Gly Pro Leu Ser Pro Ala Lys Pro Lys Thr Leu Glu Ala Ser Gly
        115                 120                 125

Ala Val Gly Leu Gly Ser Gln Met Met Pro Gly Pro Lys Lys Thr Lys
    130                 135                 140

Val Met Thr Thr Lys Gly Ala Ile Ser Ala Thr Thr Gly Lys Glu Gly
145                 150                 155                 160

Glu Ala Gly Ala Ala Met Gln Glu Lys Lys Gly Val Gln Lys Glu Lys
                165                 170                 175

Lys Ala Ala Gly Gly Gly Lys Asp Glu Thr Arg Pro Arg Ala Pro Lys
            180                 185                 190

Ile Asn Asn Cys Met Asp Ser Leu Glu Ala Ile Asp Gln Glu Leu Ser
        195                 200                 205

Asn Val Asn Ala Gln Ala Asp Arg Ala Phe Leu Gln Leu Glu Arg Lys
    210                 215                 220

Phe Gly Arg Met Arg Arg Leu His Met Gln Arg Arg Ser Phe Ile Ile
225                 230                 235                 240

Gln Asn Ile Pro Gly Phe Trp Val Thr Ala Phe Arg Asn His Pro Gln
                245                 250                 255

Leu Ser Pro Met Ile Ser Gly Gln Asp Glu Asp Met Met Arg Tyr Met
            260                 265                 270

Ile Asn Leu Glu Val Glu Glu Leu Lys His Pro Arg Ala Gly Cys Lys
        275                 280                 285
```

-continued

Phe Lys Phe Ile Phe Gln Ser Asn Pro Tyr Phe Arg Asn Glu Gly Leu
    290                 295                 300

Val Lys Glu Tyr Glu Arg Arg Ser Ser Gly Arg Val Val Ser Leu Ser
305                 310                 315                 320

Thr Pro Ile Arg Trp His Arg Gly Gln Glu Pro Gln Ala His Ile His
                325                 330                 335

Arg Asn Arg Glu Gly Asn Thr Ile Pro Ser Phe Phe Asn Trp Phe Ser
            340                 345                 350

Asp His Ser Leu Leu Glu Phe Asp Arg Ile Ala Glu Ile Ile Lys Gly
        355                 360                 365

Glu Leu Trp Ser Asn Pro Leu Gln Tyr Tyr Leu Met Gly Asp Gly Pro
    370                 375                 380

Arg Arg Gly Val Arg Val Pro Pro Arg Gln Pro Val Glu Ser Pro Arg
385                 390                 395                 400

Ser Phe Arg Phe Gln Ser Gly
                405

<210> SEQ ID NO 54
<211> LENGTH: 4148
<212> TYPE: DNA
<213> ORGANISM: Homo sapiens
<220> FEATURE:
<221> NAME/KEY: CDS
<222> LOCATION: (88)..(1329)

<400> SEQUENCE: 54
ggggtggtgc tagacgtttc gggcagagct cggccgctgc ggaggacaag gaactctccc     60
tctcccacta gtctgacttc ttccaaa atg agc ggc ctg gat ggg ggc aac aag    114
                              Met Ser Gly Leu Asp Gly Gly Asn Lys
                                1               5 ctc cct ctc gcc caa acc ggc ggc ctg gct gct ccc gac cat gcc tca      162
Leu Pro Leu Ala Gln Thr Gly Gly Leu Ala Ala Pro Asp His Ala Ser
 10                  15                  20                  25 gga gat ccg gac cta gac cag tgc caa ggg ctc cgt gaa gaa acc gag      210
Gly Asp Pro Asp Leu Asp Gln Cys Gln Gly Leu Arg Glu Glu Thr Glu
                 30                  35                  40 gcg aca cag gtg atg gcg aac aca ggt ggg ggc agc ctg gag acc gtt      258
Ala Thr Gln Val Met Ala Asn Thr Gly Gly Gly Ser Leu Glu Thr Val
             45                  50                  55 gcg gag ggg ggt gca tcc cag gat cct gtc gac tgt ggc ccc gcg ctc      306
Ala Glu Gly Gly Ala Ser Gln Asp Pro Val Asp Cys Gly Pro Ala Leu
         60                  65                  70 cgc gtc cca gtt gcc ggg agt cgc ggc ggt gca gcg acc aaa gcc ggg      354
Arg Val Pro Val Ala Gly Ser Arg Gly Gly Ala Ala Thr Lys Ala Gly
     75                  80                  85 cag gag gat gct cca cct tct acg aaa ggt ctg gaa gca gcc tct gcc      402
Gln Glu Asp Ala Pro Pro Ser Thr Lys Gly Leu Glu Ala Ala Ser Ala
 90                  95                 100                 105 gcc gag gct gct gac agc agc cag aaa aat ggc tgt cag ctt gga gag      450
Ala Glu Ala Ala Asp Ser Ser Gln Lys Asn Gly Cys Gln Leu Gly Glu
                110                 115                 120 ccc cgt ggc cct gct ggg cag aag gct cta gaa gcc tgt ggc gca ggg      498
Pro Arg Gly Pro Ala Gly Gln Lys Ala Leu Glu Ala Cys Gly Ala Gly
            125                 130                 135 ggc ttg ggg tct cag atg ata ccg ggg aag aag gcc aag gaa gtg acg      546
Gly Leu Gly Ser Gln Met Ile Pro Gly Lys Lys Ala Lys Glu Val Thr
        140                 145                 150 act aaa aaa cgc gcc atc tcg gca gca gtg gaa aag gag gga gaa gca      594

-continued

```
Thr Lys Lys Arg Ala Ile Ser Ala Ala Val Glu Lys Glu Gly Glu Ala
    155                 160                 165

ggg gcg gcg atg gag gaa aag aag gta gtg cag aag gaa aaa aag gtg      642
Gly Ala Ala Met Glu Glu Lys Lys Val Val Gln Lys Glu Lys Lys Val
170                 175                 180                 185

gca gga ggg gtg aaa gag gag aca cgg ccc agg gcc ccg aag atc aat      690
Ala Gly Gly Val Lys Glu Glu Thr Arg Pro Arg Ala Pro Lys Ile Asn
                190                 195                 200

aac tgc atg gac tca ctg gag gcc atc gat caa gag ttg tca aac gta      738
Asn Cys Met Asp Ser Leu Glu Ala Ile Asp Gln Glu Leu Ser Asn Val
            205                 210                 215

aat gcc cag gct gac agg gcc ttc ctt cag ctt gag cgc aag ttt ggc      786
Asn Ala Gln Ala Asp Arg Ala Phe Leu Gln Leu Glu Arg Lys Phe Gly
        220                 225                 230

cgc atg cga agg ctc cac atg cag cgc aga agt ttc att atc cag aat      834
Arg Met Arg Arg Leu His Met Gln Arg Arg Ser Phe Ile Ile Gln Asn
    235                 240                 245

atc cca ggt ttc tgg gtt act gcc ttt cga aac cac ccc cag ctg tca      882
Ile Pro Gly Phe Trp Val Thr Ala Phe Arg Asn His Pro Gln Leu Ser
250                 255                 260                 265

cct atg atc agt ggc caa gat gaa gac atg ctg agg tac atg atc aat      930
Pro Met Ile Ser Gly Gln Asp Glu Asp Met Leu Arg Tyr Met Ile Asn
                270                 275                 280

ttg gag gtg gag gag ctt aaa cac ccc aga gca ggc tgc aaa ttc aag      978
Leu Glu Val Glu Glu Leu Lys His Pro Arg Ala Gly Cys Lys Phe Lys
            285                 290                 295

ttc atc ttt cag ggc aac ccc tac ttc cga aat gag ggg ctt gtc aag     1026
Phe Ile Phe Gln Gly Asn Pro Tyr Phe Arg Asn Glu Gly Leu Val Lys
        300                 305                 310

gaa tat gaa cgc aga tcc tct ggc cgg gtg gtg tct ctt tcc act cca     1074
Glu Tyr Glu Arg Arg Ser Ser Gly Arg Val Val Ser Leu Ser Thr Pro
    315                 320                 325

atc cgc tgg cac cga ggc caa gac ccc cag gct cat atc cac aga aac     1122
Ile Arg Trp His Arg Gly Gln Asp Pro Gln Ala His Ile His Arg Asn
330                 335                 340                 345

cgg gaa ggg aac act atc cct agt ttc ttc aac tgg ttt tca gac cac     1170
Arg Glu Gly Asn Thr Ile Pro Ser Phe Phe Asn Trp Phe Ser Asp His
                350                 355                 360

agc ctt cta gaa ttc gac aga att gca gag att atc aaa gga gaa ctg     1218
Ser Leu Leu Glu Phe Asp Arg Ile Ala Glu Ile Ile Lys Gly Glu Leu
            365                 370                 375

tgg ccc aat ccc cta caa tac tac ctg atg ggt gaa ggg ccc cgt aga     1266
Trp Pro Asn Pro Leu Gln Tyr Tyr Leu Met Gly Glu Gly Pro Arg Arg
        380                 385                 390

gga att cga ggc cca cca agg cag cca gtg gag agc gcc aga tcc ttc     1314
Gly Ile Arg Gly Pro Pro Arg Gln Pro Val Glu Ser Ala Arg Ser Phe
    395                 400                 405

agg ttc cag tct ggc taatctctgt cctgtgagaa gcttctgcac aagtttcctt     1369
Arg Phe Gln Ser Gly
410

accacctcct cttggaccta tgcttggcca acagcatgca gtcttccatc tgctttctct   1429

tcatactgtg gattatcttt tcctttggtt ctaaatcttc agtaatcggt tgcaagattg   1489

ttggcttacc tgcctgtgcc attcttcctc tgggccttca tgcttttctg cattgtgtta   1549

acatgtttca agtgcatggc cttctacggc ttctatgcca agcgtatgat actatagata   1609

tagtgtacca tactgccttt ctttgcatgg cttggaccct atctgtgacc atgctcttct   1669

cccaatttaa gtggttctgt accacaaaga atcttgatac attttcacaa ataactgatt   1729
```

-continued

```
gggcttcata ctttatgctg gctgtgtcct gatacccatg tacttatggt aagctatttg   1789
ggtattacca ctgcaagaca aaactgatat cttaacccgg ccatcaaccc aaattggaca   1849
ttccagacta ccaccaactg gatcccagct gccttcctgg gcttgtgcca tccaccctac   1909
tggttatctg atagaacaag ctggtggctg atgggtgact gctaggcgtg actgaggtaa   1969
tagatgaaaa gtgttctatg ttatcacatt ggttttcctg tacctttggt tactctacgt   2029
catgaccagc tgctggtgag tatgaagcct gtgctatagc ccacccctac tcactctcac   2089
cttctggttg aactttgctt aggccaccat tgtctgcctc atcaggaact atctgtagac   2149
gtagctccca gggagctcac agcaacaccc cctaccacca ggatgggcag taatatgtga   2209
cagagcccaa agcaaggctg gaacgcagtc ccttccagct tagtctttct gactcctagc   2269
caacaaacca tccttaatgt gagcaacttc tttaggcatt tcctcttttc cccgcctgca   2329
cccactctga acatgacaaa agttgccaga gttggggcat tgaggaagag atatttctgg   2389
aatgtgagac ttgttatgcc tctgtctctt tctctccctc cccctcccct ctccctcccc   2449
ctctccctcc catccctttt cttccctttc actctgaagc agttttagct tattaacaga   2509
aaacaaaact ggcaaagcag gctttttgtt taatttgctc tttccctgat tgtgttcaga   2569
gagaaaggtt atgattaaat gggctccaga tctcttattg cccttattcc tccaccccac   2629
ttcttttagc aaggtctgaa agtttcaaag ggagacctat aggttaattg tttagttata   2689
ggcagtgtta aattaggcag attttgacat atttatcttt ttaccccatc cattctacca   2749
aaacctgtgt atttcttgag tttttagttt gagaagctgg aaagagagag aagggcctca   2809
cagtgatggg ttcaggacgg gtcaaaggca aaggcctttg tgatgtgagc aaaggcaacc   2869
aaaacttagc ctcactccac ttttctaaag atggaaattc ttttttgggc cttggactgc   2929
ttctagggta gcattttgta ggtcactctt ctcctttgta ctattttgtt tctgccctga   2989
tgtcccttgg gtctccatcc tactgcctgg ctttcttggc cctcatttct cagcttctgc   3049
atttccttcc ctgctcctaa caaatgaaga agcaggctgc agcctgcatt gtggaagatc   3109
tccagcctcc ttgtagggga taaggggatg tgtagcatct gtgtggattt tcacggacaa   3169
gttccagtag gtgggacagt gatgccgtca aggcttagtt atgatcatgt gtggtgataa   3229
agaccatcca ccatcaccct tttccccttt ggttttgaag gccttgccct aagctacctg   3289
agggtttagg aggtctgaac acacacagtg gagaggttaa tctaggttgg gaaactgagt   3349
aaaagtccag agcaggaatg agcctgctgt ggcgtgggtt tggaaaggct cacaggaaag   3409
aacctgcagg atcaggggtg ggaggggagg cccctgaggt gctctccagg gaagaggggc   3469
tggggtttaa atagcatgct tggaggaaga ttttccttca atttttccta agtccttgaa   3529
ttcaccagta gatttttgta aacaaaatgt aagtcgatgt tttctctcaa ttatcctagg   3589
agtgaccttt atatgtgtgg aagattaatg gtatatgctc cttatgtcac tgtttttgag   3649
taaaatccat ttcctttctc tgtttcagcc tatgacaaaa ttgatgttta caggcctgct   3709
ttttgcttat aattgacaac atgtgcaaaa ataccaaatt tgtgtcctgt gcagtatgaa   3769
gaattcagtg aatattcatt aatgtattag cttgttttgc tctctgttca tatatggctc   3829
tattcttaga aatataattt gaatgtgatc tttcaatagt ctgaatattt tacaaattat   3889
agctatgtct tgtgaaaata acctcaaaaa gaaaaatacg actctgttgt cttacttgat   3949
atttcttgcc ctagtaatgt acttgacatt tatgttccta agcagtgtaa gtaccagtag   4009
aatttctctg tcaaactcaa tgatcattta gtacttttgt cttctcccat gtgcttgaag   4069
gaaaaataaa gtgtcactac cgtatttctt gttttcatca aaaaataaaa ataatttaaa   4129
```

-continued

```
aaacaaaaaa aaaaaaaaa                                              4148


<210> SEQ ID NO 55
<211> LENGTH: 414
<212> TYPE: PRT
<213> ORGANISM: Homo sapiens

<400> SEQUENCE: 55

Met Ser Gly Leu Asp Gly Gly Asn Lys Leu Pro Leu Ala Gln Thr Gly
  1               5                  10                  15

Gly Leu Ala Ala Pro Asp His Ala Ser Gly Asp Pro Asp Leu Asp Gln
             20                  25                  30

Cys Gln Gly Leu Arg Glu Glu Thr Glu Ala Thr Gln Val Met Ala Asn
         35                  40                  45

Thr Gly Gly Gly Ser Leu Glu Thr Val Ala Glu Gly Gly Ala Ser Gln
     50                  55                  60

Asp Pro Val Asp Cys Gly Pro Ala Leu Arg Val Pro Val Ala Gly Ser
 65                  70                  75                  80

Arg Gly Gly Ala Ala Thr Lys Ala Gly Gln Glu Asp Ala Pro Pro Ser
                 85                  90                  95

Thr Lys Gly Leu Glu Ala Ala Ser Ala Ala Glu Ala Ala Asp Ser Ser
            100                 105                 110

Gln Lys Asn Gly Cys Gln Leu Gly Glu Pro Arg Gly Pro Ala Gly Gln
        115                 120                 125

Lys Ala Leu Glu Ala Cys Gly Ala Gly Gly Leu Gly Ser Gln Met Ile
    130                 135                 140

Pro Gly Lys Lys Ala Lys Glu Val Thr Thr Lys Lys Arg Ala Ile Ser
145                 150                 155                 160

Ala Ala Val Glu Lys Glu Gly Glu Ala Gly Ala Ala Met Glu Glu Lys
                165                 170                 175

Lys Val Val Gln Lys Glu Lys Lys Val Ala Gly Gly Val Lys Glu Glu
            180                 185                 190

Thr Arg Pro Arg Ala Pro Lys Ile Asn Asn Cys Met Asp Ser Leu Glu
        195                 200                 205

Ala Ile Asp Gln Glu Leu Ser Asn Val Asn Ala Gln Ala Asp Arg Ala
    210                 215                 220

Phe Leu Gln Leu Glu Arg Lys Phe Gly Arg Met Arg Arg Leu His Met
225                 230                 235                 240

Gln Arg Arg Ser Phe Ile Ile Gln Asn Ile Pro Gly Phe Trp Val Thr

                245                 250                 255
Ala Phe Arg Asn His Pro Gln Leu Ser Pro Met Ile Ser Gly Gln Asp
            260                 265                 270

Glu Asp Met Leu Arg Tyr Met Ile Asn Leu Glu Val Glu Glu Leu Lys
        275                 280                 285

His Pro Arg Ala Gly Cys Lys Phe Lys Phe Ile Phe Gln Gly Asn Pro
    290                 295                 300

Tyr Phe Arg Asn Glu Gly Leu Val Lys Glu Tyr Glu Arg Arg Ser Ser
305                 310                 315                 320

Gly Arg Val Val Ser Leu Ser Thr Pro Ile Arg Trp His Arg Gly Gln
                325                 330                 335

Asp Pro Gln Ala His Ile His Arg Asn Arg Glu Gly Asn Thr Ile Pro
            340                 345                 350

Ser Phe Phe Asn Trp Phe Ser Asp His Ser Leu Leu Glu Phe Asp Arg
        355                 360                 365
```

-continued

```
Ile Ala Glu Ile Ile Lys Gly Glu Leu Trp Pro Asn Pro Leu Gln Tyr
    370                 375                 380

Tyr Leu Met Gly Glu Gly Pro Arg Arg Gly Ile Arg Gly Pro Pro Arg
385                 390                 395                 400

Gln Pro Val Glu Ser Ala Arg Ser Phe Arg Phe Gln Ser Gly
                405                 410


<210> SEQ ID NO 56
<211> LENGTH: 2643
<212> TYPE: DNA
<213> ORGANISM: Rattus sp.
<220> FEATURE:
<221> NAME/KEY: CDS
<222> LOCATION: (1)..(801)

<400> SEQUENCE: 56

ctg aaa ggg gcg agg ccc agg gtg gtg aac tcc acc tgc agt gac ttc       48
Leu Lys Gly Ala Arg Pro Arg Val Val Asn Ser Thr Cys Ser Asp Phe
  1               5                  10                  15

aac cat ggc tca gct ctg cac atc gct gcc tcg aat ctg tgc ctg ggc       96
Asn His Gly Ser Ala Leu His Ile Ala Ala Ser Asn Leu Cys Leu Gly
             20                  25                  30

gcc gcc aaa tgt tta ctg gag cat ggt gcc aac cca gcg ctg agg aat      144
Ala Ala Lys Cys Leu Leu Glu His Gly Ala Asn Pro Ala Leu Arg Asn
         35                  40                  45

cga aaa gga cag gta cca gcg gaa gtg gtc cca gac ccc atg gac atg      192
Arg Lys Gly Gln Val Pro Ala Glu Val Val Pro Asp Pro Met Asp Met
     50                  55                  60

tcc ctt gac aag gca gag gca gcc ctg gtg gcc aag gaa ttg cgg acg      240
Ser Leu Asp Lys Ala Glu Ala Ala Leu Val Ala Lys Glu Leu Arg Thr
 65                  70                  75                  80

ctg cta gaa gag gct gtg cca ctg tcc tgc acc ctt cct aaa gtc aca      288
Leu Leu Glu Glu Ala Val Pro Leu Ser Cys Thr Leu Pro Lys Val Thr
                 85                  90                  95

cta ccc aac tat gac aac gtc cca ggc aat ctc atg ctc agc gcg ctg      336
Leu Pro Asn Tyr Asp Asn Val Pro Gly Asn Leu Met Leu Ser Ala Leu
            100                 105                 110

ggc ctg cgt cta gga gac cga gtg ctc ctc gat ggc cag aag acg ggc      384
Gly Leu Arg Leu Gly Asp Arg Val Leu Leu Asp Gly Gln Lys Thr Gly
        115                 120                 125

acg ctg agg ttc tgc ggg acc acc gag ttc gcc agt ggc cag tgg gtg      432
Thr Leu Arg Phe Cys Gly Thr Thr Glu Phe Ala Ser Gly Gln Trp Val
    130                 135                 140

ggc gtg gag cta gat gaa ccg gaa ggc aag aac gac ggc agc gtt ggg      480
Gly Val Glu Leu Asp Glu Pro Glu Gly Lys Asn Asp Gly Ser Val Gly
145                 150                 155                 160

ggt gtc cgg tac ttc atc tgc cct ccc aag cag ggt ctc ttt gca tct      528
Gly Val Arg Tyr Phe Ile Cys Pro Pro Lys Gln Gly Leu Phe Ala Ser
                165                 170                 175

gtg tcc aag gtc tcc aag gca gtg gat gca ccc ccc tca tct gtt acc      576
Val Ser Lys Val Ser Lys Ala Val Asp Ala Pro Pro Ser Ser Val Thr
            180                 185                 190

tcc acg ccc cgc act ccc cgg atg gac ttc tcc cgt gta acg ggc aaa      624
Ser Thr Pro Arg Thr Pro Arg Met Asp Phe Ser Arg Val Thr Gly Lys
        195                 200                 205

ggc cgg agg gaa cac aaa ggg aag aag aag tcc cca tct tcc cca tct      672
Gly Arg Arg Glu His Lys Gly Lys Lys Lys Ser Pro Ser Ser Pro Ser
    210                 215                 220

ctg ggc agc ctg cag cag cgt gaa ggg gcc aaa gct gaa gtt gga gac      720
Leu Gly Ser Leu Gln Gln Arg Glu Gly Ala Lys Ala Glu Val Gly Asp
```

-continued

```
225                 230                 235                 240

caa gtc ctt gtg gca ggc cag aac agg gat tgt gcg ttt cta tgg gaa      768
Gln Val Leu Val Ala Gly Gln Asn Arg Asp Cys Ala Phe Leu Trp Glu
                245                 250                 255

gac aga ctt tgc tcc agg tta ctg gta tgg cat tgaactggac cagcccacgg    821
Asp Arg Leu Cys Ser Arg Leu Leu Val Trp His
            260                 265

gcaagcatga cggctctgtg ttcggtgtcc ggtactttac ctgtgccccg aggcacgggg    881

tctttgcacc agcatctcgt atccagagga ttggtggatc cactgatccc cctggagaca    941

gtgttggagc aaaaaaagtg catcaagtga caatgacaca gcccaaacgc accttcacaa   1001

cagtccggac cccaaaggac attgcatcag agaactctat ctccaggtta ctcttctgct   1061

gctggtttcc ttggatgctg agggcggaga tgcagtctta gagacctgga tacctgacac   1121

agagacagag tcccctctag catctcctga cacaaggaga ccccagtcac cctaagatag   1181

agattcccag tgacacctcc agaatagaaa ccccgttagc cagccctcga ttactgaggt   1241

cccattatta acagatctcc catgacgact cccccaaata cagacctcat gttaccccaa   1301

aagagattcc ctgagtagca ccttcaggct agtccctgtc ccctacccct cagagcagat   1361

ttcccccaat aaacattttc cacatcaccc aagggatgct gaccctctcc acgacaggac   1421

gttcttgagt taccagtgga ttagagtccc atgaatgaag acccccccca ccccggttct   1481

ccttaagcat aggtcatacc tccagaatag ccagccacat cactatcccc atgtaacatc   1541

agtctcctca aaatggcgtg aggtcactag aaagacctta tactctcctc tccttctcag   1601

agatgccctc cattcactta agtccctgtt ctcaccccctg aacaagacac ctaattaacc  1661

ggcccactca cctcaattac aaacaccaaa atcgtcctgg aagcatgaat tacaggacag   1721

caagtcttcc tgccctctgc acccttgaga aacccccagt gccttgtatg aagcccaccc   1781

cacatggccc acagtccctg tgctggccaa ggctcccaga aaattctcta ttttttaaag   1841

taataacttc cccccctttg gggggatccc caaatttgga gaccccattc tagaacactg   1901

gggagttcaa attccagaga gaatatatat tatatataat ccccaattcc ccatgcttcc   1961

aagccctaca atctctagaa gaccccaaat ttctaattcc caggacttcc cctacccaag   2021

tcacagaatc ttcaaatccc cagggaatcc caaacttaag ataccaatcc caaaccctca   2081

ggaaatcccc caacacaagg tccttaggac cgggaggaag gaacctgttg ccaggagaac   2141

atcccaggct ctcagggcat ctcaaacctg actcccaggc accaggagac cccaaacaga   2201

aagtcccatc tttggaacaa ggataggact ctaataccct tagtccatgg atctttaatt   2261

tcccaacctc caaactccat gggccccacc ctcaagggaa cccccaagat ccaaatctct   2321

gataactaat atgtgcaggg ccccagggct ctaacaggac cccaaatcat ggagtcccta   2381

cttcaatcta ccttctggtc acaggtccaa gacactaaat ctgagtcatt ggccccaaag   2441

gacttcacag cacctgggcc agactaacag cctgagggag aacctgaggg ccccgtgggt   2501

ccagagcaga cctggggccc tgaccaccaa ggacagctca cgactgcccc ttcactgcat   2561

gtccctaaac tcagcatgac tcctgtcctc ttcaataaag acgtttctat ggcaaaaaaa   2621

aaaaaaaaaa aaaaaaaaaa aa                                            2643

<210> SEQ ID NO 57
<211> LENGTH: 267
<212> TYPE: PRT
<213> ORGANISM: Rattus sp.

<400> SEQUENCE: 57
```

-continued

```
Leu Lys Gly Ala Arg Pro Arg Val Val Asn Ser Thr Cys Ser Asp Phe
  1               5                  10                  15

Asn His Gly Ser Ala Leu His Ile Ala Ala Ser Asn Leu Cys Leu Gly
             20                  25                  30

Ala Ala Lys Cys Leu Leu Glu His Gly Ala Asn Pro Ala Leu Arg Asn
         35                  40                  45

Arg Lys Gly Gln Val Pro Ala Glu Val Val Pro Asp Pro Met Asp Met
     50                  55                  60

Ser Leu Asp Lys Ala Glu Ala Ala Leu Val Ala Lys Glu Leu Arg Thr
 65                  70                  75                  80

Leu Leu Glu Glu Ala Val Pro Leu Ser Cys Thr Leu Pro Lys Val Thr
                 85                  90                  95

Leu Pro Asn Tyr Asp Asn Val Pro Gly Asn Leu Met Leu Ser Ala Leu
            100                 105                 110

Gly Leu Arg Leu Gly Asp Arg Val Leu Leu Asp Gly Gln Lys Thr Gly
        115                 120                 125

Thr Leu Arg Phe Cys Gly Thr Thr Glu Phe Ala Ser Gly Gln Trp Val
    130                 135                 140

Gly Val Glu Leu Asp Glu Pro Glu Gly Lys Asn Asp Gly Ser Val Gly
145                 150                 155                 160

Gly Val Arg Tyr Phe Ile Cys Pro Pro Lys Gln Gly Leu Phe Ala Ser
                165                 170                 175

Val Ser Lys Val Ser Lys Ala Val Asp Ala Pro Pro Ser Ser Val Thr
            180                 185                 190

Ser Thr Pro Arg Thr Pro Arg Met Asp Phe Ser Arg Val Thr Gly Lys
        195                 200                 205

Gly Arg Arg Glu His Lys Gly Lys Lys Lys Ser Pro Ser Ser Pro Ser
    210                 215                 220

Leu Gly Ser Leu Gln Gln Arg Glu Gly Ala Lys Ala Glu Val Gly Asp
225                 230                 235                 240

Gln Val Leu Val Ala Gly Gln Asn Arg Asp Cys Ala Phe Leu Trp Glu
                245                 250                 255

Asp Arg Leu Cys Ser Arg Leu Leu Val Trp His
            260                 265


<210> SEQ ID NO 58
<211> LENGTH: 2929
<212> TYPE: DNA
<213> ORGANISM: Rattus sp.
<220> FEATURE:
<221> NAME/KEY: CDS
<222> LOCATION: (1)..(810)

<400> SEQUENCE: 58

gct gac tct acc tct aga tgg gct gag gcc ctc aga gaa atc tct ggt        48
Ala Asp Ser Thr Ser Arg Trp Ala Glu Ala Leu Arg Glu Ile Ser Gly
  1               5                  10                  15

cgc tta gct gaa atg cct gca gat agt gga tac cct gca tac ctt ggt        96
Arg Leu Ala Glu Met Pro Ala Asp Ser Gly Tyr Pro Ala Tyr Leu Gly
             20                  25                  30

gcc cga ctg gct tct ttc tat gag cga gca ggc aga gtg aaa tgt ctt       144
Ala Arg Leu Ala Ser Phe Tyr Glu Arg Ala Gly Arg Val Lys Cys Leu
         35                  40                  45

gga aac cct gag aga gaa ggg agt gtc agc att gta gga gca gtt tct       192
Gly Asn Pro Glu Arg Glu Gly Ser Val Ser Ile Val Gly Ala Val Ser
     50                  55                  60
```

-continued

```
cca cct ggt ggt gat ttt tct gat cca gtc aca tct gct act ctg ggt      240
Pro Pro Gly Gly Asp Phe Ser Asp Pro Val Thr Ser Ala Thr Leu Gly
 65                  70                  75                  80

att gtt cag gtg ttc tgg ggc ttg gat aag aag cta gct cag cgc aag      288
Ile Val Gln Val Phe Trp Gly Leu Asp Lys Lys Leu Ala Gln Arg Lys
                 85                  90                  95

cac ttc ccg tcc gtc aac tgg ctc att agc tac agc aag tac atg cgc      336
His Phe Pro Ser Val Asn Trp Leu Ile Ser Tyr Ser Lys Tyr Met Arg
            100                 105                 110

gcc ctg gac gag tac tat gac aaa cac ttc aca gag ttc gtg cct ctg      384
Ala Leu Asp Glu Tyr Tyr Asp Lys His Phe Thr Glu Phe Val Pro Leu
        115                 120                 125
agg acc aaa gct aag gag att ctg cag gaa gag gag gat ctg gcg gaa      432
Arg Thr Lys Ala Lys Glu Ile Leu Gln Glu Glu Glu Asp Leu Ala Glu
    130                 135                 140

atc gtg cag ctc gtg gga aag gcg tct tta gca gag aca gat aaa atc      480
Ile Val Gln Leu Val Gly Lys Ala Ser Leu Ala Glu Thr Asp Lys Ile
145                 150                 155                 160

acc ctg gag gta gca aaa ctt atc aaa gat gac ttc cta caa caa aat      528
Thr Leu Glu Val Ala Lys Leu Ile Lys Asp Asp Phe Leu Gln Gln Asn
                165                 170                 175

ggg tac act cct tat gac agg ttc tgt cca ttc tat aag acg gtg ggg      576
Gly Tyr Thr Pro Tyr Asp Arg Phe Cys Pro Phe Tyr Lys Thr Val Gly
            180                 185                 190

atg ctg tcc aac atg att tca ttc tat gat atg gcc cgc cgg gct gtg      624
Met Leu Ser Asn Met Ile Ser Phe Tyr Asp Met Ala Arg Arg Ala Val
        195                 200                 205

gag acc acc gcc cag agt gac aat aag atc aca tgg tcc att atc cgt      672
Glu Thr Thr Ala Gln Ser Asp Asn Lys Ile Thr Trp Ser Ile Ile Arg
    210                 215                 220

gag cac atg ggg gag att ctc tat aaa ctt tcc tcc atg aaa ttc aag      720
Glu His Met Gly Glu Ile Leu Tyr Lys Leu Ser Ser Met Lys Phe Lys
225                 230                 235                 240

gat cca gtg aag gat ggc gag gca aag atc aag gcc gac tac gca cag      768
Asp Pro Val Lys Asp Gly Glu Ala Lys Ile Lys Ala Asp Tyr Ala Gln
                245                 250                 255

ctt ctt gaa gat atg cag aac gca ttc cgt agc ctg gaa gat              810
Leu Leu Glu Asp Met Gln Asn Ala Phe Arg Ser Leu Glu Asp
            260                 265                 270

tagaactgtg acttctctcc tcctcttccg cagctcatat gtgtatattt tcctgaattt    870

ctcatctcca accctttgct tccatattgt gcagctttga gactagtgcc tcgtgcgttc    930

tcgttcattt tgctgtttct ttggtaggtc ttataaaaca cacattcctg tgctccgctg    990

tctgaaggag ctcctgacct ttgtctgaag tggtgaatgt agtgcatatg atacacagtg   1050

taacatacac attgtaacat atacgttctg taaacttgta tgtaaggtga ctaccccttc   1110

cctcctctcc agtaaactgt aaacaggact actgcatgtg ctctattggg gatggaaggc   1170

cagatctcca taccgtggac aggtacataa ggaaactaga ccacttgcaa cttagtgttt   1230

gttgagtaac cattttgcag gaagtatttc catttaaaaa acaaaagatt aatgttccaa   1290

ttatttgtag cttccccagt atcaatcagg actgtttgtg gcgcacttgg gaactatttt   1350

gttttcctaa cagacgtttg caaggctgaa cgtaatagat aaatcagttc cctctgaaag   1410

tgtgaaagta aaaagagagc taggtggtca gacttaaatt gacatcgtct tgtttaagca   1470

tattttattt cactgagaga tttaatatca aggactttta tatactcaat tactaggaaa   1530

tctttttttta agtacaattt aaaaatcatt gaaaatgtga tccacatcat agccattttc   1590

cttatattta gtcagatgag ctcagagtgg ggagggtgtg ggttagaata ccacaaggac   1650
```

-continued

```
acgcagcagt gcctgcaggc agtgtggccg ggggccagag cggcattgtt ttcacgaggt   1710

acgtgtgtgg cgtgtgtgtt tgcttgttga cactctgaaa acagcaagct taccagttcc   1770

aggaaatatt ttgttttctt tcactggctc agaaagctcc tcaaagtacc tggtccctga   1830

agcttcctat ctgttaatag agacgagaga ggttcttaaa tttaactggt gacaaaacaa   1890

aaagaaaaaa aagatcgatt tttgtcttgc tgttttggtg tgtttaaata ataattccat   1950

atttgcataa cgaggctcgc ttctgagagc ttggagatcg tgctccctct tcactctccg   2010

gggtgataat gctggcgcca tgctacctct tcaggagggg aaggggattg aacatggcta   2070

acactctcaa gtacacaagc gtaacgacaa agtatttatt ttaagccttg gtatgttgtt   2130

taaattatta ggtggtgcat ttcttatggt cttttgggta gacatagtat acacttcaga   2190

tgtaatgtgt aaatccttgc tagtgcatgt ctacacgata gactgctatt caagaaggat   2250

attcttccac ataacaattt aaaaactatt aaatcagata tggattatgc aatgacttgt   2310

tgagaggtgg attaacggtg ctgcttaatc agtttgcttc caatatggct tcgtatccag   2370

aagccctgac tagtggagat gagaaagatt tcaaaacctg tctgcctaca cctaccagca   2430

acctaggctt gtgatcagaa tgaatgatcc caagaaacta cttgaccaag tgtgttttgt   2490

tgtcctggat ttgagatgtg cgttcttcct ccctctgaga ctgttgatgt atgagtgtga   2550

agaagttaca gaaacaacgc tcagattttc acggtaactt tccctctgcc cacactgtag   2610

agtttcagat tgttcactga tagtgcttct ttcgtaagga tgtgttaaaa tatagcagtc   2670

tttttaaaag attatgcagt tctctattta ttgtgctgtg cctggtccta agtgcagccg   2730

gttaaacaag tttcatatgt atttttccag tgttaaatct catacctatg ccctttggaa   2790

agctccatcc tgaacaatga atagaagagg ctatataaat tgcctcctta tccttaagat   2850

ttcactatct ttatgttaag agtaatgtat aattattaaa atctatgaaa aataaaaagt   2910

ggatttaaat taagagatc                                                2929


<210> SEQ ID NO 59
<211> LENGTH: 270
<212> TYPE: PRT
<213> ORGANISM: Rattus sp.

<400> SEQUENCE: 59

Ala Asp Ser Thr Ser Arg Trp Ala Glu Ala Leu Arg Glu Ile Ser Gly
  1               5                  10                  15

Arg Leu Ala Glu Met Pro Ala Asp Ser Gly Tyr Pro Ala Tyr Leu Gly
             20                  25                  30

Ala Arg Leu Ala Ser Phe Tyr Glu Arg Ala Gly Arg Val Lys Cys Leu
         35                  40                  45

Gly Asn Pro Glu Arg Glu Gly Ser Val Ser Ile Val Gly Ala Val Ser
     50                  55                  60

Pro Pro Gly Gly Asp Phe Ser Asp Pro Val Thr Ser Ala Thr Leu Gly
 65                  70                  75                  80

Ile Val Gln Val Phe Trp Gly Leu Asp Lys Lys Leu Ala Gln Arg Lys
                 85                  90                  95

His Phe Pro Ser Val Asn Trp Leu Ile Ser Tyr Ser Lys Tyr Met Arg
            100                 105                 110

Ala Leu Asp Glu Tyr Tyr Asp Lys His Phe Thr Glu Phe Val Pro Leu
        115                 120                 125

Arg Thr Lys Ala Lys Glu Ile Leu Gln Glu Glu Glu Asp Leu Ala Glu
    130                 135                 140
```

-continued

```
Ile Val Gln Leu Val Gly Lys Ala Ser Leu Ala Glu Thr Asp Lys Ile
145                 150                 155                 160

Thr Leu Glu Val Ala Lys Leu Ile Lys Asp Asp Phe Leu Gln Gln Asn
                165                 170                 175

Gly Tyr Thr Pro Tyr Asp Arg Phe Cys Pro Phe Tyr Lys Thr Val Gly
            180                 185                 190

Met Leu Ser Asn Met Ile Ser Phe Tyr Asp Met Ala Arg Arg Ala Val
        195                 200                 205

Glu Thr Thr Ala Gln Ser Asp Asn Lys Ile Thr Trp Ser Ile Ile Arg
    210                 215                 220

Glu His Met Gly Glu Ile Leu Tyr Lys Leu Ser Ser Met Lys Phe Lys
225                 230                 235                 240

Asp Pro Val Lys Asp Gly Glu Ala Lys Ile Lys Ala Asp Tyr Ala Gln
                245                 250                 255

Leu Leu Glu Asp Met Gln Asn Ala Phe Arg Ser Leu Glu Asp
            260                 265                 270


<210> SEQ ID NO 60
<211> LENGTH: 1489
<212> TYPE: DNA
<213> ORGANISM: Rattus sp.
<220> FEATURE:
<221> NAME/KEY: CDS
<222> LOCATION: (1)..(1053)

<400> SEQUENCE: 60

gca cgg ctc ccg gcc ccg gag cat gcg cga cag cag ccc ctc ctc tcc       48
Ala Arg Leu Pro Ala Pro Glu His Ala Arg Gln Gln Pro Leu Leu Ser
  1               5                  10                  15

ggc cct gag ccc gga tcg tcc gcc cgg gtt cca gtt ccc ggc gtg gcc       96
Gly Pro Glu Pro Gly Ser Ser Ala Arg Val Pro Val Pro Gly Val Ala
             20                  25                  30

agt agg cgg cag ccg cga ggc ggc aag cca ccc agc ggg gac ggc ctg      144
Ser Arg Arg Gln Pro Arg Gly Gly Lys Pro Pro Ser Gly Asp Gly Leu
         35                  40                  45

gag tcg ggc ccc tct cca cgc ccc ctt ctc cac gcg cgc ggg gag gca      192
Glu Ser Gly Pro Ser Pro Arg Pro Leu Leu His Ala Arg Gly Glu Ala
     50                  55                  60

ggg ctc cac cgc cag tct gga agg gtt cca cat aca gga acg gcc tac      240
Gly Leu His Arg Gln Ser Gly Arg Val Pro His Thr Gly Thr Ala Tyr
 65                  70                  75                  80

ttc gca gat gag ccc acc gag gct cag gct ccg ggc gga ttc tgc gtg      288
Phe Ala Asp Glu Pro Thr Glu Ala Gln Ala Pro Gly Gly Phe Cys Val
                 85                  90                  95

tca ccc tcg ctc ctt ggg gtc cgc tgg ccg gcc tgt gcc acc cgg acg      336
Ser Pro Ser Leu Leu Gly Val Arg Trp Pro Ala Cys Ala Thr Arg Thr
            100                 105                 110

ccc ggc tca ctg cct ctg tct ccc cca tca gcg cag ccc cgg acg cta      384
Pro Gly Ser Leu Pro Leu Ser Pro Pro Ser Ala Gln Pro Arg Thr Leu
        115                 120                 125

tgg ccc acc cct cca gct ggc ccc tcg agt agg atg gta gca cgt aac      432
Trp Pro Thr Pro Pro Ala Gly Pro Ser Ser Arg Met Val Ala Arg Asn
    130                 135                 140

cag gtg gca gcc gac aat gcg atc tcc ccg gca tca gag ccc cga cgg      480
Gln Val Ala Ala Asp Asn Ala Ile Ser Pro Ala Ser Glu Pro Arg Arg
145                 150                 155                 160

cgg cca gag cca tcc tcg tcc tcg tct tcg tcc tcg ccg gcg gcc ccg      528
Arg Pro Glu Pro Ser Ser Ser Ser Ser Ser Ser Ser Pro Ala Ala Pro
                165                 170                 175
```

-continued

```
gcg cgt ccc cgg ccc tgc ccg gtg gtc ccg gcc ccg gct ccg ggc gac      576
Ala Arg Pro Arg Pro Cys Pro Val Val Pro Ala Pro Ala Pro Gly Asp
            180                 185                 190

act cac ttc cgc acc ttc cgc tcc cac tct gat tac cgg cgc atc acg      624
Thr His Phe Arg Thr Phe Arg Ser His Ser Asp Tyr Arg Arg Ile Thr
        195                 200                 205

cgg acc agc gct ctc ctg gac gcc tgc ggc ttc tac tgg gga ccc ctg      672
Arg Thr Ser Ala Leu Leu Asp Ala Cys Gly Phe Tyr Trp Gly Pro Leu
    210                 215                 220

agc gtg cat ggg gcg cac gaa cgg ctg cgt gcc gag ccc gtg ggc acc      720
Ser Val His Gly Ala His Glu Arg Leu Arg Ala Glu Pro Val Gly Thr
225                 230                 235                 240

ttc ttg gtg cgc gac agt cgc cag cgg aac tgc ttc ttc gcg ctc agc      768
Phe Leu Val Arg Asp Ser Arg Gln Arg Asn Cys Phe Phe Ala Leu Ser
                245                 250                 255

gtg aag atg gct tcg ggc ccc acg agc att cgt gtg cac ttc cag gcc      816
Val Lys Met Ala Ser Gly Pro Thr Ser Ile Arg Val His Phe Gln Ala
            260                 265                 270

ggc cgc ttc cac ctg gac ggc agc cgc gag acc ttc gac tgc ctc ttc      864
Gly Arg Phe His Leu Asp Gly Ser Arg Glu Thr Phe Asp Cys Leu Phe
        275                 280                 285

gag ctg ctg gag cac tac gtg gcg gcg ccg cgc cgc atg ttg ggg gcc      912
Glu Leu Leu Glu His Tyr Val Ala Ala Pro Arg Arg Met Leu Gly Ala
    290                 295                 300

cca ctg cgc cag cgc cgc gtg cgg ccg ctg cag gag ctg tgt cgc cag      960
Pro Leu Arg Gln Arg Arg Val Arg Pro Leu Gln Glu Leu Cys Arg Gln
305                 310                 315                 320

cgc atc gtg gcc gcc gtg ggt cgc gag aac ctg gca cgc atc cct ctt     1008
Arg Ile Val Ala Ala Val Gly Arg Glu Asn Leu Ala Arg Ile Pro Leu
                325                 330                 335

aac ccg gta ctc cgt gac tac ctg agt tcc ttc ccc ttc cag atc         1053
Asn Pro Val Leu Arg Asp Tyr Leu Ser Ser Phe Pro Phe Gln Ile
            340                 345                 350

tgaccggctg ccgccgtgcc cgcagcatta agtgggagcg ccttattatt tcttattatt   1113

aattattatt atttttctgg aaccacgtgg gagccctccc cgcctaggtc ggagggagtg   1173

ggtgtggagg gtgagatgcc tcccacttct ggctggagac cttatcccgc ctctcggggg   1233

gcctcccctc ctggtgctcc ctcccggtcc ccctggttgt agcagcttgt gtctggggcc   1293

aggacctgaa ctccacgcct acctctccat gtttacatgt tcccagtatc tttgcacaaa   1353

ccaggggtgg gggagggtct ctggcttcat ttttctgctg tgcagaatat tctattttat   1413

atttttacat ccagtttaga taataaactt tattatgaaa gttttttttt taaagaaaaa   1473

aaaaaaaaaa aaaaaa                                                   1489


<210> SEQ ID NO 61
<211> LENGTH: 351
<212> TYPE: PRT
<213> ORGANISM: Rattus sp.

<400> SEQUENCE: 61

Ala Arg Leu Pro Ala Pro Glu His Ala Arg Gln Gln Pro Leu Leu Ser
  1               5                  10                  15

Gly Pro Glu Pro Gly Ser Ser Ala Arg Val Pro Val Pro Gly Val Ala
             20                  25                  30

Ser Arg Arg Gln Pro Arg Gly Gly Lys Pro Pro Ser Gly Asp Gly Leu
         35                  40                  45

Glu Ser Gly Pro Ser Pro Arg Pro Leu Leu His Ala Arg Gly Glu Ala
     50                  55                  60
```

-continued

```
Gly Leu His Arg Gln Ser Gly Arg Val Pro His Thr Gly Thr Ala Tyr
 65                  70                  75                  80

Phe Ala Asp Glu Pro Thr Glu Ala Gln Ala Pro Gly Gly Phe Cys Val
                 85                  90                  95

Ser Pro Ser Leu Leu Gly Val Arg Trp Pro Ala Cys Ala Thr Arg Thr
            100                 105                 110

Pro Gly Ser Leu Pro Leu Ser Pro Pro Ser Ala Gln Pro Arg Thr Leu
        115                 120                 125

Trp Pro Thr Pro Pro Ala Gly Pro Ser Ser Arg Met Val Ala Arg Asn
    130                 135                 140

Gln Val Ala Ala Asp Asn Ala Ile Ser Pro Ala Ser Glu Pro Arg Arg
145                 150                 155                 160

Arg Pro Glu Pro Ser Ser Ser Ser Ser Ser Ser Ser Pro Ala Ala Pro
                165                 170                 175

Ala Arg Pro Arg Pro Cys Pro Val Val Pro Ala Pro Ala Pro Gly Asp
            180                 185                 190

Thr His Phe Arg Thr Phe Arg Ser His Ser Asp Tyr Arg Arg Ile Thr
        195                 200                 205

Arg Thr Ser Ala Leu Leu Asp Ala Cys Gly Phe Tyr Trp Gly Pro Leu
    210                 215                 220

Ser Val His Gly Ala His Glu Arg Leu Arg Ala Glu Pro Val Gly Thr
225                 230                 235                 240

Phe Leu Val Arg Asp Ser Arg Gln Arg Asn Cys Phe Phe Ala Leu Ser
                245                 250                 255

Val Lys Met Ala Ser Gly Pro Thr Ser Ile Arg Val His Phe Gln Ala
            260                 265                 270

Gly Arg Phe His Leu Asp Gly Ser Arg Glu Thr Phe Asp Cys Leu Phe
        275                 280                 285

Glu Leu Leu Glu His Tyr Val Ala Ala Pro Arg Arg Met Leu Gly Ala
    290                 295                 300

Pro Leu Arg Gln Arg Arg Val Arg Pro Leu Gln Glu Leu Cys Arg Gln
305                 310                 315                 320

Arg Ile Val Ala Ala Val Gly Arg Glu Asn Leu Ala Arg Ile Pro Leu
                325                 330                 335

Asn Pro Val Leu Arg Asp Tyr Leu Ser Ser Phe Pro Phe Gln Ile
            340                 345                 350


<210> SEQ ID NO 62
<211> LENGTH: 1194
<212> TYPE: DNA
<213> ORGANISM: Rattus sp.
<220> FEATURE:
<221> NAME/KEY: CDS
<222> LOCATION: (130)..(765)

<400> SEQUENCE: 62

ggcacggctc ccggccccgg agcatgcgcg acagcagccc cggaaccccc agccgcggcg      60

ccccgcgtcc cgccgccagc gcagccccgg acgctatggc ccacccctcc agctggcccc     120

tcgagtagg atg gta gca cgt aac cag gtg gca gcc gac aat gcg atc tcc     171
          Met Val Ala Arg Asn Gln Val Ala Ala Asp Asn Ala Ile Ser
            1               5                  10

ccg gca tca gag ccc cga cgg cgg cca gag cca tcc tcg tcc tcg tct       219
Pro Ala Ser Glu Pro Arg Arg Arg Pro Glu Pro Ser Ser Ser Ser Ser
 15                  20                  25                  30

tcg tcc tcg ccg gcg gcc ccg gcg cgt ccc cgg ccc tgc ccg gtg gtc       267
```

-continued

```
Ser Ser Ser Pro Ala Ala Pro Ala Arg Pro Arg Pro Cys Pro Val Val
                35                  40                  45

ccg gcc ccg gct ccg ggc gac act cac ttc cgc acc ttc cgc tcc cac      315
Pro Ala Pro Ala Pro Gly Asp Thr His Phe Arg Thr Phe Arg Ser His
            50                  55                  60

tct gat tac cgg cgc atc acg cgg acc agc gct ctc ctg gac gcc tgc      363
Ser Asp Tyr Arg Arg Ile Thr Arg Thr Ser Ala Leu Leu Asp Ala Cys
        65                  70                  75

ggc ttc tac tgg gga ccc ctg agc gtg cat ggg gcg cac gaa cgg ctg      411
Gly Phe Tyr Trp Gly Pro Leu Ser Val His Gly Ala His Glu Arg Leu
    80                  85                  90

cgt gcc gag ccc gtg ggc acc ttc ttg gtg cgc gac agt cgc cag cgg      459
Arg Ala Glu Pro Val Gly Thr Phe Leu Val Arg Asp Ser Arg Gln Arg
95                  100                 105                 110

aac tgc ttc ttc gcg ctc agc gtg aag atg gct tcg ggc ccc acg agc      507
Asn Cys Phe Phe Ala Leu Ser Val Lys Met Ala Ser Gly Pro Thr Ser
                115                 120                 125

att cgt gtg cac ttc cag gcc ggc cgc ttc cac ctg gac ggc agc cgc      555
Ile Arg Val His Phe Gln Ala Gly Arg Phe His Leu Asp Gly Ser Arg
            130                 135                 140

gag acc ttc gac tgc ctc ttc gag ctg ctg gag cac tac gtg gcg gcg      603
Glu Thr Phe Asp Cys Leu Phe Glu Leu Leu Glu His Tyr Val Ala Ala
        145                 150                 155

ccg cgc cgc atg ttg ggg gcc cca ctg cgc cag cgc cgc gtg cgg ccg      651
Pro Arg Arg Met Leu Gly Ala Pro Leu Arg Gln Arg Arg Val Arg Pro
    160                 165                 170

ctg cag gag ctg tgt cgc cag cgc atc gtg gcc gcc gtg ggt cgc gag      699
Leu Gln Glu Leu Cys Arg Gln Arg Ile Val Ala Ala Val Gly Arg Glu
175                 180                 185                 190

aac ctg gca cgc atc cct ctt aac ccg gta ctc cgt gac tac ctg agt      747
Asn Leu Ala Arg Ile Pro Leu Asn Pro Val Leu Arg Asp Tyr Leu Ser
                195                 200                 205

tcc ttc ccc ttc cag atc tgaccggctg ccgccgtgcc cgcagcatta             795
Ser Phe Pro Phe Gln Ile
            210

agtgggagcg ccttattatt tcttattatt aattattatt atttttctgg aaccacgtgg    855

gagccctccc cgcctaggtc ggagggagtg ggtgtggagg gtgagatgcc tcccacttct    915

ggctggagac cttatcccgc ctctcggggg gcctcccctc ctggtgctcc ctcccggtcc    975

ccctggttgt agcagcttgt gtctggggcc aggacctgaa ctccacgcct acctctccat   1035

gtttacatgt tcccagtatc tttgcacaaa ccaggggtgg gggagggtct ctggcttcat   1095

ttttctgctg tgcagaatat tctattttat atttttacat ccagtttaga taataaactt   1155

tattatgaaa gttttttttt taaaaaaaaa aaaaaaaaa                          1194


<210> SEQ ID NO 63
<211> LENGTH: 212
<212> TYPE: PRT
<213> ORGANISM: Rattus sp.

<400> SEQUENCE: 63

Met Val Ala Arg Asn Gln Val Ala Ala Asp Asn Ala Ile Ser Pro Ala
  1               5                  10                  15

Ser Glu Pro Arg Arg Arg Pro Glu Pro Ser Ser Ser Ser Ser Ser Ser
            20                  25                  30

Ser Pro Ala Ala Pro Ala Arg Pro Arg Pro Cys Pro Val Val Pro Ala
        35                  40                  45

Pro Ala Pro Gly Asp Thr His Phe Arg Thr Phe Arg Ser His Ser Asp
```

-continued

```
     50                  55                  60

Tyr Arg Arg Ile Thr Arg Thr Ser Ala Leu Leu Asp Ala Cys Gly Phe
 65                  70                  75                  80

Tyr Trp Gly Pro Leu Ser Val His Gly Ala His Glu Arg Leu Arg Ala
                85                  90                  95

Glu Pro Val Gly Thr Phe Leu Val Arg Asp Ser Arg Gln Arg Asn Cys
            100                 105                 110

Phe Phe Ala Leu Ser Val Lys Met Ala Ser Gly Pro Thr Ser Ile Arg
        115                 120                 125

Val His Phe Gln Ala Gly Arg Phe His Leu Asp Gly Ser Arg Glu Thr
    130                 135                 140

Phe Asp Cys Leu Phe Glu Leu Leu Glu His Tyr Val Ala Ala Pro Arg
145                 150                 155                 160

Arg Met Leu Gly Ala Pro Leu Arg Gln Arg Arg Val Arg Pro Leu Gln
                165                 170                 175

Glu Leu Cys Arg Gln Arg Ile Val Ala Ala Val Gly Arg Glu Asn Leu
            180                 185                 190

Ala Arg Ile Pro Leu Asn Pro Val Leu Arg Asp Tyr Leu Ser Ser Phe
        195                 200                 205

Pro Phe Gln Ile
    210


<210> SEQ ID NO 64
<211> LENGTH: 600
<212> TYPE: DNA
<213> ORGANISM: Rattus sp.
<220> FEATURE:
<221> NAME/KEY: CDS
<222> LOCATION: (52)..(336)

<400> SEQUENCE: 64

cttccaaaga ctgcagcgcc tcagggccca ggtttcaaca gattcttcaa a atg cca      57
                                                         Met Pro
                                                           1

tcc caa atg gag cat gcc atg gaa acc atg atg ctt aca ttt cac agg      105
Ser Gln Met Glu His Ala Met Glu Thr Met Met Leu Thr Phe His Arg
          5                  10                  15

ttt gca ggg gaa aaa aac tac ttg aca aag gag gac ctg aga gtg ctc      153
Phe Ala Gly Glu Lys Asn Tyr Leu Thr Lys Glu Asp Leu Arg Val Leu
     20                  25                  30

atg gaa agg gag ttc cct ggg ttt ttg gaa aat caa aag gac cct ctg      201
Met Glu Arg Glu Phe Pro Gly Phe Leu Glu Asn Gln Lys Asp Pro Leu
 35                  40                  45                  50

gct gtg gac aaa ata atg aaa gac ctg gac cag tgc cga gat gga aaa      249
Ala Val Asp Lys Ile Met Lys Asp Leu Asp Gln Cys Arg Asp Gly Lys
                55                  60                  65

gtg ggc ttc cag agc ttt cta tca cta gtg gcg ggg ctc atc att gca      297
Val Gly Phe Gln Ser Phe Leu Ser Leu Val Ala Gly Leu Ile Ile Ala
            70                  75                  80

tgc aat gac tat ttt gta gta cac atg aag cag aag aag taggccaact       346
Cys Asn Asp Tyr Phe Val Val His Met Lys Gln Lys Lys
         85                  90                  95

ggagccctgg tacccacacc ttgatgcgtc ctctcccatg ggtcaactg aggaatctgc     406

cccactgctt cctgtgagca gatcaggacc cttaggaaat gtgcaaataa catccaactc    466

caattcgaca agcagagaaa gaaaagttaa tccaatgaca gaggagcttt cgagttttat    526

attgtttgca tccggttgcc ctcaataaag aaagtctttt tttttaagtt ccgaaaaaaa    586
```

-continued

```
aaaaaaaaaa aaaa                                                         600


<210> SEQ ID NO 65
<211> LENGTH: 95
<212> TYPE: PRT
<213> ORGANISM: Rattus sp.

<400> SEQUENCE: 65

Met Pro Ser Gln Met Glu His Ala Met Glu Thr Met Met Leu Thr Phe
  1               5                  10                  15

His Arg Phe Ala Gly Glu Lys Asn Tyr Leu Thr Lys Glu Asp Leu Arg
             20                  25                  30

Val Leu Met Glu Arg Glu Phe Pro Gly Phe Leu Glu Asn Gln Lys Asp
         35                  40                  45

Pro Leu Ala Val Asp Lys Ile Met Lys Asp Leu Asp Gln Cys Arg Asp
     50                  55                  60

Gly Lys Val Gly Phe Gln Ser Phe Leu Ser Leu Val Ala Gly Leu Ile
 65                  70                  75                  80

Ile Ala Cys Asn Asp Tyr Phe Val Val His Met Lys Gln Lys Lys
                 85                  90                  95


<210> SEQ ID NO 66
<211> LENGTH: 639
<212> TYPE: DNA
<213> ORGANISM: Rattus sp.
<220> FEATURE:
<221> NAME/KEY: CDS
<222> LOCATION: (1)..(636)

<400> SEQUENCE: 66

atg gcg tac gcc tat ctc ttc aag tac atc atc atc ggc gac aca ggt       48
Met Ala Tyr Ala Tyr Leu Phe Lys Tyr Ile Ile Ile Gly Asp Thr Gly
  1               5                  10                  15

gtt ggt aaa tcg tgc tta ttg cta cag ttt aca gac aag agg ttt cag       96
Val Gly Lys Ser Cys Leu Leu Leu Gln Phe Thr Asp Lys Arg Phe Gln
             20                  25                  30

ccg gtg cat gac ctc aca att ggt gta gag ttt ggt gct cga atg ata      144
Pro Val His Asp Leu Thr Ile Gly Val Glu Phe Gly Ala Arg Met Ile
         35                  40                  45

acc att gat ggg aaa cag ata aaa ctc cag atc tgg gat aca gca ggg      192
Thr Ile Asp Gly Lys Gln Ile Lys Leu Gln Ile Trp Asp Thr Ala Gly
     50                  55                  60

cag gag tcc ttt cgt tct atc aca agg tca tat tac aga ggt gca gcg      240
Gln Glu Ser Phe Arg Ser Ile Thr Arg Ser Tyr Tyr Arg Gly Ala Ala
 65                  70                  75                  80

ggg gct tta cta gtg tat gat att aca agg aga gac acg ttc aac cac      288
Gly Ala Leu Leu Val Tyr Asp Ile Thr Arg Arg Asp Thr Phe Asn His
                 85                  90                  95

ttg aca acc tgg tta gaa gac gcc cgt cag cat tcc aat tcc aac atg      336
Leu Thr Thr Trp Leu Glu Asp Ala Arg Gln His Ser Asn Ser Asn Met
            100                 105                 110

gtc atc atg ctt att gga aat aaa agt gac tta gaa tct agg aga gaa      384
Val Ile Met Leu Ile Gly Asn Lys Ser Asp Leu Glu Ser Arg Arg Glu
        115                 120                 125

gtg aaa aag gaa gaa ggt gaa gct ttt gca cga gag cat gga ctt atc      432
Val Lys Lys Glu Glu Gly Glu Ala Phe Ala Arg Glu His Gly Leu Ile
    130                 135                 140

ttc atg gaa act tct gcc aag act gct tct aat gta gag gag gca ttt      480
Phe Met Glu Thr Ser Ala Lys Thr Ala Ser Asn Val Glu Glu Ala Phe
145                 150                 155                 160
```

-continued

```
att aac aca gca aaa gaa att tat gaa aaa atc caa gaa ggg gtc ttt      528
Ile Asn Thr Ala Lys Glu Ile Tyr Glu Lys Ile Gln Glu Gly Val Phe
            165                 170                 175

gac att aat aat gag gca aac ggc atc aaa att ggc cct cag cat gct      576
Asp Ile Asn Asn Glu Ala Asn Gly Ile Lys Ile Gly Pro Gln His Ala
        180                 185                 190

gct acc aat gca tct cac gga ggc aac caa gga ggg cag cag gca ggg      624
Ala Thr Asn Ala Ser His Gly Gly Asn Gln Gly Gly Gln Gln Ala Gly
    195                 200                 205

gga ggc tgc tgc tga                                                  639
Gly Gly Cys Cys
    210
```

<210> SEQ ID NO 67
<211> LENGTH: 212
<212> TYPE: PRT
<213> ORGANISM: Rattus sp.

<400> SEQUENCE: 67

```
Met Ala Tyr Ala Tyr Leu Phe Lys Tyr Ile Ile Ile Gly Asp Thr Gly
  1               5                  10                  15

Val Gly Lys Ser Cys Leu Leu Leu Gln Phe Thr Asp Lys Arg Phe Gln
            20                  25                  30

Pro Val His Asp Leu Thr Ile Gly Val Glu Phe Gly Ala Arg Met Ile
        35                  40                  45

Thr Ile Asp Gly Lys Gln Ile Lys Leu Gln Ile Trp Asp Thr Ala Gly
    50                  55                  60

Gln Glu Ser Phe Arg Ser Ile Thr Arg Ser Tyr Tyr Arg Gly Ala Ala
 65                  70                  75                  80

Gly Ala Leu Leu Val Tyr Asp Ile Thr Arg Arg Asp Thr Phe Asn His
                 85                  90                  95

Leu Thr Thr Trp Leu Glu Asp Ala Arg Gln His Ser Asn Ser Asn Met
            100                 105                 110

Val Ile Met Leu Ile Gly Asn Lys Ser Asp Leu Glu Ser Arg Arg Glu
        115                 120                 125

Val Lys Lys Glu Glu Gly Glu Ala Phe Ala Arg Glu His Gly Leu Ile
    130                 135                 140

Phe Met Glu Thr Ser Ala Lys Thr Ala Ser Asn Val Glu Glu Ala Phe
145                 150                 155                 160

Ile Asn Thr Ala Lys Glu Ile Tyr Glu Lys Ile Gln Glu Gly Val Phe
            165                 170                 175

Asp Ile Asn Asn Glu Ala Asn Gly Ile Lys Ile Gly Pro Gln His Ala
        180                 185                 190

Ala Thr Asn Ala Ser His Gly Gly Asn Gln Gly Gly Gln Gln Ala Gly
    195                 200                 205

Gly Gly Cys Cys
    210
```

<210> SEQ ID NO 68
<211> LENGTH: 816
<212> TYPE: DNA
<213> ORGANISM: Rattus sp.
<220> FEATURE:
<221> NAME/KEY: CDS
<222> LOCATION: (1)..(813)

<400> SEQUENCE: 68

```
atg gtg ctg ctc aag gaa tat cgg gtc atc ctg cct gtg tct gta gat       48
Met Val Leu Leu Lys Glu Tyr Arg Val Ile Leu Pro Val Ser Val Asp
```

-continued

```
 1               5                  10                  15

gag tat caa gtg ggg cag ctg tac tct gtg gct gaa gcc agt aaa aat       96
Glu Tyr Gln Val Gly Gln Leu Tyr Ser Val Ala Glu Ala Ser Lys Asn
             20                  25                  30

gaa act ggt ggt ggg gaa ggt gtg gag gtc ctg gtg aac gag ccc tac      144
Glu Thr Gly Gly Gly Glu Gly Val Glu Val Leu Val Asn Glu Pro Tyr
        35                  40                  45

gag aag gat gat ggc gag aaa ggc cag tac aca cac aag atc tac cac      192
Glu Lys Asp Asp Gly Glu Lys Gly Gln Tyr Thr His Lys Ile Tyr His
    50                  55                  60

tta cag agc aaa gtt ccc acg ttt gtt cga atg ctg gcc cca gaa ggc      240
Leu Gln Ser Lys Val Pro Thr Phe Val Arg Met Leu Ala Pro Glu Gly
 65                  70                  75                  80

gcc ctg aat ata cat gag aaa gcc tgg aat gcc tac cct tac tgc aga      288
Ala Leu Asn Ile His Glu Lys Ala Trp Asn Ala Tyr Pro Tyr Cys Arg
                 85                  90                  95

acc gtt att aca aat gag tac atg aag gaa gac ttt ctc att aaa att      336
Thr Val Ile Thr Asn Glu Tyr Met Lys Glu Asp Phe Leu Ile Lys Ile
            100                 105                 110

gaa acc tgg cac aag cca gac ctt ggc acc cag gag aat gtg cat aaa      384
Glu Thr Trp His Lys Pro Asp Leu Gly Thr Gln Glu Asn Val His Lys
        115                 120                 125

ctg gag cct gag gca tgg aaa cat gtg gaa gct ata tat ata gac atc      432
Leu Glu Pro Glu Ala Trp Lys His Val Glu Ala Ile Tyr Ile Asp Ile
    130                 135                 140

gct gat cga agc caa gta ctt agc aag gat tac aag gca gag gaa gac      480
Ala Asp Arg Ser Gln Val Leu Ser Lys Asp Tyr Lys Ala Glu Glu Asp
145                 150                 155                 160

cca gca aaa ttt aaa tct atc aaa aca gga cga gga cca ttg ggc ccg      528
Pro Ala Lys Phe Lys Ser Ile Lys Thr Gly Arg Gly Pro Leu Gly Pro
                165                 170                 175

aat tgg aag caa gaa ctt gtc aat cag aag gac tgc cca tat atg tgt      576
Asn Trp Lys Gln Glu Leu Val Asn Gln Lys Asp Cys Pro Tyr Met Cys
            180                 185                 190

gca tac aaa ctg gtt act gtc aag ttc aag tgg tgg ggc ttg cag aac      624
Ala Tyr Lys Leu Val Thr Val Lys Phe Lys Trp Trp Gly Leu Gln Asn
        195                 200                 205

aaa gtg gaa aac ttt ata cat aag caa gag aag cgt ctg ttt aca aac      672
Lys Val Glu Asn Phe Ile His Lys Gln Glu Lys Arg Leu Phe Thr Asn
    210                 215                 220

ttt cac agg cag ctg ttc tgt tgg ctt gat aaa tgg gtt gat ctg act      720
Phe His Arg Gln Leu Phe Cys Trp Leu Asp Lys Trp Val Asp Leu Thr
225                 230                 235                 240

atg gat gac att cgg agg atg gaa gaa gag acg aag aga cag ctg gat      768
Met Asp Asp Ile Arg Arg Met Glu Glu Glu Thr Lys Arg Gln Leu Asp
                245                 250                 255

gag atg aga caa aag gac ccc gtg aaa gga atg aca gca gat gac tag      816
Glu Met Arg Gln Lys Asp Pro Val Lys Gly Met Thr Ala Asp Asp
            260                 265                 270
```

```
<210> SEQ ID NO 69
<211> LENGTH: 2263
<212> TYPE: DNA
<213> ORGANISM: Simian sp.

<400> SEQUENCE: 69

cgctctcctc ctcccctttc tctagcagta gccttcttaa tgtagtttaa tggctttaca     60

aagaaagcca ggcagaggag cacttctcag tggctgtggt cggaccatga cctagctgac    120

catgaacttg gaagggcttg aaatgatagc agttctgatc gtcattgtgc tttttgttaa    180
```

-continued

```
attattggaa cagtttgggc tgattgaagc aggtttagaa gacagcgtgg aagatgaact    240
ggagatggcc actgtcaggc atcggcctga ggcccttgag cttctggaag cccagagcaa    300
atttaccaag aaagagcttc agatccttta cagaggattt aagaacgaat gccccagtgg    360
tgttgttaat gaagaaacct tcaaagagat ttactcgcag ttctttccac agggagactc    420
tacaacatat gcacattttc tgttcaatgc gtttgatacg gaccacaatg gagctgtgag    480
tttcgaggat ttcatcaaag gtctttccat tttgctccgg gggacagtac aagaaaaact    540
caattgggca tttaatctgt atgatataaa taaagatggc tacatcacta aagaggaaat    600
gcttgatata atgaaagcaa tatacgacat gatgggtaaa tgtacatatc ctgtcctcaa    660
agaagatgca cccagacaac acgtcgaaac atttttcag aaaatggaca aaaataaaga    720
tggggttgtt accatagatg agttcattga aagctgccaa aaagatgaaa acataatgcg    780
ctccatgcag ctctttgaaa atgtgattta acttgtcaac tagatcctga atccaacaga    840
caaatgtgaa ctattctacc acccttaaag tcggagctac cacttttagc atagattgct    900
cagcttgaca ctgaagcata ttatgcaaac aagctttgtt ttaatataaa gcaatcccca    960
aaagatttga gtttctcagt tataaatttg catcctttcc ataatgccac tgagttcatg   1020
ggatgttcta actcatttca tactctgtga atattcaaaa gtaatagaat ctggcatata   1080
gttttattga ttccttagcc atgggattat tgaggctttc acatatcagt gattttaaaa   1140
taccagtgtt ttttgctact catttgtatg tattcagtcc taggattttg aatggttttc   1200
taatatactg acatctgcat ttaatttcca gaaattaaat taattttcat gtctgaatgc   1260
tgtaattcca tttatatact ttaagtaaac aaataagatt actacaatta aacacatagt   1320
tccagtttct atggccttca cttcccacct tctattagaa attaatttta tctggtattt   1380
ttaaacattt aaaaatttat catcagatat cagcatatgc ctaattatgc ctaatgaaac   1440
ttaataagca tttaattttc catcatacat tatagtcaag gcctatatac tatatataat   1500
tttggatttg tttaatctta caggctgttt tccattgtat catcaagtgg aagttcaaga   1560
cggcatcaaa caaaacaagg atgtttacag acatatgcaa agggtcagga tatctatcct   1620
ccagtatatg ttaatgctta ataacaagta atcctaacag cattaaaggc caaatctgtc   1680
ctctttcccc tgacttcctt acagcatgtt tatattacaa gccattcagg gacaaagaaa   1740
ccttgactac cccactgtct actaggaaca aacaaacagc aagcaaaatt cactttgaaa   1800
gcaccagtgg ttccattaca ttgacaacta ctaccaagat tcagtagaaa ataagtgctc   1860
aacaactaat ccagattaca atatgattta gtgcatcata aaattccaac aattcagatt   1920
atttttaatc acctcagcca caactgtaaa gttgccacat tactaaagac acacacatcg   1980
tccctgtttt gtagaaatat cacaaagacc aagaggctac agaaggagga aatttgcaac   2040
tgtctttgca acaataaatc aggtatctat tctggtgtag agataggatg ttgaaagctg   2100
ccctgctatc accagtgtag aaattaagag tagtacaata catgtacact gaaatttgcc   2160
atcgcgtgtt tgtgtaaact caatgtgcac attttgtatt tcaaaaagaa aaaataaaag   2220
caaaataaaa tgtttataac tctaaaaaaa aaaaaaaaaa aaa                     2263
```

<210> SEQ ID NO 70
<211> LENGTH: 229
<212> TYPE: PRT
<213> ORGANISM: Simian sp.

<400> SEQUENCE: 70

-continued

```
Met Asn Leu Glu Gly Leu Glu Met Ile Ala Val Leu Ile Val Ile Val
  1               5                  10                  15

Leu Phe Val Lys Leu Leu Glu Gln Phe Gly Leu Ile Glu Ala Gly Leu
             20                  25                  30

Glu Asp Ser Val Glu Asp Glu Leu Glu Met Ala Thr Val Arg His Arg
         35                  40                  45

Pro Glu Ala Leu Glu Leu Leu Glu Ala Gln Ser Lys Phe Thr Lys Lys
     50                  55                  60

Glu Leu Gln Ile Leu Tyr Arg Gly Phe Lys Asn Glu Cys Pro Ser Gly
 65                  70                  75                  80

Val Val Asn Glu Glu Thr Phe Lys Glu Ile Tyr Ser Gln Phe Phe Pro
                 85                  90                  95

Gln Gly Asp Ser Thr Thr Tyr Ala His Phe Leu Phe Asn Ala Phe Asp
            100                 105                 110

Thr Asp His Asn Gly Ala Val Ser Phe Glu Asp Phe Ile Lys Gly Leu
        115                 120                 125

Ser Ile Leu Leu Arg Gly Thr Val Gln Glu Lys Leu Asn Trp Ala Phe
    130                 135                 140

Asn Leu Tyr Asp Ile Asn Lys Asp Gly Tyr Ile Thr Lys Glu Glu Met
145                 150                 155                 160

Leu Asp Ile Met Lys Ala Ile Tyr Asp Met Met Gly Lys Cys Thr Tyr
                165                 170                 175

Pro Val Leu Lys Glu Asp Ala Pro Arg Gln His Val Glu Thr Phe Phe
            180                 185                 190

Gln Lys Met Asp Lys Asn Lys Asp Gly Val Val Thr Ile Asp Glu Phe
        195                 200                 205

Ile Glu Ser Cys Gln Lys Asp Glu Asn Ile Met Arg Ser Met Gln Leu
    210                 215                 220

Phe Glu Asn Val Ile
225
```

<210> SEQ ID NO 71
<211> LENGTH: 2259
<212> TYPE: DNA
<213> ORGANISM: Simian sp.

<400> SEQUENCE: 71

```
gtcgacagac gcccctggcc ggtggactcc tgagtcttac tcctgcaccc tgcgtcccca     60

gacatgaatg tgaggagagt ggaaagcatt tcggctcagc tggaggaggc cagctccaca    120

ggcggtttcc tgtatgctca gaacagcacc aagcgcagca ttaaagagcg gctcatgaag    180

ctcttgccct gctcagctgc caaaacatcg tctcctgcta ttcaaaacag cgtggaagat    240

gaactggaga tggccactgt caggcatcgg cctgaggccc ttgagcttct ggaagcccag    300

agcaaattta ccaagaaaga gcttcagatc ctttacagag gatttaagaa cgaatgcccc    360

agtggtgttg ttaatgaaga aaccttcaaa gagatttact cgcagttctt tccacaggga    420

gactctacaa catatgcaca ttttctgttc aatgcgtttg atacggacca caatggagct    480

gtgagtttcg aggatttcat caaaggtctt tccattttgc tccgggggac agtacaagaa    540

aaactcaatt gggcatttaa tctgtatgat ataaataaag atggctacat cactaaagag    600

gaaatgcttg atataatgaa agcaatatac gacatgatgg gtaaatgtac atatcctgtc    660

ctcaaagaag atgcacccag acaacacgtc gaaacatttt ttcagaaaat ggacaaaaat    720

aaagatgggg ttgttaccat agatgagttc attgaaagct gccaaaaaga tgaaaacata    780
```

-continued

```
atgcgctcca tgcagctctt tgaaaatgtg atttaacttg tcaactagat cctgaatcca    840

acagacaaat gtgaactatt ctaccaccct taaagtcgga gctaccactt ttagcataga    900

ttgctcagct tgacactgaa gcatattatg caaacaagct ttgttttaat ataaagcaat    960

ccccaaaaga tttgagtttc tcagttataa atttgcatcc tttccataat gccactgagt   1020

tcatgggatg ttctgactca tttcatactc tgtgaatatt caaaagtaat agaatctggc   1080

atatagtttt attgattcct tagccatggg attattgagg ctttcacata tcagtgattt   1140

taaaatacca gtgtttttg ctactcattt gtatgtattc agtcctagga ttttgaatgg   1200

ttttctaata tactgacatc tgcatttaat ttccagaaat taaattaatt ttcatgtctg   1260

aatgctgtaa ttccatttat atactttaag taaacaaata agattactac aattaaacac   1320

atagttccag tttctatggc cttcacttcc caccttctat tagaaattaa ttttatctgg   1380

tatttttaaa catttaaaaa tttatcatca gatatcagca tatgcctaat tatgcctaat   1440

gaaacttaat aagcatttaa ttttccatca tacattatag tcaaggccta tatactatat   1500

ataattttgg atttgtttaa tcttacaggc tgttttccat tgtatcatca agtggaagtt   1560

caagacggca tcaaacaaaa caaggatgtt tacagacata tgcaaagggt caggatatct   1620

atcctccagt atatgttaat gcttaataac aagtaatcct aacagcatta aaggccaaat   1680

ctgtcctctt tcccctgact tccttacagc atgtttatat tacaagccat tcagggacaa   1740

agaaaccttg actaccccac tgtctactag gaacaaacaa acagcaagca aaattcactt   1800

tgaaagcacc agtggttcca ttacattgac aactactacc aagattcagt agaaaataag   1860

tgctcaacaa ctaatccaga ttacaatatg atttagtgca tcataaaatt ccaacaattc   1920

agattatttt taatcacctc agccacaact gtaaagttgc cacattacta aagacacaca   1980

catcgtccct gttttgtaga aatatcacaa agaccaagag gctacagaag gaggaaattt   2040

gcaactgtct ttgcaacaat aaatcaggta tctattctgg tgtagagata ggatgttgaa   2100

agctgccctg ctatcaccag tgtagaaatt aagagtagta caatacatgt acactgaaat   2160

ttgccatcgc gtgtttgtgt aaactcaatg tgcacatttt gtatttcaaa aagaaaaaat   2220

aaaagcaaaa taaaatgtta aaaaaaaaaa aaaaaaaaa                          2259
```

<210> SEQ ID NO 72
<211> LENGTH: 250
<212> TYPE: PRT
<213> ORGANISM: Simian sp.

<400> SEQUENCE: 72

```
Met Asn Val Arg Arg Val Glu Ser Ile Ser Ala Gln Leu Glu Glu Ala
  1               5                  10                  15

Ser Ser Thr Gly Gly Phe Leu Tyr Ala Gln Asn Ser Thr Lys Arg Ser
             20                  25                  30

Ile Lys Glu Arg Leu Met Lys Leu Leu Pro Cys Ser Ala Ala Lys Thr
         35                  40                  45

Ser Ser Pro Ala Ile Gln Asn Ser Val Glu Asp Glu Leu Glu Met Ala
     50                  55                  60

Thr Val Arg His Arg Pro Glu Ala Leu Glu Leu Leu Glu Ala Gln Ser
 65                  70                  75                  80

Lys Phe Thr Lys Lys Glu Leu Gln Ile Leu Tyr Arg Gly Phe Lys Asn
                 85                  90                  95

Glu Cys Pro Ser Gly Val Val Asn Glu Glu Thr Phe Lys Glu Ile Tyr
            100                 105                 110
```

-continued

```
Ser Gln Phe Phe Pro Gln Gly Asp Ser Thr Thr Tyr Ala His Phe Leu
        115                 120                 125

Phe Asn Ala Phe Asp Thr Asp His Asn Gly Ala Val Ser Phe Glu Asp
    130                 135                 140

Phe Ile Lys Gly Leu Ser Ile Leu Leu Arg Gly Thr Val Gln Glu Lys
145                 150                 155                 160

Leu Asn Trp Ala Phe Asn Leu Tyr Asp Ile Asn Lys Asp Gly Tyr Ile
                165                 170                 175

Thr Lys Glu Glu Met Leu Asp Ile Met Lys Ala Ile Tyr Asp Met Met
            180                 185                 190

Gly Lys Cys Thr Tyr Pro Val Leu Lys Glu Asp Ala Pro Arg Gln His
        195                 200                 205

Val Glu Thr Phe Phe Gln Lys Met Asp Lys Asn Lys Asp Gly Val Val
    210                 215                 220

Thr Ile Asp Glu Phe Ile Glu Ser Cys Gln Lys Asp Glu Asn Ile Met
225                 230                 235                 240

Arg Ser Met Gln Leu Phe Glu Asn Val Ile
                245                 250
```

POTASSIUM CHANNEL INTERACTORS AND USES THEREFOR

RELATED APPLICATIONS

This application claims priority to U.S. provisional Application No. 60/110,033, filed on Nov. 25, 1998, U.S. provisional Application No. 60/109,333, filed on Nov. 20, 1998, U.S. provisional Application No. 60/110,277, filed on Nov. 30, 1998, and which is also a continuation-in-part of U.S. patent application Ser. No.: 09/298,731, filed on Apr. 23, 1999, now U.S. Pat. No. 6,369,197, incorporated herein in their entirety by this reference.

BACKGROUND OF THE INVENTION

Mammalian cell membranes are important to the structural integrity and activity of many cells and tissues. Of particular interest in membrane physiology is the study of trans-membrane ion channels which act to directly control a variety of pharmacological, physiological, and cellular processes. Numerous ion channels have been identified including calcium, sodium, and potassium channels, each of which have been investigated to determine their roles in vertebrate and insect cells.

Because of their involvement in maintaining normal cellular homeostasis, much attention has been given to potassium channels. A number of these potassium channels open in response to changes in the cell membrane potential. Many voltage-gated potassium channels have been identified and characterized by their electrophysiological and pharmcological properties. Potassium currents are more diverse than sodium or calcium currents and are further involved in determining the response of a cell to external stimuli.

The diversity of potassium channels and their important physiological role highlights their potential as targets for developing therapeutic agents for various diseases. One of the best characterized classes of potassium channels are the voltage-gated potassium channels. The prototypical member of this class is the protein encoded by the Shaker gene in *Drosophila melanogaster*. Proteins of the Shal or Kv4 family are a type of voltage-gated potassium channels that underlies many of the native A type currents that have been recorded from different primary cells. Kv4 channels have a major role in the repolarization of cardiac action potentials. In neurons, Kv4 channels and the A currents they may comprise play an important role in modulation of firing rate, action potential initiation and in controlling dendritic responses to synaptic inputs.

The fundamental function of a neuron is to receive, conduct, and transmit signals. Despite the varied purpose of the signals carried by different classes of neurons, the form of the signal is always the same and consists of changes in the electrical potential across the plasma membrane of the neuron. The plasma membrane of a neuron contains voltage-gated cation channels, which are responsible for propagating this electrical potential (also referred to as an action potential or nerve impulse) across and along the plasma membrane.

The Kv family of channels includes, among others: (1) the delayed-rectifier potassium channels, which repolarize the membrane after each action potential to prepare the cell to fire again; and (2) the rapidly inactivating (A-type) potassium channels, which are active predominantly at subthreshold voltages and and act to reduce the rate at which excitable cells reach firing threshold. In addition to being critical for action potential conduction, Kv channels also control the response to depolarizing, e.g., synaptic, inputs and play a role in neurotransmitter release. As a result of these activities, voltage-gated potassium channels are key regulators of neuronal excitability (Hille B., Ionic Channels of Excitable Membranes, Second Edition, Sunderland, Mass.: Sinauer, (1992)).

There is tremendous structural and functional diversity within the Kv potassium channel superfamily. This diversity is generated both by the existence of multiple genes and by alternative splicing of RNA transcripts produced from the same gene. Nonetheless, the amino acid sequences of the known Kv potassium channels show high similarity. All appear to be comprised of four, pore forming α-subunits and some are known to have four cytoplasmic (β-subunit) polypeptides (Jan L. Y. et al. (1990) *Trends Neurosci* 13:415–419, and Pongs, O. et al. (1995) *Sem Neurosci*. 7:137–146). The known Kv channel (α-subunits fall into four sub-families named for their homology to channels first isolated from Drosophila: the Kv1, or Shaker-related subfamily; the Kv2, or Shab-related subfamily; the Kv3, or Shaw-related subfamily; and the Kv4, or Shal-related subfamily. Kv4.2 and Kv4.3 are examples of Kv channel (α-subunits of the Shal-related subfamily. Kv4.3 has a unique neuroanatomical distribution in that its mRNA is highly expressed in brainstem monoaminergic and forebrain cholinergic neurons, where it is involved in the release of the neurotransmitters dopamine, norepinephrine, serotonin, and acetylcholine.

This channel is also highly expressed in cortical pyramidal cells and in interneurons. (Serdio P. et al. (1996) *J. Neurophys* 75:2174–2179). Interestingly, the Kv4.3 polypeptide is highly expressed in neurons which express the corresponding mRNA. The Kv4.3 polypeptide is expressed in the somatodendritic membranes of these cells, where it is thought to contribute to the rapidly inactivating K+ conductance. Kv4.2 mRNA is widely expressed in brain, and the corresponding polypeptide also appears to be concentrated in somatodendritic membranes where it also contributes to the rapidly inactivating K+ conductance (Sheng et al. (1992) Neuron 9:271–84). These somatodendritic A-type Kv channels, like Kv4.2 and Kv4.3, are likely involved in processes which underlie leaming and memory, such as integration of sub-threshold synaptic responses and the conductance of back-propagating action potentials (Hoffman D. A. et al. (1997) *Nature* 387:869–875).

Thus, proteins which interact with and modulate the activity of potassium channel proteins e.g., potassium channels having a Kv4.2 or Kv4.3 subunit, provide novel molecular targets to modulate neuronal excitability, e.g., action potential conduction, somatodendritic excitability and neurotransmitter release, in cells expressing these channels. In addition, detection of genetic lesions in the gene encoding these proteins could be used to diagnose and treat central nervous system disorders such as epilepsy, anxiety, depression, age-related memory loss, migraine, obesity, Parkinsons disease or Alzheimer's disease.

SUMMARY OF THE INVENTION

The present invention is based, at least in part, on the discovery of novel nucleic acid molecules which encode gene products that interact with potassium channel proteins or possess substantial homology to the gene products of the invention that interact with potassium channel proteins (paralogs). Potassium channel proteins are, for example, potassium channels having a Kv4.2 or Kv4.3 subunit. The nucleic acid molecules of the invention and their gene products are referred to herein as "Potassium Channel Interacting Proteins", "PCIP", or "KChIP" nucleic acid and protein molecules. The PCIP proteins of the present invention interact with, e.g., bind to a potassium channel protein, modulate the activity of a potassium channel protein, and/or modulate a potassium channel mediated activity in a cell, e.g., a neuronal cell. The PCIP molecules of the present invention are useful as modulating agents to regulate a variety of cellular processes, e.g., neuronal cell processes. Accordingly, in one aspect, this invention provides isolated nucleic acid molecules encoding PCIP proteins or biologically active portions thereof, as well as nucleic acid fragments suitable as primers or hybridization probes for the detection of PCIP-encoding nucleic acids.

In one embodiment, a PCIP nucleic acid molecule of the invention is at least 50%, 55%, 60%, 65%, 70%, 75%, 80%, 85%, 90%, 95%, 98% or more identical to the nucleotid sequence (e.g., to the entire length of the nucleotide sequence) shown in SEQ ID NO:1, SEQ ID NO:3 SEQ ID NO:5, SEQ ID NO:7, SEQ ID NO:9, SEQ ID NO:=1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a complement thereof.

In another preferred embodiment, the isolated nucleic acid molecule includes the nucleotide sequence shown SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or a complement thereof. In another preferred embodiment, the nucleic acid molecule includes a fragment of at least 300, 350, 400, 426, 471, or 583 nucleotides of the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or a complement thereof.

In another embodiment, a PCIP nucleic acid molecule includes a nucleotide sequence encoding a protein having an amino acid sequence sufficiently identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, or an amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In a preferred embodiment, a PCIP nucleic acid molecule includes a nucleotide sequence encoding a protein having an amino acid sequence at least 50%, 55%, 60%, 65%, 70%, 75%, 80%, 85%, 90%, 95% or more identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

In another preferred embodiment, an isolated nucleic acid molecule encodes the amino acid sequence of 1v, 9q, p19, W28559, KChIP4a, KChIP4b, 33b07, 1p, and rat 7s protein. In yet another preferred embodiment, the nucleic acid molecule includes a nucleotide sequence encoding a protein having the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In yet another preferred embodiment, the nucleic acid molecule is at least 426, 471, or 583 nucleotides in length and encodes a protein having a PCIP activity (as described herein).

Another embodiment of the invention features nucleic acid molecules, preferably PCIP nucleic acid molecules, which specifically detect PCIP nucleic acid molecules relative to nucleic acid molecules encoding non-PCIP proteins. For example, in one embodiment, such a nucleic acid molecule is at least 426, 400–450, 471, 450–500, 500–550, 583, 550–600, 600–650, 650–700, 700–750, 750–800 or more nucleotides in length and hybridizes under stringent conditions to a nucleic acid molecule comprising the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a complement thereof. In preferred embodiments, the nucleic acid molecules are at least 15 (e.g., contiguous) nucleotides in length and hybridize under stringent conditions to nucleotides 93–126, 360–462, 732–825, 1028–1054, or 1517–1534 of SEQ ID NO:7. In other preferred embodiments, the nucleic acid molecules comprise nucleotides 93–126, 360–462, 732–825, 1028–1054, or 1517–1534 of SEQ ID NO:7.

In other preferred embodiments, the nucleic acid molecules are at least 15 (e.g., contiguous) nucleotides in length and hybridize under stringent conditions to nucleotides 1–14, 49–116, 137–311, 345–410, 430–482, 503–518, 662–693, 1406–1421, 1441–1457, 1478–494, or 1882–1959 of SEQ ID NO:13. In other preferred embodiments, the nucleic acid molecules comprise nucleotides 1–14, 49–116, 137–311, 345–410, 430–482, 503–518, 662–693, 1406–1421, 1441–1457, 1478–1494, or 1882–1959of SEQ ID NO:13.

In preferred embodiments, the nucleic acid molecules are at least 15 (e.g., contiguous) nucleotides in length and hybridize under stringent conditions to nucleotides 932–1527, 1548–1765, 1786–1871, 1908–2091, 2259–2265, or 2630–2654 of SEQ ID NO:35.

In other preferred embodiments, the nucleic acid molecules comprise nucleotides 932–1527, 1548–1765, 1786–1871, 1908–2091, 2259–2265, or 2630–2654 of SEQ ID NO:35.

In other preferred embodiments, the nucleic acid molecule encodes a naturally occurring allelic variant of a polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72 or an amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, wherein the nucleic acid molecule hybridizes to a nucleic acid molecule comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71 under stringent conditions.

Another embodiment of the invention provides an isolated nucleic acid molecule which is antisense to a PCIP nucleic acid molecule, e.g., the coding strand of a PCIP nucleic acid molecule.

Another aspect of the invention provides a vector comprising a PCIP nucleic acid molecule. In certain embodiments, the vector is a recombinant expression vector. In another embodiment, the invention provides a host cell containing a vector of the invention. The invention also provides a method for producing a protein, preferably a PCIP protein, by culturing in a suitable medium, a host cell, e.g., a mammalian host cell such as a non-human mammalian cell, of the invention containing a recombinant expression vector, such that the protein is produced.

Another aspect of this invention features isolated or recombinant PCIP proteins and polypeptides. In one embodiment, the isolated protein, preferably a PCIP protein, includes at least one calcium binding domain. In a preferred embodiment, the protein, preferably a PCIP protein, includes at least one calcium binding domain and has an arnino acid sequence at least about 50%, 55%, 60%, 65%, 70%, 75%, 80%, 85%, 90%, 95% or more identical t the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In another preferred embodiment, the protein, preferably a PCIP protein, includes at least one calcium binding domain and modulates a potassium channel mediated activity. In yet another preferred embodiment, the protein, preferably a PCIP protein, includes at least one calcium binding domain and is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71.

In another embodiment, the invention features fragments of the proteins having the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, wherein the fragment comprises at least 15 amino acids (e.g., contiguous amino acids) of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID. NO:55, SEQ ID NO:57, SEQ ID NO:59, SEQ ID NO:70, or SEQ ID NO:72, or an amino acid sequence encoded by the DNA insert of the plasmid deposited with the ATCC as Accession Number 98936, 98937, 98938, 98939, 98940, 98941, 98942, 98943, 98944, 98945, 98946, 98947, 98948, 98949, 98950, 98951, 98991, 98993, or 98994. In another embodiment, the protein, preferably a PCIP protein, has the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:25, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72.

In another embodiment, the invention features an isolated protein, preferably a PCIP protein, which is encoded by a nucleic acid molecule having a nucleotide sequence at least about 50%, 55%, 60%, 65%, 70%, 75%, 80%, 85%, 90%, 95% or more identical to a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQID NO:71, or a complement thereof.

The proteins of the present invention or biologically active portions thereof, can be operatively linked to a non-PCIP polypeptide (e.g., heterologous amino acid sequences) to form fusion proteins. The invention further features antibodies, such as monoclonal or polyclonal antibodies, that specifically bind proteins of the invention, preferably PCIP proteins. In addition, the PCIP proteins or biologically active portions thereof can be incorporated into pharmaceutical compositions, which optionally include pharmaceutically acceptable carriers.

In another aspect, the present invention provides a method for detecting the presence of a PCIP nucleic acid molecule, protein or polypeptide in a biological sample by contacting the biological sample with an agent capable of detecting a PCIP nucleic acid molecule, protein or polypeptide such that the presence of a PCIP nucleic acid molecule, protein or polypeptide is detected in the biological sample.

In another aspect, the present invention provides a method for detecting the presence of PCIP activity in a biological sample by contacting the biological sample with an agent capable of detecting an indicator of PCIP activity such that the presence of PCIP activity is detected in the biological sample.

In another aspect, the invention provides a method for modulating PCIP activity comprising contacting a cell capable of expressing PCIP with an agent that modulates PCIP activity such that PCIP activity in the cell is modulated. In one embodiment, the agent inhibits PCIP activity. In another embodiment, the agent stimulates PCIP activity. In one embodiment, the agent is an antibody that specifically binds to a PCIP protein. In another embodiment, the agent modulates expression of PCIP by modulating transcription of a PCIP gene or translation of a PCIP mRNA. In yet another embodiment, the agent is a nucleic acid molecule having a nucleotide sequence that is antisense to the coding strand of a PCIP mRNA or a PCIP gene.

In one embodiment, the methods of the present invention are used to treat a subject having a disorder characterized by aberrant PCIP protein or nucleic acid expression or activity by administering an agent which is a PCIP modulator to the subject. In one embodiment, the PCIP modulator is a PCIP protein. In another embodiment the PCIP modulator is a PCIP nucleic acid molecule. In yet another embodiment, the PCIP modulator is a peptide, peptidomimetic, or other small molecule. In a preferred embodiment, the disorder characterized by aberrant PCIP protein or nucleic acid expression is a CNS disorder.

The present invention also provides a diagnostic assay for identifying the presence or absence of a genetic alteration characterized by at least one of (i) aberrant modification or mutation of a gene encoding a PCIP protein; (ii) misregulation of the gene; and (iii) aberrant post-translational modification of a PCIP protein, wherein a wild-type form of the gene encodes a protein with a PCIP activity.

In another aspect the invention provides a method for identifying a compound that binds to or modulates the activity of a PCIP protein, by providing an indicator composition comprising a PCIP protein having PCIP activity, contacting the indicator composition with a test compound, and determining the effect of the test compound on PCIP activity in the indicator composition to identify a compound that modulates the activity of a PCIP protein.

Other features and advantages of the invention will be apparent from the following detailed description and claims.

BRIEF DESCRIPTION OF THE DRAWINGS

FIG. 1 depicts the cDNA sequence and predicted amino acid sequence of human 1v. The nucleotide sequence corresponds to nucleic acids 1 to 1463 of SEQ ID NO:1. The amino acid sequence corresponds to amino acids 1 to 216 of SEQ ID NO:2.

FIG. 2 depicts the cDNA sequence and predicted amino acid sequence of rat 1v. The nucleotide sequence corresponds to nucleic acids 1 to 1856 of SEQ ID NO:3. The amino acid sequence corresponds to amino acids 1 to 245 of SEQ ID NO:4.

FIG. 3 depicts the cDNA sequence and predicted amino acid sequence of mouse 1v. The nucleotide sequence corresponds to nucleic acids 1 to 1907 of SEQ ID NO:5. The amino acid sequence corresponds to amino acids 1 to 216 of SEQ ID NO:6.

FIG. 4 depicts the cDNA sequence and predicted amino acid sequence of rat 1vl. The nucleotide sequence corresponds to nucleic acids 1 to 1534 of SEQ ID NO:7. The amino acid sequence corresponds to amino acids 1 to 227 of SEQ ID NO:8.

FIG. 5 depicts the cDNA sequence and predicted amino acid sequence of mouse 1vl. The nucleotide sequence corresponds to nucleic acids 1 to 1540 of SEQ ID NO:9. The amino acid sequence corresponds to amino acids 1 to 227 of SEQ ID NO:10.

FIG. 6 depicts the cDNA sequence and predicted amino acid sequence of rat 1vn. The nucleotide sequence corresponds to nucleic acids 1 to 955 of SEQ ID NO:11. The amino acid sequence corresponds to amino acids 1 to 203 of SEQ ID NO:12.

FIG. 7 depicts the cDNA sequence and predicted amino acid sequence of human 9ql. The nucleotide sequence corresponds to nucleic acids 1 to 2009 of SEQ ID NO:13. The amino acid sequence corresponds to amino acids 1 to 270 of SEQ ID NO:14.

FIG. 8 depicts the cDNA sequence and predicted amino acid sequence of rat 9ql. The nucleotide sequence corresponds to nucleic acids 1 to 1247 of SEQ ID NO:15. The amino acid sequence corresponds to amino acids 1 to 257 of SEQ ID NO:16.

FIG. 9 depicts the cDNA sequence and predicted amino acid sequence of mouse 9ql. The nucleotide sequence corresponds to nucleic acids 1 to 2343 of SEQ ID NO:17. The amino acid sequence corresponds to amino acids 1 to 270 of SEQ ID NO:18.

FIG. 10 depicts the cDNA sequence and predicted amino acid sequence of human 9qm. The nucleotide sequence corresponds to nucleic acids 1 to 1955 of SEQ ID NO:19. The amino acid sequence corresponds to amino acids 1 to 252 of SEQ ID NO:20.

FIG. 11 depicts the cDNA sequence and predicted amino acid sequence of rat 9qm. The nucleotide sequence corresponds to nucleic acids 1 to 2300 of SEQ ID NO:21. The amino acid sequence corresponds to amino acids 1 to 252 of SEQ ID NO:22.

FIG. 12 depicts the cDNA sequence and predicted amino acid sequence of human 9qs. The nucleotide sequence corresponds to nucleic acids 1 to 1859 of SEQ ID NO:23. The amino acid sequence corresponds to amino acids 1 to 220 of SEQ ID NO:24.

FIG. 13 depicts the cDNA sequence and predicted amino acid sequence of monkey 9qs. The nucleotide sequence corresponds to nucleic acids 1 to 2191 of SEQ ID NO:25. The amino acid sequence corresponds to amino acids 1 to 220 of SEQ ID NO:26.

FIG. 14 depicts the cDNA sequence and predicted amino acid sequence of rat 9qc. The nucleotide sequence corresponds to nucleic acids 1 to 2057 of SEQ ID NO:27. The amino acid sequence corresponds to amino acids 1 to 252 of SEQ ID NO:28.

FIG. 15 depicts the cDNA sequence and predicted amino acid sequence of rat 8t. The nucleotide sequence corresponds to nucleic acids 1 to 1904 of SEQ ID NO:29. The amino acid sequence corresponds to amino acids 1 to 225 of SEQ ID NO:30.

FIG. 16 depicts the cDNA sequence and predicted amino acid sequence of human p19. The nucleotide sequence corresponds to nucleic acids 1 to 619 of SEQ ID NO:31. The amino acid sequence corresponds to amino acids 1 to 200 of SEQ ID NO:32.

FIG. 17 depicts the cDNA sequence and predicted amino acid sequence of rat p19. The nucleotide sequence corresponds to nucleic acids 1 to 442 of SEQ ID NO:33. The amino acid sequence corresponds to amino acids 1 to 109 of SEQ ID NO:34.

FIG. 18 depicts the cDNA sequence and predicted amino acid sequence of mouse p19. The nucleotide sequence corresponds to nucleic acids 1 to 2644 of SEQ ID NO:35. The amino acid sequence corresponds to amino acids 1 to 256 of SEQ ID NO:36.

FIG. 19 depicts the cDNA sequence and predicted amino acid sequence of human W28559. The nucleotide sequence corresponds to nucleic acids 1 to 380 of SEQ ID NO:37. The amino acid sequence corresponds to amino acids 1 to 126 of SEQ ID NO:38.

FIG. 20 depicts the cDNA sequence and predicted amino acid sequence of human P193. The nucleotide sequence corresponds to nucleic acids 1 to 2176 of SEQ ID NO:39. The amino acid sequence corresponds to amino acids 1 to 41 of SEQ ID NO:40.

FIG. 22A depicts the genomic DNA sequence of human 9q. FIG. 22B depicts exon 1 and its flanking intron sequences (SEQ ID NO:46). FIG. 22C depicts exons 2–11 and the flanking intron sequences (SEQ ID NO:47).

FIG. 23 depicts the cDNA sequence and predicted amino acid sequence of monkey KChIP4a. The nucleotide sequence corresponds to nucleic acids 1 to 2413 of SEQ ID NO:48. The amino acid sequence corresponds to amino acids 1 to 233 of SEQ ID NO:49.

FIG. 24 depicts the cDNA sequence and predicted amino acid sequence of monkey KChIP4b. The nucleotide sequence corresponds to nucleic acids 1 to 1591 of SEQ ID NO:50. The amino acid sequence corresponds to amino acids 1 to 233 of SEQ ID NO:51.

FIG. 25 depicts an alignment of KChIP4a, KChIP4b, 9ql, 1v, p19, and related human paralog (hsncspara) W28559. Amino acids identical to the consensus are shaded in black, conserved amino acids are shaded in gray.

FIG. 26 depicts the cDNA sequence and predicted amino acid sequence of rat 33b07. The nucleotide sequence corresponds to nucleic acids 1 to 2051 of SEQ ID NO:52. The amino acid sequence corresponds to amino acids 1 to 407 of SEQ ID NO:53.

FIG. 27 depicts the cDNA sequence and predicted amino acid sequence of human 33b07. The nucleotide sequence corresponds to nucleic acids 1 to 4148 of SEQ ID NO:54. The amino acid sequence corresponds to amino acids 1 to 414 of SEQ ID NO:55.

FIG. 28 depicts the cDNA sequence and predicted amino acid sequence of rat 1p. The nucleotide sequence corresponds to nucleic acids 1 to 2643 of SEQ ID NO:56. The amino acid sequence corresponds to amino acids 1 to 267 of SEQ ID NO:57.

FIG. 29 depicts the cDNA sequence and predicted amino acid sequence of rat 7s. The nucleotide sequence corresponds to nucleic acids 1 to 2929 of SEQ ID NO:58. The amino acid sequence corresponds to amino acids 1 to 270 of SEQ ID NO:59.

FIG. 30 depicts the cDNA sequence and predicted amino acid sequence of rat 29x. The nucleotide sequence corresponds to nucleic acids 1 to 1489 of SEQ ID NO:60. The amino acid sequence corresponds to amino acids 1 to 351 of SEQ ID NO:61.

FIG. 31 depicts the cDNA sequence of rat 25r. The nucleotide sequence corresponds to nucleic acids 1 to 1194 of SEQ ID NO:62.

FIG. 32 depicts the cDNA sequence and predicted amino acid sequence of rat 5p. The nucleotide sequence corresponds to nucleic acids 1 to 600 of SEQ ID NO:63. The amino acid sequence corresponds to amino acids 1 to 95 of SEQ ID NO:64.

FIG. 33 depicts the cDNA sequence and predicted amino acid sequence of rat 7q. The nucleotide sequence corresponds to nucleic acids 1 to 639 of SEQ ID NO:65. The amino acid sequence corresponds to amino acids 1 to 212 of SEQ ID NO:66.

FIG. 34 depicts the cDNA sequence and predicted amino acid sequence of rat 19r. The nucleotide sequence corresponds to nucleic acids 1 to 816 of SEQ ID NO:67. The amino acid sequence corresponds to amino acids 1 to 271 of SEQ ID NO:68.

FIG. 35 depicts the cDNA sequence and predicted amino acid sequence of monkey KChIP4c. The nucleotide sequence corresponds to nucleic acids 1 to 2263 of SEQ ID NO:69. The amino acid sequence corresponds to amino acids 1 to 229 of SEQ ID NO:70.

FIG. 36 depicts the cDNA sequence and predicted amino acid sequence of monkey KChIP4d. The nucleotide sequence corresponds to nucleic acids 1 to 2259 of SEQ ID NO:71. The amino acid sequence corresponds to amino acids 1 to 250 of SEQ ID NO:72.

FIG. 37 depicts an alignment of KChIP4a, KChIP4b, KChIP4c, and KChIP4d.

FIG. 38 further depicts a table showing the amplitude and kinetic effects of KChIP2 (9ql) on Kv4.2. KchIP2 expression alters the peak current amplitude, inactivation and recovery from inactivation time constants, and activation $V_{1/12}$.

FIG. 39 further depicts a table showing the amplitude and kinetic effects of KchIP3 (p19) on Kv4.2. KchIP3 causes alterations in peak current and inactivation and recovery from inactivation time constants.

DETAILED DESCRIPTION OF THE INVENTION

Figure 21:
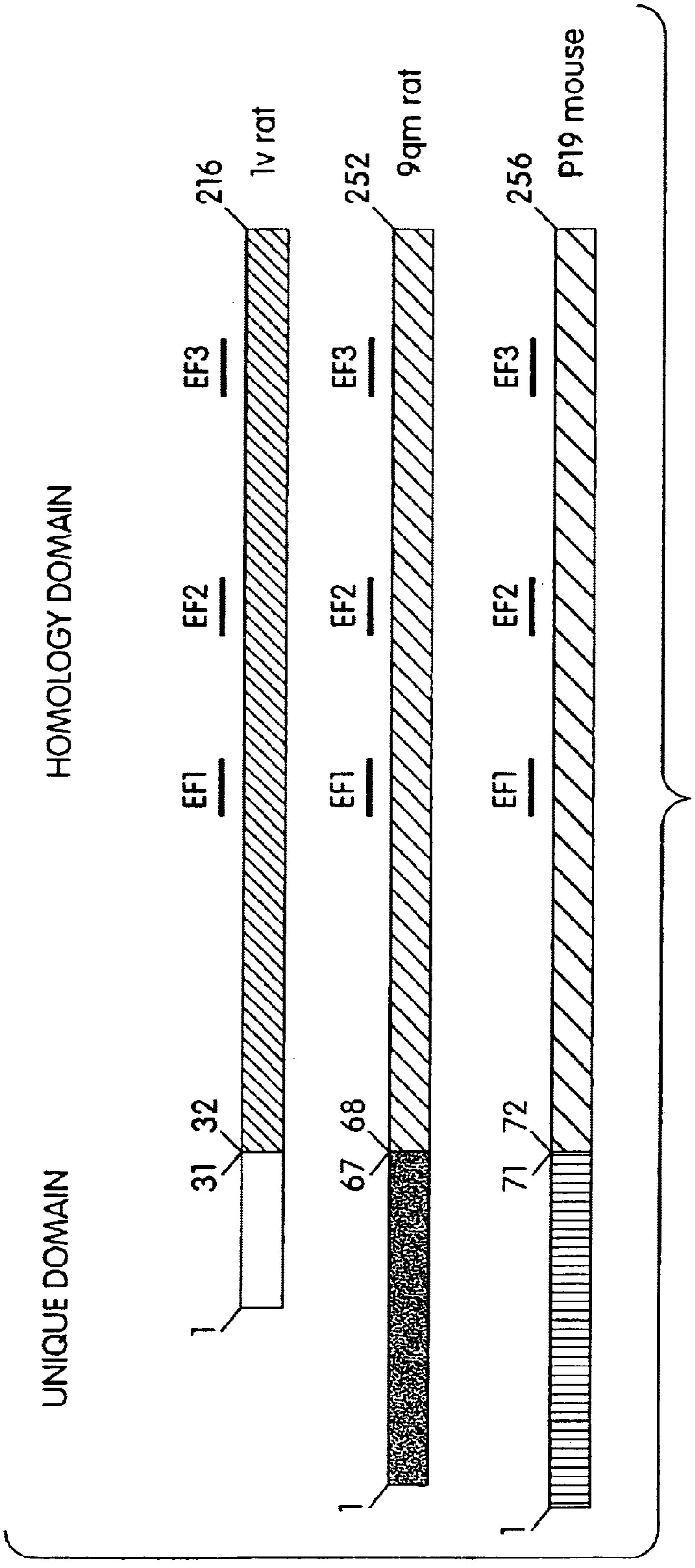
FIG. 21 depicts a schematic representation of the rat 1v, the rat 9qm, and the mouse P19 proteins, aligned to indicate the conserved domains among these proteins.

| | | |
|---|---|---|
| I. | Isolated Nucleic Acid Molecules | 22 |
| II. | Isolated PCIP Proteins and Anti-PCIP Antibodies | 37 |
| III. | Recombinant Expression Vectors and Host Cells | 47 |
| IV. | Pharmaceutical Compositions | 54 |
| V. | Uses and Methods of the Invention | 60 |
| | A. Screening Assays | 61 |
| | B. Detection Assays | 68 |
| | 1. Chromosome Mapping | 68 |
| | 2. Tissue Typing | 70 |
| | 3. Use of Partial PCIP Sequences in Forensic Biology | 70 |
| | C. Predictive Medicine | 71 |
| | 1. Diagnostic Assays | 72 |
| | 2. Prognostic Assays | 73 |
| | 3. Monitoring of Effects During Clinical Trials | 78 |
| | D. Methods of Treatment | 79 |
| | 1. Prophylactic Methods | 79 |
| | 2. Therapeutic Methods | 80 |
| | 3. Pharmacogenomics | 81 |

The present invention is based, at least in part, on the discovery of novel nucleic acid molecules which encode gene products that interact with potassium channel proteins or possess substantial homology to the gene products of the invention that interact with potassium channel proteins (paralogs). Potassium channel proteins are, for example, potassium channels having a Kv4.2 or Kv4.3 subunit. The nucleic acid molecules of the invention and their gene products are referred to herein as "Potassium Channel Interacting Proteins", "PCIP", or "KChIP4" nucleic acid and protein molecules. Preferably, the PCIP proteins of the present invention interact with, e.g., bind to a potassium channel protein, modulate the activity of a potassium channel protein, and/or modulate a potassium channel mediated activity in a cell, e.g., a neuronal cell.

As used herein, the term "PCIP family" when referring to the protein and nucleic acid molecules of the invention is intended to mean two or more proteins or nucleic acid molecules having a PCIP activity as defined herein. Such PCIP family members can be naturally or non-naturally occurring and can be from either the same or different species. For example, a PCIP family can contain a first protein of human origin, as well as other, distinct proteins of human origin or alternatively, can contain homologues of non-human origin.

As used interchangeably herein, a "PCIP activity", "biological activity of PCIP" or "functional activity of PCIP", refers to an activity exerted by a PCIP protein, polypeptide or nucleic acid molecule on a PCIP responsive cell or on a PCIP protein substrate, as determined in vivo, or in vitro, according to standard techniques. In one embodiment, a PCIP activity is a direct activity, such as an association with a PCIP-target molecule. As used herein, a "target molecule" or "binding partner" is a molecule with which a PCIP protein binds or interacts in nature, such that PCIP-mediated function is achieved. A PCIP target molecule can be a non-PCIP molecule or a PCIP protein or polypeptide of the present invention. In an exemplary embodiment, a PCIP target molecule is a PCIP ligand. Alternatively, a PCIP activity is an indirect activity, such as a cellular signaling activity mediated by interaction of the PCIP protein with a PCIP ligand. The biological activities of PCIP are described herein.

For example, the PCIP proteins of the present invention can have one or more of the following activities: (1) they can interact with (e.g., bind to) a potassium channel protein or portion thereof; (2) they can regulate the phosphorylation state of a potassium channel protein or portion thereof; (3) they can associate with (e.g., bind) calcium and can, for example, act as calcium dependent kinases, e.g., phosphorylate a potassium channel or a G-protein coupled receptor in a calcium-dependent manner; (4) they can modulate a potassium channel mediated activity in a cell (e.g., a neuronal cell such as a sensory neuron cell or a motor neuron cell) to, for example, beneficially affect the cell; (5) they can modulate chromatin formation in a cell, e.g., a neuronal cell; (6) they can modulate vesicular traffic and protein transport in a cell, e.g., a neuronal cell; (7) they can modulate cytokine signaling in a cell, e.g., a neuronal cell; (8) they can regulate the association of a potassium channel protein or portion thereof with the cellular cytoskeleton; (9) they can modulate cellular proliferation; (10) they can modulate the release of neurotransmitters; (11) they can modulate membrane excitability; (12) they can influence the resting potential of membranes; (13) they can modulate wave forms and frequencies of action potentials; and (14) they can modulate thresholds of excitation.

As used herein, a "potassium channel" includes a protein or polypeptide that is involved in receiving, conducting, and transmitting signals in an excitable cell. Potassium channels are typically expressed in electrically excitable cells, e.g., neurons, cardiac, skeletal and smooth muscle, renal, endocrine, and egg cells, and can form heteromultimeric structures, e.g., composed of pore-forming and cytoplasmic subunits. Examples of potassium channels include: (1) the voltage-gated potassium channels, (2) the ligand-gated potassium channels, and (3) the mechanically-gated potassium channels. For a detailed description of potassium channels, see Kandel E. R. et al., Principles of Neural Science, second edition, (Elsevier Science Publishing Co., Inc., N.Y. (1985)), the contents of which are incorporated herein by reference. The PCIP proteins of the present invention have been shown to interact with, for example, potassium channels having a Kv4.3 subunit or a Kv4.2 subunit.

As used herein, a "potassium channel mediated activity" includes an activity which involves a potassium channel, e.g., a potassium channel in a neuronal cell or a muscle cell, associated with receiving, conducting, and transmitting signals in, for example, the nervous system. Potassium channel mediated activities include release of neurotransmitters, e.g., dopamine or norepinephrine, from cells, e.g., neuronal cells; modulation of resting potential of membranes, wave forms and frequencies of action potentials, and thresholds of excitation; and modulation of processes such as integration of sub-threshold synaptic responses and the conductance of back-propagating action potentials in, for example, neuronal cells or muscle cells. As the PCIP proteins of the present invention modulate potassium channel mediated activities, they may be useful as novel diagnostic and therapeutic agents for potassium channel associated disorders and/or nervous system related disorders.

As used herein, a "potassium channel associated disorder" includes a disorder, disease or condition which is characterized by a misregulation of a potassium channel mediated activity. Potassium channel associated disorders can detrimentally affect conveyance of sensory impulses from the periphery to the brain and/or conductance of motor impulses from the brain to the periphery; integration of reflexes; interpretation of sensory impulses; and emotional, intellectual (e.g., learning and memory), or motor processes. As used herein, a "nervous system related disorder" includes a disorder, disease or condition which affects the nervous system. Examples of potassium channel associated disorders and nervous system related disorders include cognitive disorders, e.g., memory and learning disorders, such as amnesia, apraxia, agnosia, amnestic dysnomia, amnestic spatial disorientation, Kluver-Bucy syndrome, Alzheimer's related memory loss (Eglen R. M. (1996) *Pharmacol. and Toxicol.* 78(2):59–68; Perry E. K. (1995) *Brain and Cognition* 28(3):240–58) and learning disability; disorders affecting consciousness, e.g., visual hallucinations, perceptual disturbances, or delerium associated with Lewy body dementia; schitzo-effective disorders (Dean B. (1996) *Mol. Psychiatry* 1(1):54–8), schizophrenia with mood swings (Bymaster F. P. (1997) *J. Clin. Psychiatry* 58 (suppl.10):28–36; Yeomans J. S. (1995) *Neuropharmacol.* 12(1):3–16; Reimann D. (1994) *J. Psychiatric Res.* 28(3):195–210), depressive illness (primary or secondary); affective disorders (Janowsky D. S. (1994) *Am. J. Med. Genetics* 54(4):335–44); sleep disorders (Kimura F. (1997) *J. Neurophysiol.* 77(2):709–16), e.g., REM sleep abnormalities in patients suffering from, for example, depression (Riemann D. (1994) *J. Psychosomatic Res.* 38 Suppl. 1:15–25; Bourgin P. (1995) *Neuroreport* 6(3): 532–6), paradoxical sleep abnormalities (Sakai K. (1997) *Eur. J. Neuroscience* 9(3):415–23), sleep-wakefulness, and body temperature or respiratory depression abnormalities during sleep (Shuman S. L. (1995) Am. J. Physiol. 269(2 Pt 2):R308–17; Mallick B. N. (1997) *Brain Res.* 750(1–2):311–7). Other examples of nervous system related disorders include disorders affecting pain generation mechanisms, e.g., pain related to irritable bowel syndrome (Mitch C. H. (1997) J. Med. Chem. 40(4):538–46; Shannon H. E. (1997) *J. Pharmac. and Exp. Therapeutics* 281(2):884–94; Bouaziz H. (1995) *Anesthesia and Analgesia* 80(6): 1140–4; or Guimaraes A. P. (1994) *Brain Res.* 647(2):220–30) or chest pain; movement disorders (Monassi C. R. (1997) *Physiol. and Behav.* 62(1):53–9), e.g., Parkinson's disease related movement disorders (Finn M. (1997) *Pharmacol. Biochem. & Behavior* 57(1–2):243–9; Mayorga A. J. (1997) *Pharmacol. Biochem. & Behavior* 56(2):273–9); eating disorders, e.g., insulin hypersecretion related obesity (Maccario M. (1997) *J. Endocrinol. Invest.* 20(1):8–12; Premawardhana L. D. (1994) *Clin. Endocrinol.* 40(5):617–21); drinking disorders, e.g., diabetic polydipsia (Murzi E. (1997) *Brain Res.* 752(1–2):184–8; Yang X. (1994) *Pharmacol. Biochem. & Behavior* 49(1):1–6); neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, epileptic syndromes, and Jakob-Creutzfieldt disease; psychiatric disorders, e.g., depression, schizophrenic disorders, Korsakoffs psychosis, mania, anxiety disorders, bipolar affective disorders, or phobic disorders; neurological disorders, e.g., migraine; spinal cord injury; stroke; and head trauma.

Some members of a PCIP family may also have common structural characteristics, such as a common structural domain or motif or a sufficient amino acid or nucleotide sequence homology as defined herein. Such PCIP family members can be naturally or non-naturally occurring and can be from either the same or different species. For example, a PCIP family can contain a first protein of human origin, as well as other, distinct proteins of human origin or alternatively, can contain homologues of non-human origin.

For example, members of a PCIP family which have common structural characteristics, may comprise at least one "calcium binding domain". As used herein, the term "calcium binding domain" includes an amino acid domain, e.g., an EF hand (Baimbridge K. G. et al. (1992) TINS 15(8): 303–308), which is involved in calcium binding. Preferably, a calcium binding domain has a sequence, which is substantially identical to the consensus sequence:

EO••OO••ODKDGDG•OO•••EF••OO. (SEQ ID NO:41).

O can be I, L, V or M, and "•" indicates a position with no strongly preferred residue. Each residue listed is present in more than 25% of sequences, and those underlined are present in more than 80% of sequences. Amino acid residues 126–154 and 174–202 of the human 1v protein, amino acid residues 126–154 and 174–202 of the rat 1v protein, amino acid residues 137–165 and 185–213 of the rat 1vl protein, amino acid residues 142–170 of the rat 1vn protein, amino acid residues 126–154 and 174–202 of the mouse 1v protein, amino acid residues 137–165 and 185–213 of the mouse 1vl protein, amino acid residues 144–172, 180–208, and 228–256 of the human 9ql protein, amino acid residues 126–154, 162–190, and 210–238 of the human 9qm protein, amino acid residues 94–122, 130–158, and 178–206 of the human 9qs protein, amino acid residues 126–154, 162–190, and 210–238 of the rat 9qm protein, amino acid residues 131–159, 167–195, and 215–243 of the rat 9ql protein, amino acid residues 126–154, 162–190, and 210–238 of the rat 9qc protein, amino acid residues 99–127, 135–163, and 183–211 of the rat 8t protein, amino acid residues 144–172, 180–208, and 228–256 of the mouse 9ql protein, amino acid residues 94–122, 130–158, and 178–206 of the monkey 9qs protein, amino acid residues 94–122, 130–158, and 178–206 of the human p19 protein, amino acid residues 19–47 and 67–95 of the rat p19 protein, and amino acid residues 130–158, 166–194, and 214–242 of the mouse p19 protein comprise calcium binding domains (EF hands) (see FIG. 21). Amino acid residues 116–127 and 152–163 of the monkey KChIP4a and KChIP4b proteins comprise calcium binding domains.

Members of the PCIP family which also have common structural characteristics are listed in Table I and described below. The invention provides full length human, mouse, and rat 1v cDNA clones, full length mouse and rat cDNA clones of 1v splice variant 1vl, a partial rat cDNA clone of 1v splice variant 1vn, and the proteins encoded by these cDNAs. The invention further provides full length human and mouse and partial rat 9ql cDNA clones, full length human and rat cDNA clones of 9ql splice variant 9qm, full length human and monkey cDNA clones of 9ql splice variant 9qs, a full length rat cDNA clone of 9ql splice variant 9qc, a partial rat cDNA clone of 9ql splice variant 8t, and the proteins encoded by these cDNAs. The invention also provides full length mouse and human and partial rat p19 cDNA clones and the proteins encoded by these cDNAs. A full length human cDNA clone of p19 is provided, and a partial clone p193, representing the 3' end of the human p19 cDNA. In addition, the invention provides a partial human W28559 cDNA clone and the protein encoded by this cDNA. The invention further provides a full length monkey clone, KChIP4a, and a corresponding full length splice variant, KChIP4b and the proteins encoded by these cDNAs.

Other members of the PCIP family, e.g., members of the PCIP family which do not have common structural characteristics, are listed in Table II and are described below. The present invention provides a full length human and a partial length rat 33b07 clone and the proteins encoded by these cDNAs. The present invention further provides partial length rat 1p clone and the protein encoded by this cDNA. In addition, the present invention provides a partial length rat 7s clone and the protein encoded by this cDNA.

The present invention further provides PCIP family members which represent previously identified cDNAs (29x, 25r, 5p, 7q, and 19r). These previously identified cDNAs are identified herein as PCIP family members, i.e., as molecules which have a PCIP activity, as described herein. Accordingly, the present invention provides methods for using these previously identified cDNAs, e.g., methods for using these cDNAs in the screening assays, the diagnostic assays, the prognostic assays, and the methods of treatment described herein.

The PCIP molecules of the present invention were initially identified based on their ability, as determined using yeast two-hybrid assays (described in detail in Example 1), to interact with the amino-terminal 180 amino acids of rat Kv4.3 subunit. Further binding studies with other potassium subunits were performed to demonstrate specificity of the PCIP for Kv4.3 and Kv4.2. In situ localization, immunohistochemical methods, co-immunoprecipitation and patch clamping methods were then used to clearly demonstrate that the PCIPs of the present invention interact with and modulate the activity of potassium channels, particularly those comprising a 4.3 or 4.2 subunit.

Several novel human, mouse, monkey, and rat PCIP family members have been identified, referred to herein as 1v, 9q, p19, W28559, KChIP4, 33b07, 1p, and rat 7s proteins and nucleic acid molecules. The human, rat, and mouse cDNAs encoding the 1v polypeptide are represented by SEQ ID NOs:1, 3, and 5, and shown in FIGS. 1, 2, and 3, respectively. In the brain, 1v mRNA is highly expressed in neocortical and hippocampal interneurons, in the thalamic reticular nucleus and medial habenula, in basal forebrain and striatal cholinergic neurons, in the superior colliculus, and in cerebellar granule cells. The 1v polypeptide is highly expressed in the somata, dendrites, axons and axon terminals of cells that express 1v mRNA. Splice variants of the 1v gene have been identified in rat and mouse and are represented by SEQ ID NOs: 7, 9, and 11 and shown in FIGS. 4, 5, and 6, respectively. Iv polypeptide interacts with potassium channels comprising Kv4.3 or Kv4.2 subunits, but not with Kv1.1 subunits. As determined by Northern blot, the 1v transcripts (mRNA) are expressed predominantly in the brain.

The 8t cDNA (SEQ ID NO:29) encodes a polypeptide having a molecular weight of approximately 26 kD corresponding to SEQ ID NO:30 (see FIG. 15). The 8t polypeptide interacts with potassium channel comprising Kv4.3 or Kv4.2 subunits, but not with Kv1.1 subunits. As determined by Northern blot and in situ data, the 8t mRNA is expressed predominantly in the heart and the brain. The 8t cDNA is a splice variant of 9q.

Human, rat, monkey, and mouse 9q cDNA were also isolated. Splice variants include human 9ql (SEQ ID NO:13; FIG. 7) rat 9ql (SEQ ID NO:15; FIG. 8), mouse 9ql (SEQ ID NO:17; FIG. 9), human 9qm (SEQ ID NO:19; FIG. 10), rat 9qm (SEQ ID NO:21; FIG. 11), human 9qs (SEQ ID NO:23; FIG. 12), monkey 9qs (SEQ ID NO:25; FIG. 13), and rat 9qc (SEQ ID NO:27; FIG. 14). The genomic DNA sequence of 9q has also be determined. Exon 1 and its flanking intron sequences (SEQ ID NO:46) are shown in FIG. 22A. Exons 2–11 and the flanking intron sequences (SEQ ID NO:47) are shown in FIG. 22B. 9q polypeptides interact with potassium channels comprising Kv4.3 or Kv4.2 subunits, but not with Kv1.1 subunits. As determined by Northern blot and in situ data, the 9q proteins are expressed predominantly in the heart and the brain. In the brain, 9q mRNA is highly expressed in the neostriatum, hippocampal formation, neocortical pyramidal cells and interneurons, and in the thalamus, superior colliculus, and cerebellum.

Human, rat, and mouse P19 cDNA was also isolated. Human P19 is shown in SEQ ID NO:31 and FIG. 16; and in SEQ ID NO:39 and FIG. 20 (the 3' sequence). Rat P19 is shown in SEQ ID NO:33 and FIG. 17, and mouse P19 is shown in SEQ ID NO:35 and FIG. 18. P19 polypeptides interact with potassium channels comprising Kv4.3 or Kv4.2 subunits, but not with Kv1.1 subunits. As determined by northern blot analysis, the P19 transcripts (mRNA) are expressed predominantly in the brain.

A partial human paralog of the PCIP molecules was also identified. This paralog is referred to herein as W28559 and is shown in SEQ ID NO:37 and FIG. 19.

Monkey KChIP4a and its splice variants KChIP4b, KChIP4c, and KChIP4d were also identified. Monkey KChIP4a is shown in SEQ ID NO:48 and FIG. 23. Monkey KChIP4b is shown in SEQ ID NO:50 and FIG. 24. Monkey KChIP4c is shown in SEQ ID NO:69 and FIG. 35. Monkey KChIP4d is shown in SEQ ID NO:71 and FIG. 36.

The nucleotide sequence of the full length rat 33b07 cDNA and the predicted amino acid sequence of the rat 33b07 polypeptide are shown in FIG. 26 and in SEQ ID NOs:52 and 53, respectively. The rat 33b07 cDNA encodes a protein having a molecular weight of approximately 44.7 kD and which is 407 amino acid residues in length. Rat 33b07 binds rKv4.3N and rKv4.2N with slight preference for rKv4.2N in yeast 2-hybrid assays.

The nucleotide sequence of the full length human 33b07 cDNA and the predicted amino acid sequence of the human 33b07 polypeptide are shown in FIG. 27 and in SEQ ID NOs:54 and 55, respectively.

The nucleotide sequence of the partial length rat 1p cDNA and the predicted amino acid sequence of the rat 1p polypeptide are shown in FIG. 28 and in SEQ ID NOs:56 and 57, respectively. The rat 1p cDNA encodes a protein having a molecular weight of approximately 28.6 kD and which is 267 amino acid residues in length. Rat 1p binds rKv4.3N and rKv4.2N with slight preference for rKv4.3N in yeast two-hybrid assays.

The nucleotide sequence of the partial length rat 7s cDNA and the predicted amino acid sequence of the rat 7s polypeptide are shown in FIG. 29 and in SEQ ID NOs:58 and 59, respectively. The rat 7s cDNA encodes a protein having a molecular weight of approximately 28.6 kD and which is 270 amino acid residues in length. Rat 7s binds rKv4.3N and rKv4.2N with preference for rKv4.3N in yeast two-hybrid assays.

The sequences of the present invention are summarized below, in Tables I and II.

TABLE I

| | Novel Polynucleotides and Polypeptides of the Present Invention (full length except where noted) | | | | |
|---|---|---|---|---|---|
| PCIP | Nucleic Acid Molecule Form | Source | SEQ ID NO: DNA | SEQ ID NO: PROTEIN | ATCC |
| 1v | 1v | human (225–875)* | 1 | 2 | 98994 |
| | 1v | rat (210–860) | 3 | 4 | 98946 |
| | 1v | mouse (477–1127) | 5 | 6 | 98945 |
| | 1v1 | rat (31–714) | 7 | 8 | 98942 |
| | 1v1 | mouse (77–760) | 9 | 10 | 98943 |
| | 1vn (partial) | rat (345–955) | 11 | 12 | 98944 |
| 9q | Genomic DNA sequence (Exon 1 and flanking intron sequences) | human | 46 | | |
| | Genomic DNA sequence (Exons 2–11 and flanking intron sequences) | human | 47 | | |
| | 9q1 | human (207–1019) | 13 | 14 | 98993 98991 |
| | 9q1 (partial) | rat (2–775) | 15 | 16 | 98948 |
| | 9q1 | mouse (181–993) | 17 | 18 | 98937 |
| | 9qm | human (207–965) | 19 | 20 | 98993 98991 |
| | 9qm | rat (214–972) | 21 | 22 | 98941 |
| | 9qs | human (207–869) | 23 | 24 | 98951 |
| | 9qs | monkey (133–795) | 25 | 26 | 98950 |
| | 9qc | rat (208–966) | 27 | 28 | 98947 |
| | 8t (partial) | rat (1–678) | 29 | 30 | 98939 |
| p19 | p19 | Human (1–771) | 31 | 32 | PTA-316 |
| | p19 (partial) | rat (1–330) | 33 | 34 | 98936 |
| | p19 | mouse (49–819) | 35 | 36 | 98940 |
| | p193 (partial) | Human (2–127) | 39 | 40 | 98949 |
| W28559 | W28559 (partial) | human (1–339) | 37 | 38 | |
| KChIP4 | KChIP4a | Monkey (265–966) | 48 | 49 | |
| | KChIP4b C-terminal splice variant | Monkey (265–966) | 50 | 51 | |
| | KChIP4c splice variant | Monkey (122–811) | 69 | 70 | |
| | KChIP4d splice variant | Monkey (64–816) | 71 | 72 | |

*The coordinates of the coding sequence are shown in parenthesis.

The first column indicates the PCIPs which were identified and column 2 indicates the various nucleic acid forms identified for each PCIP.

TABLE II

| Polynucleotides and Polypeptides of the Present Invention (full length except where noted) | | | | | |
|---|---|---|---|---|---|
| PCIP | Nucleic Acid Molecule Form | Source | SEQ ID NO: DNA | SEQ ID NO: PROTEIN | ATCC |
| 33b07 Novel | 33b07 | Human (88–1332) | 52 | 53 | |
| | 33b07 | Rat (85–1308) | 54 | 55 | |
| 1p Novel | 1p (partial) | Rat (1–804) | 56 | 57 | |
| 7s Novel | 7s (partial) | Rat (1–813) | 58 | 59 | |
| 29x | 29x | Rat (433–1071) | 60 | 61 | |
| | 25r splice variant of 29x | Rat (130–768) | 62 | | |
| 5p | 5p | Rat (52–339) | 63 | 64 | |
| 7q | 7q | Rat (1–639) | 65 | 66 | |
| 19r | 19r | Rat (1–816) | 67 | 68 | |

*The coordinates of the coding sequence are shown in parenthesis.
The first column indicates the four families of PCIPs which were identified and column 2 indicates the various nucleic acid forms identified for each family.
Novel molecules are also indicated.

Plasmids containing the nucleotide sequences encoding human, rat and monkey PCIPs were deposited with American Type Culture Collection (ATCC), 10801 University Boulevard, Manassas, Va. 20110–2209, on Nov. 17, 1998, and assigned the Accession Numbers described above. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Clones containing cDNA molecules encoding human p19 (clone EphP19) and human 33b07 (clone Eph33b07) were deposited with American Type Culture Collection (Manassas, Va.) on Jul. 8,1998 as Accession Number PTA-316, as part of a composite deposit representing a mixture of two strains, each carrying one recombinant plasmid harboring a particular cDNA clone. (The ATCC strain designation for the mixture of hP19 and h33b07 is EphP19h33b07mix.

To distinguish the strains and isolate a strain harboring a particular cDNA clone, an aliquot of the mixture can be streaked out to single colonies on LB plates supplemented with 100 ug/ml ampicillin, single colonies grown, and then plasmid DNA extracted using a standard minipreparation procedure. Next, a sample of the DNA minipreparation can be digested with NotI and the resultant products resolved on a 0.8% agarose gel using standard DNA electrophoresis conditions. The digest gives the following band patterns: EphP19:7 kb 9 (single band), Eph33b07: 5.8 kb (single band).

Various aspects of the invention are described in further detail in the following subsections:

I. Isolated Nucleic Acid Molecules

One aspect of the invention pertains to isolated nucleic acid molecules that encode PCIP proteins or biologically active portions thereof, as well as nucleic acid fragments sufficient for use as hybridization probes to identify PCIP-encoding nucleic acid molecules (e.g., PCIP mRNA) and fragments for use as PCR primers for the amplification or mutation of PCIP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PCIP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion thereof, can be isolated using standard molecular biology techniques and the sequence information provided herein. Using all or portion of the nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, as a hybridization probe, PCIP nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 can be isolated by the polymerase chain reaction (PCR) using synthetic oligonucleotide primers designed based upon the sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to PCIP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences.

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:5, SEQ ID NO:7, SEQID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences. A nucleic acid molecule which is complementary to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, is one which is sufficiently complementary to the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, such that it can hybridize to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95% or more identical to the entire length of the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the entire length of the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences.

Moreover, the nucleic acid molecule of the invention can comprise only a portion of the nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:213, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, for example a fragment which can be used as a probe or primer or a fragment encoding a biologically active portion of a PCIP protein. The nucleotide sequence determined from the cloning of the PCIP gene allows for the generation of probes and primers designed for use in identifying and/or cloning other PCIP family members, as well as PCIP homologues from other species.

The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, of an anti-sense sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or of a naturally occurring allelic variant or mutant of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In an exemplary embodiment, a nucleic acid molecule of the present invention comprises a nucleotide sequence which is 350–400, 400–450, 450–500, 500–550, 550–600, 600–650, 650–700, 700–750, 750–800, 800–850, 850–900, 949, 950–1000, or more nucleotides in length and hybridizes under stringent hybridization conditions to a nucleic acid molecule of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

Probes based on the PCIP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PCIP protein, such as by measuring a level of a PCIP-encoding nucleic acid in a sample of cells from a subject e.g., detecting PCIP mRNA levels or determining whether a genomic PCIP gene has been mutated or deleted.

A nucleic acid fragment encoding a "biologically active portion of a PCIP protein" can be prepared by isolating a portion of the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, which encodes a polypeptide having a PCIP biological activity (the biological activities of the PCIP proteins are described herein), expressing the encoded portion of the PCIP protein (e.g., by recombinant expression in vitro) and assessing the activity of the encoded portion of the PCIP protein.

The invention further encompasses nucleic acid molecules that differ from the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71 or the nucleotide sequence of the DNA insert of the plasmid deposited with 98936, 98937, 98938, 98939, 98940, 98941, 98942, 98943, 98944, 98945, 98946, 98947, 98948, 98949, 98950, 98951, 98991, 98993, or 98994, due to degeneracy of the genetic code and thus encode the same PCIP proteins as those encoded by the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID N:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In another embodiment, an isolated nucleic acid molecule of the invention has a nucleotide sequence encoding a protein having an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72.

In addition to the PCIP nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, it will be appreciated by those skilled in the art that DNA sequence polymorphisms that lead to changes in the amino acid sequences of the PCIP proteins may exist within a population (e.g., the human population). Such genetic polymorphism in the PCIP genes may exist among individuals within a population due to natural allelic variation. As used herein, the terms "gene" and "recombinant gene" refer to nucleic acid molecules which include an open reading frame encoding a PCIP protein, preferably a mammalian PCIP protein, and can further include non-coding regulatory sequences, and introns.

Allelic variants of human PCIP include both functional and non-functional PCIP proteins. Functional allelic variants are naturally occurring amino acid sequence variants of the human PCIP protein that maintain the ability to bind a PCIP ligand and/or modulate any of the PCIP activities described herein. Functional allelic variants will typically contain only conservative substitution of one or more amino acids of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72 or substitution, deletion or insertion of non-critical residues in non-critical regions of the protein.

Non-functional allelic variants are naturally occurring amino acid sequence variants of the human PCIP protein that do not have the ability to either bind a PCIP ligand and/or modulate any of the PCIP activities described herein. Non-functional allelic variants will typically contain a non-conservative substitution, a deletion, or insertion or premature truncation of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72 or a substitution, insertion or deletion in critical residues or critical regions.

The present invention further provides non-human orthologues of the human PCIP protein. Orthologues of the human PCIP protein are proteins that are isolated from non-human organisms and possess the same PCIP ligand binding and/or modulation of potassium channel mediated activities of the human PCIP protein. Orthologues of the human PCIP protein can readily be identified as comprising an amino acid sequence that is substantially identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72.

Moreover, nucleic acid molecules encoding other PCIP family members and, thus, which have a nucleotide sequence which differs from the PCIP sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 are intended to be within the scope of the invention. For example, another PCIP cDNA can be identified based on the nucleotide sequence of human PCIP. Moreover, nucleic acid molecules encoding PCIP proteins from different species, and thus which have a nucleotide sequence which differs from the PCIP sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 are intended to be within the scope of the invention. For example, a mouse PCIP cDNA can be identified based on the nucleotide sequence of a human PCIP.

Nucleic acid molecules corresponding to natural allelic variants and homologues of the PCIP cDNAs of the invention can be isolated based on their homology to the PCIP nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In other embodiment, the nucleic acid is at least 30, 50, 100, 150, 200, 250, 300, 307, 350, 400, 450, 500, 550, 600, 650, 700, 750, 800, 850, 900, 949, or 950 nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6X sodium chloride/sodium citrate (SSC) at about 45C, followed by one or more washes in 0.2X SSC, 0.1% SDS at 50° C., preferably at 55° C., and more preferably at 60° C. or 65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the PCIP sequences that may exist in the population, the skilled artisan will further appreciate that changes can be introduced by mutation into the nucleotide sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, thereby leading to changes in the amino acid sequence of the encoded PCIP proteins, without altering the functional ability of the PCIP proteins. For example, nucleotide substitutions leading to amino acid substitutions at "non-essential" amino acid residues can be made in the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. A "non-essential" amino acid residue is a residue that can be altered from the wild-type sequence of PCIP (e.g., the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72) without altering the biological activity, whereas an "essential" amino acid residue is required for biological activity. For example, amino acid residues that are conserved among the PCIP proteins of the present invention, are predicted to be particularly unamenable to alteration. Furthermore, additional amino acid residues that are conserved between the PCIP proteins of the present invention and other members of the PCIP family of proteins are not likely to be amenable to alteration.

Accordingly, another aspect of the invention pertains to nucleic acid molecules encoding PCIP proteins that contain changes in amino acid residues that are not essential for activity. Such PCIP proteins differ in amino acid sequence from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95% or more identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72.

An isolated nucleic acid molecule encoding a PCIP protein homologous to the protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72 can be created by introducing one or more nucleotide substitutions, additions or deletions into the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, such that one or more amino acid substitutions, additions or deletions are introduced into the encoded protein. Mutations can be introduced into SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PCIP protein is preferably replaced with another amino acid residue from the same side chain family. Alternatively, in another embodiment, mutations can be introduced randomly along all or part of a PCIP coding sequence, such as by saturation mutagenesis, and the resultant mutants can be screened for PCIP biological activity to identify mutants that retain activity. Following mutagenesis of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, the encoded protein can be expressed recombinantly and the activity of the protein can be determined.

In a preferred embodiment, a mutant PCIP protein can be assayed for the ability to (1) interact with (e.g., bind to) a potassium channel protein or portion thereof; (2) regulate the phosphorylation state of a potassium channel protein or portion thereof; (3) associate with (e.g., bind) calcium and, for example, act as a calcium dependent kinase, e.g., phosphorylate a potassium channel in a calcium-dependent manner; (4) modulate a potassium channel mediated activity in a cell (e.g., a neuronal cell) to, for example, beneficially affect the cell; (5) modulate the release of neurotransmitters; (6) modulate membrane excitability; (7) influence the resting potential of membranes; (8) modulate wave forms and frequencies of action potentials; and (9) modulate thresholds of excitation.

In addition to the nucleic acid molecules encoding PCIP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PCIP coding strand, or to only a portion thereof. In one embodiment, an antisense nucleic acid molecule is antisense to a "coding region" of the coding strand of a nucleotide sequence encoding PCIP. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PCIP. The term "noncoding region" refers to 5' and 3' sequences which flank the coding region that are not translated into amino acids (i.e., also referred to as 5' and 3' untranslated regions).

Given the coding strand sequences encoding PCIP disclosed herein, antisense nucleic acids of the invention can be designed according to the rules of Watson and Crick base pairing. The antisense nucleic acid molecule can be complementary to the entire coding region of PCIP mRNA, but more preferably is an oligonucleotide which is antisense to only a portion of the coding or noncoding region of PCIP mRNA. For example, the antisense oligonucleotide can be complementary to the region surrounding the translation start site of PCIP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PCIP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an (α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave PCIP mRNA transcripts to thereby inhibit translation of PCIP mRNA. A ribozyme having specificity for a PCIP-encoding nucleic acid can be designed based upon the nucleotide sequence of a PCIP cDNA disclosed herein (i.e., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994). For example, a derivative of a Tetrahymena L-19 IVS RNA can be constructed in which the nucleotide sequence of the active site is complementary to the nucleotide sequence to be cleaved in a PCIP-encoding mRNA. See, e.g., Cech et al. U.S. Pat. No. 4,987,071; and Cech et al. U.S. Pat. No. 5,116,742. Alternatively, PCIP mRNA can be used to select a catalytic RNA having a specific ribonuclease activity from a pool of RNA molecules. See, e.g., Bartel, D. and Szostak, J. W. (1993) *Science* 261:1411–1418.

Alternatively, PCIP gene expression can be inhibited by targeting nucleotide sequences complementary to the regulatory region of the PCIP (e.g., the PCIP promoter and/or enhancers) to form triple helical structures that prevent transcription of the PCIP gene in target cells. See generally, Helene, C. (1991) *Anticancer Drug Des.* 6(6):569–84; Helene, C. et al. (1992) *Ann. N. Y. Acad Sci.* 660:27–36; and Maher, L. J. (1992) *Bioassays* 14(12):807–15.

In yet another embodiment, the PCIP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of PCIP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PCIP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of PCIP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PCIP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated PCIP Proteins and Anti-PCIP Antibodies

One aspect of the invention pertains to isolated PCIP proteins, and biologically active portions thereof, as well as polypeptide fragments suitable for use as immunogens to raise anti-PCIP antibodies. In one embodiment, native PCIP proteins can be isolated from cells or tissue sources by an appropriate purification scheme using standard protein purification techniques. In another embodiment, PCIP proteins are produced by recombinant DNA techniques. Alternative to recombinant expression, a PCIP protein or polypeptide can be synthesized chemically using standard peptide synthesis techniques.

An "isolated" or "purified" protein or biologically active portion thereof is substantially free of cellular material or other contaminating proteins from the cell or tissue source from which the PCIP protein is derived, or substantially free from chemical precursors or other chemicals when chemically synthesized. The language "substantially free of cellular material" includes preparations of PCIP protein in which the protein is separated from cellular components of the cells from which it is isolated or recombinantly produced. In one embodiment, the language "substantially free of cellular material" includes preparations of PCIP protein having less than about 30% (by dry weight) of non-PCIP protein (also referred to herein as a "contaminating protein"), more preferably less than about 20% of non-PCIP protein, still more preferably less than about 10% of non-PCIP protein, and most preferably less than about 5% non-PCIP protein. When the PCIP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PCIP protein in which the protein is separated from chemical precursors or other chemicals which are involved in the synthesis of the protein. In one embodiment, the language "substantially free of chemical precursors or other chemicals" includes preparations of PCIP protein having less than about 30% (by dry weight) of chemical precursors or non-PCIP chemicals, more preferably less than about 20% chemical precursors or non-PCIP chemicals, still more preferably less than about 10% chemical precursors or non-PCIP chemicals, and most preferably less than about 5% chemical precursors or non-PCIP chemicals.

As used herein, a "biologically active portion" of a PCIP protein includes a fragment of a PCIP protein which participates in an interaction between a PCIP molecule and a non-PCIP molecule. Biologically active portions of a PCIP protein include peptides comprising amino acid sequences sufficiently identical to or derived from the amino acid sequence of the PCIP protein, e.g., the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, which include less amino acids than the full length PCIP proteins, and exhibit at least one activity of a PCIP protein. Typically, biologically active portions comprise a domain or motif with at least one activity of the PCIP protein, e.g., binding of a potassium channel subunit. A biologically active portion of a PCIP protein can be a polypeptide which is, for example, 10, 25, 50, 100, 200, or more amino acids in length. Biologically active portions of a PCIP protein can be used as targets for developing agents which modulate a potassium channel mediated activity.

In one embodiment, a biologically active portion of a PCIP protein comprises at least one calcium binding domain.

It is to be understood that a preferred biologically active portion of a PCIP protein of the present invention may contain at least one of the above-identified structurali domains. A more preferred biologically active portion of a PCIP protein may contain at least two of the above-identified structural domains. Moreover, other biologically active portions, in which other regions of the protein are deleted, can be prepared by recombinant techniques and evaluated for one or more of the functional activities of a native PCIP protein.

In a preferred embodiment, the PCIP protein has an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72. In other embodiments, the PCIP protein is substantially homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, and retains the functional activity of the protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, yet differs in amino acid sequence due to natural allelic variation or mutagenesis, as described in detail in subsection I above. Accordingly, in another embodiment, the PCIP protein is a protein which comprises an amino acid sequence at least about 50%, 55%, 60%, 65%, 70%, 75%, 80%, 85%, 90%, 95% or more identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72.

Isolated proteins of the present invention, preferably 1v, 9q, p19, W28559, KChIP4a, KChIP4b, 33b07, 1p, or 7s proteins, have an amino acid sequence sufficiently identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72 or are encoded by a nucleotide sequence sufficiently identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:21, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% identity, preferably 60% identity, more preferably 70%–80%, and even more preferably 90–95% identity across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% identity and share a common functional activity are defined herein as sufficiently identical.

Preferred proteins are PCIP proteins having at least one calcium binding domain and, preferably, a PCIP activity. Other preferred proteins are PCIP proteins having at least one calcium binding domain, and are, preferably, encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the PCIP amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http:/lwww.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to PCIP nucleic acid molecules of the invention. BLAST protein searches can be performed with the XBLAST program, score=50, wordlength=3 to obtain amino acid sequences homologous to PCIP protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http:H/www.ncbi.nlm.nih.gov.

The invention also provides PCIP chimeric or fusion proteins. As used herein, a PCIP "chimeric protein" or "fusion protein" comprises a PCIP polypeptide operatively linked to a non-PCIP polypeptide. An "PCIP polypeptide" refers to a polypeptide having an amino acid sequence corresponding to PCIP, whereas a "non-PCIP polypeptide" refers to a polypeptide having an amino acid sequence corresponding to a protein which is not substantially homologous to the PCIP protein, e.g., a protein which is different from the PCIP protein and which is derived from the same or a different organism. Within a PCIP fusion protein the PCIP polypeptide can correspond to all or a portion of a PCIP protein. In a preferred embodiment, a PCIP fusion protein comprises at least one biologically active portion of a PCIP protein. In another preferred embodiment, a PCIP fusion protein comprises at least two biologically active portions of a PCIP protein. Within the fusion protein, the term "operatively linked" is intended to indicate that the PCIP polypeptide and the non-PCIP polypeptide are fused in-frame to each other. The non-PCIP polypeptide can be fused to the N-terminus or C-terminus of the PCIP polypeptide.

For example, in one embodiment, the fusion protein is a GST-PCIP fusion protein in which the PCIP sequences are fused to the C-terminus of the GST sequences. Such fusion proteins can facilitate the purification of recombinant PCIP.

In another embodiment, the fusion protein is a PCIP protein containing a heterologous signal sequence at its N-terminus. In certain host cells (e.g., mammalian host cells), expression and/or secretion of PCIP can be increased through use of a heterologous signal sequence.

The PCIP fusion proteins of the invention can be incorporated into pharmaceutical compositions and administered to a subject in vivo. The PCIP fusion proteins can be used to affect the bioavailability of a PCIP substrate. Use of PCIP fusion proteins may be useful therapeutically for the treatment of potassium channel associated disorders such as CNS disorders, e.g., neurodegenerative disorders such as Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; psychiatric disorders, e.g., depression, schizophrenic disorders, Korsakoffs psychosis, mania, anxiety disorders, or phobic disorders; learning or memory disorders, e.g., amnesia or age-related memory loss; and neurological disorders; e.g., migraine.

Moreover, the PCIP-fusion proteins of the invention can be used as immunogens to produce anti-PCIP antibodies in a subject, to purify PCIP ligands and in screening assays to identify molecules which inhibit the interaction of PCIP with a PCIP substrate.

Preferably, a PCIP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PCIP-encoding nucleic acid can be cloned into such an expression vector such that the fusion moiety is linked in-frame to the PCIP protein.

The present invention also pertains to variants of the PCIP proteins which function as either PCIP agonists (mimetics) or as PCIP antagonists. Variants of the PCIP proteins can be generated by mutagenesis, e.g., discrete point mutation or truncation of a PCIP protein. An agonist of the PCIP proteins can retain substantially the same, or a subset, of the biological activities of the naturally occurring form of a PCIP protein. An antagonist of a PCIP protein can inhibit one or more of the activities of the naturally occurring form of the PCIP protein by, for example, competitively modulating a potassium channel mediated activity of a PCIP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PCIP protein.

In one embodiment, variants of a PCIP protein which function as either PCIP agonists (mimetics) or as PCIP antagonists can be identified by screening combinatorial libraries of mutants, e.g., truncation mutants, of a PCIP protein for PCIP protein agonist or antagonist activity. In one embodiment, a variegated library of PCIP variants is generated by combinatorial mutagenesis at the nucleic acid level and is encoded by a variegated gene library. A variegated library of PCIP variants can be produced by, for example, enzymatically ligating a mixture of synthetic oligonucleotides into gene sequences such that a degenerate set of potential PCIP sequences is expressible as individual polypeptides, or alternatively, as a set of larger fusion proteins (e.g., for phage display) containing the set of PCIP sequences therein. There are a variety of methods which can be used to produce libraries of potential PCIP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PCIP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a PCIP protein coding sequence can be used to generate a variegated population of PCIP fragments for screening and subsequent selection of variants of a PCIP protein. In one embodiment, a library of coding sequence fragments can be generated by treating a double stranded PCR fragment of a PCIP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PCIP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PCIP proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify PCIP variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated PCIP library. For example, a library of expression vectors can be transfected into a cell line which ordinarily possesses a potassium channel mediated activity. The effect of the PCIP mutant on the potassium channel mediated activity can then be detected, e.g., by any of a number of enzymatic assays or by detecting the release of a neurotransmitter. Plasmid DNA can then be recovered from the cells which score for inhibition, or alternatively, potentiation of the potassium channel mediated activity, and the individual clones further characterized.

An isolated PCIP protein, or a portion or fragment thereof, can be used as an immunogen to generate antibodies that bind PCIP using standard techniques for polyclonal and monoclonal antibody preparation. A full-length PCIP protein can be used or, alternatively, the invention provides antigenic peptide fragments of PCIP for use as immunogens. The antigenic peptide of PCIP comprises at least 8 amino acid residues of the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72 and encompasses an epitope of PCIP such that an antibody raised against the peptide forms a specific immune complex with PCIP.

Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of PCIP that are located on the surface of the protein, e.g., hydrophilic regions, as well as regions with high antigenicity.

A PCIP immunogen typically is used to prepare antibodies by immunizing a suitable subject, (e.g., rabbit, goat, mouse or other mammal) with the immunogen. An appropriate immunogenic preparation can contain, for example, recombinantly expressed PCIP protein or a chemically synthesized PCIP polypeptide. The preparation can further include an adjuvant, such as Freund's complete or incomplete adjuvant, or similar immunostimulatory agent. Immunization of a suitable subject with an immunogenic PCIP preparation induces a polyclonal anti-PCIP antibody response.

Accordingly, another aspect of the invention pertains to anti-PCIP antibodies. The term "antibody" as used herein refers to immunoglobulin molecules and immunologically active portions of immunoglobulin molecules, i.e., molecules that contain an antigen binding site which specifically binds (immunoreacts with) an antigen, such as PCIP. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind PCIP. The term "monoclonal antibody" or "monoclonal antibody composition", as used herein, refers to a population of antibody molecules that contain only one species of an antigen binding site capable of immunoreacting with a particular epitope of PCIP. A monoclonal antibody composition thus typically displays a single binding affinity for a particular PCIP protein with which it immunoreacts.

Polyclonal anti-PCIP antibodies can be prepared as described above by immunizing a suitable subject with a PCIP immunogen. The anti-PCIP antibody titer in the immunized subject can be monitored over time by standard techniques, such as with an enzyme linked immunosorbent assay (ELISA) using immobilized PCIP. If desired, the antibody molecules directed against PCIP can be isolated from the mammal (e.g., from the blood) and further purified by well known techniques, such as protein A chromatography to obtain the IgG fraction. At an appropriate time after immunization, e.g., when the anti-PCIP antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet*. 3:231–36). Briefly, an immortal cell line (typically a myeloma) is fused to lymphocytes (typically splenocytes) from a mammal immunized with a PCIP immunogen as described above, and the culture supernatants of the resulting hybridoma cells are screened to identify a hybridoma producing a monoclonal antibody that binds PCIP.

Any of the many well known protocols used for fusing lymphocytes and immortalized cell lines can be applied for the purpose of generating an anti-PCIP monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PCIP, e.g., using a standard ELISA assay.

Alternative to preparing monoclonal antibody-secreting hybridomas, a monoclonal anti-PCIP antibody can be identified and isolated by screening a recombinant combinatorial immunoglobulin library (e.g., an antibody phage display library) with PCIP to thereby isolate immunoglobulin library members that bind PCIP. Kits for generating and screening phage display libraries are commercially available (e.g., the *Pharmacia Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J*12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad Sci. USA* 88:7978–7982; and McCafferty et al. *Nature* (1990) 348:552–554.

Additionally, recombinant anti-PCIP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *Bio Techniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-PCIP antibody (e.g., monoclonal antibody) can be used to isolate PCIP by standard techniques, such as affinity chromatography or immunoprecipitation. An anti-PCIP antibody can facilitate the purification of natural PCIP from cells and of recombinantly produced PCIP expressed in host cells. Moreover, an anti-PCIP antibody can be used to detect PCIP protein (e.g., in a cellular lysate or cell supernatant) in order to evaluate the abundance and pattern of expression of the PCIP protein. Anti-PCIP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a PCIP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PCIP proteins, mutant forms of PCIP proteins, fusion proteins, and the like).

The recombinant expression vectors of the invention can be designed for expression of PCIP proteins in prokaryotic or eukaryotic cells. For example, PCIP proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PCIP activity assays, (e.g., direct assays or competitive assays described in detail below), or to generate antibodies specific for PCIP proteins, for example. In a preferred embodiment, a PCIP fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gnl). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the PCIP expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, PCIP proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning. A Laboratory Manual. 2nd, ed, Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PCIP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PCIP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning, A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PCIP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a PCIP protein. Accordingly, the invention further provides methods for producing a PCIP protein using the host cells of the invention. In one embodiment, the method comprises culturing the host cell of invention (into which a recombinant expression vector encoding a PCIP protein has been introduced) in a suitable medium such that a PCIP protein is produced. In another embodiment, the method further comprises isolating a PCIP protein from the medium or the host cell.

The host cells of the invention can also be used to produce non-human transgenic animals. For example, in one embodiment, a host cell of the invention is a fertilized oocyte or an embryonic stem cell into which PCIP-coding sequences have been introduced. Such host cells can then be used to create non-human transgenic animals in which exogenous PCIP sequences have been introduced into their genome or homologous recombinant animals in which endogenous PCIP sequences have been altered. Such animals are useful for studying the function and/or activity of a PCIP and for identifying and/or evaluating modulators of PCIP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PCIP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a PCIP-encoding nucleic acid into the male pronuclei of a fertilized oocyte, e.g., by microinjection, retroviral infection, and allowing the oocyte to develop in a pseudopregnant female foster animal. The PCIP cDNA sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71 can be introduced as a transgene into the genome of a non-human animal. Alternatively, a nonhuman homologue of a human PCIP gene, such as a mouse or rat PCIP gene, can be used as a transgene. Alternatively, a PCIP gene homologue, such as another PCIP family member, can be isolated based on hybridization to the PCIP cDNA sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71 or the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 (described further in subsection I above) and used as a transgene. Intronic sequences and polyadenylation signals can also be included in the transgene to increase the efficiency of expression of the transgene. A tissue-specific regulatory sequence(s) can be operably linked to a PCIP transgene to direct expression of a PCIP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a PCIP transgene in its genome and/or expression of PCIP mRNA in tissues or cells of the animals. A transgenic founder animal can then be used to breed additional animals carrying the transgene. Moreover, transgenic animals carrying a transgene encoding a PCIP protein can further be bred to other transgenic animals carrying other transgenes.

To create a homologous recombinant animal, a vector is prepared which contains at least a portion of a PCIP gene into which a deletion, addition or substitution has been introduced to thereby alter, e.g., functionally disrupt, the PCIP gene. The PCIP gene can be a human gene (e.g., the cDNA of SEQ ID NO:1), but more preferably, is a non-human homologue of a human PCIP gene (e.g., the cDNA of SEQ ID NO:3 or 5). For example, a mouse PCIP gene can be used to construct a homologous recombination vector suitable for altering an endogenous PCIP gene in the mouse genome. In a preferred embodiment, the vector is designed such that, upon homologous recombination, the endogenous PCIP gene is functionally disrupted (i.e., no longer encodes a functional protein; also referred to as a "knock out" vector). Alternatively, the vector can be designed such that, upon homologous recombination, the endogenous PCIP gene is mutated or otherwise altered but still encodes functional protein (e.g., the upstream regulatory region can be altered to thereby alter the expression of the endogenous PCIP protein). In the homologous recombination vector, the altered portion of the PCIP gene is flanked at its 5' and 3' ends by additional nucleic acid sequence of the PCIP gene to allow for homologous recombination to occur between the exogenous PCIP gene carried by the vector and an endogenous PCIP gene in an embryonic stem cell. The additional flanking PCIP nucleic acid sequence is of sufficient length for successful homologous recombination with the endogenous gene. Typically, several kilobases of flanking. DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced PCIP gene has homologously recombined with the endogenous PCIP gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of Saccharomyces cerevisiae (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided-through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The PCIP nucleic acid molecules, fragments of PCIP proteins, and anti-PCIP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a PCIP protein or an anti-PCIP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about Imicrogram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to Form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a PCIP protein of the invention has one or more of the following activities: (1) interaction with (e.g., bind to) a potassium channel protein or portion thereof; (2) regulation of the phosphorylation state of a potassium channel protein or portion thereof; (3) association with (e.g., bind) calcium and can, for example, act as calcium dependent kinases, e.g., phosphorylate a potassium channel or a G-protein coupled receptor in a calcium-dependent manner; (4) modulation of a potassium channel mediated activity in a cell (e.g., a neuronal cell) to, for example, beneficially affect the cell; (5) modulation of chromatin formation in a cell, e.g., a neuronal cell; (6)

modulation of vesicular traffic and protein transport in a cell, e.g., a neuronal cell; (7) modulation of cytokine signaling in a cell, e.g., a neuronal cell; (8) regulation of the association of a potassium channel protein or portion thereof with the cellular cytoskeleton; (9) modulation of cellular proliferation; (10) modulation of the release of neurotransmitters; (11) modulation of membrane excitability; (12) influencing of the resting potential of membranes; (13) modulation of wave forms and frequencies of action potentials; and (14) modulation of thresholds of excitation and, thus, can be used to, for example, (1) modulate the activity of a potassium channel protein or portion thereof; (2) modulate the phosphorylation state of a potassium channel protein or portion thereof; (3) modulate the phosphorylation state of a potassium channel or a G-protein coupled receptor in a calcium-dependent manner; (4) modulate a potassium channel mediated activity in a cell (e.g., a neuronal cell) to, for example, beneficially affect the cell; (5) modulate chromatin formation in a cell, e.g., a neuronal cell; (6) modulate vesicular traffic and protein transport in a cell, e.g., a neuronal cell; (7) modulate cytokine signaling in a cell, e.g., a neuronal cell; (8) regulate the association of a potassium channel protein or portion thereof with the cellular cytoskeleton; (9) modulate cellular proliferation; (10) modulate the release of neurotransmitters; (11) modulate membrane excitability; (12) influence the resting potential of membranes; (13) modulate wave forms and frequencies of action potentials; and (14) modulate thresholds of excitation.

The isolated nucleic acid molecules of the invention can be used, for example, to express PCIP protein (e.g., via a recombinant expression vector in a host cell in gene therapy applications), to detect PCIP mRNA (e.g., in a biological sample) or a genetic alteration in a PCIP gene, and to modulate PCIP activity, as described further below. The PCIP proteins can be used to treat disorders characterized by insufficient or excessive production of a PCIP substrate or production of PCIP inhibitors. In addition, the PCIP proteins can be used to screen for naturally occurring PCIP substrates, to screen for drugs or compounds which modulate PCIP activity, as well as to treat disorders characterized by insufficient or excessive production of PCIP protein or production of PCIP protein forms which have decreased or aberrant activity compared to PCIP wild type protein (e.g., CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; psychiatric disorders, e.g., depression, schizophrenic disorders, Korsakoffs psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma). Moreover, the anti-PCIP antibodies of the invention can be used to detect and isolate PCIP proteins, regulate the bioavailability of PCIP proteins, and modulate PCIP activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to PCIP proteins, have a stimulatory or inhibitory effect on, for example, PCIP expression or PCIP activity, or have a stimulatory or inhibitory effect on, for example, the expression or activity of PCIP substrate.

In one embodiment, the invention provides assays for screening candidate or test compounds which are substrates of a PCIP protein or polypeptide or biologically active portion thereof. In another embodiment, the invention provides assays for screening candidate or test compounds which bind to or modulate the activity of a PCIP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner USP '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a PCIP protein or biologically active portion thereof is contacted with a test compound and the ability of the test compound to modulate PCIP activity, e.g., binding to a potassium channel or a portion thereof, is determined. Determining the ability of the test compound to modulate PCIP activity can be accomplished by monitoring, for example, the release of a neurotransmitter, e.g., dopamine, form a cell which expresses PCIP such as a neuronal cell, e.g., a substantia nigra neuronal cell. The cell, for example, can be of mammalian origin. Determining the ability of the test compound to modulate the ability of PCIP to bind to a substrate can be accomplished, for example, by coupling the PCIP substrate with a radioisotope or enzymatic label such that binding of the PCIP substrate to PCIP can be determined by detecting the labeled PCIP substrate in a complex. For example, compounds (e.g., PCIP substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., PCIP substrate) to interact with PCIP without the labeling of any of the interactants. For example, a microphysiometer can be used to detect the interaction of a compound with PCIP without the labeling of either the compound or the PCIP. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PCIP.

In another embodiment, an assay is a cell-based assay comprising contacting a cell expressing a PCIP target molecule (e.g., a potassium channel or a fragment thereof) with a test compound and determining the ability of the test compound to modulate (e.g. stimulate or inhibit) the activity of the PCIP target molecule. Determining the ability of the test compound to modulate the activity of a PCIP target molecule can be accomplished, for example, by determining the ability of the PCIP protein to bind to or interact with the PCIP target molecule, e.g., a potassium channel or a fragment thereof.

Determining the ability of the PCIP protein or a biologically active fragment thereof, to bind to or interact with a PCIP target molecule can be accomplished by one of the methods described above for determining direct binding. In a preferred embodiment, determining the ability of the PCIP protein to bind to or interact with a PCIP target molecule can be accomplished by determining the activity of the target molecule. For example, the activity of the target molecule can be determined by detecting induction of a cellular second messenger of the target (i.e., intracellular $Ca^2$+, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response such as the release of a neurotransmitter.

In yet another embodiment, an assay of the present invention is a cell-free assay in which a PCIP protein or biologically active portion thereof is contacted with a test compound and the ability of the test compound to bind to the PCIP protein or biologically active portion thereof is determined. Preferred biologically active portions of the PCIP proteins to be used in assays of the present invention include fragments which participate in interactions with non-PCIP molecules, e.g., potassium channels or fragments thereof, or fragments with high surface probability scores. Binding of the test compound to the PCIP protein can be determined either directly or indirectly as described above. In a preferred embodiment, the assay includes contacting the PCIP protein or biologically active portion thereof with a known compound which binds PCIP to form an assay mixture, contacting the assay mixture with a test compound, and determining the ability of the test compound to interact with a PCIP protein, wherein determining the ability of the test compound to interact with a PCIP protein comprises determining the ability of the test compound to preferentially bind to PCIP or biologically active portion thereof as compared to the known compound.

In another embodiment, the assay is a cell-free assay in which a PCIP protein or biologically active portion thereof is contacted with a test compound and the ability of the test compound to modulate (e.g., stimulate or inhibit) the activity of the PCIP protein or biologically active portion thereof is determined. Determining the ability of the test compound to modulate the activity of a PCIP protein can be accomplished, for example, by determining the ability of the PCIP protein to bind to a PCIP target molecule by one of the methods described above for determining direct binding. Determining the ability of the PCIP protein to bind to a PCIP target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PCIP protein can be accomplished by determining the ability of the PCIP protein to further modulate the activity of a downstream effector of a PCIP target molecule. For example, the activity of the effector molecule on an appropriate target can be determined or the binding of the effector to an appropriate target can be determined as previously described.

In yet another embodiment, the cell-free assay involves contacting a PCIP protein or biologically active portion thereof with a known compound which binds the PCIP protein to form an assay mixture, contacting the assay mixture with a test compound, and determining the ability of the test compound to interact with the PCIP protein, wherein determining the ability of the test compound to interact with the PCIP protein comprises determining the ability of the PCIP protein to preferentially bind to or modulate the activity of a PCIP target molecule.

The cell-free assays of the present invention are amenable to use of both soluble and/or membrane-bound forms of isolated proteins. In the case of cell-free assays in which a membrane-bound form of an isolated protein is used (e.g., a potassium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize either PCIP or its target molecule to facilitate separation of complexed from uncomplexed forms of one or both of the proteins, as well as to accommodate automation of the assay. Binding of a test compound to a PCIP protein, or interaction of a PCIP protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/PCIP fusion proteins or glutathione-S-transferase/target fusion proteins can be adsorbed onto glutathione sepharose beads (Sigma Chemical, St. Louis, MO) or glutathione derivatized microtitre plates, which are then combined with the test compound or the test compound and either the non-adsorbed target protein or PCIP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PCIP binding or activity determined using standard techniques.

Other techniques for immobilizing proteins on matrices can also be used in the screening assays of the invention. For example, either a PCIP protein or a PCIP target molecule can be immobilized utilizing conjugation of biotin and streptavidin. Biotinylated PCIP protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PCIP protein or target molecules but which do not interfere with binding of the PCIP protein to its target molecule can be derivatized to the wells of the plate, and unbound target or PCIP protein trapped in the wells by antibody conjugation. Methods for detecting such complexes, in addition to those described above for the GST-immobilized complexes, include immunodetection of complexes using antibodies reactive with the PCIP protein or target molecule, as well as enzyme-linked assays which rely on detecting an enzymatic activity associated with the PCIP protein or target molecule.

In a preferred embodiment, candidate or test compounds or agents are tested for their ability to inhibit or stimulate a PCIP molecule's ability to modulate vesicular traffic and protein transport in a cell, e.g., a neuronal cell, using the assays described in, for example, Komada M. et al. (1999) *Genes Dev*. 13(11):1475–85, and Roth M. G. et al. (1999) *Chem. Phys. Lipids*. 98(1–2):141–52, the contents of which are incorporated herein by reference.

In another preferred embodiment, candidate or test compounds or agents are tested for their ability to inhibit or stimulate a PCIP molecule's ability to regulate the phosphorylation state of a potassium channel protein or portion thereof, using for example, an in vitro kinase assay. Briefly, a PCIP target molecule, e.g., an immunoprecipitated potassium channel from a cell line expressing such a molecule, can be incubated with the PCIP protein and radioactive ATP, e.g., [$\gamma$-$^{32}$P] ATP, in a buffer containing $MgCl_2$ and $MnCl_2$, e.g., 10 mM $MgCl_2$ and 5 mM $MnCl_2$. Following the incubation, the immunoprecipitated PCIP target molecule, e.g., the potassium channel, can be separated by SDS-polyacrylamide gel electrophoresis under reducing conditions, transferred to a membrane, e.g., a PVDF membrane, and autoradiographed. The appearance of detectable bands on the autoradiograph indicates that the PCIP substrate, e.g., the potassium channel, has been phosphorylated. Phosphoaminoacid analysis of the phosphorylated substrate can also be performed in order to determine which residues on the PCIP substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards. Assays such as those described in, for example, Tamaskovic R. et al. (1999) *Biol. Chem*. 380(5):569–78, the contents of which are incorporated herein by reference, can also be used.

In another preferred embodiment, candidate or test compounds or agents are tested for their ability to inhibit or stimulate a PCIP molecule's ability to associate with (e.g., bind) calcium, using for example, the assays described in Liu L. (1999) *Cell Signal*. 11 (5):317–24 and Kawai T. et al. (1999) *Oncogene* 18(23):3471–80, the contents of which are incorporated herein by reference.

In another preferred embodiment, candidate or test compounds or agents are tested for their ability to inhibit or stimulate a PCIP molecule's ability to modulate chromatin formation in a cell, using for example, the assays described in Okuwaki M. et al. (1998) *J. Biol. Chem*. 273(51):34511–8 and Miyaji-Yamaguchi M. (1999) J. Mol. Biol. 290(2): 547–557, the contents of which are incorporated herein by reference.

In yet another preferred embodiment, candidate or test compounds or agents are tested for their ability to inhibit or stimulate a PCIP molecule's ability to modulate cellular proliferation, using for example, the assays described in Baker F. L. et al. (1995) *Cell Prolif*. 28(1):1–15, Cheviron N. et al. (1996) *Cell Prolif*. 29(8):437–46, Hu Z. W. et al. (1999) *J. Pharmacol. Exp. Ther*. 290(1):28–37 and Elliott K. et al. (1999) *Oncogene* 18(24):3564–73, the contents of which are incorporated herein by reference.

In a preferred embodiment, candidate or test compounds or agents are tested for their ability to inhibit or stimulate a PCIP molecule's ability to regulate the association of a potassium channel protein or portion thereof with the cellular cytoskeleton, using for example, the assays described in Gonzalez C. et al. (1998) *Cell Mol. Biol*. 44(7):1117–27 and Chia C. P. et al. (1998) *Exp. Cell Res*. 244(1):340–8, the contents of which are incorporated herein by reference.

In another preferred embodiment, candidate or test compounds or agents are tested or their ability to inhibit or stimulate a PCIP molecule's ability to modulate membrane excitability, using for example, the assays described in Bar-Sagi D. et al. (1985) *J. Biol. Chem*. 260(8):4740–4 and Barker J. L. et al. (1984) *Neurosci. Lett*. 47(3):313–8, the contents of which are incorporated herein by reference.

In another preferred embodiment, candidate or test compounds or agents are tested or their ability to inhibit or stimulate a PCIP molecule's ability to modulate cytokine ignaling in a cell, e.g., a neuronal cell, the assays described in Nakashima Y. et al. (1999) *J. Bone Joint Surg. Am*. 81(5):603–15, the contents of which are incorporated herein by reference.

In another embodiment, modulators of PCIP expression are identified in a method wherein a cell is contacted with a candidate compound and the expression of PCIP mRNA or protein in the cell is determined. The level of expression of PCIP mRNA or protein in the presence of the candidate compound is compared to the level of expression of PCIP mRNA or protein in the absence of the candidate compound. The candidate compound can then be identified as a modulator of PCIP expression based on this comparison. For example, when expression of PCIP mRNA or protein is greater (statistically significantly greater) in the presence of the candidate compound than in its absence, the candidate compound is identified as a stimulator of PCIP mRNA or protein expression. Alternatively, when expression of PCIP mRNA or protein is less (statistically significantly less) in the presence of the candidate compound than in its absence, the candidate compound is identified as an inhibitor of PCIP mRNA or protein expression. The level of PCIP mRNA or protein expression in the cells can be determined by methods described herein for detecting PCIP mRNA or protein.

In yet another aspect of the invention, the PCIP proteins can be used as "bait proteins" in a two-hybrid assay or three-hybrid assay (see, e.g., U.S. Pat. No. 5,283,317; Zervos et al. (1993) *Cell* 72:223–232, Madura et al. (1993) *J. Biol. Chem*. 268:12046–12054; Bartel et al. (1993) *Biotech-*

*niques* 14:920–924; Iwabuchi et al. (1993) *Oncogene* 8:1693–1696; and Brent WO94/10300), to identify other proteins, which bind to or interact with PCIP ("PCIP-binding proteins" or "PCIP-bp") and are involved in PCIP activity (described in more detail in the Examples section below). Such PCIP-binding proteins are also likely to be involved in the propagation of signals by the PCIP proteins or PCIP targets as, for example, downstream elements of a PCIP-mediated signaling pathway. Alternatively, such PCIP-binding proteins are likely to be PCIP inhibitors.

The two-hybrid system is based on the modular nature of most transcription factors, which consist of separable DNA-binding and activation domains. Briefly, the assay utilizes two different DNA constructs. In one construct, the gene that codes for a PCIP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PCIP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PCIP protein.

This invention further pertains to novel agents identified by the above-described screening assays. Accordingly, it is within the scope of this invention to further use an agent identified as described herein in an appropriate animal model. For example, an agent identified as described herein (e.g., a PCIP modulating agent, an antisense PCIP nucleic acid molecule, a PCIP-specific antibody, or a PCIP-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments, e.g., treatments of a CNS disorder, as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the PCIP nucleotide sequences, described herein, can be used to map the location of the PCIP genes on a chromosome. The mapping of the PCIP sequences to chromosomes is an important first step in correlating these sequences with genes associated with disease.

Briefly, PCIP genes can be mapped to chromosomes by preparing PCR primers (preferably 15–25 bp in length) from the PCIP nucleotide sequences. Computer analysis of the PCIP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PCIP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mousecchromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PCIP nucleotide sequences to design oligonucleotide primers, sublocalization can be achieved with panels of fragments from specific chromosomes. Other mapping strategies which can similarly be used to map a PCIP sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the PCIP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The PCIP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PCIP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PCIP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. Non-coding sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from PCIP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial PCIP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the PCIP nucleotide sequences or portions thereof, having a length of at least 20 bases, preferably at least 30 bases.

The PCIP nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such PCIP probes can be used to identify tissue by species and/or by organ type.

In a similar fashion, these reagents, e.g., PCIP primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PCIP protein and/or nucleic acid expression as well as PCIP activity, in the context of a biological sample (e.g., blood, serum, cells, tissue) to thereby determine whether an individual is afflicted with a disease or disorder, or is at risk of developing a disorder, associated with aberrant PCIP expression or activity. The invention also provides for prognostic (or predictive) assays for determining whether an individual is at risk of developing a disorder associated with PCIP protein, nucleic acid expression or activity. For example, mutations in a PCIP gene can be assayed in a biological sample. Such assays can be used for prognostic or predictive purpose to thereby phophylactically treat an individual prior to the onset of a disorder characterized by or associated with PCIP protein, nucleic acid expression or activity.

Another aspect of the invention pertains to monitoring the influence of agents (e.g., drugs, compounds) on the expression or activity of PCIP in clinical trials.

These and other agents are described in further detail in the following sections.

1. Diagnostic Assays

An exemplary method for detecting the presence or absence of PCIP protein or nucleic acid in a biological sample involves obtaining a biological sample from a test subject and contacting the biological sample with a compound or an agent capable of detecting PCIP protein or nucleic acid (e.g., mRNA, genomic DNA) that encodes PCIP protein such that the presence of PCIP protein or nucleic acid is detected in the biological sample. A preferred agent for detecting PCIP mRNA or genomic DNA is a labeled nucleic acid probe capable of hybridizing to PCIP mRNA or genomic DNA. The nucleic acid probe can be, for example, a full-length PCIP nucleic acid, such as the nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, or SEQ ID NO:71, or the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion thereof, such as an oligonucleotide of at least 15, 30, 50, 100, 250 or 500 nucleotides in length and sufficient to specifically hybridize under stringent conditions to PCIP mRNA or genomic DNA. Other suitable probes for use in the diagnostic assays of the invention are described herein.

A preferred agent for detecting PCIP protein is an antibody capable of binding to PCIP protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PCIP mRNA, protein; or geniomic DNA in a biological sample in vitro as well as in vivo. For example, in vitro techniques for detection of PCIP mRNA include Northern hybridizations and in situ hybridizations. In vitro techniques for detection of PCIP protein include enzyme linked immunosorbent assays (ELISAs), Western blots, immunoprecipitations and immunofluorescence. In vitro techniques for detection of PCIP genomic DNA include Southern hybridizations. Furthermore, in vivo techniques for detection of PCIP protein include introducing into a subject a labeled anti-PCIP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting PCIP protein, mRNA, or genomic DNA, such that the presence of PCIP protein, mRNA or genomic DNA is detected in the biological sample, and comparing the presence of PCIP protein, mRNA or genomic DNA in the control sample with the presence of PCIP protein, mRNA or genomic DNA in the test sample.

The invention also encompasses kits for detecting the presence of PCIP in a biological sample. For example, the kit can comprise a labeled compound or agent capable of detecting PCIP protein or mRNA in a biological sample; means for determining the amount of PCIP in the sample; and means for comparing the amount of PCIP in the sample with a standard. The compound or agent can be packaged in a suitable container. The kit can further comprise instructions for using the kit to detect PCIP protein or nucleic acid.

2. Prognostic Assays

The diagnostic methods described herein can furthermore be utilized to identify subjects having or at risk of developing a disease or disorder associated with aberrant PCIP expression or activity. For example, the assays described herein, such as the preceding diagnostic assays or the following assays, can be utilized to identify a subject having or at risk of developing a disorder associated with a misregulation in PCIP protein activity or nucleic acid expression, such as a neurodegenerative disorder, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; a psychiatric disorder, e.g., depression, schizophrenic disorders, Korsakoff s psychosis, mania, anxiety disorders, bipolar affective disorders, or phobic disorders; a learning or memory disorder, e.g., amnesia or age-related memory loss; a neurological disorder, e.g., migraine; a pain disorder, e.g., hyperalgesia or pain associated with muscoloskeletal disorders; spinal cord injury; stroke; and head trauma.

Alternatively, the prognostic assays can be utilized to identify a subject having or at risk for developing a disorder associated with a misregulation in PCIP protein activity or nucleic acid expression, such as a potassium channel associated disorder. Thus, the present invention provides a method for identifying a disease or disorder associated with aberrant PCIP expression or activity in which a test sample is obtained from a subject and PCIP protein or nucleic acid (e.g., mRNA or genomic DNA) is detected, wherein the presence of PCIP protein or nucleic acid is diagnostic for a subject having or at risk of developing a disease or disorder associated with aberrant PCIP expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant PCIP expression or activity. For example, such methods can be used to determine whether a subject can be effectively treated with an agent for a CNS disorder. Thus, the present invention provides methods for determining whether a subject can be effectively treated with an agent for a disorder associated with aberrant PCIP expression or activity in which a test sample is obtained and PCIP protein or nucleic acid expression or activity is detected (e.g., wherein the abundance of PCIP protein or nucleic acid expression or activity is diagnostic for a subject that can be administered the agent to treat a disorder associated with aberrant PCIP expression or activity).

The methods of the invention can also be used to detect genetic alterations in a PCIP gene, thereby determining if a subject with the altered gene is at risk for a disorder characterized by misregulation in PCIP protein activity or nucleic acid expression, such as a CNS disorder. In preferred embodiments, the methods include detecting, in a sample of cells from the subject, the presence or absence of a genetic alteration characterized by at least one of an alteration affecting the integrity of a gene encoding a PCIP-protein, or the mis-expression of the PCIP gene. For example, such genetic alterations can be detected by ascertaining the existence of at least one of 1) a deletion of one or more nucleotides from a PCIP gene; 2) an addition of one or more nucleotides to a PCIP gene; 3) a substitution of one or more nucleotides of a PCIP gene, 4) a chromosomal rearrangement of a PCIP gene; 5) an alteration in the level of a messenger RNA transcript of a PCIP gene, 6) aberrant modification of a PCIP gene, such as of the methylation pattern of the genomic DNA, 7) the presence of a non-wild type splicing pattern of a messenger RNA transcript of a PCIP gene, 8) a non-wild type level of a PCIP-protein, 9) allelic loss of a PCIP gene, and 10) inappropriate post-translational modification of a PCIP-protein. As described herein, there are a large number of assays known in the art which can be used for detecting alterations in a PCIP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the PCIP-gene (see Abravaya et al. (1995) *Nucleic Acids Res*. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a PCIP gene under conditions such that hybridization and amplification of the PCIP-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PCIP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PCIP can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in PCIP can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PCIP gene and detect mutations by comparing the sequence of the sample PCIP with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO94/16101; Cohen et al. (1996) *Adv. Chromatogr*. 36:127–162; and Griffin et al. (1993) *Appl. Biochem. Biotechnol*. 38:147–159).

Other methods for detecting mutations in the PCIP gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type PCIP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then'separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PCIP cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a PCIP sequence, e.g., a wild-type PCIP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in PCIP genes. For example, single strand conformation polymorphism (SSCP) may be used to detect differences in electrophoretic mobility between mutant and wild type nucleic acids (Orita et al. (1989) *Proc. Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control PCIP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PCIP gene.

Furthermore, any cell type or tissue in which PCIP is expressed may be utilized in the prognostic assays described herein.

3. Monitoring of Effects During Clinical Trials

Monitoring the influence of agents (e.g., drugs) on the expression or activity of a PCIP protein (e.g., the modulation of membrane excitability or resting potential) can be applied not only in basic drug screening, but also in clinical trials. For example, the effectiveness of an agent determined by a screening assay as described herein to increase PCIP gene expression, protein levels, or upregulate PCIP activity, can be monitored in clinical trials of subjects exhibiting decreased PCIP gene expression, protein levels, or downregulated PCIP activity. Alternatively, the effectiveness of an agent determined by a screening assay to decrease PCIP gene expression, protein levels, or downregulate PCIP activity, can be monitored in clinical trials of subjects exhibiting increased PCIP gene expression, protein levels, or upregulated PCIP activity. In such clinical trials, the expression or activity of a PCIP gene, and preferably, other genes that have been implicated in, for example, a potassium channel associated disorder can be used as a "read out" or markers of the phenotype of a particular cell.

For example, and not by way of limitation, genes, including PCIP, that are modulated in cells by treatment with an agent (e.g., compound, drug or small molecule) which modulates PCIP activity (e.g., identified in a screening assay as described herein) can be identified. Thus, to study the effect of agents on potassium channel associated disorders, for example, in a clinical trial, cells can be isolated and RNA prepared and analyzed for the levels of expression of PCIP and other genes implicated in the potassium channel associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of PCIP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a PCIP protein, mRNA, or genomic DNA in the preadministration sample; (iii) obtaining one or more post-administration samples from the subject; (iv) detecting the level of expression or activity of the PCIP protein, mRNA, or genomic DNA in the post-administration samples; (v) comparing the level of expression or activity of the PCIP protein, mRNA, or genomic DNA in the pre-administration sample with the PCIP protein, mRNA, or genomic DNA in the post administration sample or samples; and (vi) altering the administration of the agent to the subject accordingly. For example, increased administration of the agent may be desirable to increase the expression or activity of PCIP to higher levels than detected, i.e., to increase the effectiveness of the agent. Alternatively, decreased administration of the agent may be desirable to decrease expression or activity of PCIP to lower levels than detected, i.e. to decrease the effectiveness of the agent. According to such an embodiment, PCIP expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant PCIP expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the PCIP molecules of the present invention or PCIP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant PCIP expression or activity, by administering to the subject a PCIP or an agent which modulates PCIP expression or at least one PCIP activity. Subjects at risk for a disease which is caused or contributed to by aberrant PCIP expression or activity can be identified by, for example, any or a combination of diagnostic or prognostic assays as described herein. Administration of a prophylactic agent can occur prior to the manifestation of symptoms characteristic of the PCIP aberrancy, such that a disease or disorder is prevented or, alternatively, delayed in its progression. Depending on the type of PCIP aberrancy, for example, a PCIP, PCIP agonist or PCIP antagonist agent can be used for treating the subject. The appropriate agent can be determined based on screening assays described herein.

2. Therapeutic Methods

Another aspect of the invention pertains to methods of modulating PCIP expression or activity for therapeutic purposes. Accordingly, in an exemplary embodiment, the modulatory method of the invention involves contacting a cell with a PCIP or agent that modulates one or more of the activities of PCIP protein activity associated with the cell. An agent that modulates PCIP protein activity can be an agent as described herein, such as a nucleic acid or a protein, a naturally-occurring target molecule of a PCIP protein (e.g., a PCIP substrate), a PCIP antibody, a PCIP agonist or antagonist, a peptidomimetic of a PCIP agonist or antagonist, or other small molecule. In one embodiment, the agent stimulates one or more PCIP activities. Examples of such stimulatory agents include active PCIP protein and a nucleic acid molecule encoding PCIP that has been introduced into the cell. In another embodiment, the agent inhibits one or more PCIP activities. Examples of such inhibitory agents include antisense PCIP nucleic acid molecules, anti-PCIP antibodies, and PCIP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a PCIP protein or nucleic acid molecule. Examples of such disorders include CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, Korsakoff's psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma. In one embodiment, the method involves administering an agent (e.g., an agent identified by a screening assay described herein), or combination of agents that modulates (e.g., upregulates or downregulates) PCIP expression or activity. In another embodiment, the method involves administering a PCIP protein or nucleic acid molecule as therapy to compensate for reduced or aberrant PCIP expression or activity.

A preferred embodiment of the present invention involves a method for treatment of a PCIP associated disease or disorder which includes the step of administering a therapeutically effective amount of a PCIP antibody to a subject. As defined herein, a therapeutically effective amount of antibody (i. e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Stimulation of PCIP activity is desirable in situations in which PCIP is abnormally downregulated and/or in which increased PCIP activity is likely to have a beneficial effect. For example, stimulation of PCIP activity is desirable in situations in which a PCIP is downregulated and/or in which increased PCIP activity is likely to have a beneficial effect. Likewise, inhibition of PCIP activity is desirable in situations in which PCIP is abnormally upregulated and/or in which decreased PCIP activity is likely to have a beneficial effect.

3. Pharmacogenomics

The PCIP molecules of the present invention, as well as agents, or modulators which have a stimulatory or inhibitory effect on PCIP activity (e.g., PCIP gene expression) as identified by a screening assay described herein can be administered to individuals to treat (prophylactically or therapeutically) potassium channel associated disorders associated with aberrant PCIP activity (e.g, CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, Korsakoff s psychosis, mania, anxiety disorders, bipolar affective disorders, or phobic disorders; learning or memory disorders, e.g., amnesia or age-related memory loss, neurological disorders, e.g., migraine; pain disorders, e.g., hyperalgesia or pain associated with muscoloskeletal disorders; spinal cord injury; stroke; and head trauma). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a PCIP molecule or PCIP modulator as well as tailoring the dosage and/or therapeutic regimen of treatment with a PCIP molecule or PCIP modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a PCIP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a PCIP molecule or PCIP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a PCIP molecule or PCIP modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing are incorporated herein by reference.

EXAMPLES

The following materials and methods were used in the Examples.

Strains, Plasmids, Bait cDNAs, and General Microbiological Techniques

Basic yeast strains (HF7c, Y187,) bait (pGBT9) and fish (pACT2) plasmids used in this work were purchased from Clontech (Palo Alto, Calif.). cDNAs encoding rat Kv4.3, Kv4.2, and Kv1.1, were provided by Wyeth-Ayerst Research (865 Ridge Rd., Monmouth Junction, N.J. 08852) Standard yeast media including synthetic complete medium lacking L-leucine, L-tryptophan, and L-histidine were prepared and yeast genetic manipulations were performed as described (Sherman (1991) *Meth. Enzymol.* 194:3–21). Yeast transformations were performed using standard protocols (Gietz et al. (1992) *Nucleic Acids Res.* 20:1425; Ito et al (1983) *J. Bacteriol.* 153:163–168). Plasmid DNAs were isolated from yeast strains by a standard method (Hoffman and Winston (1987) *Gene* 57:267–272).

Bait and Yeast Strain Construction

The first 180 amino acids of rKv4.3 (described in Serdio P. et al. (1996) *J. Neurophys* 75:2174–2179) were amplified by PCR and cloned in frame into pGBT9 resulting in plasmid pFWA2, (hereinafter "bait"). This bait was transformed into the two-hybrid screening strain HF7c and tested for expression and self-activation. The bait was validated for expression by Western blotting. The rKv4.3 bait did not self-activate in the presence of 10 mM 3-amino-1,2,3-Triazole (3-AT).

Library Construction

Rat mid brain tissue was provided by Wyeth-Ayerst Research (Monmouth Junction, N.J.). Total cellular RNA was extracted from the tissues using standard techniques (Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., (1989)). mRNA was prepared using a Poly-A Spin mRNA Isolation Kit from New England Biolabs (Beverly, Mass.). cDNA from the mRNA sample was synthesized using a cDNA Synthesis Kit from Stratagene (La Jolla, Calif.) and ligated into pACT2's EcoRI and XhoI sites, giving rise to a two-hybrid library.

Two-Hybrid Screening

Two-hybrid screens were carried out essentially as described in Bartel, P. et al. (1993) "Using the Two-Hybrid System to Detect Polypeptide-Polypeptide Interactions" in Cellular Interactions in Development: A Practical Approach, Hartley, D. A. ed. Oxford University Press, Oxford, pp. 153–179, with a bait-library pair of rkv4.3 bait-rat mid brain library. A filter disk beta-galactosidase (beta-gal) assay was performed essentially as previously described (Brill et al. (1994) *Mol. Biol. Cell.* 5:297–312). Clones that were positive for both reporter gene activity (His and beta-galactosidase) were scored and fish, plasmids were isolated from yeast, transformed into *E. coli* strain KC8, DNA plasmids were purified and the resulting plasmids were sequenced by conventional methods (Sanger F. et al. (1977) PNAS, 74: 5463–67).

Specificity Test

Positive interactor clones were subjected to a binding specificity test where they were exposed to a panel of related and unrelated baits by a mating scheme previously described (Finley R. L. Jr. et al. (1994) *PNAS*, 91(26):12980–12984). Briefly, positive fish plasmids were transformed into Y187 and the panel of baits were transformed into HF7c. Transformed fish and bait cells were streaked out as stripes on selective medium plates, mated on YPAD plates, and tested for reporter gene activity.

Analysis

PCIP nuleotides were analyzed for nucleic acid hits by the BLASTN 1.4.8MP program (Altschul et al. (1990) Basic Local Alignment Search Tool. *J. Mol. Biol.* 215: 403–410). PCIP proteins were analyzed for polypeptide hits by the BLASTP 1.4.9MP program.

Example 1

Identification of Rat PCIP cDNAs

The Kv4.3 gene coding sequence (coding for the first 180 amino acids) was amplified by PCR and cloned into pGBT9 creating a GAL4 DNA-binding domain-Kv4.3(1–180) gene fusion (plasmid pFWA2). HF7c was transformed with this construct. The resulting strain grew on synthetic complete medium lacking L-tryptophan but not on synthetic complete medium lacking L-tryptophan and L-histidine in the presence of 10 mM 3-AT demonstrating that the {GAL4 DNA-binding domain}-{vKv4.3(1–180)} gene fusion does not have intrinsic transcriptional activation activity higher than the threshhold allowed by 10 mM 3-AT.

In this example, a yeast two-hybrid assay was performed in which a plasmid containing a {GAL4 DNA-binding domain}-{rKv4.3(1–180)} gene fusion was introduced into the yeast two-hybrid screening strain HF7c described above. HF7c was then transformed with the rat mid brain two-hybrid library. Approximately six million transformants were obtained and plated in selection medium. Colonies that grew in the selection medium and expressed the beta-galactosidase reporter gene were further characterized and subjected to retransformation and specificity assays. The retransformation and specificity tests yielded three PCIP clones (rat 1v, 8t, and 9qm) that were able to bind to the Kv4.3 polypeptide.

The full length sequences for the rat 1v gene, and partial sequences for 8t and 9q genes were derived as follows. The partial rat PCIP sequences were used to prepare probes, which were then used to screen, for example, rat mid brain cDNA libraries. Positive clones were identified, amplified and sequenced using standard techniques, to obtain the full length sequence. Additionally, a rapid amplification of the existing rat PCIP cDNA ends (using for example, 5' RACE, by Gibco, BRL) was used to complete the 5' end of the transcript.

Example 2

Identification of Human 1v cDNA

To obtain the human 1v nucleic acid molecule, a cDNA library made from a human hippocampus (Clontech, Palo Alto, Calif.) was screened under low stringency conditions as follows: Prehybridization for 4 hours at 42° C. in Clontech Express Hyb solution, followed by overnight hybridization at 42° C. The probe used was a PCR-generated fragment including nucletides 49–711 of the rat sequence labeled with $^{32}$p dCTP. The filters were washed 6 times in 2XSSC/0.1% SDS at 55° C. The same conditions were used for secondary screening of the positive isolates. Clones thus obtained were sequenced using an ABI automated DNA Sequencing system, and compared to the rat sequences shown in SEQ ID NO:3 as well as to known sequences from the GenBank database. The largest clone from the library screen was subsequently subcloned into pBS-KS+ (Stratagene, La Jolla, Calif.) for sequence verification. The 515 base pair clone was determined to represent the human homolog of the 1v gene, encompasing 211 base pairs of 5' UTR and a 304 base pair coding region. To generate the full-length cDNA, 3' RACE was used according to the manufacturers instructions (Clontech Advantage PCR kit).

Example 3

Isolation and Characterization of 1v Splice Variants

The mouse 1v shown in SEQ ID NO:5 and the rat 1vl splice variant shown in SEQ ID NO:7 was isolated using a two-hybrid assay as described in Example 1. The mouse 1vl splice variant shown in SEQ ID NO: 7 was isolated by screening a mouse brain cDNA library, and the rat 1vn splice variant shown in SEQ ID NO:11 was isolated by BLAST searching.

Example 4

Isolation and Identification of 9q and Other PCIPs

Rat 9ql (SEQ ID NO: 15) was isolated by database mining, rat 9qm (SEQ ID NO: 21) was isolated by a two-hybrid assay, and rat 9qc (SEQ ID NO:27) was identified by database mining. Human 9ql (SEQ ID NO: 13), and human 9qs (SEQ ID NO:23) were identified as described in Example 2. Mouse 9ql (SEQ ID NO:17), monkey 9qs (SEQ ID NO:25), human p193 (SEQ ID NO:39), rat p19 (SEQ ID NO:33), and mouse p19 (SEQ ID NO:35) were identified by database mining. Rat 8t (SEQ ID NO:29) was identified using a two-hybrid assay. The sequence of W28559 (SEQ ID NO:37) was identified by database mining and sequencing of the identified EST with Genbank Accession Number A1352454. The protein sequence was found to contain a 41 amino acid region with strong homology to 1v, 9ql, and p19 (see alignment in FIG. 25). However, downstream of this homologous region the sequence diverges from that of the PCIP family. This sequence could represent a gene which possesses a 41 amino acid domain with homology to a similar domain found in the PCIP family members.

The human genomic 9q sequence (SEQ ID NOs:46 and 47) was isolated by screening a BAC genomic DNA library (Reasearch Genetics) using primers which were designed based on the sequence of the human 9qm cDNA. Two positive clones were identified (44802 and 721117) and sequenced.

Example 5

Expression of 1v, 8t, and 9q mRNA in Rat Tissues

Rat and mouse multiple tissue Northern blots (Clontech) were probed with a [$^{32}$P]-labeled cDNA probe directed at the 5'-untranslated and 5'- coding region of the rat 1v sequence (nucleotides 35–124; SEQ ID NO:3) (this probe is specific for rat 1v and rat 1vl), the 5' coding region of the 8t sequence (nucleotides 1–88; SEQ ID NO:29) (this probe is specific for 8t), or the 5' end of the rat 9qm sequence (nucleotides 1–195; SEQ ID NO:21) (this probe is specific for all 9q isoforms, besides 8t). Blots were hybridize using standard techniques. Northern blots hybridized with the rat 1v probe revealed a single band at 2.3 kb only in the lane containing brain RNA, suggesting that 1v expression is brain specific. Northern blots probed with the rat 8t probe revealed a major band at 2.4 kb. The rat 8t band was most intense in the lane containing heart RNA and there was also a weaker band in the lane containing brain RNA. Northern blots hybridized with the 9q cDNA probe revealed a major band at 2.5 kb and a minor band at over 4 kb with predominant expression in brain and heart. The minor band may represent incompletely spliced or processed 9q mRNA. The results from the northern blots further indicated that p19 is expressed predominantly in the heart.

Example 6

Expression of 1v, 8t, and 9q in Brain

Expression of the rat 1v and 8t/9q genes in the brain was examined by in situ hybridization histochemistry (ISHH) using [$^{35}$S]-labeled cRNA probes and a hybridization procedure identical to that described in Rhodes et al. (1996) J. Neurosci., 16:4846–4860. Templates for preparing the cRNA probes were generated by standard PCR methods. Briefly, oligonucleotide primers were designed to amplify a fragment of 3'- or 5'-untranslated region of the target cDNA and in addition, add the promoter recognition sequences for T7 and T3 polymerase. Thus, to generate a 300 nucleotide probe directed at the 3'-untranslated region of the 1v mRNA, we used the following primers:

5-TAATACGACTCACTATAGGGACTGGCCATCCT GCTCTCAG-3 (T 7, forward, sense; SEQ ID NO:42)

5-ATTAACCCTCACTAAAGGGACACTACTGTTTA AGCTCAAG-3 (T 3, reverse, antisense; SEQ ID NO:43). The underlined bases correspond to the T7 and T3 promoter sequences. To generate a probe directed at a 325 bp region of 3'-untranslated sequence shared by the 8t and 9q mRNAs, the following primers were used:

5-TAATACGACTCACTATAGGGCACCTCCCCTCC GGCTGTTC-3 (T 7, forward, sense; SEQ ID NO:44)

5-ATTAACCCTCACTAAAGGGAGAGCAGCAGC ATGGCAGGGT-3 (T 3, reverse, antisense; SEQ ID NO:45).

Autoradiograms of rat brain tissue sections processed for ISHH localization of 1v or 8t/9q mRNA expression revealed that 1v mRNA is expressed widely in brain in a pattern consistent with labeling of neurons as opposed to glial or endothelial cells. 1v mRNA is highly expressed in cortical, hippocampal, and striatal interneurons, the reticlar nucleus of the thalamus, the medial habenula, and in cerebellar granule cells. 1v mRNA is expressed at moderate levels in midbrain nuclei including the substantia nigra and superior colliculus, in several other thalamic nuclei, and in the medial septal and diagonal band nuclei of the basal forebrain.

Because the probe used to analyze the expression of 8t and 9q hybridizes to a region of the 3-untranslated region that is identical in the 8t and 9q mRNAs, this probe generates a composite image that reveals that 8t/9q mRNA is expressed widely in brain in a pattern that partly overlaps with that for 1v as described above. However, 8t/9q mRNA is highly expressed in the striatum, hippocampal formation, cerebellar granule cells, and neocortex. 8t/9q mRNA is expressed at moderate levels in the midbrain, thalamus, and brainstem. In may of these areas, 8t/9q mRNA appears to be concentrated in interneurons in addition to principal cells, and in all regions 8t/9q expression appears to be concentrated in neurons as apposed to glial cells.

Single- and double-label immunohistochemistry revealed that the PCIP and Kv4 polypeptides are precisely colocalized in many of the cell types and brain regions where PCIP and Kv4 mRNAs are coexpressed. For example, 9qm colocalized with Kv4.2 in the somata and dendrites of hippocampal granule and pyramidal cells, neurons in the medial habenular nucleus and in cerebellar basket cells, while 1v colocalized with Kv4.3 in layer II neurons of posterior cingulate cortex, hippocampal interneurons, and in a subset of cerebellar granule cells. Immunoprecipitation analyses indicated that 1v and 9qm are coassociated with Kv4 α-subunits in rat brain membranes.

Example 7

Co-association 1v and Kv4.3 in COS Cells

COS1 cells were transiently transfected with rat Kv4.3 alone, rat Kv4.3 +rat 1v, and rat 1v alone using the lipofectamine plus procedure essentially as described by the manufacturer (Boehringer Mannheim). Forty-eight hours after the transfection, cells were washed, fixed, and processed for immunofluorescent visualization as described previously (Bekele-Arcuri et al. (1996) Neuropharmacology, 35:851–865). Affinity-purified rabbit polyclonal or mouse monoclonal antibodies to the Kv4.3 or rat 1v protein were used for immunofluorescent detection of the target proteins. Cells transfected with 1v alone and stained with 1v-specific revealed that 1v is diffusely distributed throughout the cytoplasm of transiently transfected cells, as expected for a cytoplasmic protein. Cells transiently transfected with Kv4.3 alone and stained with antibodies specific for Kv4.3 revealed that although much of the expressed channel protein is trapped within intracellular organelles, Kv4.3 expression is also concentrated at the outer margins of the cell and is presumed to be associated with the cell membrane. When the 1v protein is coexpressed with Kv4.3 in COS1 cells, the subcellular distribution of 1v is dramatically different than it is in cells transfected with 1v alone. In cells cotransfected with 1v and Kv4.3, 1v protein expression appears to be trapped in intracellular organelles and becomes concentrated at the outer margins of the cell. Double-label immunofluorescence of these co-transfected cells indicates that the pattern of 1v immunofluorecence is identical that for Kv4.3, indicating that these two proteins are extensively colocalized in cotransfected cells. Moreover, the extensive and dramatic change in the subcellular distribution of 1v when it is coexpressed with Kv4.3 suggests that the proteins coassociate when they are coexpressed.

To further demonstrate that 1v and Kv4.3 directly associate in cotransfected cells, COS1 cells were cotransfected with 1v and Kv4.3 cDNAs as described above. The cells were then lysed in buffer containing detergent and protease inhibitors, and prepared for immunoprecipitation reactions essentially as described previously (Nakahira et al. (1996) J. Biol. Chem., 271:7084–7089). Antibodies specific for 1v or Kv4.3 were used to immunoprecipitate the corresponding polypeptide from the transfected cell lysates essentially as described in Nakahira et al. (1996) J. Biol. Chem., 271:7084–7089 and in Harlow E. and Lane, D., Antibodies:A Laboratory Manual, Cold Spring Harbor Laboratory, c1988. The products resulting from the immunoprecipitation were size fractionated by SDS-PAGE and transferred to nitrocellulose filters using standard procedures. Immunoblots performed using Kv4.3-specific antibodies revealed that 1v co-immunoprecipitates Kv4.3 from lysates prepared from co-transfected cells, indicating that the two proteins are tightly co-associated. Taken together, these data suggest that 1v may promote the transit of the Kv4.3 subunits to the cell surface, and that this chaperone-like effect may underlie the enhancement of Kv4 current density by 1v.

Example 8

Electrophysiological Characterization of PCIPs

Currents flowing through rKv4.2 were measured electrophysiologically after transiently transfecting the channels (with or without rat 1v) in CHO cells or microinjecting in vitro transcribed mRNA into Xenopus oocytes. Currents in CHO cells were measured using the patch-clamp technique (Hamill et al. 1981. Pfluegers Arch. 391: 85–100), while currents in oocytes were measured with two-electrode voltage clamp. CHO cells were transiently-transfected with cDNA using the DOTAP lipofection method as described by the manufacturer. (Boehringer Mannheim, Inc.). Transfected cells were identified by cotransfecting enhanced GFP along with the genes of interest and subsequently determining if the cells contained green GFP fluorescence. Alternatively, oocytes were injected with 1–3 ng/oocyte cRNA which was prepared using standard in vitro transcription techniques (Sambrook et al. 1989. Molecular Cloning: a laboratory manual, Cold Spring Harbor Press). When CHO cells were transfected with 1 μg rKv4.2 cDNA, current levels averaged about 539 pA/cell, or 23.1 pA/pF (Table 2). When 1v was coexpressed with rKv4.2, however, the current amplitude increased by 8.5 fold to an average of 3076 pA/cell or 197.2 pA/pF (see below).

TABLE 2

| | CHO | | Oocytes | | Oocytes | |
|---|---|---|---|---|---|---|
| Parameter | rKv4.2 | rKv4.2 + 1v | hKv4.3 | hKv4.3 + 1v | hKv1.4 | hKv1.4 + 1v |
| Peak Current (pA/cell) | 538.8 | 3076.3 | 7.7 A | 18.1 A | 8.3 A | 6.5 A |
| Peak Current (pA/pF) | 23.1 | 197.2 | — | — | — | — |
| Inactivation time constant (ms, at 40 mV) | 20.4 | 90.9 | 58.5 | 137.0 | 52.3 | 57.8 |
| Recovery from Inactivation time constant (ms, at −80 mV) | 247.3 | 39.7 | 327.0 | 34.5 | 132.6, 666.8 | 210.7, 821.9 |
| Activation $V_{1/2}$ (mV) | 13.1 | −15.9 | −19.2 | −45.5 | −21.0 | −13.5 |
| Steady-state Inactivation $V_{1/2}$ (mV) | −54.1 | −59.7 | −57.4 | −56.8 | −47.5 | −48.1 |

Coexpression of 1v also caused a number of changes in other kinetic parameters of the rKv4.2 current. The voltage at which half of the channels are activated is a measure of the voltage dependence of the channels. This half activation voltage for rKv4.2 was relatively high at 13 mV. Coexpression of 1v with rKv4.2 shifted the half activation voltage by 29 mV to the more negative potential of −16 mV (Table 2). The voltage at which channels inactivate during a long (1 second) pulse only shifted slightly from −54 to −60 mV with 1v coexpression.

The modulatory effects observed with 1v coexpression were not limited to the rKv4.2 channel or to CHO cells. A similar modulation by 1v of hKv4.3 expressed in Xenopus oocytes has also been observed (see Table 2). Co-injection of 1v into oocytes induced an increase in hKv4.3 current, a slowing of inactivation, a speeding of the recovery from inactivation, and a leftward shift in the activation curve. The effects of 1v, however, did not translate to all inactivating channel types, as the inactivating hKv1.4 channel was not effected by coinjection of 1v mRNA into oocytes (Table 2).

Co-expression of 1v or 9qm with Kv4 α-subunits in CHO cells or Xenopus oocytes revealed that the corresponding polypeptides co-associate with Kv4 subunits and dramatically modulate the current density, rate of inactivation and rate of recovery from inactivation of Kv4 channels.

Figure 38:
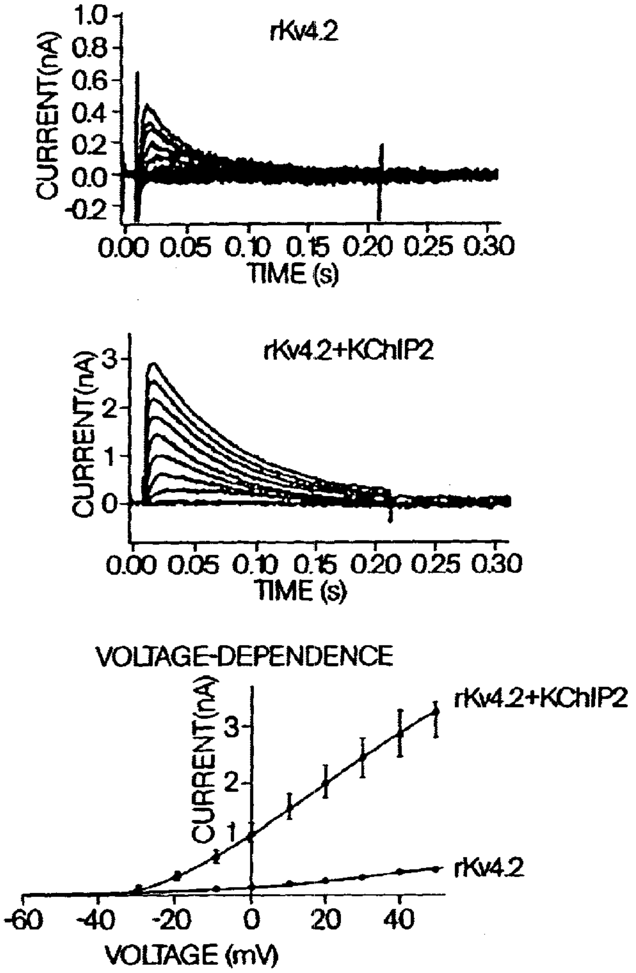
FIG. 38 depicts a graph showing the current traces from CHO cells which express Kv4.2 with or without KChIP2 (9ql). Cells are voltage clamped at −80 mV and stepped from −60 mV to +50 mV for 200 ms. Peak current amplitudes at the various test voltages are shown in the right panel.
Figure 39:
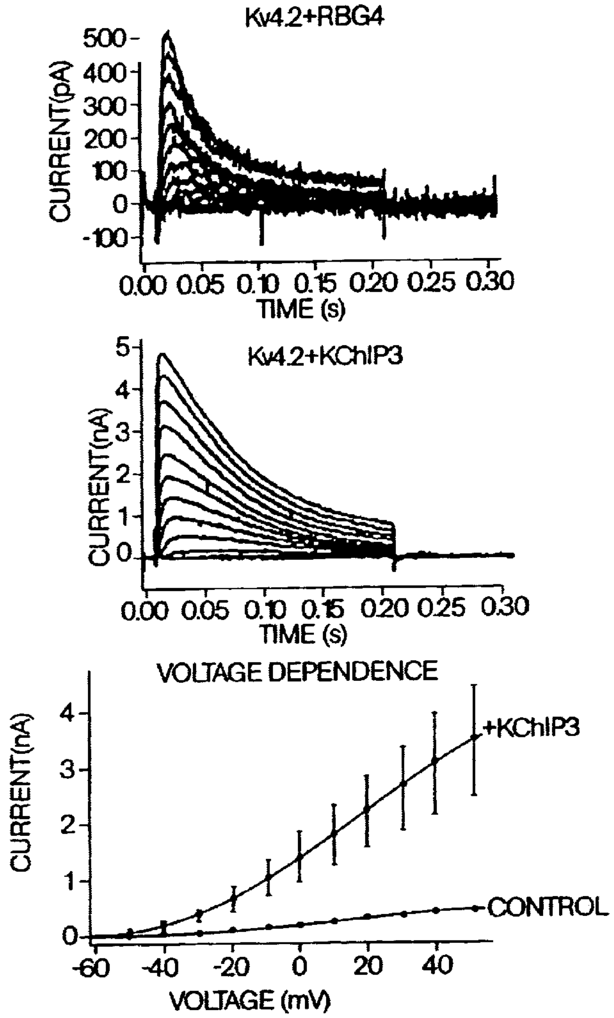
FIG. 39 depicts a graph showing the current traces from CHO cells which express Kv4.2 with or without KChIP3 (p19). Cells are voltage clamped at −80 mV and stepped from −60 mV to +50 mV for 200 ms. Peak current amplitudes at the various test voltages are shown in the right panel.

Co-expression of Kv4.3 with 9q or p19 also gives rise to a current that is almost identical to the native current $I_{to}$ (see FIGS. 38 and 39).

Deletion of the N-terminus of the two PCIP proteins 1v and 9qm (the first 31 amino acids were deleted from 1v and the first 67 amino acids were deleted from 9qm) did not alter their modulatory actions on Kv4.2 current amplitude and kinetics when co-expressed in CHO cells. Thus, the variable N-terminus of these genes is not responsible for their modulatory actions on Kv4 channels. Point mutations were then constructed in the EF-hand domains of the 1v gene to remove its putative ability to bind calcium. Two different mutants were created: one has point mutations in the first two EF hands ($D_{199}$ to A, $G_{104}$ to A, $D_{135}$ to A, and $G_{140}$ to A) and the other one has point muations in all three EF hands ($D_{199}$ to A, $G_{104}$ to A, $D_{135}$ to A, $G_{140}$ to A, $D_{183}$ to A, and $G_{188}$ to A). These mutations had a large effect on the modulatory function of this gene; co-expression with Kv4.2 produced a much smaller increase in current than the wild type 1v and very little effect on the other kinetic parameters of the channel. Thus, the EF-hand, or putative $Ca^{2+}$ binding domains, of 1v appear to have a critical role in the modulatory actions of the PCIP genes.

Example 9

Characterization of the PCIP Proteins

In this example, the amino acid sequences of the PCIP proteins were compared to amino acid sequences of known proteins and various motifs were identified.

The 1v polypeptide, the amino acid sequence of which is shown in SEQ ID NO:3 is a novel polypeptide which includes 216 amino acid residues. Domains that are putatively involved in calcium binding (Linse, S. and Forsen, S. (1995) *Advances in Second Messenger and Phosphoprotein Research* 30, Chapter 3, p89–151, edited by Means, A R., Raven Press, Ltd., New York), were identified by sequence alignment (see FIG. 21).

The 8t polypeptide, the amino acid sequence of which is shown in SEQ ID NO:30 is a novel polypeptide which includes 225 amino acid residues. Calcium binding domains that are putatively involved in calcium binding (Linse, S. and Forsen, S. (1995) *Advances in Second Messenger and Phosphoprotein Research* 30, Chapter 3, p89–151, edited by Means, A R., Raven Press, Ltd., New York), were identified by sequence alignment (see FIG. 21).

The 9q polypeptide is a novel polypeptide which includes calcium binding domains that are putatively involved in calcium binding (Linse, S. and Forsen, S. (1995) *Advances in Second Messenger and Phosphoprotein Research* 30, Chapter 3, p89–151, edited by Means, A R., Raven Press, Ltd., New York (see FIG. 21).

The p19 polypeptide is a novel polypeptide which includes calcium binding domains that are putatively involved in calcium binding (Linse, S. and Forsen, S. (1995) *Advances in Second Messenger and Phosphoprotein Research* 30, Chapter 3, p89–15 1, edited by Means, A R., Raven Press, Ltd., New York (see FIG. 21).

A BLASTN 2.0.7 search (Altschul et al. (1990) *J. Mol. Biol.* 215:403) of the nucleotide sequence of rat 1vl revealed that the rat 1vl is similar to the rat cDNA clone RMUAH89 (Accession Number AA849706). The rat 1vl nucleic acid molecule is 98% identical to the rat cDNA clone RMUAH89 (Accession Number AA849706) over nucleotides 1063 to 1488.

A BLASTN 2.0.7 search (Altschul et al. (1990) *J. Mol. Biol.* 215:403) of the nucleotide sequence of human 9ql revealed that the human 9ql is similar to the human cDNA clone 1309405 (Accession Number AA757119). The human 9ql nucleic acid molecule is 98% identical to the human cDNA clone 1309405 (Accession Number AA757119) over nucleotides 937 to 1405.

A BLASTN 2.0.7 search (Altschul et al. (1990) *J. Mol. Biol.* 215:403) of the nucleotide sequence of mouse P19 revealed that the mouse P19 is similar to the Mus musculus cDNA clone MNCb-7005 (Accession Number AU035979). The mouse P19 nucleic acid molecule is 98% identical to the Mus musculus cDNA clone MNCb-7005 (Accession Number AU035979) over nucleotides 1 to 583.

Example 10

Expression of Recombinant PCIP Proteins in Bacterial Cells

In this example, PCIP is expressed as a recombinant glutathione-S-transferase (GST) fusion polypeptide in *E.*

*coli* and the fusion polypeptide is isolated and characterized. Specifically, PCIP is fused to GST and this fusion polypeptide is expressed in *E. coli*, e.g., strain B121. Expression of the GST-PCIP fusion protein in B121 is induced with IPTG. The recombinant fusion polypeptide is purified from crude bacterial lysates of the induced B121 strain by affinity chromatography on glutathione beads. Using polyacrylamide gel electrophoretic analysis of the polypeptide purified from the bacterial lysates, the molecular weight of the resultant fusion polypeptide is determined.

Rat 1v and 9ql were cloned into pGEX-6p-2 (Pharmacia). The resulting recombinant fusion proteins were expressed in *E. coli* cells and purified following art known methods (described in, for example, *Current Protocols in Molecular Biology*, eds. Ausubel et al. John Wiley & Sons: 1992). The identities of the purified proteins were verified by western blot analysis using antibodies raised against peptide epitopes of rat 1v and 9ql.

Example 11

Expression of Recombinant PCIP Proyeins in COS Cells

To express the PCIP gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire PCIP protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the PCIP DNA sequence is amplified by PCR using two primers. The 5' primer contains the restriction site of interest followed by approximately twenty nucleotides of the PCIP coding sequence starting from the initiation codon; the 3' end sequence contains complementary sequences to the other restriction site of interest, a translation stop codon, the HA tag or FLAG tag and the last 20 nucleotides of the PCIP coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the PCIP gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the PCIP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989. The expression of the PCIP polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the PCIP coding sequence is cloned directly into the polylinker of the pCDNA/Amp vector using the appropriate restriction sites. The resulting plasmid is transfected into COS cells in the manner described above, and the expression of the PCIP polypeptide is detected by radiolabelling and immunoprecipitation using a PCIP specific monoclonal antibody.

Rat 1v was cloned into the mammalian expresssion vector pRBG4. Transfections into COS cells were performed using LipofectAmine Plus (Gibco BRL) following the manufacturer's instructions. The expressed 1v protein was detected by immunocytochemistry and/or western blot analysis using antibodies raised against 1v in rabbits or mice.

Example 12

Identification and Characterization of Human Full Length p19

The human full length p19 sequence was identified using RACE PCR. The sequence of p19 (also referred to as KChIP3) is shown in FIG. 16. The amino acid sequence of human p19 is 92% identical to the mouse p19 gene (SEQ ID NO:35).

TBLASTN searches using the protein sequence of human p19 revealed that human p19 is homologous to two sequences, Calsenilin (described in (1998) *Nature Medicine* 4: 1177–1181) and DREAM (described in Carrion et al. (1999) *Nature* 398: 80–84). Human p19 is 100% identical at the nucleotide level to Calsenilin (but extends 3' to the published sequence) and 99% identical at the nucleotide level to DREAM.

The ability of p19 (as well as other PCIP family members) to co-localize with presenilin and act as transcription factors is determined using art known techniques such as northern blots, in situ hybridization, β-gal assays, DNA mobility assays (described in, for example, Carrion et al. (1999) *Nature* 398:80) and DNA mobility supershift assays, using antibodies specific for KchIPs.

Other assays suitable for evaluating the association of PCIP family members with presenilins is co-immunoprecipitation (described in, for example, Buxbaum et al. (1998) *Nature Medicine* 4:1177).

Example 13

Identification and Characterization of Monkey KChIP4

In this example, the identification and characterization of the genes encoding monkey KChIP4a Olkbd352e01tl) and alternatively spliced monkey KChIP4b (jlkbb231c04tl), KChIP4c (jlkxa053c02), and KChIP4d (jlkx015b10) is described. TBLASTN searches in proprietary databases with the sequence of the known PCIP family members, lead to the identification of four clones jlkbb231c04tl, jlkbd352e01tl, jlkxa053c02, and jlkx015b10. The four monkey clones were obtained and sequenced.

The sequences of proprietary monkey clones jlkbb231c04tl and jlkbd352e01tl were found to correspond to alternately spliced variants of an additional PCIP family member, referred to herein as KChIP4. Clone jlkbb231c04tl contains a 822bp deletion relative to jlkbd352e01tl (presumably due to splicing out of an exon), resulting in the loss of the final EF hand domain. In clone jlkbd352e01tl, the final EF hand domain is preserved, and the C-terminus is highly homologous to that of PCIP family members 1v, 9ql, and p19. Overall identity in the homologous C-termini among KChIP4, 1v, 9ql, and p19 ranged from 71%–80% at the amino acid level (alignments were performed using the CLUSTALW).

Monkey KChIP4c and KChIP4d were discovered by BLASTN search using monkey KChIP4a as a query for searching a proprietary database.

The nucleotide sequence of the monkey KChIP4a cDNA and the predicted amino acid sequence of the KChIP4a polypeptide are shown in FIG. 23 and in SEQ ID NOs:48 and 49, respectively.

The nucleotide sequence of the monkey KChIP4b cDNA and the predicted amino acid sequence of the KChIP4b polypeptide are shown in FIG. 24 and in SEQ ID NOs:50 and 51, respectively.

The nucleotide sequence of the monkey KChIP4c cDNA and the predicted amino acid sequence of the KChIP4c polypeptide are shown in FIG. 35 and in SEQ ID NOs:69 and 70, respectively.

The nucleotide sequence of the monkey KChIP4d cDNA and the predicted amino acid sequence of the KChIP4d polypeptide are shown in FIG. 36 and in SEQ ID NOs:71 and 72, respectively.

FIG. 37 depicts an alignment of the protein sequences of KChIP4a, KChIP4b, KChIP4c, and KChIP4d.

Example 14

Identification and Characterization of Human and Rat 33b07

In this example, the identification and characterization of the genes encoding rat and human 33b07 is described. Partial rat 33b07 (clone name 9o) was isolated as a positive clone from the yeast two-hybrid screen described above, using rKv4.3N as bait. The full length rat 33b07 clone was identified by mining of proprietary databases.

The nucleotide sequence of the full length rat 33b07 cDNA and the predicted amino acid sequence of the rat 33b07 polypeptide are shown in FIG. 26 and in SEQ ID NOs:52 and 53, respectively. The rat 33b07 cDNA encodes a protein having a molecular weight of approximately 44.7 kD and which is 407 amino acid residues in length.

Rat 33b07 binds rKv4.3N and rKv4.2N with slight preference for rKv4.2N in yeast 2-hybrid assays. In contrast, rat 33b07 does not bind rKv1.1N, indicating that the rat 33b07-Kv4N interaction is specific.

Rat 33b07 is expressed predominantly in the brain as determined by northern blot analysis.

The human 33b07 ortholog (clone 106d5) was also identified by mining of proprietary databases. The nucleotide sequence of the full length human 33b07 cDNA and the predicted amino acid sequence of the human 33b07 polypeptide are shown in FIG. 27 and in SEQ ID NOs:54 and 55, respectively. The human 33b07 cDNA encodes a protein having a molecular weight of approximately 45.1 kD and which is 414 amino acid residues in length.

Human 33b07 is 99% identical to the human KIAA0721 protein (GenBank Accession Number: AB018264) at the amino acid level. However, GenBank Accession Number: AB018264 does not have a functional annotation. Human 33b07 is also homologous to Testes-specific (Y-encoded) proteins (TSP(Y)s), SET, and Nucleosome Assembly Proteins (NAPs). The human 33b07 is 38% identical to human SET protein (GenBank Accession Number Q01105=U51924) over amino acids 204 to 337 and 46% identical over amino acids 334 to 387.

Human SET is also called HLA-DR associated protein II (PHAPII) (Hoppe-Seyler (1994) *Biol. Chem.* 375:113–126) and in some cases is associated with acute undifferentiated leukemia (AUL) as a result of a translocation event resulting in the formation of a SET-CAN fusion gene (Von Lindern M. et al. (1992) *Mol. Cell. Biol.* 12:3346–3355). An alternative spliced form of SET is also called Template Activating Factor-I alpha (TAF). TAF is found to be associated with myeloid leukemogenesis (Nagata K. et aL (1995) *Proc. Natl. Acad. Sci. U.S.A.* 92 (10), 4279–4283). Human SET is also a potent protein inhibitor of phosphatase 2A (Adachi Y. et al. (1994) *J. Biol. Chem.* 269:2258–2262). NAPs may be involved in modulating chromatin formation and contribute to regulation of cell proliferation (Simon H. U. et al. (1994) *Biochem. J.* 297, 389–397).

Thus, due to its homology to the above identified proteins, 33b07 may function as a protein inhibitor of phosphatase, an oncogene, and/or a chromatin modulator. The homology of 33b07 to SET, a protein phosphatase inhibitor, is of particular interest. Many channels, in particular the Kv4 channels (with which 33b07 is associated), are known to be regulated by phosphorylation by PKC and PKA ((1998) *J. Neuroscience* 18(10): 3521–3528; Am J Physiol 273: H1775–86 (1997)). Thus, 33b07 may modulate Kv4 activity by regulating the phosphorylation status of the potassium channel.

Example 15

Identification and Characterization of Rat 1p

In this example, the identification and characterization of the gene encoding rat 1p is described. Partial rat 1p was isolated as a positive clone from the yeast two-hybrid screen described above, using rKv4.3N as a bait.

The nucleotide sequence of the partial length rat 1p cDNA and the predicted amino acid sequence of the rat 1p polypeptide are shown in FIG. 28 and in SEQ ID NOs:56 and 57, respectively. The rat 1p cDNA encodes a protein having a molecular weight of approximately 28.6 kD and which is 267 amino acid residues in length.

Rat 1p binds rKv4.3N and rKv4.2N with slight preference for rKv4.3N in yeast two-hybrid assays. In contrast, 1p does not bind rKv1.1N, indicating that the 1p-Kv4N interaction is specific.

Rat 1p is predominantly expressed in the brain as determined by northern blot analysis.

A BLASTP 1.4 search, using a score of 100 and a word length of 3 (Altschul et al. (1990) *J. Mol. Biol.* 215:403) of the amino acid sequences of rat 1p revealed that rat 1p is similar to the human Restin (GenBank Accession Number P30622; also named cytoplasmic linker protein-170 alpha-2 (CLIP-170), M97501)). The rat 1p protein is 58% identical to the human Restin over amino acid residues 105 to 182, 55% identical to the human Restin over amino acid residues 115 to 186, 22% identical to the human Restin over amino acid residues 173 to 246, 22% identical to the human Restin over amino acid residues 169 to 218, and 58% identical to the human Restin over amino acid residues 217 to 228.

Restin is also named Reed-Stemberg intermediate filament associated protein. Reed-Sternberg cells are the tumoral cells diagnostic for Hodgkin's disease. It is suggested that Restin overexpression may be a contributing factor in the progression of Hodgkin's disease (Bilbe G. et al. (1992) *EMBO J.* 11: 2103–13) and Restin appears to be an intermediate filament associated protein that links endocytic vesicles to microtubules (Pierre P, et al. (1992) *Cell* 70 (6), 887–900).

The cytoskeleton regulates the activity of potassium channels (see, for example, Honore E, et al. (1992) *EMBO J.* 11:2465–2471 and Levin G, et al. (1996) *J. Biol. Chem.* 271:29321–29328), as well as the activity of other channels, e.g., $Ca^{-+}$ channels (Johnson B. D. et al (1993) *Neuron* 10:797–804); or $Na^{-}$ channels (Fukuda J. et al. (1981) *Nature* 294:82–85).

Accordingly, based on its homology to the Restin protein, the rat 1p protein may be associated with the cytoskeleton and may modulate the activity of potassium channels, e.g., Kv4, via its association to the cytoskeleton.

Example 16

Identification and Characterization of Rat 7s

In this example, the identification and characterization of the gene encoding rat 7s is described. Partial rat 7s was isolated as a positive clone from the yeast two-hybrid screen described above, using rKv4.3N as a bait. Rat 7s is the rat ortholog of the human vacuolar H(+)-ATPase catalytic subunit A (Accession Number P38606 and B46091) described in, for example, van Hille B. et al. (1993) *J. Biol. Chem.* 268 (10), 7075–7080.

The nucleotide sequence of the partial length rat 7s cDNA and the predicted amino acid sequence of the rat 7s polypeptide are shown in FIG. 29 and in SEQ ID NOs:58 and 59, respectively. The rat 7s cDNA encodes a protein having a molecular weight of approximately 28.6 kD and which is 270 amino acid residues in length.

Rat 7s binds rKv4.3N and rKv4.2N with preference for rKv4.3N in yeast two-hybrid assays. In contrast, 7s does not bind rKv1.1N, indicating that the 7s-Kv4N interaction is specific.

Rat 7s is expressed at significantly higher levels in the brain and the kidney than in the lung, liver, heart, testes, and skeletal muscle, as determined by northern blot analysis.

Example 17

Identification and Characterization of Rat 29x and 25r

In this example, the identification and characterization of the gene encoding rat 29x is described. Rat 29x was isolated as a positive clone from the yeast two-hybrid screen described above, using rKv4.3N as a bait. Rat 25r is a splice variant of 29x. They differ in the 5' untranslated region, but are identical in the coding region and at the amino acid level.

The nucleotide sequence of the rat 29x cDNA and the predicted amino acid sequence of the rat 29x polypeptide are shown in FIG. 30 and in SEQ ID NOs:60 and 61, respectively. The rat 29x cDNA encodes a protein having a molecular weight of approximately 40.4 kD and which is 351 amino acid residues in length.

The nucleotide sequence of the rat 25r cDNA is shown in FIG. 31 and in SEQ ID NO:62. The rat 25r cDNA encodes a protein having a molecular weight of approximately 40.4 kD and which is 351 amino acid residues in length.

Rat 29x is expressed in the spleen, lung, kidney, heart, brain, testes, skeletal muscle and liver, with the highest level of expression being in the spleen and the lowest being in the liver.

Rat 29x binds rKv4.3N and rKv4.2N with slight preference for rKv4.3N in yeast two-hybrid assays. In contrast, 29x does not bind rKv1.1N, indicating that the 29x-Kv4N interaction is specific.

Rat 29x is identical at the amino acid level to rat SOCS-1 (Suppressor Of Cytokine Signaling) described in Starr R. et al. (1997) *Nature* 387: 917–921; to JAB described in Endo T. A. et al. (1997) *Nature* 387: 921–924; and to SSI-1 (STAT-induced STAT inhibitor-1) described in Naka T. el al. (1997) *Nature* 387:924–928. These proteins are characterized in that they have an SH2 domain, bind to and inhibit JAK kinase, and, as a result, regulate cytokine signaling.

As used herein, the term "SH2 domain", also referred to a Src Homology 2 domain, includes a protein domain of about 100 amino acids in length which is involved in binding of phosphotyrosine residues, e.g., phosphotyrosine residues in other proteins. The target site is called an SH2-binding site. The SH2 domain has a conserved 3D structure consisting of two alpha helices and six to seven beta-strands. The core of the SH2 domain is formed by a continuous beta-meander composed of two connected beta-sheets (Kuriyan J. et al. (1997) *Curr. Opin. Struct. Biol.* 3:828–837). SH2 domains function as regulatory modules of intracellular signaling cascades by interacting with high affinity to phosphotyrosine-containing target peptides in a sequence-specific and strictly phosphorylation-dependent manner (Pawson T. (1995) *Nature* 373:573–580). Some proteins contain multiple SH2 domains, which increases their affinity for binding to phosphoproteins or confers the ability to bind to different phosphoproteins. Rat 29x contains an SH2 domain at amino acid residues 219–308 of SEQ ID NO:61.

Tyrosine phosphorylation regulates potassium channel activity (Prevarskaya N. B. et al. (1995) *J. Biol. Chem.* 270:24292–24299). JAK kinase phoshorylates proteins at tyrosines and is implicated in the regulation of channel activity (Prevarskaya N. B. et al. supra). Accordingly, based on its homology to SOCS-1, JAB, and SSI-1, rat 29x may modulate the activity of potassium channels, e.g., Kv4, by modulating JAK kinase activity.

Example 18

Identification and Characterization of Rat 5p

In this example, the identification and characterization of the gene encoding rat 5p is described. Rat 5p was isolated as a positive clone from the yeast two-hybrid screen described above, using rKv4.3N as a bait.

The nucleotide sequence of the rat Spc DNA and the predicted amino acid sequence of the rat 5p polypeptide are shown in FIG. 32 and in SEQ ID NOs:63 and 64, respectively. The rat 5p cDNA encodes a protein having a molecular weight of approximately 11.1 kD and which is 95 amino acid residues in length.

Rat 5p binds rKv4.3N and rKv4.2N with similar strength in yeast two-hybrid assays. In contrast, 5p does not bind rKv1.1N, indicating that the 5p-Kv4N interaction is specific.

Rat 5p is expressed in the spleen, lung, skeletal muscle, heart, kidney, brain, liver, and testes, as determined by northern blot analysis.

The rat 5p is identical to rat Calpactin I light chain or P10 (Accession Number P05943). P10 binds and induces the dimerization of annexin II (p36). P10 may function as a regulator of protein phosphorylation in that the p36 monomer is the preferred target of a tyrosine-specific kinase (Masiakowski P. et al. (1998) *Proc. Natl. Acad. Sci. U.S.A.* 85 (4): 1277–1281).

Tyrosine phosphorylation regulates the activity of potassium channels (Prevarskaya N. B. et al. supra). Thus, due to its identity to P10, rat 5p may modulate the activity of potassium channels, e.g., Kv4, by modulating the activity of a tyrosine-specific kinase.

Example 19

Identification and Characterization of Rat 7q

In this example, the identification and characterization of the gene encoding rat 7q is described. Rat 7q was isolated as a positive clone from the yeast two-hybrid screen described above, using rKv4.3N as a bait. Full length rat 7q was obtained by RACE PCR.

The nucleotide sequence of the rat 7q cDNA and the predicted amino acid sequence of the rat 7q polypeptide are shown in FIG. 33 and in SEQ ID NOs:65 and 66, respectively. The rat 7q cDNA encodes a protein having a molecular weight of approximately 23.5 kD and which is 212 amino acid residues in length.

Rat 7q binds rKv4.3N and rKv4.2N with same strength in yeast two-hybrid assays. In contrast, 7q does not bind rKv1.1N, indicating that the 7q-Kv4N interaction is specific.

Rat 7q is expressed in the heart, brain, spleen, lung, liver, skeletal muscle, kidney, and testes, as determined by northern blot analysis.

Rat 7q is identical to RAB2 (rat RAS-related protein, Accession Number P05712) at the amino acid level. RAB2 appears to be involved in vesicular traffic and protein transport (Touchot N. et al. (1987) *Proc. Natl. Acad. Sci. U.S.A.* 84 (23): 8210–8214). Accordingly, based on its homology to RAB2, rat 7q may be involved in potassium channel, e.g., Kv4, trafficking.

Example 20

Identification and Characterization of Rat 19r

In this example, the identification and characterization of the gene encoding rat 19r is described. Partial rat 19r was isolated as a positive clone from the yeast two-hybrid screen described above, using rKv4.3N as a bait. Full length rat 19r was obtained by RACE PCR.

The nucleotide sequence of the rat 19r cDNA and the predicted amino acid sequence of the rat 19r polypeptide are shown in FIG. 34 and in SEQ ID NOs:67 and 68, respectively. The rat 19r cDNA encodes a protein having a molecular weight of approximately 31.9 kD and which is 271 amino acid residues in length.

Rat 19r is expressed in the heart, brain, spleen, lung, liver, skeletal muscle, kidney, and testes, as determined by northern blot analysis.

Rat 19r binds rKv4.3N and rKv4.2N with slight preference for rKv4.3N in yeast two-hybrid assays. In contrast, 19r does not bind rKv1.1N, indicating that the 19r-Kv4N interaction is specific.

Rat 19r is identical to Rat phosphatidylinositol (PTDINS) transfer protein alpha (PTDINSTP, Accession Number M25758 or P16446) described in Dickeson S. K. et al. (1989) *J. Biol. Chem.* 264:16557–16564. PTDINSTP is believed to be involved in phospholipase C-beta (PLC-beta) signaling, phosphatidylinositol transfer protein (PtdIns-TP) synthesis, secrettory vesicle formation, and enhancement of phosphatidylinositol 3-kinase (PtdIns 3-kinase) activity (Cunningham E. et al. (1995) *Curr. Biol.* 5 (7): 775–783; (1995) *Nature* 377 (6549): 544–547; and Panaretou C. et al. (1997) *J. Biol. Chem.* 272 (4): 2477–2485).

Accordingly, based on its homology with PTDINSTP, rat 19r may modulate potassium channel, e.g., Kv4, activity via the PLC-beta signaling pathway and/or the PtdIns 3-kinase signaling pathway. Rat p19r may also be involved in potassium channel, e.g., Kv4, trafficking.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated nucleic acid molecule comprising a nucleotide sequence which is at least 90% identical to the nucleotide sequence of SEQ ID NO:31, SEQ ID NO:33, SEQ ID NO:35, or SEQ ID NO:39, or a complement thereof, wherein said isolated nucleic acid molecule encodes a polypeptide that binds to a potassium channel.

2. An isolated nucleic acid molecule comprising a nucleotide sequence which is at least 90% identical to the nucleotide sequence of the DNA insert of the plasmid deposited with ATCC as Accession Number 98936, 98940, 98949 or PTA-316, or a complement thereof, wherein said isolated nucleic acid molecule encodes a polypeptide that binds to a potassium channel.

3. An isolated nucleic acid molecule which encodes a polypeptide comprising an amino acid sequence at least 90% identical to the amino acid sequence of SEQ ID NO:32, SEQ ID NO.34, SEQ ID NO:36, or SEQ ID NO:40, wherein said isolated nucleic acid molecule encodes a polypeptide that binds to a potassium channel.

4. An isolated nucleic acid molecule comprising the nucleotide sequence of SEQ ID NO:31, SEQ ID NO:33, SEQ ID NO:35, or SEQ ID NO:39, or a complement thereof.

5. The isolated nucleic acid molecule of claim 4, wherein the nucleic acid molecule comprises the nucleotide sequence of SEQ ID NO:31, or a complement thereof.

6. The isolated nucleic acid molecule of claim 4, wherein the nucleic acid molecule comprises the nucleotide sequence of SEQ ID NO:33, or a complement thereof.

7. The isolated nucleic acid molecule of claim 4, wherein the nucleic acid molecule comprises the nucleotide sequence of SEQ ID NO:35, or a complement thereof.

8. The isolated nucleic acid molecule of claim 4, wherein the nucleic acid molecule comprises the nucleotide sequence of SEQ ID NO:39, or a complement thereof.

9. An isolated nucleic acid molecule consisting of the nucleotide sequence of SEQ ID NO:31, SEQ ID NO:33, SEQ ID NO:35, or SEQ ID NO:39, or a complement thereof.

10. The isolated nucleic acid molecule of claim 9, wherein the nucleic acid molecule consists of the nucleotide sequence of SEQ ID NO:31, or a complement thereof.

11. The isolated nucleic acid molecule of claim 9, wherein the nucleic acid molecule consists of the nucleotide sequence of SEQ ID NO:33, or a complement thereof.

12. The isolated nucleic acid molecule of claim 9, wherein the nucleic acid molecule consists of the nucleotide sequence of SEQ ID NO:35, or a complement thereof.

13. The isolated nucleic acid molecule of claim 9, wherein the nucleic acid molecule consists of the nucleotide sequence of SEQ ID NO:39, or a complement thereof.

14. An isolated nucleic acid molecule comprising the nucleotide sequence of the DNA insert of the plasmid deposited with ATCC as Accession Number 98936, 98940, 98949 or PTA-316, or a complement thereof.

15. The isolated nucleic acid molecule of claim 14, wherein the nucleic acid molecule comprises the nucleotide sequence of the DNA insert of the plasmid deposited with ATCC as Accession Number 98936, or a complement thereof.

16. The isolated nucleic acid molecule of claim 14, wherein the nucleic acid molecule comprises the nucleotide sequence of the DNA insert of the plasmid deposited with ATCC as Accession Number 98940, or a-complement thereof.

17. The isolated nucleic acid molecule of claim 14, wherein the nucleic acid molecule comprises the nucleotide sequence of the DNA insert of the plasmid deposited with ATCC as Accession Number 98949, or a complement thereof.

18. The isolated nucleic acid molecule of claim 14, wherein the-nucleic acid molecule comprises the nucleotide sequence of the DNA insert of the plasmid deposited with ATCC as Accession Number PTA-316, or a complement thereof.

19. An isolated nucleic acid molecule consisting of the nucleotide sequence of the DNA insert of the plasmid deposited with ATCC as Accession Number 98936, 98940, 98949 or PTA-316, or a complement thereof.

20. The isolated nucleic acid molecule of claim 19, wherein the nucleic acid molecule consists of the nucleotide sequence of the DNA insert of the plasmid deposited with ATCC as Accession Number 98936, or a complement thereof.

21. The isolated nucleic acid molecule of claim 19, wherein the nucleic acid molecule consists of the nucleotide sequence of the DNA insert of the plasmid deposited with ATCC as Accession Number 98940, or a complement thereof.

22. The isolated nucleic acid molecule of claim 19, wherein the nucleic acid molecule consists of the nucleotide sequence of the DNA insert of the plasmid deposited with ATCC as Accession Nurmber 98949, or a complement thereof.

23. The isolated nucleic acid molecule of claim 19, wherein the nucleic acid molecule consists of the nucleotide sequence of the DNA insert of the plasmid deposited with ATCC as Accession Number PTA-316, or a complement thereof.

24. An isolated nucleic acid molecule which encodes a polypeptide comprising the amino acid sequence of SEQ ID NO:32, SEQ ID NO:34, SEQ ID NO:36, or SEQ ID NO:40.

25. The isolated nucleic acid molecule of claim 24, which encodes a polypeptide comprising the amino acid sequence of SEQ ID NO:32.

26. The isolated nucleic acid molecule of claim 24, which encodes a polypeptide comprising the amino acid sequence of SEQ ID NO:34.

27. The isolated nucleic acid molecule of claim 24, which encodes a polypeptide comprising the amino acid sequence of SEQ ID NO:36.

28. The isolated nucleic acid molecule of claim 24, which encodes a polypeptide comprising the amino acid sequence of SEQ ID NO:40.

29. An isolated nucleic acid molecule which encodes a polypeptide consisting of the amino acid sequence of SEQ ID NO:32, SEQ ID NO:34, SEQ ID NO:36, or SEQ ID NO:40.

30. The isolated nucleic acid molecule of claim 29, which encodes a polypeptide consisting of the amino acid sequence of SEQ ID NO:32.

31. The isolated nucleic acid molecule of claim 29, which encodes a polypeptide consisting of the amiino acid sequence of SEQ ID NO:34.

32. The isolated nucleic acid molecule of claim 29, which encodes a polypeptide consisting of the amino acid sequence of SEQ ID NO:36.

33. The isolated nucleic acid molecule of claim 29, which encodes a polypeptide consisting of the amino acid sequence of SEQ ID NO:40.

34. An isolated nucleic acid molecule comprising a nucleotide sequence which is at least 95% identical to the nucleotide sequence of SEQ ID NO31, SEQ ID NO:33, SEQ ID NO:35, or SEQ ID NO:39, or a complement thereof, wherein said isolated nucleic acid molecule encodes a polypeptide that binds to a potassium channel.

35. An isolated nucleic acid molecule comprising a nucleotide sequence which is at least 95% identical to the nucleotide sequence of the DNA insert of the plasmid deposited with ATCC as Accession Number 98936, 98940, 98949 or PTA-316, or a complement thereof, wherein said isolated nucleic acid molecule encodes a polypeptide that binds to a potassium channel.

36. An isolated nucleic acid molecule which encodes a polypeptide comprising an amino acid sequence at least 95% identical To the amino acid sequence of SEQ ID NO:32, SEQ ID NO:34, SEQ ID NO:36, or SEQ ID NO:40, wherein said isolated nucleic acid molecule encodes a polypeptide that binds to a potassium channel.

37. An isolated nucleic acid molecule comprising a nucleotide sequence which is at least 90% identical to the nucleotide sequence of SEQ ID NO:31, SEQ ID NO:33, SEQ ID NO:35, or SEQ ID NO:39, or a comnplement thereof, wherein said isolated nucleic acid molecule encodes a polypeptide that modulates intracellular calcium concentration.

38. An isolated nucleic acid molecule comnprising a nucleotide sequence which is at least 90% identical to the nucleotide sequence of the DNA insert of the plasmid deposited with ATCC as Accession Number 98936, 98940, 98949 or PTA-316, or a complement thereof, wherein said isolated nucleic acid molecule encodes a polypeptide that modulates intracellular calcium concentration.

39. An isolated nucleic acid molecule which encodes a polypeptide comprising an amino acid sequence at least 90% identical to the amino acid sequence of SEQ ID NQ:32, SEQ ID NO:34, SEQ ID NO:36, or SEQ ID NO:40, wherein said isolated nucleic acid molecule encodes a polypeptide that modulates intracellular calcium concentration.

40. An isolated nucleic acid molecule comprising a nucleotide sequence which is at least 95% identical to the nucleotide sequence of SEQ ID NO:31, SEQ ID NO:33, SEQ ID NO:35, or SEQ ID NO:39, or a complement thereof, wherein said isolated nucleic acid molecule encodes a polypeptide that modulates intracellular calcium concentration.

41. An isolated nucleic acid molecule comprising a nucleotide sequence which is at least 95% identical to the nucleotide sequence of the DNA insert of the plasmid deposited with ATCC as Accession Number 98936, 98940, 98949 or PTA-316, or a complement thereof, wherein said isolated nucleic acid molecule encodes a polypeptide that modulates intracellular calcium concentration.

42. An isolated nucleic acid molecule which encodes a polypeptide comprising an amino acid sequence at least 95% identical To the amino acid sequence of SEQ ID NO:32, SEQ ID NO:34, SEQ ID NO:36, or SEQ ID NO:40, wherein said isolated nucleic acid molecule encodes a polypeptide that modulates intracellular calciun concentration.

43. An isolated nucleic acid molecule comprising a nucleotide sequence which is at least 90% identical to the nucleotide sequence of SEQ ID NO:31, SEQ ID NO:33, SEQ ID NO:35, or SEQ ID NO:39, or a complement thereof, wherein said isolated nucleic acid molecule encodes a polypeptide that modulates Kv4.2 or Kv4.3 currents.

44. An isolated nucleic acid molecule comprising a nucleotide sequence which is at least 90% identical to the nucleotide sequence of the DNA insert of the plasmid deposited with ATCC as Accession Number 98936, 98940, 98949 or PTA-316, or a complement thereof, wherein said isolated nucleic acid molecule encodes a polypeptide that modulates Kv4.2 or Kv4.3 currents.

45. An isolated nucleic acid molecule which encodes a polypeptide comprising an amino acid sequence at least 90% identical to the amino acid sequence of SEQ ID NO:32, SEQ ID NO:34, SEQ ID NO:36, or SEQ ID NO:40, wherein said isolated nucleic acid molecule encodes a polypeptide that modulates Kv4.2 or Kv4.3 currents.

46. An isolated nucleic acid molecule cornprising a nucleotide sequence which is at least 95% identical to the nucleotide sequence of SEQ ID NO:31, SEQ ID NO:33, SEQ ID NO:35, or SEQ ID NO:39, or a complement tereof, wherein said isolated nucleic acid molecule encodes a polypeptide that modulates Kv4.2 or Kv4.3 currents.

47. An isolated nucleic acid molecule comprising a nucleotide sequence which is at least 95% identical to the nucleotide sequence of the DNA insert of the plasmid deposited with ATCC as Accession Number 98936, 98940, 98949 or PTA-316, or a compler thereof, wherein said isolated nucleic acid molecule encodes a polypeptide that modulates or Kv4.3 currents.

48. An isolated nucleic acid molecule which encodes a polypeptide comprising an amino acid sequence at least 90% identical to the amino acid sequence of SEQ ID NO:32, SEQ ID NO:34, SEQ ID NO:36, or SEQ ID NO:40, wherein said isolated nucleic acid molecule encodes a polypeptide that modulates Kv4.2 or Kv4.3 currents.

49. The nucleic acid molecule of any of claims 1, 2, 3, 4, 9, 14, 19, 24, 29, 34, 47, or 48, further comprising vector nucleic acid sequences.

50. The nucleic acid molecule of any of claims 1, 2, 3, 4, 9, 14, 19, 24, 29, 34, 47 or 48, further comprising nucleic acid sequences encoding a heterologous polypeptide.

51. An isolated host cell which contains the nucleic acid molecule of any of claims 1, 2, 3, 4, 9, 14, 19, 24, 29, 34, 47 or 48.

52. The host cell of claim 51 which is a mammalian host cell.

53. A method for producing a polypeptide comprising culturing the host cell of claim 51 under conditions in which the nucleic acid molecule is expressed and the polypeptide is produced.

* * * * *